United States Patent
Burgess et al.

(10) Patent No.: US 8,962,596 B2
(45) Date of Patent: Feb. 24, 2015

(54) 5,7-SUBSTITUTED-IMIDAZO[1,2-C]PYRIMIDINES AS INHIBITORS OF JAK KINASES

(75) Inventors: Laurence E. Burgess, Boulder, CO (US); Mark Laurence Boys, Boulder, CO (US); Robert D. Groneberg, Boulder, CO (US); Darren M. Harvey, Acton, MA (US); Timothy Kercher, Boulder, CO (US); Christopher F. Kraser, Boulder, CO (US); Ellen Laird, Boulder, CO (US); Eugene Tarlton, Lafayette, CO (US); Qian Zhao, Louisville, CO (US); Lily Huang, Austin, TX (US)

(73) Assignee: Array BioPharma Inc., Boulder, CO (US)

( * ) Notice: Subject to any disclaimer, the term of this patent is extended or adjusted under 35 U.S.C. 154(b) by 297 days.

(21) Appl. No.: 13/640,099

(22) PCT Filed: Apr. 11, 2011

(86) PCT No.: PCT/US2011/031896
§ 371 (c)(1),
(2), (4) Date: Jan. 8, 2013

(87) PCT Pub. No.: WO2011/130146
PCT Pub. Date: Oct. 20, 2011

(65) Prior Publication Data
US 2013/0131039 A1    May 23, 2013

Related U.S. Application Data

(60) Provisional application No. 61/324,186, filed on Apr. 14, 2010.

(51) Int. Cl.
| C07D 487/04 | (2006.01) |
| A61K 31/519 | (2006.01) |
| A61P 29/00 | (2006.01) |
| A61P 35/00 | (2006.01) |
| A61P 37/06 | (2006.01) |
| C07D 498/04 | (2006.01) |

(52) U.S. Cl.
CPC ............ C07D 487/04 (2013.01); C07D 498/04 (2013.01)
USPC ...................... 514/63; 514/259.1; 514/210.21; 514/252.16; 514/233.2; 514/210.8; 514/230.5; 514/249; 514/64; 544/230; 544/281; 544/117; 544/105; 548/364.1

(58) Field of Classification Search
CPC ........................... C07D 487/04; A61K 31/519
USPC ........................ 544/281; 514/259.1
See application file for complete search history.

(56) References Cited

U.S. PATENT DOCUMENTS

| 6,210,654 | B1 | 4/2001 | Ihle et al. |
| 7,598,257 | B2 | 10/2009 | Rodgers et al. |
| 8,158,616 | B2 | 4/2012 | Rodgers et al. |
| 2008/0312258 | A1 | 12/2008 | Rodgers et al. |
| 2009/0181959 | A1 | 7/2009 | Rodgers et al. |

FOREIGN PATENT DOCUMENTS

| WO | WO 2007/070514 A1 | 6/2007 |
| WO | WO 2008/064157 A1 | 5/2008 |
| WO | WO 2010/083283 A2 | 7/2010 |

OTHER PUBLICATIONS

Patent Cooperation Treaty, International Searching Authority, Search Report and Written Opinion for PCT/US2011/031896, 9 pages, dated May 30, 2011.

Primary Examiner — Susanna Moore
(74) Attorney, Agent, or Firm — Sarah S. Mastous; Viksnins Harris & Padys

(57) ABSTRACT

Compounds of Formula I:

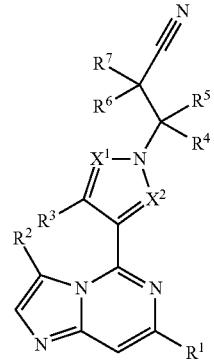

and stereoisomers and pharmaceutically acceptable salts and solvates thereof in which $R^1, R^2, R^3, R^4, R^5, R^6, R^7, X^1$ and $X^2$ have the meanings given in the specification, are inhibitors of one or more JAK kinases and are useful in the treatment of autoimmune diseases, inflammatory diseases, rejection of transplanted organs, tissues and cells, as well as hematologic disorders and malignancies and their co-morbidities.

38 Claims, No Drawings

5,7-SUBSTITUTED-IMIDAZO[1,2-C]PYRIMIDINES AS INHIBITORS OF JAK KINASES

The present invention relates to novel compounds, to pharmaceutical compositions comprising the compounds, to processes for making the compounds, and to the use of the compounds in therapy. More particularly, it relates to certain 5,7-substituted-imidazo[1,2-c]pyrimidine compounds which are inhibitors of JAK kinases. In particular, the compounds are inhibitors of Tyk2, JAK1, JAK2, and/or JAK3, and are useful in the treatment of JAK kinase-associated diseases such as autoimmune diseases, inflammatory diseases, organ, tissue and cell transplant rejection, and hematological disorders and malignancies.

The members of the Janus kinase (JAK) family of non-receptor, intracellular tyrosine kinases are components of cytokine signal transduction. Four family members have been identified: JAK1, JAK2, JAK3 and Tyk2. The JAKs play a key role in the intracellular signaling mediated through Type I and Type II cytokine receptors. Specific cytokine receptor chains are associated with particular JAK kinases (reviewed in O'Sullivan et al., Mol. Immunol. 2007 44:2497; Murray J., Immunol. 2007 178:2623). Upon binding of cytokines to their receptors, JAKs are activated and phosphorylate the receptors, creating docking sites for other signaling molecules, in particular members of the signal transducer and activator of transcription (STAT) family. Upon phosphorylation, STATs dimerize, translocate to the nucleus and activate expression of genes involved in development, growth, differentiation, and maintenance of a variety of cell types. The cytokine-induced responses mediated by JAK kinases are important in host defense and, when dysregulated, play a role in pathogenesis of immune or inflammatory diseases, immune deficiencies, and malignancy (O'Sullivan et al., Mol. Immunol. 2007, 44:2497). Elevated or decreased levels of JAK/STAT-utilizing cytokines have been implicated in a number of disease states. In addition, mutations or polymorphisms in Type 1 and II cytokine receptors, JAK kinases, STAT proteins, and JAK/STAT regulatory proteins such as phosphotyrosine phosphatases, SOCS proteins, PIAS proteins have been reported in a variety of diseases. When dysregulated, JAK-mediated responses can positively or negatively effect cells leading to over-activation and malignancy or immune and hematopoietic deficiencies, respectively, and suggests the utility for use of inhibitors of JAK kinases. The JAK/STAT signaling pathway is involved in a variety of hyperproliferative and cancer-related processes including cell-cycle progression, apoptosis, angiogenesis, invasion, metastasis and evasion of the immune system (Haura et al., Nature Clinical Practice Oncology, 2005, 2(6), 315-324; Verna et al., Cancer and Metastasis Reviews, 2003, 22, 423-434). In addition, the JAK/STAT signaling pathway is important in the genesis and differentiation of hematopoietic cells and regulating both pro- and anti-inflammatory and immune responses (O'Sullivan et al., Molecular Immunology 2007, 44:2497. Because cytokines utilize different patterns of JAK kinases (O'Sullivan et al., Mol. Immunol. 2007 44:2497; Murray J., Immunol. 2007 178:2623), there may be utility for antagonists of JAK kinases with differing intra-family selectivity profiles in diseases associated with particular cytokines or in diseases associated with mutations or polymorphisms in the JAK/STAT pathways.

JAK3 deficient mice exhibit a severe combined immunodeficiency syndrome (scid). The failure of lymphocyte development in an otherwise healthy animal supports the utility of targeting JAK3 for diseases associated with lymphocyte activation.

In addition to the scid phenotype of the JAK3-deficient mice, the elevated expression of cytokines which signal through the JAK3-associated gamma common chain in inflammatory and immune responses suggests that inhibitors of JAK3 could impede T-cell activation and prevent rejection of grafts following transplant surgery, or to provide therapeutic benefit to patients suffering autoimmune or inflammatory disorders (reviewed in O'Sullivan et al., Mol. Immunol. 2007 44:2497; Murray J., Immunol. 2007 178:2623).

Inhibitors of the tyrosine kinase JAK3 have been described to be useful as immunosuppressants (see, for example, U.S. Pat. No. 6,313,129; Borie et al., 2003 Curr. Opin. Investigational Drugs 4:1297). JAK3 has also been shown to play a role in mast-cell mediated allergic reactions and inflammatory diseases.

JAK1- and JAK2-deficient animals are not viable. Studies have identified a high prevalence of an acquired activating JAK2 mutation (JAK2V617F) in myeloproliferative disorders such as polycythemia vera, essential thrombocythemia and idiopathic myelofibrosis and to a lesser extent in several other diseases. The mutant JAK2 protein is able to activate downstream signaling in the absence of cytokine stimulation, resulting in autonomous growth and/or hypersensitivity to cytokines and is believed to play a role in driving these diseases (M J Percy and McMullin M F, Hematological Oncology 2005, 23(3-4), 91-93). Additional mutations or translocations resulting dysregulated JAK2 function have been described in other malignancies (Ihle J N and Gilliland D G, Curr. Opin. Genet. Dev. 2007 17:8; Sayyah J and Sayeski P P 2009 Curr. Oncol. Rep. 11:117) Inhibitors of JAK2 have been described to be useful in myeloproliferative diseases (Santos et al., Blood 2010 115:1131; Barosi G. and Rosti V., Curr. Opin. Hematol. 2009 16:129, Atallah E. and Versotvsek S., 2009 Exp. Rev. Anticancer Ther. 9:663). More rarely, mutations in JAK1 and JAK3 have been reported in hematologic malignancies (Vainchecker et al., Semin. Cell Dev. Biol. 2008 Aug. 1; 9(4):385-93). JAK family kinase inhibitors may be useful in these settings (Sayyah J and Sayeski P P 2009 Curr. Oncol. Rep. 11:117). In addition, over expression of cytokines which utilize JAK2 for signaling have been implicated in disease states (JAK2 utilizing cytokines are reviewed in O'Sullivan et al., Mol. Immunol. 2007 44:2497; Murray J., Immunol. 2007 178:2623).

JAK1 has been reported to signal with other JAK1 molecules or in collaboration with JAK2 or JAK3 depending on the cytokine input (JAK1 utilizing cytokines reviewed in O'Sullivan 2007, Murray 2007). Elevated levels of cytokines which signal through JAK1 have been implicated in a number of immune and inflammatory diseases. JAK1 or JAK family kinase antagonists may be useful for modulating or treating in such diseases.

Tyk2-deficient animals exhibit blunted immune responses to several types of pathogens and are less susceptible to some autoimmune diseases. This phenotype supports the utility of inhibiting Tyk2 in particular disease settings. Particularly, targeting Tyk2 appears to be a promising strategy for the treatment of IL-12-, IL-23- or Type 1 IFN-mediated diseases or diseases. These include but are not limited to rheumatoid arthritis, multiple sclerosis, lupus, psoriasis, psoriatic arthritis, inflammatory bowel disease, uveitis, and sarcoidosis (Shaw, M. et al., Proc. Natl. Acad. Sci. USA, 2003, 100, 11594-11599; Ortmann, R. A., and Shevach, E. M. Clin. Immunol., 2001, 98, 109-118; Watford et al., Immunol. Rev. 2004 202:139).

There remains a need for compounds and methods for the treatment of autoimmune diseases, inflammatory diseases, organ, tissue and cell transplant rejection, and hematologic disorders and malignancies.

SUMMARY OF THE INVENTION

It has now been found that certain 5,7-substituted-imidazo [1,2-c]pyrimidine compounds are inhibitors of one or more JAK kinases and are useful for treating autoimmune diseases, inflammatory diseases, rejection of transplanted organs, tissues and cells, as well as hematologic disorders and malignancies and their co-morbidities.

More specifically, one aspect of the present invention provides compounds of Formula I:

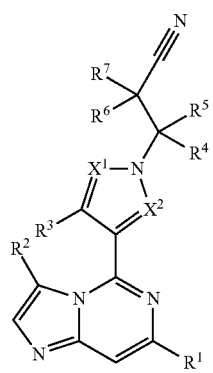

and stereoisomers and pharmaceutically acceptable salts and solvates thereof, wherein $R^1$, $R^2$, $R^3$, $R^4$, $R^5$, $R^6$, $R^7$, $X^1$ and $X^2$ are as defined herein.

Another aspect of the present invention provides methods of treating a disease or disorder modulated by one or more JAK kinases, comprising administering to a mammal in need of such treatment an effective amount of a compound of this invention or pharmaceutically acceptable salt or solvate thereof. In one embodiment, the disease or disorder is selected from autoimmune diseases, inflammatory diseases, and organ, tissue and cell transplant rejection. In another embodiment, the disease or disorder is selected from hematological disorders and malignancies.

Another aspect of the present invention provides a pharmaceutical composition comprising a compound of the present invention or a pharmaceutically acceptable salt or solvate thereof.

Another aspect of the present invention provides compounds of the present invention for use in therapy.

Another aspect of the present invention provides compounds of the present invention for use in the treatment of diseases or disorders selected from autoimmune diseases, inflammatory diseases, and organ, tissue and cell transplant rejection.

Another aspect of the present invention provides compounds of the present invention for use in the treatment of hematological disorders and malignancies.

Another aspect of the present invention provides the use of a compound of this invention in the manufacture of a medicament for the treatment of diseases or disorders selected from autoimmune diseases, inflammatory diseases, and organ, tissue and cell transplant rejection.

Another aspect of the present invention provides the use of a compound of this invention in the manufacture of a medicament for the treatment of hematological disorders and malignancies.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical compositions thereof, which are useful in the treatment of disease and disorders selected from autoimmune diseases, inflammatory diseases, organ, tissue and cell transplant rejection, and hematological disorders and malignancies.

Accordingly, one embodiment of this invention provides a compound of the general Formula I

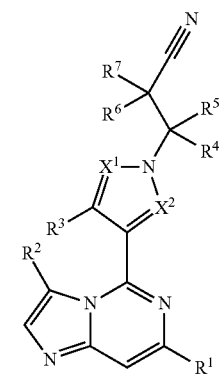

and stereoisomers and pharmaceutically acceptable salts and solvates thereof, wherein:

$X^1$ is N or $CR^{3a}$ and $X^2$ is N or $CR^{3b}$;

$R^{3a}$ and $R^{ab}$ are independently H, (1-6C alkyl), $CF_3$, F, Cl, CN, or (3-6C)cycloalkyl;

$R^1$ is $hetAr^1$, $hetAr^2$, $hetAr^3$, $Ar^1$, $Ar^2$, $C(=O)NR^aR^b$, (3-6C)cycloalkyl, or N-(1-3C alkyl)pyridinonyl;

$hetAr^1$ is a 5 membered heteroaryl ring having 1-3 ring heteroatoms independently selected from N, O and S and optionally substituted with one or more substituents independently selected from (1-6C)alkyl, fluoro(1-6C)alkyl, difluoro (1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, $hetCyc^a$(1-2C)alkyl, $hetAr^a$(1-2C)alkyl and (1-4C alkylsulfonyl)(1-6C alkyl);

$hetCyc^a$ is a 6 membered heterocycle having 1-2 ring heteroatoms independently selected from N and O and is optionally substituted with (1-6C)alkyl;

$hetAr^a$ is a 6 membered heteroaryl having 1-2 ring nitrogen atoms;

$hetAr^2$ is a 9-membered bicyclic partially unsaturated or fully unsaturated heterocyclic ring having 3 ring nitrogen atoms and optionally substituted with one or more substituents independently selected from (1-6C)alkyl;

$hetAr^3$ is a 6 membered heteroaryl having 1-2 ring nitrogen atoms and optionally substituted with one or more substituents independently selected from (1-6C)alkyl, $hetCyc^b$ and (1-6C)alkoxy;

$hetCyc^b$ is a 6-membered heterocycle having 1-2 ring nitrogen atoms and optionally substituted with one or more substituents independently selected from (1-6C)alkyl;

$Ar^1$ is phenyl substituted with a substituent selected from $hetCyc^c$, $hetCyc^d$, $hetAr^b$, trifluoro(1-6C)alkyl and (1-6C) alkoxy;

hetCyc$^c$ is a 6 membered heterocycle having 1-2 ring heteroatoms independently selected from N and O and optionally substituted with one or more substituents independently selected from (1-6C)alkyl;

hetCyc$^d$ is an 8-membered bridged heterocyclic ring having 1-2 ring heteroatoms independently selected from N and O;

hetAr$^b$ is a 5-membered heteroaryl ring having 1-2 ring nitrogen atoms and optionally substituted with one or more substituents independently selected from (1-6C)alkyl;

Ar$^2$ is a benzo ring fused to a 5-6 membered azacyclic ring and is optionally substituted with one or more substituents independently selected from (1-6C)alkyl;

R$^a$ is H;

R$^b$ is (1-6C)alkyl, (3-6C)cycloalkyl or hetAr$^c$;

hetAr$^c$ is a 6-membered heteroaryl having 1-2 ring N atoms;

R$^2$ is hydrogen, halogen, (1-4C)alkyl, CF$_3$, CN, (3-4C)cycloalkyl, azetidinyl or oxetanyl;

R$^3$ is hydrogen, (1-6C)alkyl, CF$_3$, F, Cl, CN or (3-6C)cycloalkyl;

R$^4$ is H or (1-6C)alkyl, and

R$^5$ is H, (1-6C)alkyl, —CH$_2$CN, (3-6C)cycloalkyl (optionally substituted by one or more halogens), hetCyc$^e$, Ar$^a$ or hetAr$^d$, or R$^4$ and R$^5$ together with the carbon atom to which they are attached form a 4-6 membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cyclo alkyl), —CH$_2$hetCyc$^f$, —C(=O)O(1-6C alkyl), —C(=O)(1-6C alkyl), —C(=O)(CR'R")CF$_3$, hetAr$^e$, (3-6C)cycloalkyl, a 4-6 membered oxacyclic ring and —SO$_2$R$^c$, or R$^4$ and R$^5$ together with the carbon atom to which they are attached form a 4-membered oxacyclic ring, or R$^4$ and R$^5$ together with the carbon atom to which they are attached form a 3-6 membered carbocyclic ring optionally substituted with (1-6C)alkyl, or R$^4$ and R$^5$ together with the carbon atom to which they are attached form a 7-9 membered bicyclic Spiro carbocycle, or R$^4$ and R$^5$ together with the carbon atom to which they are attached form a 7-9 membered bicyclic spiro heterocycle having a ring heteroatom selected from O and N, wherein said ring nitrogen atom when present is optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl and —SO$_2$R$^c$;

hetCyc$^e$ is a 5-6-membered heterocycle having a ring N atom and substituted with a substituents selected from C(=O)(1-6C)alkyl;

Ar$^a$ is phenyl optionally substituted with one or more substituents independently selected from halogen, CF$_3$, (1-6C)alkyl and (1-6C)alkoxy;

hetAr$^d$ is a 6-membered heteroaryl having 1-2 ring nitrogen atoms and optionally substituted with one or more substituents independently selected from halogen, (1-6C)alkoxy, (1-6C)alkyl and CF$_3$;

hetCyc$^f$ is a 6-membered oxacyclic ring;

R' and R" are independently hydrogen or methyl, or R' and R" together with the carbon atom to which they are attached form a cyclopropylidine ring;

hetAr$^e$ is a 6-membered heteroaryl ring having 1-2 ring nitrogen atoms;

R$^c$ is (1-6C)alkyl, fluoro(1-3C)alkyl, difluoro(1-3C)alkyl trifluoro(1-3C)alkyl, tetrafluoro(1-3C)alkyl, pentafluoro(1-3C)alkyl, (3-6C)cyclo alkyl (optionally substituted with (1-6C)alkyl), or phenyl (optionally substituted with one or more groups independently selected from (1-6C alkyl), CF$_3$, CF$_3$O— and halogen);

R$^6$ is hydrogen or methyl; and

R$^7$ is hydrogen or (1-6C)alkyl.

In one embodiment of Formula I,

X$^1$ is N or CR$^{3a}$ and X$^2$ is N or CR$^{3b}$, wherein only one of X$^1$ and X$^2$ may be N;

R$^{3a}$ and R$^{3b}$ are independently H, (1-6C alkyl) or CF$_3$;

R$^1$ is hetAr$^1$, hetAr$^2$, hetAr$^3$, Ar$^1$, Ar$^2$ or C(=O)NR$^a$R$^b$;

hetAr$^1$ is a 5 membered heteroaryl ring having 1-3 ring heteroatoms independently selected from N, O and S and optionally substituted with one or more substituents independently selected from (1-6C)alkyl, fluoro(1-6C)alkyl, difluoro (1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc$^a$(1-2C)alkyl and hetAr$^a$(1-2C)alkyl;

hetCyc$^a$ is a 6 membered heterocycle having 1-2 ring heteroatoms independently selected from N and O and is optionally substituted with (1-6C)alkyl;

hetAr$^a$ is a 6 membered heteroaryl having 1-2 ring nitrogen atoms;

hetAr$^2$ is a 9-membered bicyclic partially unsaturated or fully unsaturated heterocyclic ring having 3 ring nitrogen atoms and optionally substituted with one or more substituents independently selected from (1-6C)alkyl;

hetAr$^3$ is a 6 membered heteroaryl having 1-2 ring nitrogen atoms and optionally substituted with one or more substituents independently selected from (1-6C)alkyl and hetCyc$^b$;

hetCyc$^b$ is a 6-membered heterocycle having 1-2 ring nitrogen atoms and optionally substituted with one or more substituents independently selected from (1-6C)alkyl;

Ar$^1$ is phenyl substituted with a substituent selected from hetCyc$^c$, hetCyc$^d$ and hetAr$^b$;

hetCyc$^c$ is a 6 membered heterocycle having 1-2 ring heteroatoms independently selected from N and O and optionally substituted with one or more substituents independently selected from (1-6C)alkyl;

hetCyc$^d$ is an 8-membered bridged heterocyclic ring having 1-2 ring heteroatoms independently selected from N and O;

hetAr$^b$ is a 5-membered heteroaryl ring having 1-2 ring nitrogen atoms and optionally substituted with one or more substituents independently selected from (1-6C)alkyl;

Ar$^2$ is a benzo ring fused to a 5-6 membered azacyclic ring and is optionally substituted with one or more substituents independently selected from (1-6C)alkyl;

R$^a$ is H;

R$^b$ is (1-6C)alkyl, (3-6C)cycloalkyl or hetAr$^c$;

hetAr$^c$ is a 6-membered heteroaryl having 1-2 ring N atoms;

R$^2$ is hydrogen, F, Cl or CN;

R$^3$ is hydrogen or (1-6C)alkyl;

R$^4$ is H or (1-6C)alkyl, and

R$^5$ is H, (1-6C)alkyl, —CH$_2$CN, (3-6C)cycloalkyl, hetCyc$^e$, Ar$^a$ or hetAr$^d$, or R$^4$ and R$^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cyclo alkyl), —CH$_2$hetCyc$^f$, —C(=O)O(1-6C alkyl), —C(=O)(1-6C alkyl), —C(=O)(CR'R")CF$_3$, hetAr$^e$, (3-6C)cycloalkyl, a 4-6 membered oxacyclic ring and —SO$_2$R$^c$, or $R^4$ and $R^5$ together with the carbon atom to which they are attached form a 6-membered azacyclic ring substituted with a substituent selected from (1-6C)alkyl, fluoro(1-6C)alkyl, difluoro(1-6C)alkyl, trifluoro(1-6C)alkyl, tetrafluoro (1-6C)alkyl, pentafluoro(1-6C)alkyl, (3-4C)alkynyl, cyano(1-4C)alkyl, benzyl, —CH$_2$(3-6C cycloalkyl), —CH$_2$hetCyc$^f$, —C(=O)O(1-6Calkyl), —C(=O)(1-6Calkyl), —C(=O)(CR'R'')CF$_3$, hetAr$^e$, (3-6C)cycloalkyl, a 4-6 membered oxacyclic ring and —SO$_2$R$^c$, or $R^4$ and $R^5$ together with the carbon atom to which they are attached form a 4-membered oxacyclic ring, or $R^4$ and $R^5$ together with the carbon atom to which they are attached form a 3-6 membered carbocyclic ring;

hetCyc$^e$ is a 5-6-membered heterocycle having a ring N atom and substituted with a substituents selected from C(=O)(1-6C)alkyl;

Ar$^a$ is phenyl optionally substituted with one or more substituents independently selected from halogen, CF$_3$, (1-6C) alkyl and (1-6C)alkoxy;

hetAr$^d$ is a 6-membered heteroaryl having 1-2 ring nitrogen atoms and optionally substituted with one or more substituents independently selected from halogen, (1-6C)alkoxy, (1-6C)alkyl and CF$_3$;

hetCyc$^f$ is a 6-membered oxacyclic ring;

R' and R'' are independently hydrogen or methyl, or

R' and R'' together with the carbon atom to which they are attached form a cyclopropylidine ring;

hetAr$^e$ is a 6-membered heteroaryl ring having 1-2 ring nitrogen atoms;

R$^c$ is (1-6C)alkyl, fluoro(1-3C)alkyl, difluoro(1-3C)alkyl trifluoro(1-3C)alkyl, tetrafluoro(1-3C)alkyl, pentafluoro(1-3C)alkyl, (3-6C)cycloalkyl or phenyl;

R$^6$ is hydrogen; and

R$^7$ is hydrogen or (1-6C)alkyl.

In one embodiment of Formula I, R$^1$ is hetAr$_1$, wherein hetAr$^1$ is a 5 membered heteroaryl ring having 1-3 ring heteroatoms independently selected from N, O and S and optionally substituted with one or more substituents independently selected from (1-6C)alkyl, fluoro(1-6C)alkyl, difluoro(1-6C) alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc$^a$(1-2C)alkyl, hetAr$^a$(1-2C)alkyl and (1-4C alkylsulfonyl)(1-6C alkyl).

In one embodiment of Formula I, R$^1$ is hetAr$^1$, wherein hetAr$^1$ is a 5 membered heteroaryl ring having 1-3 ring heteroatoms independently selected from N, O and S and optionally substituted with one or more substituents independently selected from (1-6C)alkyl, fluoro(1-6C)alkyl, difluoro(1-6C) alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc$^a$(1-2C)alkyl and hetAr$^a$(1-2C)alkyl.

In one embodiment, hetAr$^1$ is pyrazolyl, thiazolyl, oxazolyl, thiadiazolyl, imidazolyl, pyrrolyl or thiophenyl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc$^a$(1-2C)alkyl, hetAr$^a$(1-2C)alkyl and (1-4C alkylsulfonyl)(1-6C alkyl).

In one embodiment, hetAr$^1$ is pyrazolyl, thiazolyl, oxazolyl, thiadiazolyl, imidazolyl, pyrrolyl or thiophenyl optionally substituted with one or more substituents independently selected from (1-6C)alkyl, fluoro(1-6C)alkyl, difluoro (1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc$^a$(1-2C)alkyl and hetAr$^a$(1-2C)alkyl.

In one embodiment, hetAr$^1$ is substituted with one or two of said substituents. In one embodiment, hetAr$^1$ is substituted with one of said substituents.

Particular examples of (1-6C)alkyl substituents for hetAr$^1$ include methyl, ethyl, propyl, isopropyl, butyl, isobutyl, and tert-butyl.

Particular examples of fluoro(1-6C)alkyl substituents for hetAr$^1$ include fluoromethyl and fluoroethyl.

Particular examples of difluoro(1-6C)alkyl substituents for hetAr$^1$ include difluoromethyl and difluoroethyl.

Particular examples of trifluoro(1-6C)alkyl substituents for hetAr$^1$ include trifluoromethyl and 2,2,2-trifluoroethyl.

Particular examples of (1-4C alkoxy)(1-6C)alkyl substituents for hetAr$^1$ include methoxymethyl, ethoxyethyl, ethoxyethyl and (2-isopropoxy)ethyl.

A particular example of a trimethylsilyl(1-4C alkoxy)(1-6C)alkyl substituent for hetAr$^1$ is trimethylsilylethoxymethyl.

Particular examples of (3-6C)cycloalkyl substituents for hetAr$^1$ include cyclopropyl, cyclobutyl, cyclopentyl and cyclohexyl.

Particular examples of 4-6 membered oxacyclic ring substituents for hetAr$^1$ include oxetanyl, tetrahydropyranyl and tetrahydropyranyl groups.

Particular examples of hetCyc$^a$(1-2C)alkyl substituents for hetAr$^1$ include piperidinylmethyl, piperidinylethyl, piperazinylmethyl, piperazinylmethyl and morpholinylmethyl. A particular example is (4-methylpiperazinyl)ethyl.

Particular examples of hetAr$^a$(1-2C)alkyl substituents for hetAr$^1$ include pyridinylmethyl, pyridinylethyl, pyrimidinylmethyl and pyrimidinylethyl. A particular example is pyrid-3-ylmethyl.

Particular examples of (1-4C alkylsulfonyl)(1-6C alkyl) substituents for hetAr$^1$ include CH$_3$SO$_2$(1-6C alkyl), for example CH$_3$SO$_2$CH$_2$CH$_2$—.

In one embodiment, hetAr$^1$ is optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, 4-tetrahydro-2H-pyranyl, (4-methylpiperazinyl)ethyl, pyrid-3-ylmethyl and CH$_3$SO$_2$CH$_2$CH$_2$—.

In one embodiment, hetAr$^1$ is optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, 4-tetrahydro-2H-pyranyl, (4-methylpiperazinyl)ethyl and pyrid-3-ylmethyl.

In one embodiment, hetAr$^1$ is pyrazolyl, thiazolyl, oxazolyl, thiadiazolyl or imidazolyl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl (1-4C alkoxy)(1-6C)alkyl, (3-6C)cycloalkyl, a 4-6 membered oxacyclic ring, hetCyc$^a$(1-2C)alkyl, hetAr$^a$(1-2C)alkyl and (1-4C alkylsulfonyl)(1-6C alkyl).

In one embodiment, hetAr$^1$ is pyrazolyl, thiazolyl, oxazolyl, thiadiazolyl or imidazolyl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl (1-4C alkoxy)(1-6C)alkyl, (3-6C)cycloalkyl, a 4-6 membered oxacyclic ring, hetCyc$^a$(1-2C)alkyl and hetAr$^a$(1-2C)alkyl.

In one embodiment, hetAr¹ is pyrazol-4-yl, thiazol-5-yl, imidazol-1-yl or 1,3,4-thiadiazol-2-yl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl (1-4C alkoxy)(1-6C)alkyl, (3-6C)cycloalkyl, a 4-6 membered oxacyclic ring, hetCyc^a(1-2C)alkyl, hetAr^a(1-2C)alkyl and (1-4C alkylsulfonyl)(1-6C alkyl).

In one embodiment, hetAr¹ is pyrazol-4-yl, thiazol-5-yl, imidazol-1-yl or 1,3,4-thiadiazol-2-yl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl (1-4C alkoxy)(1-6C)alkyl, (3-6C)cycloalkyl, a 4-6 membered oxacyclic ring, hetCyc^a(1-2C)alkyl and hetAr^a(1-2C) alkyl.

In one embodiment, hetAr¹ is pyrazol-4-yl, thiazol-5-yl, or imidazol-1-yl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc^a (1-2C)alkyl, hetAr^a(1-2C)alkyl and (1-4C alkylsulfonyl)(1-6C alkyl).

In one embodiment, hetAr¹ is pyrazol-4-yl, thiazol-5-yl, or imidazol-1-yl optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, hetCyc^a (1-2C)alkyl and hetAr^a(1-2C)alkyl.

In one embodiment, hetAr¹ is pyrazol-4-yl, thiazol-5-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, 4-tetrahydro-2H-pyranyl, (4-methylpiperazinyl)ethyl, pyrid-3-ylmethyl and $CH_3SO_2CH_2CH_2$—.

In one embodiment, hetAr¹ is pyrazol-4-yl, thiazol-5-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, 4-tetrahydro-2H-pyranyl, (4-methylpiperazinyl)ethyl and pyrid-3-ylmethyl.

In one embodiment, hetAr¹ is pyrazol-4-yl, thiazol-5-yl or imidazol-1-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, 4-tetrahydro-2H-pyranyl, (4-methylpiperazinyl)ethyl, pyrid-3-ylmethyl and $CH_3SO_2CH_2CH_2$—.

In one embodiment, hetAr¹ is pyrazol-4-yl, thiazol-5-yl or imidazol-1-yl optionally substituted with one or more substituents independently selected from methyl, ethyl, isopropyl, isobutyl, 2,2,2-trifluoro ethyl, (2-isopropoxy)ethyl, trimethylsilylethoxymethyl, cyclobutyl, 4-tetrahydro-2H-pyranyl, (4-methylpiperazinyl)ethyl and pyrid-3-ylmethyl.

In one embodiment, hetAr¹ is pyrazol-4-yl optionally substituted a substituent selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl, pyrid-3-ylmethyl and $CH_3SO_2CH_2CH_2$—.

In one embodiment, hetAr¹ is pyrazol-4-yl optionally substituted a substituent selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl.

In one embodiment, hetAr¹ is pyrazol-4-yl optionally substituted a substituent selected from methyl, ethyl, isopropyl, isobutyl and 2,2,2-trifluoroethyl.

Particular examples of R¹ when represented by hetAr¹ include the structures:

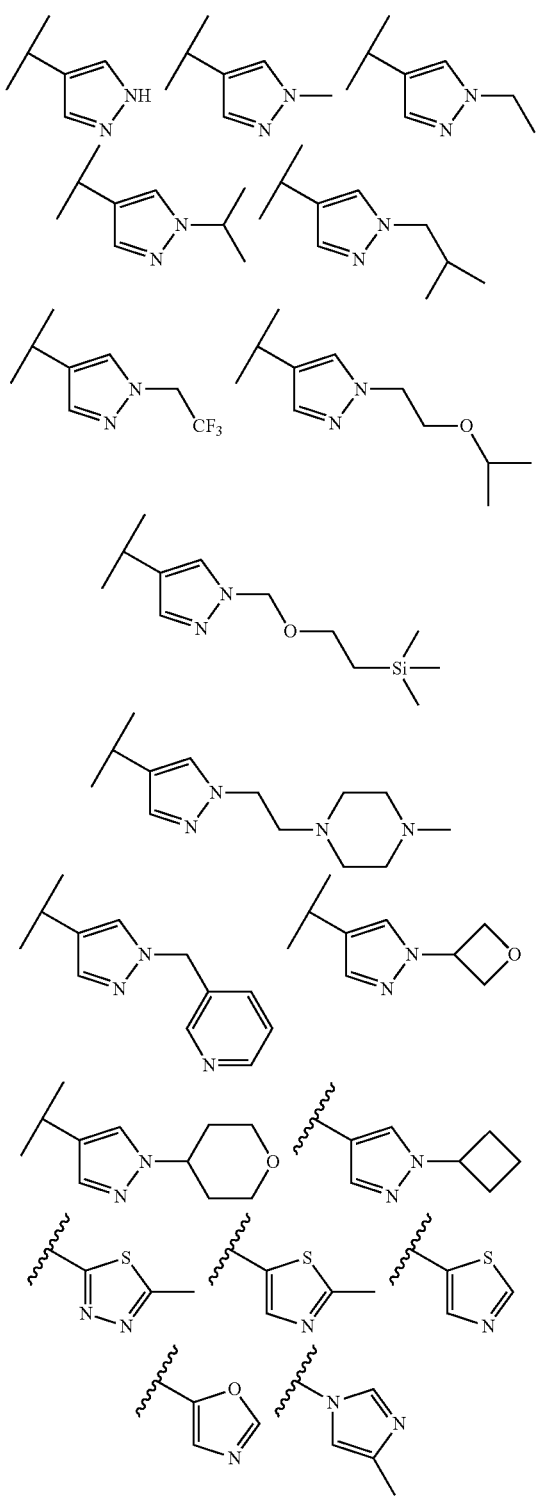

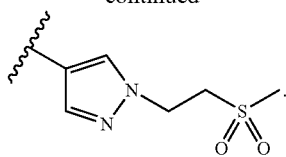

In one embodiment, R¹ is hetAr², wherein hetAr² is a 9-membered bicyclic partially unsaturated or fully unsaturated heterocyclic ring having 3 ring nitrogen atoms and optionally substituted with one or more substituents independently selected from (1-6C)alkyl.

In one embodiment, hetAr² is 5,6,7,8-tetrahydroimidazo[1,2-a]pyrazinyl optionally substituted with one or more substituents independently selected from (1-6C)alkyl, such as methyl or ethyl.

Particular examples of R¹ when represented by hetAr² include the structures:

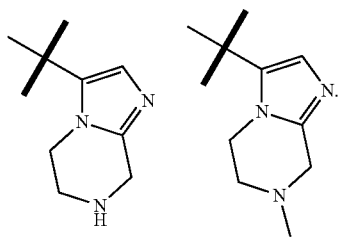

In one embodiment, R¹ is hetAr³, wherein hetAr³ is a 6 membered heteroaryl having 1-2 ring nitrogen atoms and optionally substituted with one or more substituents independently selected from (1-6C)alkyl, hetCyc$^b$ and (1-6C)alkoxy.

In one embodiment, R¹ is hetAr³, wherein hetAr³ is a 6 membered heteroaryl having 1-2 ring nitrogen atoms and optionally substituted with one or more substituents independently selected from (1-6C)alkyl and hetCyc$^b$.

In one embodiment, hetAr³ is pyridyl or pyrimidyl optionally substituted with one or more substituents independently selected from (1-6C)alkyl, hetCyc$^b$ and (1-6C)alkoxy.

In one embodiment, hetAr³ is pyridyl or pyrimidyl optionally substituted with one or more substituents independently selected from (1-6C)alkyl and hetCyc$^b$.

Examples of (1-6C)alkyl substituents for hetAr³ include methyl and ethyl.

Examples of hetCyc$^b$ substituents for hetAr³ include piperidinyl and piperazinyl rings optionally substituted with one or more substituents independently selected from (1-6C)alkyl, such as methyl or ethyl. A particular example of hetCyc$^b$ includes 4-methylpiperazinyl.

Examples of (1-6C)alkoxy substituents for hetAr³ include methoxy and ethoxy.

In one embodiment, hetAr³ is pyridyl optionally substituted with methyl, 4-methylpiperazinyl or methoxy.

In one embodiment, hetAr³ is pyridyl optionally substituted with methyl or 4-methylpiperazinyl.

Particular examples of R¹ when represented by hetAr³ include the structures:

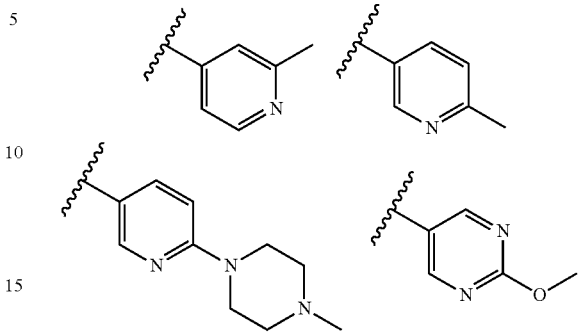

In one embodiment, R¹ is Ar¹, wherein Ar¹ is phenyl substituted with a substituent selected from hetCyc$^c$, hetCyc$^d$, hetAr$^b$, trifluoro(1-6C)alkyl and (1-6C)alkoxy.

In one embodiment, R¹ is Ar¹, wherein Ar¹ is phenyl substituted with a substituent selected from hetCyc$^c$, hetCyc$^d$ and hetAr$^b$.

In one embodiment, Ar¹ is phenyl substituted with hetCyc$^c$, wherein hetCyc$^c$ is a 6 membered heterocycle having 1-2 ring heteroatoms independently selected from N and O and optionally substituted with one or more substituents independently selected from (1-6C)alkyl. Examples of hetCyc$^c$ include piperidinyl, piperazinyl and morpholinyl rings optionally substituted with one or more substituents independently selected from (1-6C)alkyl, for example methyl and ethyl. Particular examples of hetCyc$^c$ include 1-methylpiperidin-4-yl, 1-methylpiperazin-4-yl and morpholinyl.

In one embodiment, Ar¹ is phenyl substituted with hetCyc$^d$, where hetCyc$^d$ is an 8-membered bridged heterocyclic ring having 1-2 ring heteroatoms independently selected from N and O. An example of hetCyc$^d$ is 8-oxa-3-azabicyclo[3.2.1]octanyl.

In one embodiment, Ar¹ is phenyl substituted with hetAr$^b$, wherein hetAr$^b$ is a 5-membered heteroaryl ring having 1-2 ring nitrogen atoms and optionally substituted with one or more substituents independently selected from (1-6C)alkyl. Examples of hetAr$^b$ include pyrrolyl and pyrazolyl rings optionally substituted with one or more substituents independently selected from (1-6C)alkyl, for example methyl and ethyl. A particular example of hetAr$^b$ is 1-methylpyrazol-3-yl.

In one embodiment, Ar¹ is phenyl optionally substituted with a substituent selected from (i) morpholinyl, (ii) piperidinyl optionally substituted with (1-6C)alkyl, (iii) piperazinyl optionally substituted with (1-6C)alkyl, (iv) oxa-3-azabicyclo[3.2.1]octane, (v) pyrazolyl optionally substituted with (1-6C)alkyl, (vi) trifluoro(1-6C)alkyl, and (vi) (1-6C)alkoxy.

In one embodiment, Ar¹ is phenyl optionally substituted with a substituent selected from (i) morpholinyl, (ii) piperidinyl optionally substituted with (1-6C)alkyl, (iii) piperazinyl optionally substituted with (1-6C)alkyl, (iv) oxa-3-azabicyclo[3.2.1]octane, and (v) pyrazolyl optionally substituted with (1-6C)alkyl.

In one embodiment Ar¹ is phenyl substituted with a substituent selected from morpholin-4-yl, 1-methylpiperidin-4-yl, 1-methylpiperazin-4-yl, 8-oxa-3-azabicyclo[3.2.1]octanyl, 1-methyl-1H-pyrazolyl, methoxy or trifluoromethyl.

In one embodiment Ar¹ is phenyl substituted with a substituent selected from morpholin-4-yl, 1-methylpiperidin-4-yl, 1-methylpiperazin-4-yl, 8-oxa-3-azabicyclo[3.2.1]octanyl and 1-methyl-1H-pyrazolyl.

In one embodiment, Ar¹ is phenyl substituted with trifluoro (1-6C)alkyl or (1-6C)alkoxy. In one embodiment, Ar¹ is phenyl substituted with methoxy or trifluoromethyl.

Particular examples of R¹ when represented by Ar¹ include the structures:

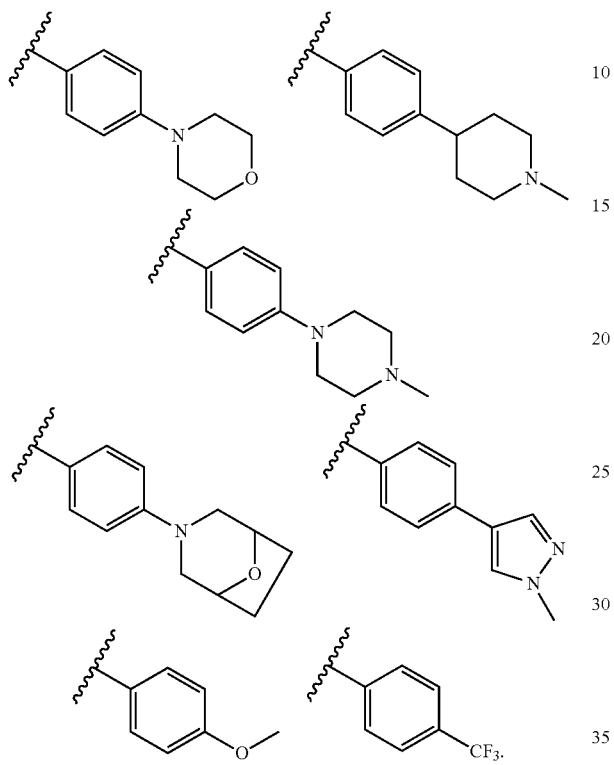

In one embodiment, R¹ is Ar², wherein Ar² is a benzo ring fused to a 5-6 membered azacyclic ring and is optionally substituted with one or more substituents independently selected from (1-6C)alkyl, such as methyl or ethyl. In one embodiment, Ar² is 1,2,3,4-tetrahydroisoquinolin-6-yl or 1,2,3,4-tetrahydroisoquinolin-7-yl optionally substituted with one or more substituents independently selected from (1-6C) alkyl. Particular examples of R¹ when represented by Ar² include the structures:

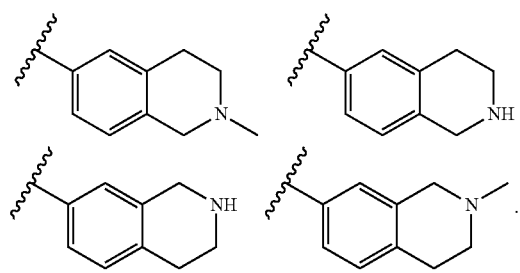

In one embodiment, R¹ is selected from hetAr¹, hetAr², hetAr³, Ar¹ and Ar².
In one embodiment, R¹ is selected from hetAr¹ and hetAr².
In one embodiment, R¹ is selected from Ar¹ and Ar².
In one embodiment, R¹ is C(=O)NR$^a$R$^b$.
In one embodiment, R$^b$ is methyl, ethyl, isopropyl, t-butyl, cyclobutyl, cyclohexyl or pyridyl.

Particular examples of R¹ when represented by C(=O)NR$^a$R$^b$ include the structures:

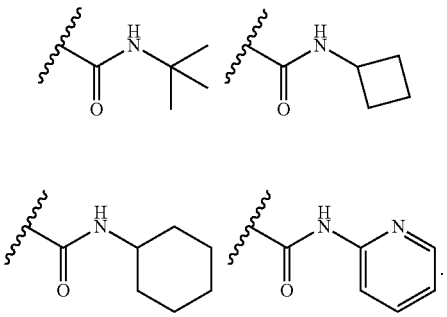

In one embodiment, R¹ is N-(1-3C alkyl)pyridinonyl. In one embodiment, R¹ is N-methylpyridonyl. In one embodiment, R¹ is 1-methylpyridin-2(1H)-on-5-yl or 1-dimethylpyridin-2(1H)-one-4-yl, which can be represented by the structures:

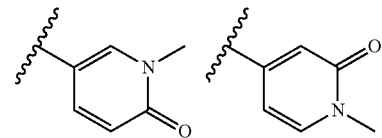

respectively.

In one embodiment, R¹ is (3-6C) cycloalkyl. In one embodiment, is cyclopropyl.

In one embodiment, X¹ is N and X² is CR$^{3b}$, such that the residue at the 5-position of the imidazo[1,2-c]pyrimidine ring has the structure shown as structure A:

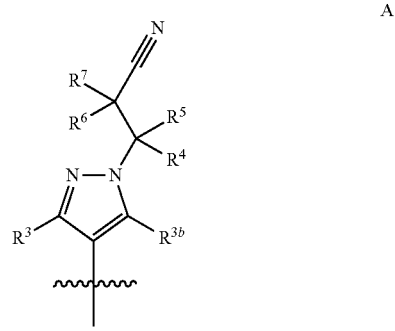

wherein the wavy line indicates the point of attachment to the 5-position of the imidazo[1,2-c]pyrimidine ring and R³, R$^{3b}$, R⁴, R⁵, R⁶ and R⁷ are as defined for Formula I. In one embodiment of structure A, R³ and R$^{3b}$ are both hydrogen.

In one embodiment, X¹ is CR$^{3a}$ and X² is CR$^{3b}$, such that the group at the 5-position of the imidazo[1,2-c]pyrimidine ring has the structure shown as structure B:

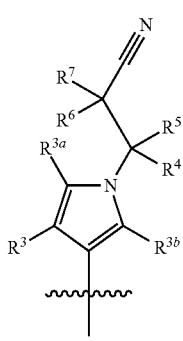

B wherein the wavy line indicates the point of attachment to the 5-position of the imidazo[1,2-c]pyrimidine ring and $R^3$, $R^{3a}$, $R^{3b}$, $R^4$, $R^5$, $R^6$ and $R^7$ are as defined for Formula I. In one embodiment of structure B, each of $R^3$, $R^{3a}$ and $R^{3b}$ is hydrogen.

In one embodiment, $X^1$ is $CR^{3a}$ and $X^2$ is N, such that the group at the 5-position of the imidazo[1,2-c]pyrimidine ring has the structure shown as structure C:

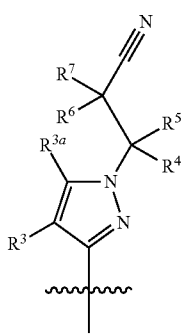

C wherein the wavy line indicates the point of attachment to the 5-position of the imidazo[1,2-c]pyrimidine ring and $R^3$, $R^{3a}$, $R^4$, $R^5$, $R^6$ and $R^7$ are as defined for Formula I. In one embodiment of structure C, $R^3$ and $R^{3a}$ are both hydrogen In one embodiment, $X^1$ is N and $X^2$ is N, such that the residue at the 5-position of the imidazo[1,2-c]pyrimidine ring has the structure shown as structure D:

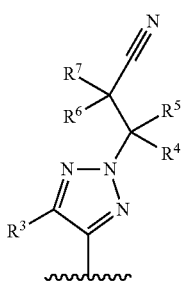

D wherein the wavy line indicates the point of attachment to the 5-position of the imidazo[1,2-c]pyrimidine ring and $R^3$, $R^4$, $R^5$, $R^6$ and $R^7$ are as defined for Formula I. In one embodiment of structure D, $R^3$ is hydrogen.

In one embodiment, $R^4$ is H or (1-6C)alkyl, and $R^5$ is H, (1-6C)alkyl, —CH$_2$CN, (3-6C)cycloalkyl (optionally substituted with one or more halogens), hetCyc$^e$, Ar$^a$ or hetAr$^d$. In one embodiment, $R^4$ is H. In one embodiment, $R^4$ is (1-6C)alkyl, for example (1-4C)alkyl, such as methyl or ethyl.

In one embodiment, $R^4$ is H or (1-6C)alkyl, and $R^5$ is H, (1-6C)alkyl, —CH$_2$CN, (3-6C)cycloalkyl, hetCyc$^e$, Ar$^a$ or hetAr$^d$. In one embodiment, $R^4$ is H. In one embodiment, $R^4$ is (1-6C)alkyl, for example (1-4C)alkyl, such as methyl or ethyl.

In one embodiment, $R^4$ is H or (1-6C)alkyl and $R^5$ is hydrogen. In one embodiment, $R^4$ is H or methyl and $R^5$ is hydrogen.

In one embodiment, $R^4$ is H or (1-6C)alkyl and $R^5$ is (1-6C)alkyl. $R^4$ is H or methyl and $R^5$ is methyl, ethyl, propyl, butyl, tert-butyl or 2,2-dimethylpropyl.

In one embodiment, $R^4$ is H or (1-6C)alkyl and $R^5$ is —CH$_2$CN.

In one embodiment, $R^4$ is H or (1-6C)alkyl and $R^5$ is (3-6C)cycloalkyl optionally substituted with one or more halogens. In one embodiment, $R^4$ is H or (1-6C)alkyl and $R^5$ is (3-6C)cycloalkyl optionally substituted with one or more fluorines. In one embodiment, $R^4$ is H or methyl and $R^5$ is cyclopropyl, 2,2-difluorocyclopropyl, cyclobutyl, cyclopentyl or cyclohexyl.

In one embodiment, $R^4$ is H or (1-6C)alkyl and $R^5$ is (3-6C)cycloalkyl. In one embodiment, $R^4$ is H or methyl and $R^5$ is cyclopropyl, cyclobutyl, cyclopentyl or cyclohexyl.

In one embodiment, $R^4$ is H or (1-6C)alkyl and $R^5$ is hetCyc$^e$, where hetCyc$^e$ is a 5-6-membered heterocycle having a ring N atom and substituted with a substituent selected from C(=O)(1-6C)alkyl. Examples of hetCyc$^e$ include pyrrolidinyl and piperidinyl rings substituted with a substituent selected from C(=O)(1-6C)alkyl. Examples of C(=O)(1-6C)alkyl substituents include C(=O)Me and C(=O)Et. A particular example of hetCyc$^e$ is 1-acetylpiperidin-4-yl.

In one embodiment, $R^4$ is H or (1-6C)alkyl, and $R^5$ is Ar$^a$, where Ar$^a$ is phenyl optionally substituted with one or more substituents independently selected from halogen, CF$_3$, (1-6C)alkyl and (1-6C)alkoxy. In one embodiment, $R^4$ is H or (1-6C)alkyl, and $R^5$ is Ar$^a$, where Ar$^a$ is phenyl optionally substituted with one or more substituents independently selected from halogen and CF$_3$. Examples of Ar$^a$ include phenyl optionally substituted with one or more substituted independently selected from Cl and CF$_3$. In one embodiment, $R^4$ is H or methyl and $R^5$ is Ar$^a$ wherein Ar$^a$ is phenyl, 2-chlorophenyl, 3-chlorophenyl, 4-chlorophenyl or 3-(trifluoromethyl)phenyl.

In one embodiment, $R^4$ is H or (1-6C)alkyl, and $R^5$ is hetAr$^d$, where hetAr$^d$ is a 6-membered heteroaryl having 1-2 ring nitrogen atoms and optionally substituted with one or more substituents independently selected from halogen, (1-6C)alkoxy, (1-6C)alkyl and CF$_3$. In one embodiment, $R^4$ is H or (1-6C)alkyl, and $R^5$ is hetAr$^d$, where hetAr$^d$ is a 6-membered heteroaryl having 1-2 ring nitrogen atoms and optionally substituted with one or more substituents independently selected from halogen and (1-6C)alkoxy. Examples of hetAr$^d$ include pyridyl and pyrimidyl optionally substituted with one or more substituents independently selected from halogen and (1-6C)alkoxy, for example one or more substituted independently selected from methoxy and bromo. In one embodiment, $R^4$ is H or methyl and $R^5$ is hetAr$^d$, wherein hetAr$^d$ is pyrid-2-yl, pyrid-3-yl, pyrid-4-yl, 5-methoxypyrid-3-yl and 5-bromopyrid-3-yl.

In one embodiment, $R^4$ is H or (1-6C)alkyl, and $R^5$ is H, methyl, t-butyl, 2,2-dimethylpropyl, cyanomethyl, cyclopropyl, 2,2-difluorocyclopropyl, cyclobutyl, cyclopentyl, 1-acetylpiperidin-4-yl, phenyl, trifluoromethylphenyl, chlorophenyl, pyridyl, methoxypyridyl or bromopyridyl. In one embodiment, $R^4$ is H or methyl. In one embodiment, $R^4$ is hydrogen.

In one embodiment, $R^4$ is H or (1-6C)alkyl, and $R^5$ is H, methyl, t-butyl, 2,2-dimethylpropyl, cyanomethyl, cyclopropyl, cyclobutyl, cyclopentyl, 1-acetylpiperidin-4-yl, phenyl, trifluoromethylphenyl, chlorophenyl, pyridyl, methoxypyridyl or bromopyridyl. In one embodiment, $R^4$ is H or methyl. In one embodiment, $R^4$ is hydrogen.

In one embodiment, $R^4$ and $R^5$ together with the carbon atom to which they are attached form a 4-6 membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —$CH_2$(3-6C cycloalkyl), —$CH_2$hetCyc$^f$, —C(=O)O(1-6C alkyl), —C(=O)(1-6C alkyl), —C(=O)(CR'R")$CF_3$, hetAr$^e$, (3-6C)cycloalkyl, a 4-6 membered oxacyclic ring and —$SO_2R^e$.

In one embodiment, $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, benzyl, —$CH_2$(3-6C cycloalkyl), —$CH_2$hetCyc$^f$, —C(=O)O(1-6Calkyl), —C(=O)(1-6C alkyl),
—C(=O)(CR'R")$CF_3$, hetAr$^e$, (3-6C)cycloalkyl, a 4-6 membered oxacyclic ring and —$SO_2R^c$. In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with any of said substituents.

In one embodiment, $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, —$CH_2$(3-6C cycloalkyl), —$CH_2$-hetCyc$^f$, (3-6C)cycloalkyl and —$SO_2R^c$. In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with any of said substituents.

In one embodiment, $R^4$ and $R^5$ together with the carbon atom to which they are attached form a 4-membered azacyclic ring optionally substituted with a substituent selected from methyl, ethyl, propyl, isopropyl, isobutyl, fluoromethyl, 3-fluoropropyl, 2-fluoro ethyl, 2,2-difluoro ethyl, 2,2,3,3-tetrafluoropropyl, 1,3-difluoroprop-2-yl, 2,2,2-trifluoroethyl, 3,3,3-trifluoropropyl, 2,2,3,3,3-pentafluoropropyl, prop-2-ynyl, but-2-ynyl, cyanomethyl, 2-cyanoethyl, benzyl, cyclopropylmethyl, cyclobutylmethyl, (tetrahydro-2H-pyran-4-yl) methyl, cyclopropyl, $SO_2CH_3$, $SO_2CH_2CH_3$, $SO_2CH_2CH_2CH_3$, $SO_2CH(CH_3)_2$, $SO_2CH_2CH_2CF_3$, $SO_2CF_3$, $SO_2CF_2CF_3$, $SO_2$(cyclopropyl), $SO_2$(cyclohexyl), and $SO_2$(phenyl). In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with any of said substituents.

In one embodiment, $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl and pentafluoro(1-6C)alkyl. In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with any of said substituents.

In one embodiment, $R^4$ and $R^5$ together with the carbon atom to which they are attached form a 4-membered azacyclic ring optionally substituted with a substituent selected from methyl, ethyl, propyl, isopropyl, isobutyl, fluoromethyl, 3-fluoropropyl, 2-fluoro ethyl, 2,2-difluoro ethyl, 2,2,3,3-tetrafluoropropyl, 1,3-difluoroprop-2-yl, 2,2,2-trifluoro ethyl, 3,3,3-trifluoropropyl and 2,2,3,3,3-pentafluoropropyl.

In one embodiment, $R^4$ and $R^5$ together with the carbon atom to which they are attached form a 4-membered azacyclic ring optionally substituted with a substituent selected from methyl, ethyl, propyl, isopropyl, and isobutyl.

In one embodiment, $R^4$ and $R^5$ together with the carbon atom to which they are attached form a 4-membered azacyclic ring optionally substituted with a substituent selected from fluoromethyl, 3-fluoropropyl, 2-fluoroethyl, 2,2-difluoroethyl, 2,2,3,3-tetrafluoropropyl, 1,3-difluoroprop-2-yl, 2,2,2-trifluoroethyl, 3,3,3-trifluoropropyl and 2,2,3,3,3-pentafluoropropyl.

In one embodiment, $R^4$ and $R^5$ together with the carbon atom to which they are attached form a 4-membered azacyclic ring optionally substituted with a substituent selected from 2,2,2-trifluoroethyl and 2,2,3,3,3-pentafluoropropyl.

In one embodiment, $R^4$ and $R^5$ together with the carbon atom to which they are attached form a 4-membered azacyclic ring optionally substituted with a 4-6 membered oxacyclic ring. In one embodiment, $R^4$ and $R^5$ together with the carbon atom to which they are attached form a 4-membered azacyclic ring optionally substituted with oxetan-3-yl.

In one embodiment, $R^4$ and $R^5$ together with the carbon atom to which they are attached form a 4-membered azacyclic ring optionally substituted with a substituent selected from —C(=O)O(1-6Calkyl), —C(=O)(1-6Calkyl) and —C(=O)(CR'R")$CF_3$. In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with any of said substituents.

In one embodiment, $R^4$ and $R^5$ together with the carbon atom to which they are attached form a 4-membered azacyclic ring optionally substituted with a substituent selected from —C(=O)OC($CH_3$)$_3$, —C(=O)$CH_3$, C(=O)$CH_2CF_3$ and C(=O)(cyclopropylidine)$CF_3$.

In one embodiment, $R^4$ and $R^5$ together with the carbon atom to which they are attached form a 4-membered azacyclic ring substituted with hetAr$^e$. Examples of hetAr$^e$ include pyridyl and pyrimidyl. A particular example of hetAr$^e$ is pyrimidin-2-yl. In one embodiment, the substituent is coupled to the nitrogen atom of the 4-membered azacyclic ring. In one embodiment, $R^4$ and $R^5$ together with the carbon atom to which they are attached form azetidin-3-yl which is optionally substituted with hetAr$^e$.

In one embodiment, $R^4$ and $R^5$ together with the carbon atom to which they are attached form a 4-membered azacyclic ring substituted with a pyrimidinyl ring. In one embodiment, $R^4$ and $R^5$ together with the carbon atom to which they are attached form azetidin-3-yl which is optionally substituted with a pyrimidinyl ring.

In one embodiment, $R^4$ and $R^5$ together with the carbon atom to which they are attached form a 4-membered azacyclic ring substituted with —$SO_2R^c$. In one embodiment, the $SO_2R^c$ group is coupled to the nitrogen atom of the azacyclic ring. In one embodiment, $R^4$ and $R^5$ together with the carbon atom to which they are attached form azetidin-3-yl which is optionally substituted with $SO_2R^e$. In one embodiment, $R^e$ is (1-6C)alkyl, fluoro(1-3C)alkyl, difluoro(1-3C)alkyl trifluoro (1-3C)alkyl, tetrafluoro(1-3C)alkyl, pentafluoro(1-3C)alkyl, (3-6C)cycloalkyl (optionally substituted with (1-6C)alkyl), or phenyl (optionally substituted with one or more groups independently selected from (1-6C alkyl), $CF_3$, $CF_3O$— and halogen). In one embodiment, $R^e$ is (1-6C)alkyl, fluoro(1-3C) alkyl, difluoro(1-3C)alkyl trifluoro(1-3C)alkyl, tetrafluoro (1-3C)alkyl, pentafluoro(1-3C)alkyl, (3-6C)cyclo alkyl or phenyl.

In one embodiment, $R^4$ and $R^5$ together with the carbon atom to which they are attached form a 4-membered azacyclic ring substituted with —$SO_2CH_3$, —$SO_2CH_2CH_3$, —$SO_2CH_2CH_2CH_3$, —$SO_2CH(CH_3)_2$, —$SO_2CH_2CH_2CF_3$, —$SO_2CF_3$, —$SO_2CF_2CF_3$, —$SO_2$-cyclopropyl, —$SO_2$-cyclohexyl or —$SO_2$-phenyl. In one embodiment, the substituent is coupled to the nitrogen atom of the 4-membered azacyclic ring.

In one embodiment, $R^4$ and $R^5$ together with the carbon atom to which they are attached form a 5-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, benzyl, —$CH_2$(3-6C cycloalkyl), —$CH_2$het$Cyc^f$, —$C(=O)O$(1-6Calkyl), —$C(=O)$(1-6Calkyl), —$C(=O)(CR'R'')CF_3$, hetAr$^e$, (3-6C)cycloalkyl, a 4-6 membered oxacyclic ring and —$SO_2R^e$. In one embodiment, the substituent is coupled to the nitrogen atom of the 5-membered azacyclic ring. In one embodiment, $R^4$ and $R^5$ together with the carbon atom to which they are attached form pyrrolidin-3-yl which is optionally substituted with any of said substituents.

In one embodiment, $R^4$ and $R^5$ together with the carbon atom to which they are attached form a 5-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, —$CH_2$(3-6C cycloalkyl), —$CH_2$-het$Cyc^f$, (3-6C)cycloalkyl and —$SO_2R^e$. In one embodiment, the substituent is coupled to the nitrogen atom of the 5-membered azacyclic ring. In one embodiment, $R^4$ and $R^5$ together with the carbon atom to which they are attached form pyrrolidin-3-yl which is optionally substituted with any of said substituents.

In one embodiment, $R^4$ and $R^5$ together with the carbon atom to which they are attached form a 5-membered azacyclic ring optionally substituted with a substituent selected from methyl, ethyl, propyl, isopropyl, isobutyl, fluoromethyl, 3-fluoropropyl, 2-fluoroethyl, 2,2-difluoroethyl, 2,2,3,3-tetrafluoropropyl, 1,3-difluoroprop-2-yl, 2,2,2-trifluoroethyl, 3,3,3-trifluoropropyl, 2,2,3,3,3-pentafluoropropyl, prop-2-ynyl, but-2-ynyl, cyanomethyl, 2-cyanoethyl, benzyl, cyclopropylmethyl, cyclobutylmethyl, (tetrahydro-2H-pyran-4-yl) methyl, cyclopropyl, $SO_2CH_3$, $SO_2CH_2CH_3$, $SO_2CH_2CH_2CH_3$, $SO_2CH(CH_3)_2$, $SO_2CH_2CH_2CF_3$, $SO_2CF_3$, $SO_2CF_2CF_3$, $SO_2$(cyclopropyl), $SO_2$(cyclohexyl), and $SO_2$(phenyl). In one embodiment, the substituent is coupled to the nitrogen atom of the 5-membered azacyclic ring. In one embodiment, $R^4$ and $R^5$ together with the carbon atom to which they are attached form pyrrolidin-3-yl which is optionally substituted with any of said substituents.

In one embodiment, $R^4$ and $R^5$ together with the carbon atom to which they are attached form a 5-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl and pentafluoro(1-6C)alkyl. In one embodiment, the substituent is coupled to the nitrogen atom of the 5-membered azacyclic ring. In one embodiment, $R^4$ and $R^5$ together with the carbon atom to which they are attached form pyrrolidin-3-yl which is optionally substituted with any of said substituents.

In one embodiment, $R^4$ and $R^5$ together with the carbon atom to which they are attached form a 5-membered azacyclic ring optionally substituted with a substituent selected from methyl, ethyl, propyl, isopropyl, isobutyl, fluoromethyl, 3-fluoropropyl, 2-fluoro ethyl, 2,2-difluoro ethyl, 2,2,3,3-tetrafluoropropyl, 1,3-difluoroprop-2-yl, 2,2,2-trifluoro ethyl, 3,3,3-trifluoropropyl and 2,2,3,3,3-pentafluoropropyl.

In one embodiment, $R^4$ and $R^5$ together with the carbon atom to which they are attached form a 5-membered azacyclic ring optionally substituted with a substituent selected from methyl, ethyl, propyl, isopropyl, and isobutyl.

In one embodiment, $R^4$ and $R^5$ together with the carbon atom to which they are attached form a 5-membered azacyclic ring optionally substituted with a substituent selected from fluoromethyl, 3-fluoropropyl, 2-fluoroethyl, 2,2-difluoroethyl, 2,2,3,3-tetrafluoropropyl, 1,3-difluoroprop-2-yl, 2,2,2-trifluoroethyl, 3,3,3-trifluoropropyl and 2,2,3,3,3-pentafluoropropyl.

In one embodiment, $R^4$ and $R^5$ together with the carbon atom to which they are attached form a 5-membered azacyclic ring optionally substituted with a substituent selected from 2,2,2-trifluoroethyl and 2,2,3,3,3-pentafluoropropyl.

In one embodiment, $R^4$ and $R^5$ together with the carbon atom to which they are attached form a 5-membered azacyclic ring optionally substituted with a 4-6 membered oxacyclic ring. In one embodiment, $R^4$ and $R^5$ together with the carbon atom to which they are attached form a 5-membered azacyclic ring optionally substituted with oxetan-3-yl.

In one embodiment, $R^4$ and $R^5$ together with the carbon atom to which they are attached form a 5-membered azacyclic ring optionally substituted with a substituent selected from —$C(=O)O$(1-6Calkyl), —$C(=O)$(1-6Calkyl) and —$C(=O)(CR'R'')CF_3$. In one embodiment, the substituent is coupled to the nitrogen atom of the 5-membered azacyclic ring. In one embodiment, $R^4$ and $R^5$ together with the carbon atom to which they are attached form azetidin-3-yl which is optionally substituted with any of said substituents. In one embodiment, $R^4$ and $R^5$ together with the carbon atom to which they are attached form a 5-membered azacyclic ring optionally substituted with —$C(=O)CH_3$.

In one embodiment, $R^4$ and $R^5$ together with the carbon atom to which they are attached form a 5-membered azacyclic ring optionally substituted with a substituent selected from —$C(=O)OC(CH_3)_3$, —$C(=O)CH_3$, $C(=O)CH_2CF_3$ and $C(=O)$(cyclopropylidine) $CF_3$.

In one embodiment, $R^4$ and $R^5$ together with the carbon atom to which they are attached form a 5-membered azacyclic ring substituted with hetAr$^e$. Examples of hetAr$^e$ include pyridyl and pyrimidyl. A particular example of hetAr$^e$ is pyrimidin-2-yl. In one embodiment, the substituent is coupled to the nitrogen atom of the 5-membered azacyclic ring. In one embodiment, $R^4$ and $R^5$ together with the carbon atom to which they are attached form pyrrolidin-3-yl which is optionally substituted with hetAr$^e$.

In one embodiment, $R^4$ and $R^5$ together with the carbon atom to which they are attached form a 5-membered azacyclic ring substituted with a pyrimidinyl ring. In one embodiment, $R^4$ and $R^5$ together with the carbon atom to which they are attached form pyrrolidin-3-yl which is optionally substituted with a pyrimidinyl ring.

In one embodiment, $R^4$ and $R^5$ together with the carbon atom to which they are attached form a 5-membered azacyclic ring substituted with —$SO_2R^c$. In one embodiment, the $SO_2R^c$ group is coupled to the nitrogen atom of the azacyclic ring. In one embodiment, $R^4$ and $R^5$ together with the carbon atom to which they are attached form pyrrolidin-3-yl which is optionally substituted with $SO_2R^c$. In one embodiment, $R^c$ is (1-6C)alkyl, fluoro(1-3C)alkyl, difluoro(1-3C)alkyl trifluoro (1-3C)alkyl, tetrafluoro(1-3C)alkyl, pentafluoro(1-3C)alkyl, (3-6C)cycloalkyl (optionally substituted with (1-6C)alkyl), or phenyl (optionally substituted with one or more groups independently selected from (1-6C alkyl), $CF_3$, $CF_3O$— and halogen). In one embodiment, $R^c$ is (1-6C)alkyl, fluoro(1-3C) alkyl, difluoro(1-3C)alkyl trifluoro(1-3C)alkyl, tetrafluoro (1-3C)alkyl, pentafluoro(1-3C)alkyl, (3-6C)cyclo alkyl or phenyl.

In one embodiment, $R^4$ and $R^5$ together with the carbon atom to which they are attached form a 5-membered azacyclic ring substituted with —$SO_2CH_3$, —$SO_2CH_2CH_3$, —$SO_2CH_2CH_2CH_3$, —$SO_2CH(CH_3)_2$, —$SO_2CH_2CH_2CF_3$, —$SO_2CF_3$, —$SO_2CF_2CF_3$, —$SO_2$-cyclopropyl, —$SO_2$-cyclohexyl or —$SO_2$-phenyl. In one embodiment, the substituent is coupled to the nitrogen atom of the 5-membered azacyclic ring.

In one embodiment, $R^4$ and $R^5$ together with the carbon atom to which they are attached form a 6-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, benzyl, —$CH_2$(3-6C cycloalkyl), —$CH_2$hetCyc$^f$, —C(=O)O(1-6C alkyl), —C(=O)(1-6C alkyl), —C(=O)(CR'R'')$CF_3$, hetAr$^e$, (3-6C)cycloalkyl, a 4-6 membered oxacyclic ring and —$SO_2R^c$. In one embodiment, the substituent is coupled to the nitrogen atom of the 6-membered azacyclic ring. In one embodiment, $R^4$ and $R^5$ together with the carbon atom to which they are attached form piperidin-4-yl which is optionally substituted with any of said substituents.

In one embodiment, $R^4$ and $R^5$ together with the carbon atom to which they are attached form a 6-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C) alkyl, (3-4C)alkynyl, cyano(1-4C)alkyl, —$CH_2$(3-6C cyclo alkyl), —$CH_2$-hetCyc$^f$, (3-6C)cycloalkyl and —$SO_2R^c$. In one embodiment, the substituent is coupled to the nitrogen atom of the 6-membered azacyclic ring. In one embodiment, $R^4$ and $R^5$ together with the carbon atom to which they are attached form piperidin-4-yl which is optionally substituted with any of said substituents.

In one embodiment, $R^4$ and $R^5$ together with the carbon atom to which they are attached form a 6-membered azacyclic ring optionally substituted with a substituent selected from methyl, ethyl, propyl, isopropyl, isobutyl, fluoromethyl, 3-fluoropropyl, 2-fluoro ethyl, 2,2-difluoro ethyl, 2,2,3,3-tetrafluoropropyl, 1,3-difluoroprop-2-yl, 2,2,2-trifluoroethyl, 3,3,3-trifluoropropyl, 2,2,3,3,3-pentafluoropropyl, prop-2-ynyl, but-2-ynyl, cyanomethyl, 2-cyanoethyl, benzyl, cyclopropylmethyl, cyclobutylmethyl, (tetrahydro-2H-pyran-4-yl) methyl, cyclopropyl, $SO_2CH_3$, $SO_2CH_2CH_3$, $SO_2CH_2CH_2CH_3$, $SO_2CH(CH_3)_2$, $SO_2CH_2CH_2$ $CF_3$, $SO_2CF_3$, $SO_2CF_2CF_3$, $SO_2$(cyclopropyl), $SO_2$(cyclohexyl), and $SO_2$ (phenyl). In one embodiment, the substituent is coupled to the nitrogen atom of the 6-membered azacyclic ring. In one embodiment, $R^4$ and $R^5$ together with the carbon atom to which they are attached form piperidin-4-yl which is optionally substituted with any of said substituents.

In one embodiment, $R^4$ and $R^5$ together with the carbon atom to which they are attached form a 6-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl and pentafluoro(1-6C)alkyl. In one embodiment, the substituent is coupled to the nitrogen atom of the 6-membered azacyclic ring. In one embodiment, $R^4$ and $R^5$ together with the carbon atom to which they are attached form piperidin-4-yl which is optionally substituted with any of said substituents.

In one embodiment, $R^4$ and $R^5$ together with the carbon atom to which they are attached form a 6-membered azacyclic ring optionally substituted with a substituent selected from methyl, ethyl, propyl, isopropyl, isobutyl, fluoromethyl, 3-fluoropropyl, 2-fluoro ethyl, 2,2-difluoro ethyl, 2,2,3,3-tetrafluoropropyl, 1,3-difluoroprop-2-yl, 2,2,2-trifluoro ethyl, 3,3,3-trifluoropropyl and 2,2,3,3,3-pentafluoropropyl.

In one embodiment, $R^4$ and $R^5$ together with the carbon atom to which they are attached form a 6-membered azacyclic ring optionally substituted with a substituent selected from methyl, ethyl, propyl, isopropyl, and isobutyl.

In one embodiment, $R^4$ and $R^5$ together with the carbon atom to which they are attached form a 6-membered azacyclic ring optionally substituted with a substituent selected from fluoromethyl, 3-fluoropropyl, 2-fluoroethyl, 2,2-difluoroethyl, 2,2,3,3-tetrafluoropropyl, 1,3-difluoroprop-2-yl, 2,2,2-trifluoroethyl, 3,3,3-trifluoropropyl and 2,2,3,3,3-pentafluoropropyl.

In one embodiment, $R^4$ and $R^5$ together with the carbon atom to which they are attached form a 6-membered azacyclic ring optionally substituted with a substituent selected from 2,2,2-trifluoroethyl and 2,2,3,3,3-pentafluoropropyl.

In one embodiment, $R^4$ and $R^5$ together with the carbon atom to which they are attached form a 6-membered azacyclic ring optionally substituted with a 4-6 membered oxacyclic ring. In one embodiment, $R^4$ and $R^5$ together with the carbon atom to which they are attached form a 6-membered azacyclic ring optionally substituted with oxetan-3-yl.

In one embodiment, $R^4$ and $R^5$ together with the carbon atom to which they are attached form a 6-membered azacyclic ring optionally substituted with a substituent selected from —C(=O)O(1-6Calkyl), —C(=O)(1-6Calkyl) and —C(=O)(CR'R'')$CF_3$. In one embodiment, the substituent is coupled to the nitrogen atom of the 6-membered azacyclic ring. In one embodiment, $R^4$ and $R^5$ together with the carbon atom to which they are attached form azetidin-3-yl which is optionally substituted with any of said substituents. In one embodiment, $R^4$ and $R^5$ together with the carbon atom to which they are attached form a 6-membered azacyclic ring optionally substituted with —C(=O)$CH_3$.

In one embodiment, $R^4$ and $R^5$ together with the carbon atom to which they are attached form a 6-membered azacyclic ring optionally substituted with a substituent selected from —C(=O)OC(CH$_3$)$_3$, —C(=O)$CH_3$, C(=O)$CH_2CF_3$ and C(=O)(cyclopropylidine) $CF_3$.

In one embodiment, $R^4$ and $R^5$ together with the carbon atom to which they are attached form a 6-membered azacyclic ring substituted with hetAr$^e$. Examples of hetAr$^e$ include pyridyl and pyrimidyl. A particular example of hetAr$^e$ is pyrimidin-2-yl. In one embodiment, the substituent is coupled to the nitrogen atom of the 6-membered azacyclic ring. In one embodiment, $R^4$ and $R^5$ together with the carbon atom to which they are attached form piperidin-4-yl which is optionally substituted with hetAr$^e$.

In one embodiment, $R^4$ and $R^5$ together with the carbon atom to which they are attached form a 6-membered azacyclic ring substituted with a pyrimidinyl ring. In one embodiment, $R^4$ and $R^5$ together with the carbon atom to which they are attached form piperidin-4-yl which is optionally substituted with a pyrimidinyl ring.

In one embodiment, $R^4$ and $R^5$ together with the carbon atom to which they are attached form a 6-membered azacyclic ring substituted with —$SO_2R^c$. In one embodiment, the $SO_2R^c$ group is coupled to the nitrogen atom of the azacyclic ring. In one embodiment, $R^4$ and $R^5$ together with the carbon atom to which they are attached form piperidin-4-yl which is optionally substituted with $SO_2R^c$. In one embodiment, $R^c$ is (1-6C)alkyl, fluoro(1-3C)alkyl, difluoro(1-3C)alkyl trifluoro(1-3C)alkyl, tetrafluoro(1-3C)alkyl, pentafluoro(1-3C)alkyl, (3-6C)cycloalkyl (optionally substituted with (1-6C)alkyl), or phenyl (optionally substituted with one or more groups independently selected from (1-6C alkyl), $CF_3$, $CF_3O$— and halogen). In one embodiment, $R^c$ is (1-6C)alkyl, fluoro(1-3C)alkyl, difluoro(1-3C)alkyl trifluoro(1-3C)alkyl, tetrafluoro(1-3C)alkyl, pentafluoro(1-3C)alkyl, (3-6C)cyclo alkyl or phenyl.

In one embodiment, $R^4$ and $R^5$ together with the carbon atom to which they are attached form a 6-membered azacyclic ring substituted with —$SO_2CH_3$, —$SO_2CH_2CH_3$, —$SO_2CH_2CH_2CH_3$, —$SO_2CH(CH_3)_2$, —$SO_2CH_2CH_2CF_3$, —$SO_2CF_3$, —$SO_2CF_2CF_3$, —$SO_2$-cyclopropyl, —$SO_2$-cyclohexyl or —$SO_2$-phenyl. In one embodiment, the substituent is coupled to the nitrogen atom of the 6-membered azacyclic ring.

In one embodiment, $R^4$ and $R^5$ together with the carbon atom to which they are attached form a 4-membered oxacyclic ring. In one embodiment, $R^4$ and $R^5$ together with the carbon atom to which they are attached form oxetan-3-yl.

In one embodiment, $R^4$ and $R^5$ together with the carbon atom to which they are attached form a 3-6 membered carbocyclic ring optionally substituted with optionally substituted with (1-6C)alkyl. In one embodiment, $R^4$ and $R^5$ together with the carbon atom to which they are attached form a 3-6 membered carbocyclic ring substituted with methyl, ethyl, or propyl. In one embodiment, $R^4$ and $R^5$ together with the carbon atom to which they are attached form a 3-6 membered carbocyclic ring which is unsubstituted. In one embodiment, $R^4$ and $R^5$ together with the carbon atom to which they are attached form a 5-6 membered carbocyclic ring which is unsubstituted.

In one embodiment, $R^4$ and $R^5$ together with the carbon atom to which they are attached form a 7-9 membered bicyclic spiro carbocycle. The term "bicyclic spiro carbocycle" as used herein refers to a carbocyclic ring system bonded to another carbocyclic ring system at the same atom. In one embodiment, the heterocyclic ring system is bonded to a carbocyclic ring system at the same atom. Examples of bicyclic spiro carbocycles include the structures:

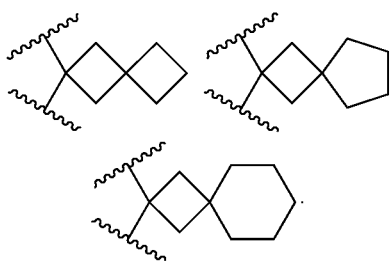

In one embodiment, $R^4$ and $R^5$ together with the carbon atom to which they are attached form a 4,4-bicyclic spiro carbocycle. In one embodiment, $R^4$ and $R^5$ together with the carbon atom to which they are attached form a 4,5-bicyclic spiro carbocycle. In one embodiment, $R^4$ and $R^5$ together with the carbon atom to which they are attached form a 4,6-bicyclic spiro carbocycle.

In one embodiment, $R^4$ and $R^5$ together with the carbon atom to which they are attached form a 7-9 membered bicyclic spiro heterocycle having a ring heteroatom selected from O and N, wherein said ring nitrogen atom when present is optionally substituted with a substituent selected from (1-6C) alkyl, fluoro(1-6C)alkyl, difluoro(1-6C)alkyl, trifluoro(1-6C)alkyl, tetrafluoro(1-6C)alkyl, pentafluoro(1-6C)alkyl and —$SO_2R^c$. The term "bicyclic spiro heterocycle" as used herein refers to at least one heterocyclic ring system bonded to another ring system at the same atom. In one embodiment, the heterocyclic ring system is bonded to a carbocyclic ring system at the same atom. Examples of bicyclic spiro heterocycles include oxa- and azabicyclic spiro heterocycles the structures such as:

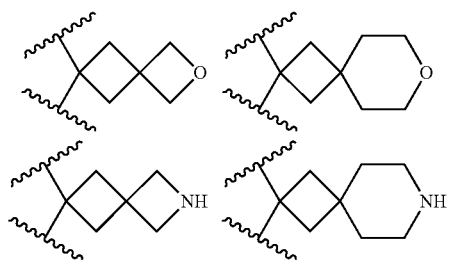

where the nitrogen atom of the azabicyclic spiro heterocycle is optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl and —$SO_2R^c$.

In one embodiment, $R^4$ and $R^5$ together with the carbon atom to which they are attached form a 4,4-bicyclic spiro heterocycle having a ring oxygen atom. In one embodiment, $R^4$ and $R^5$ together with the carbon atom to which they are attached form a 4,6-bicyclic spiro heterocycle having a ring oxygen atom. In one embodiment, the bicyclic spiro heterocycle is unsubstituted.

In one embodiment, $R^6$ is hydrogen.
In one embodiment, $R^6$ is methyl.
In one embodiment, $R^7$ is hydrogen.
In one embodiment, $R^7$ is (1-6C)alkyl. A particular example is methyl.
In one embodiment, $R^3$ is hydrogen.
In one embodiment, $R^3$ is (1-6C)alkyl. A particular example is methyl.
In one embodiment, $R^3$ is $CF_3$.
In one embodiment, $R^3$ is F.
In one embodiment, $R^3$ is Cl.
In one embodiment, $R^3$ is CN.
In one embodiment, $R^3$ is (3-6C)cycloalkyl. In one embodiment, $R^3$ is cyclopropyl.
In one embodiment, $R^3$ is H or methyl.
In one embodiment, $R^3$ is selected from hydrogen, (1-6C) alkyl, $CF_3$, F, and Cl. In one embodiment, $R^3$ is selected from hydrogen, methyl, F and Cl.
In one embodiment, $R^{3a}$ is hydrogen.
In one embodiment, $R^{3a}$ is (1-6C)alkyl. A particular example is methyl.
In one embodiment, $R^{3a}$ is $CF_3$.

In one embodiment, $R^{3a}$ is F.

In one embodiment, $R^{3a}$ is Cl.

In one embodiment, $R^{3a}$ is CN.

In one embodiment, $R^{3a}$ is (3-6C)cycloalkyl. In one embodiment, $R^{3a}$ is cyclopropyl.

In one embodiment, $R^{3b}$ is hydrogen.

In one embodiment, $R^{3b}$ is (1-6C)alkyl. A particular example is methyl.

In one embodiment, $R^{3b}$ is $CF_3$.

In one embodiment, $R^{3b}$ is F.

In one embodiment, $R^{3b}$ is Cl.

In one embodiment, $R^{3b}$ is CN.

In one embodiment, $R^{3b}$ is (3-6C)cycloalkyl. In one embodiment, $R^{3b}$ is cyclopropyl.

In one embodiment, $R^{3a}$ and $R^{3b}$ are independently selected from H, (1-6C alkyl), $CF_3$, F, and Cl. In one embodiment, $R^{3a}$ and $R^{3b}$ are independently selected from H, F, Cl, $CF_3$ and methyl. In one embodiment, $R^{3a}$ and $R^{3b}$ are independently selected from H and (1-6C alkyl). In one embodiment, $R^{3a}$ and $R^{3b}$ are independently selected from H and methyl.

Particular examples of the residue at the 5-position of the imidazo[1,2-c]pyrimidine ring when represented by the structure A

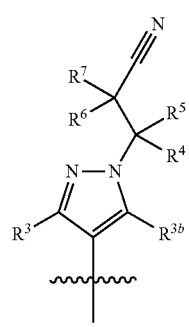

include the structures:

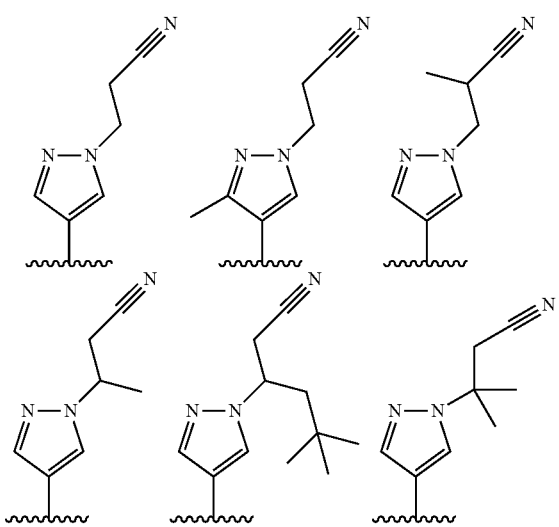

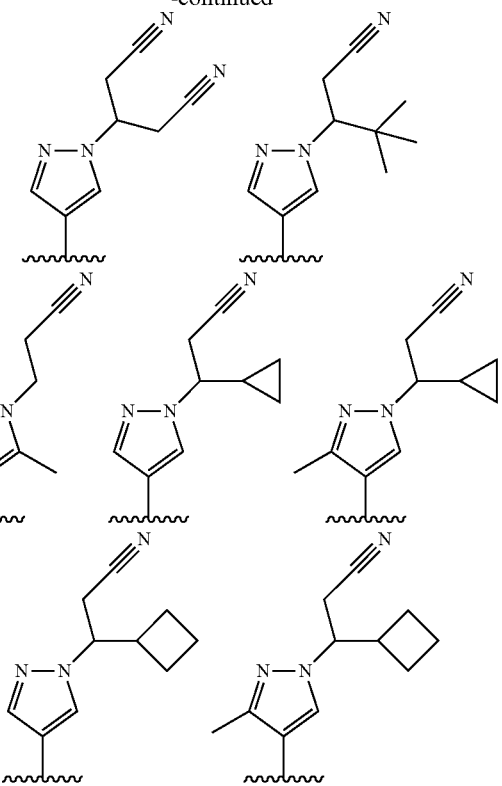

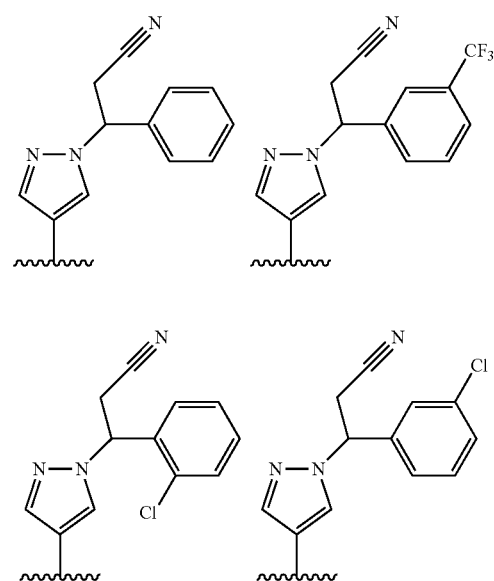

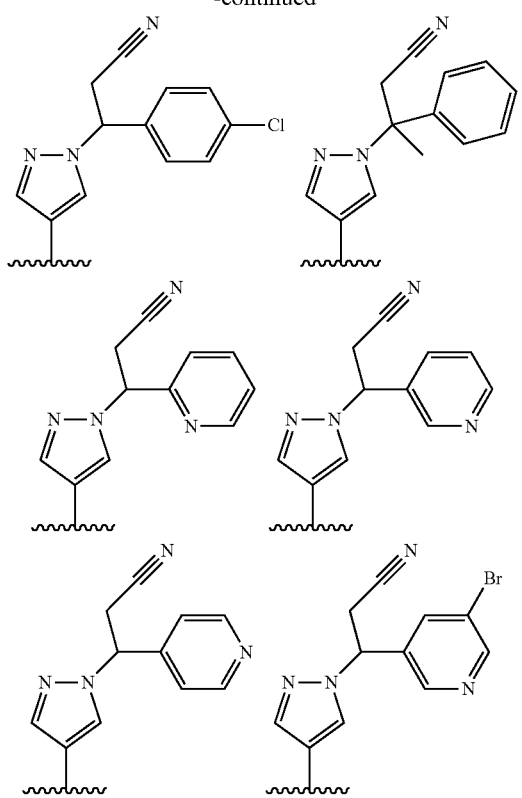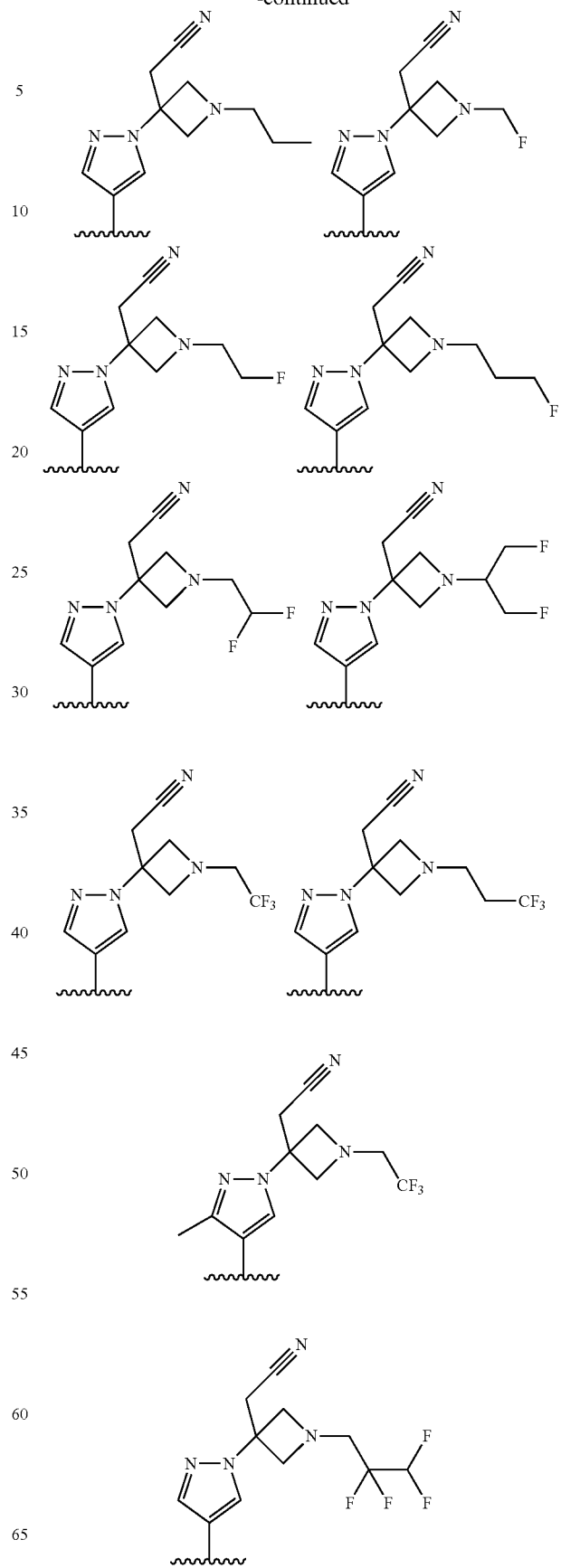

29
-continued
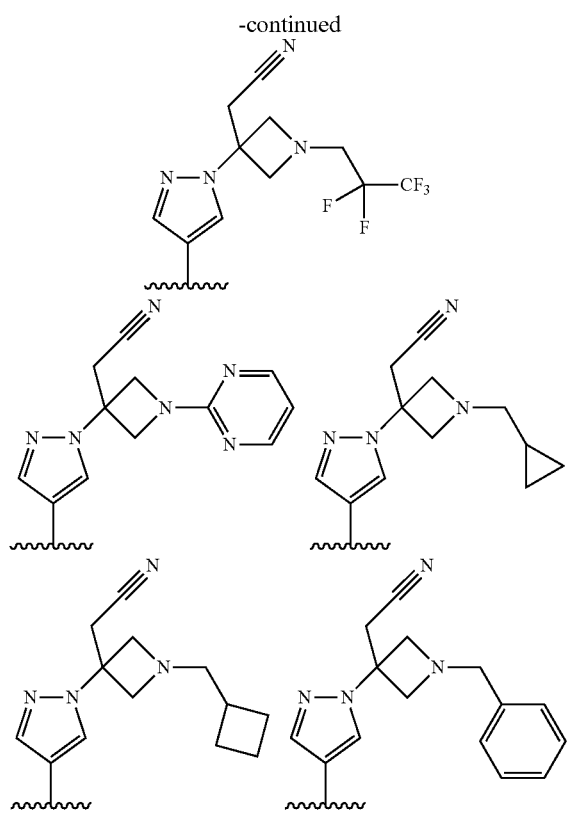
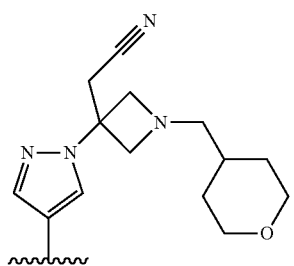
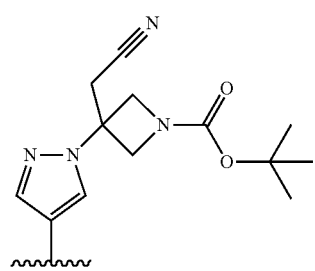
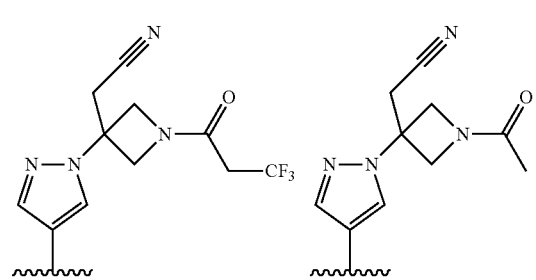
30
-continued
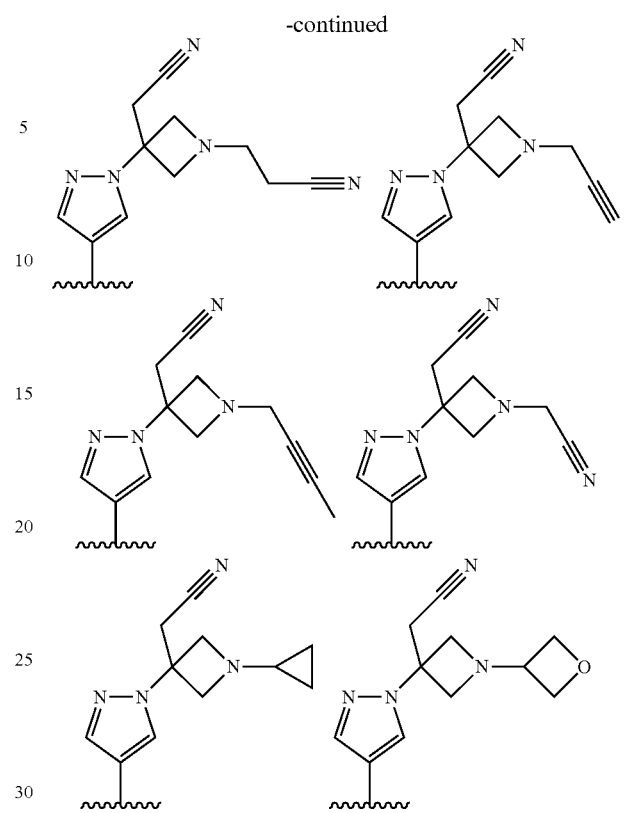
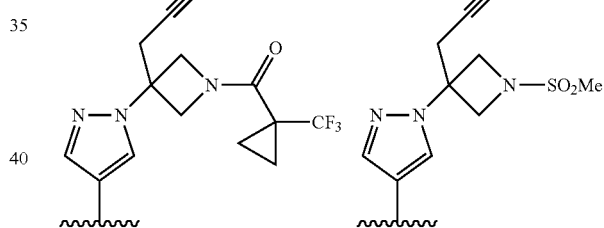
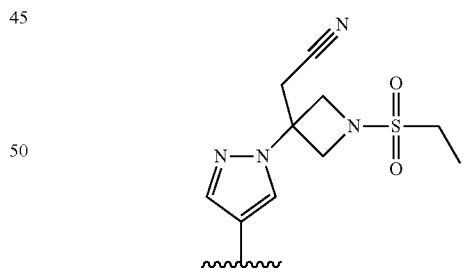
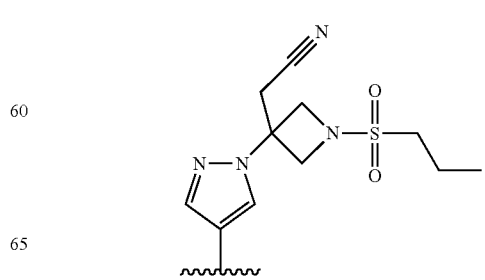

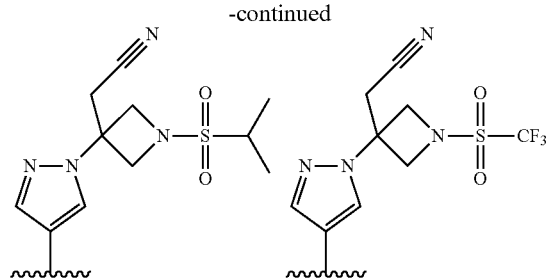
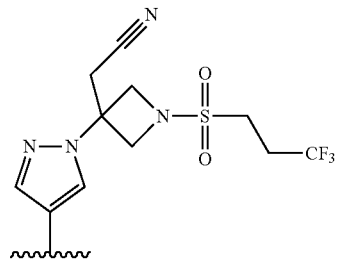
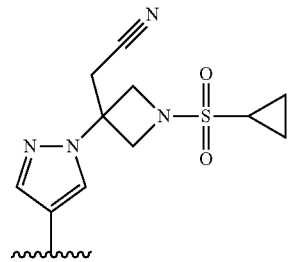
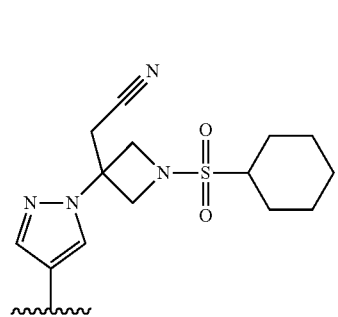
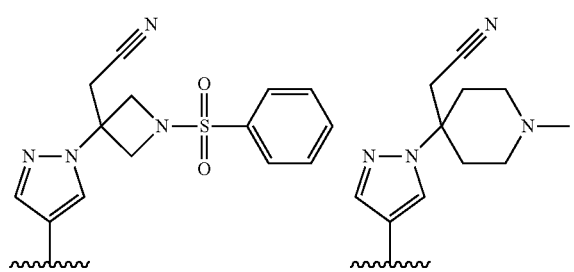
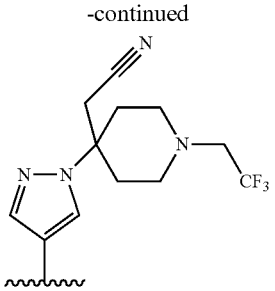
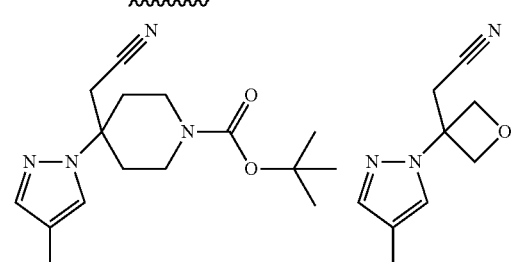
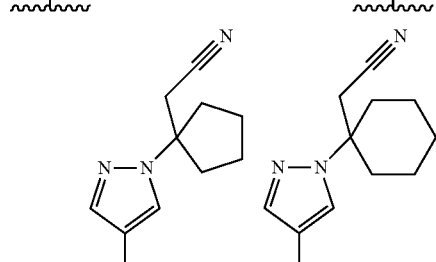
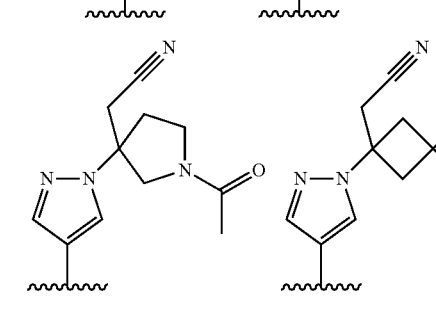
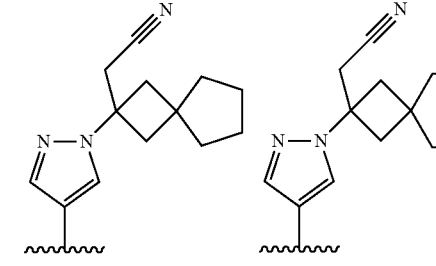
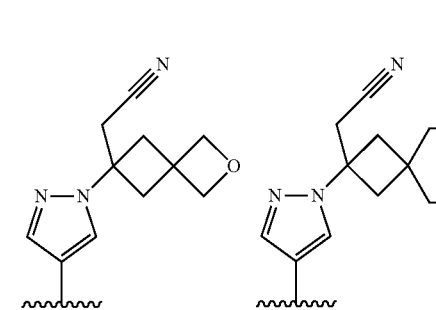

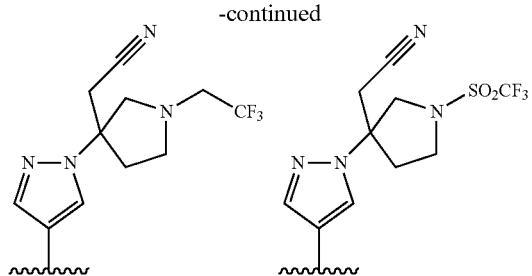

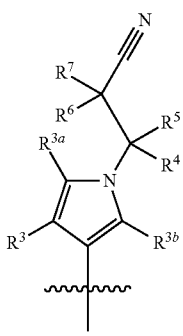

including enantiomers thereof.

Particular examples of the residue at the 5-position of the imidazo[1,2-c]pyrimidine ring when represented by the structure B

B include the structures:

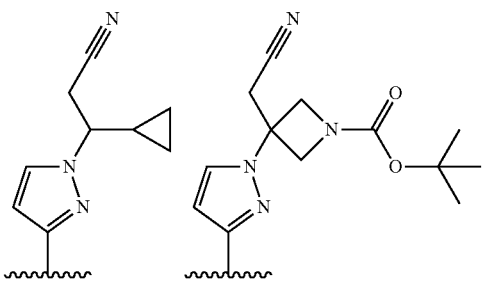

including enantiomers thereof.

Particular examples of the residue at the 5-position of the imidazo[1,2-c]pyrimidine ring when represented by the structure C

C include the structures:

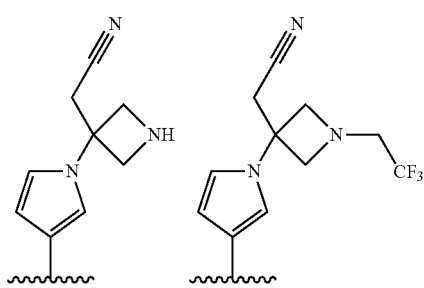

including enantiomers thereof.

In one embodiment, $R^2$ is halogen. In one embodiment, $R^2$ is F, Cl or Br. In one embodiment, $R^2$ is F or Cl. In one embodiment, $R^2$ is F. In one embodiment, $R^2$ is Cl.

In one embodiment of Formula I, $R^2$ is (1-4C)alkyl. In one embodiment, $R^2$ is methyl, ethyl, propyl, isopropyl, butyl, isobutyl or tert-butyl. In one embodiment of Formula I, $R^2$ is (1-3C)alkyl. In one embodiment, $R^2$ is methyl.

In one embodiment of Formula I, $R^2$ is $CF_3$.

In one embodiment of Formula I, $R^2$ is H, F, Cl, Br, methyl or CN.

In one embodiment of Formula I, $R^2$ is H, F, Cl or CN.

In one embodiment of Formula I, $R^2$ is hydrogen, Cl or CN.

In one embodiment of Formula I, $R^2$ is H.

In one embodiment of Formula I, $R^2$ is CN.

In one embodiment of Formula I, $R^2$ is (3-4C)cycloalkyl. In one embodiment of Formula I, $R^2$ is cyclopropyl.

In one embodiment of Formula I, $R^2$ is azetidinyl. In one embodiment of Formula I, $R^2$ is azetidin-3-yl.

In one embodiment of Formula I, $R^2$ is oxetanyl. In one embodiment of Formula I, $R^2$ is oxetan-3-yl.

In one embodiment of Formula I, $R^2$ is selected from hydrogen, halogen, (1-4C)alkyl, $CF_3$ and CN. In one embodiment of Formula I, $R^2$ is selected from hydrogen, F, Cl, methyl, $CF_3$ and CN.

In one embodiment, Formula I does not include the following compounds: 3-cyclopropyl-3-(4-(7-(3-methyl-1,2,4-oxadiazol-5-yl)imidazo[1,2-c]pyrimidin-5-yl)-1H-pyrazol-1-yl) propanenitrile; 3-cyclopropyl-3-(4-(7-(5-methyl-1H-1,2,4-triazol-3-yl)imidazo[1,2-c]pyrimidin-5-yl)-1H-pyrazol-1-yl)propanenitrile; 3-cyclopropyl-3-(4-(7-(5-methyl-1,3,4-oxadiazol-2-yl)imidazo[1,2-c]pyrimidin-5-yl)-1H-pyrazol-1-yl)propanenitrile; and 5-(1-(2-cyano-1-cyclopropylethyl)-1H-pyrazol-4-yl)-N-isopropylimidazo[1,2-c]pyrimidine-7-carboxamide.

In one embodiment of Formula I, $R^1$ is selected from $hetAr^1$, $hetAr^2$, $hetAr^3$, $Ar^1$ and $Ar^2$; $R^2$ is H; $R^3$ is H; $R^4$ is H; $R^5$ is H, (1-6C)alkyl, —$CH_2CN$, (3-6C)cycloalkyl (optionally substituted with one or more halogens), $hetCyc^e$, $Ar^a$ or $hetAr^d$; $R^6$ is H; and $R^7$ is H.

In one embodiment of Formula I, $R^1$ is selected from $hetAr^1$, $hetAr^2$, $hetAr^3$, $Ar^1$ and $Ar^2$; $R^2$ is H; $R^3$ is H; $R^4$ is H; $R^5$ is H, methyl, t-butyl, 2,2-dimethylpropyl, cyanomethyl, cyclopropyl, 2,2-difluorocyclopropyl, cyclobutyl, cyclopentyl, 1-acetylpiperidin-4-yl, phenyl, trifluoromethylphenyl, chlorophenyl, pyridyl, methoxypyridyl or bromopyridyl; $R^6$ is H; and $R^7$ is H.

In one embodiment of Formula I, $X^1$ is N or $CR^{3a}$; $X^2$ is N or $CR^{3b}$; $R^{3a}$ and $R^{3b}$ are H; $R^1$ is selected from $hetAr^1$, $hetAr^2$, $hetAr^3$, $Ar^1$ and $Ar^2$; $R^2$ is H; $R^3$ is H; $R^4$ is H; $R^5$ is H, (1-6C)alkyl, —$CH_2CN$, (3-6C)cycloalkyl, $hetCyc^e$, $Ar^a$ or $hetAr^d$; $R^6$ is H; and $R^7$ is H. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is selected from $hetAr^1$ and $hetAr^e$, $R^2$ is H; $R^3$ is H; $R^4$ is H; $R^5$ is H, (1-6C)alkyl, —$CH_2CN$, (3-6C)cycloalkyl, $hetCyc^e$, $Ar^a$ or $hetAr^d$; $R^6$ is H; and $R^7$ is H. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is $hetAr^1$; $R^2$ is H; $R^3$ is H; $R^4$ is H; $R^5$ is H, (1-6C)alkyl, —$CH_2CN$, (3-6C)cycloalkyl, $hetCyc^e$, $Ar^a$ or $hetAr^d$; $R^6$ is H; and $R^7$ is H; wherein $hetCyc^e$, $Ar^a$ or $hetAr^d$ are as defined for Formula I. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is pyrazol-4-yl, thiazol-5-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl; $R^2$ is H; $R^3$ is H; $R^4$ is H; $R^5$ is (3-6C)cycloalkyl; $R^6$ is H; and $R^7$ is H. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is $hetAr^1$; $R^2$ is H; $R^3$ is H; $R^4$ and $R^5$ together with the carbon atom to which they are attached form a 4-membered azacyclic ring optionally substituted with a substituent selected from (1-6C)alkyl, fluoro (1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, —$CH_2$(3-6C cycloalkyl), —$CH_2$-$hetCyc^f$, (3-6C)cycloalkyl and —$SO_2R^c$; $R^6$ is H; and $R^7$ is H. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is pyrazol-4-yl, thiazol-5-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl; $R^2$ is H; $R^3$ is H; $R^4$ and $R^5$ together with the carbon atom to which they are attached form a 4-membered azacyclic ring optionally substituted with a substituent selected from methyl, ethyl, propyl, isopropyl, isobutyl, fluoromethyl, 3-fluoropropyl, 2-fluoroethyl, 2,2-difluoroethyl, 2,2,3,3-tetrafluoropropyl, 1,3-difluoroprop-2-yl, 2,2,2-trifluoroethyl, 3,3,3-trifluoropropyl, and 2,2,3,3,3-pentafluoropropyl; $R^6$ is H; and $R^7$ is H. In one embodiment, $X^1$ is N and $X^2$ is CH.

In one embodiment of Formula I, $X^1$ is N or $CR^{3a}$; $X^2$ is N or $CR^{3b}$; $R^{3a}$ and $R^{3b}$ are H; $R^1$ is pyrazol-4-yl, thiazol-5-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl; $R^2$ is H; $R^3$ is H; form a 4-membered azacyclic ring substituted with —$SO_2CH_3$, —$SO_2CH_2CH_3$, —$SO_2CH_2CH_2CH_3$, —$SO_2CH(CH_3)_2$, —$SO_2CH_2CH_2CF_3$, —$SO_2CF_3$, —$SO_2CF_2CF_3$, —$SO_2$-cyclopropyl, —$SO_2$-cyclohexyl or —$SO_2$-phenyl; $R^6$ is H; and $R^7$ is H. In one embodiment, $X^1$ is N and $X^2$ is CH.

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The term "(1-6C)alkyl" as used herein refers to saturated linear or branched-chain monovalent hydrocarbon radicals of one to six carbon atoms. Examples include, but are not limited to, methyl, ethyl, 1-propyl, isopropyl, 1-butyl, isobutyl, sec-butyl, tert-butyl, 2-methyl-2-propyl, pentyl, and hexyl.

The terms "(1-4C)alkoxy" and "(1-6C)alkoxy", as used herein refer to saturated linear or branched-chain monovalent alkoxy radicals of one to four carbon atoms or one to six carbon atoms, respectively, wherein the radical is on the oxygen atom. Examples include methoxy, ethoxy, propoxy, isopropoxy, and butoxy.

The term "fluoro(1-6C)alkyl" as use herein refers to saturated linear or branched-chain monovalent radicals of one to six carbon atoms, wherein one of the hydrogen atoms is replaced by fluorine. Examples include fluoromethyl, 3-fluoropropyl and 2-fluoroethyl.

The term "difluoro(1-6C)alkyl" as use herein refers to saturated linear or branched-chain monovalent radicals of one to six carbon atoms, wherein two of the hydrogen atoms are replaced by fluorine. Examples include difluoromethyl, 2,2-difluoroethyl, and 1,3-difluoroprop-2-yl, The term "trifluoro(1-6C)alkyl" and "trifluoro(1-3C)alkyl" as use herein refers to saturated linear or branched-chain monovalent radicals of one to six carbon atoms and one to three carbon atoms, respectively, wherein three of the hydrogen atoms are replaced by fluorine. Examples include trifluoromethyl, 2,2,2-trifluoroethyl, and 3,3,3-trifluoropropyl.

The term "tetrafluoro(1-6C)alkyl" as used herein refers to saturated linear or branched-chain monovalent radicals of one to six carbon atoms, wherein four of the hydrogen atoms are replaced by fluorine. An example is 1,1,2,2-tetrafluoropropane.

The term "pentafluoro(1-6C)alkyl" as used herein refers to saturated linear or branched-chain monovalent radicals of one to six carbon atoms, wherein five of the hydrogen atoms are replaced by fluorine. An example is 2,2,3,3,3-pentafluoropropyl.

The term "(1-4C alkoxy)(1-6C)alkyl" as used herein refers to saturated linear or branched-chain monovalent radicals of one to six carbon atoms, wherein one of the hydrogen atoms is replaced by a (1-4C alkoxy) group as defined herein. Examples include methoxymethyl ($CH_3OCH_2$—) and methoxyethyl ($CH_3OCH_2CH_2$—).

The term "trimethylsilyl(1-4C alkoxy)(1-6C)alkyl" as used herein refers to saturated linear or branched-chain monovalent radicals of one to six carbon atoms, wherein one of the hydrogen atoms is replaced by a trimethylsilyl(1-4C alkoxy) group. An example includes trimethylsilylethoxymethyl ($Me_3SiCH_2CH_2OCH_2$—).

The term "trimethylsilyl(1-4C alkoxy)" as used herein refers to saturated linear or branched-chain monovalent alkoxy radicals of one to four carbon atoms in which the radical is on the oxygen atom, wherein one of the hydrogen atoms is replaced by a trimethylsilyl group.

The term "(1-4C alkylsulfonyl)(1-6C alkyl)" as used herein refers to saturated linear or branched-chain monovalent radicals of one to six carbon atoms, wherein one of the hydrogen atoms is replaced by a (1-4C alkyl)sulfonyl group, that is, a (1-4C)$SO_2$— group.

The term "halogen" includes fluoro, chloro, bromo and iodo.

In instances where the term "heterocycle" is used, the term is intended to refer to a saturated or partially unsaturated heterocyclic ring. In one embodiment, the term "heterocycle" as used herein refers to a saturated heterocyclic ring.

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I. Examples of particular salts include hydrochloride salts and trifluoroacetate salts.

The term "pharmaceutically acceptable" indicates that the substance or composition is compatible chemically and/or toxicologically, with the other ingredients comprising a formulation, and/or the mammal being treated therewith.

It will further be appreciated that the compounds of Formula I and their salts may be isolated in the form of solvates, and accordingly that any such solvate is included within the scope of the present invention.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutics, research reagents, e.g., assay reagents, and diagnostic agents, e.g., in vivo imaging agents. All isotopic variations of the compounds of the present invention, whether radioactive or not, are intended to be encompassed within the scope of the present invention.

The present invention further provides a process for the preparation of a compound of Formula I or a salt thereof as defined herein which comprises:

(a) coupling a corresponding compound having the formula II or a protected derivative thereof

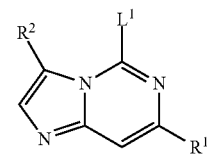

II where $L^1$ is a leaving atom and $R^1$ and $R^2$ are as defined for Formula I, with a corresponding compound having the formula III:

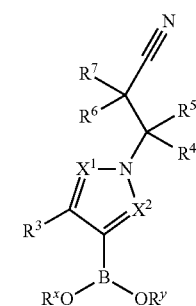

III where $R^3$, $R^4$, $R^5$, $R^6$, $R^7$, $X^1$ and $X^2$ are as defined for Formula I and Rx and $R^y$ are H or (1-6C)alkyl, or Rx and $R^y$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand; or (b) for compounds of Formula I wherein $R^2$ is hydrogen, cyclizing a corresponding compound having the formula IV or a protected derivative thereof

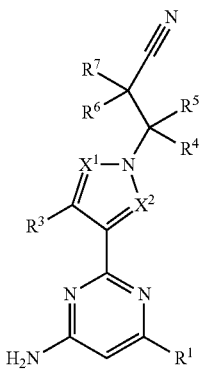

IV where $R^1$, $R^3$, $R^4$, $R^5$, $R^6$, $R^7$, $X^1$ and $X^2$ are as defined for Formula I (with the exception that $R^1$ is not $C(=O)NR^aR^b$), with 2-chloroacetaldehyde in the presence of a base; or (c) for a compound of Formula I wherein $R^1$ is hetAr$^1$, hetAr$^2$, hetAr$^3$, Ar$^1$ or Ar$^2$, and $R^2$ is hydrogen, coupling a corresponding compound having the formula V or a protected derivative thereof

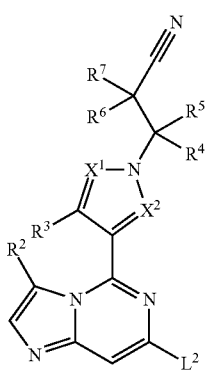

V where $R^2$ is hydrogen, $R^3$, $R^4$, $R^5$, $R^6$, $R^7$, $X^1$ and $X^2$ are as defined for Formula I and $L^2$ is a leaving atom, with a compound having the formula VIA or VIB

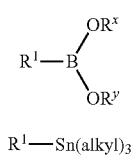

VIA

R$^1$—Sn(alkyl)$_3$

VIB wherein $R^1$ is as defined for Formula I, and $R^x$ and $R^y$ are H or (1-6C)alkyl, or $R^x$ and $R^y$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand; or (d) for compounds of Formula I wherein $R^2$ is hydrogen, $R^4$ is H or (1-6C)alkyl, and $R^5$ is H, (1-6C)alkyl, —CH$_2$CN, (3-6C)cycloalkyl, hetCyc$^e$, Ar$^a$ or hetAr$^d$, coupling a corresponding compound having the formula VII

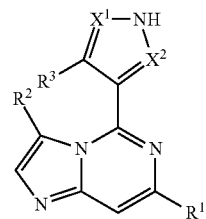

VII where $R^2$ is hydrogen, and $R^1$, $R^3$, $X^1$ and $X^2$ are as defined for Formula I, with a corresponding acrylonitrile reagent having the formula

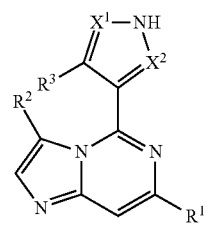

where $R^7$ is as defined for Formula I, $R^4$ is H or (1-6C)alkyl and $R^5$ is H, (1-6C)alkyl, —CH$_2$CN, (3-6C)cycloalkyl, hetCyc$^e$, Ar$^a$ or hetAr$^d$, in the presence of a base; or (e) for a compound of Formula I wherein $R^2$ is hydrogen, and $R^4$ and $R^5$ form a 4-membered oxacyclic ring, a 5-6 membered carbocyclic ring, or an unsubstituted 4 membered azacyclic ring, coupling a corresponding compound having the formula VII

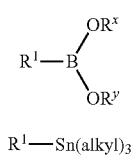

VII where $R^2$ is hydrogen, and $R^1$, $R^3$, $X^1$ and $X^2$ are as defined for Formula I, with a compound having the formula VIII-a, VIII-b, or VIII-c respectively

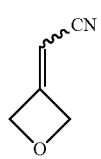

VIII-a

-continued

VIII-b
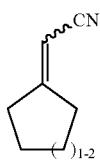

VIII-c
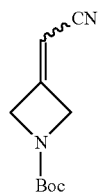

in the presence of a base; or (f) for a compound of Formula I wherein $R^4$ and $R^5$ form a 4 or 6 membered azacyclic ring substituted with (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl) or —CH$_2$hetCyc$^f$, coupling a corresponding compound having the formula IX IX
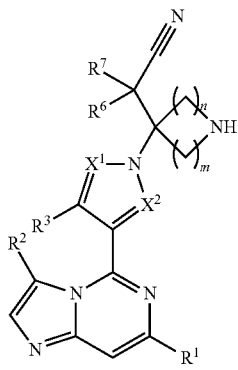

wherein m and n are each 1, or m and n are each 2, and $R^1$, $R^2$, $R^3$, $R^6$, $R^7$, $X^1$ and $X^2$ are as defined for Formula I, with a corresponding compound having the formula $L^3$-$R^{10}$, where $L^3$ is a leaving group or atom and $R^{10}$ is (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl) or —CH$_2$hetCyc$^f$, in the presence of a base; or (g) for a compound of Formula I wherein $R^4$ and $R^5$ form a 4 or 6 membered azacyclic ring substituted with (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl) or —CH$_2$hetCyc$^f$, coupling a corresponding compound having the formula IX IX
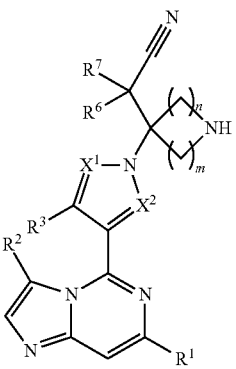

wherein m and n are each 1, or m and n are each 2, and $R^1$, $R^2$, $R^3$, $R^6$, $R^7$, $X^1$ and $X^2$ are as defined for Formula I, with a corresponding aldehyde having the formula

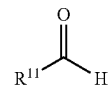

where $R^{11}$ is (1-5C)alkyl, fluoro(1-5C)alkyl, difluoro(1-5C)alkyl, trifluoro(1-5C)alkyl, tetrafluoro(1-5C)alkyl, pentafluoro(1-5C)alkyl, (3C)alkynyl, cyano(1-3C)alkyl, phenyl, -(3-6C cycloalkyl) or -hetCyc$^f$, in the presence of a base and a reducing agent; or (h) for a compound of Formula I wherein $R^4$ and $R^5$ form a 4 or 6 membered azacyclic ring substituted with cyclopropyl or oxetanyl, coupling a compound having the formula IX IX
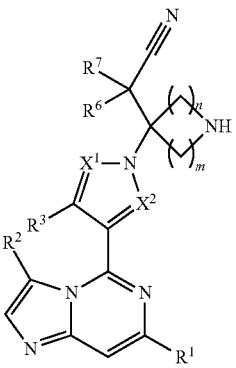

wherein m and n are each 1, or m and n are each 2, $R^1$ and $R^2$, $R^3$, $R^6$, $R^7$, $X^1$ and $X^2$ are as defined for Formula I, with a corresponding ketone having the formula

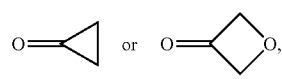

respectively, or an acetal derivative thereof, in the presence of a base and a reducing agent; or (i) for a compound of Formula I wherein $R^4$ and $R^5$ form a 4 or 6 membered azacyclic ring substituted with —C(=O)(1-6Calkyl) or —C(=O)(CR'R")CF$_3$, coupling a corresponding compound having the formula IX

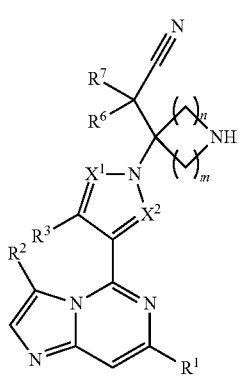

wherein m and n are each 1, or m and n are each 2, and $R^1$, $R^2$, $R^3$, $R^6$, $R^7$, $X^1$ and $X^2$ are as defined for Formula I, with a corresponding compound having the formula $R^{12}CO_2H$ or a corresponding anhydride thereof, where $R^{12}$ is -(1-6Calkyl) or —(CR'R")CF$_3$, in the presence of a base and optionally in the presence of a coupling reagent; or (j) for a compound of Formula I wherein $R^4$ and $R^5$ form a 4 or 6 membered azacyclic ring substituted with $SO_2CF_3$, reacting a compound having the formula IX

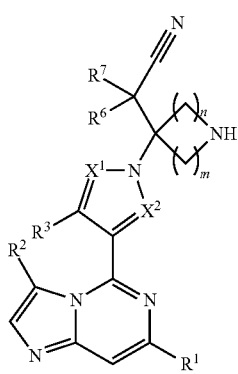

wherein m and n are each 1, or m and n are each 2, and $R^1$, $R^2$, $R^3$, $R^6$, $R^7$, $X^1$ and $X^2$ are as defined for Formula I, with triflic anhydride in the presence of a base; or (k) for a compound of Formula I wherein $R^4$ and $R^5$ form a 4 or 6 membered azacyclic ring substituted with $SO_2R^c$ where $R^c$ is as defined for Formula I, coupling a corresponding compound having the formula IX

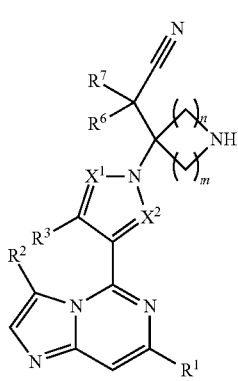

wherein m and n are 1, or m and n are 2, and $R^1$, $R^2$, $R^3$, $R^6$, $R^7$, $X^1$ and $X^2$ are as defined for Formula I, with a corresponding compound having the formula $Cl$—$SO_2R^c$ in the presence of a base; or (l) for a compound of Formula I wherein $R^1$ is C(=O)NR$^a$R$^b$, coupling a corresponding compound having the formula X

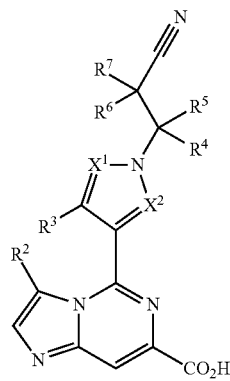

wherein $R^2$, $R^3$, $R^4$, $R^5$, $R^6$, $R^7$, $X^1$ and $X^2$ are as defined for Formula I, with a corresponding compound having the formula HNR$^a$R$^b$ in the presence of a base and a coupling agent; or (m) for a compound of Formula I wherein $R^2$ is Cl, reacting a corresponding compound of Formula XI

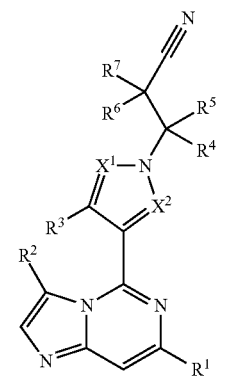

wherein $R^2$ is hydrogen, and $R^1$, $R^3$, $R^4$, $R^5$, $R^6$, $R^7$, $X^1$ and $X^2$ are as defined for Formula I, with 1-chloropyrrolidine-2,5-dione; or (n) for a compound of Formula I wherein $R^2$ is CN, reacting a corresponding compound of Formula XI

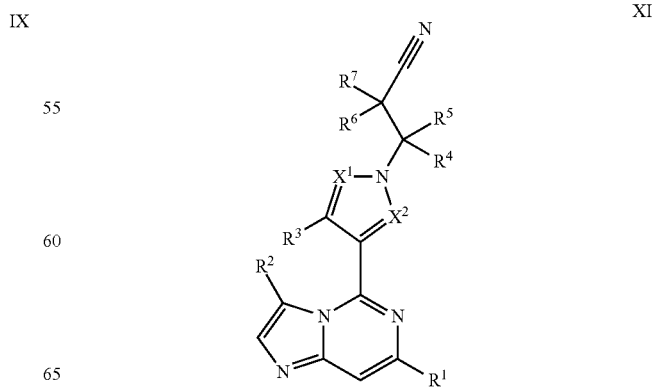

wherein R² is hydrogen, and R¹, R³, R⁴, R⁵, R⁶, R⁷, X¹ and X² are as defined for Formula I, with 1-iodopyrrolidinine-2,5-dione followed by treatment of the resulting 3-iodo-substituted derivative of X¹ with CuCN; or (o) for a compound of Formula I wherein R⁴ is hydrogen and R⁵ is CH₂CN, reacting a compound having the formula XII

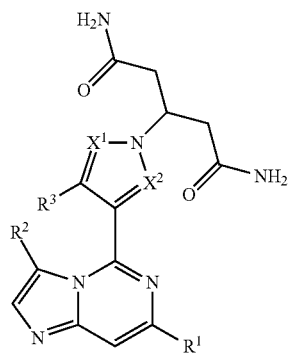

wherein R¹, R², R³, X¹ and X² are as defined for Formula I, with a dehydrating agent; or (p) for a compound of Formula I wherein R² is F, reacting a corresponding compound of Formula XI

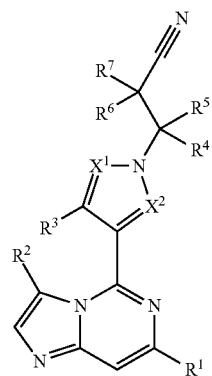

wherein R² is hydrogen, and R¹, R³, R⁴, R⁵, R⁶, R⁷, X¹ and X² are as defined for Formula I, with an electrophilic fluorinating agent; or (q) for a compound of Formula I wherein R² is F, reacting a corresponding compound of Formula XIII

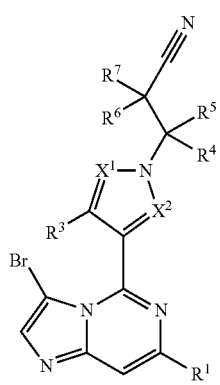

with an alkyl lithium or alkyl magnesium halide reagent, followed by treatment with an electrophilic fluorinating agent; or (r) for a compound of Formula I wherein R² is F, reacting a corresponding compound of Formula IV

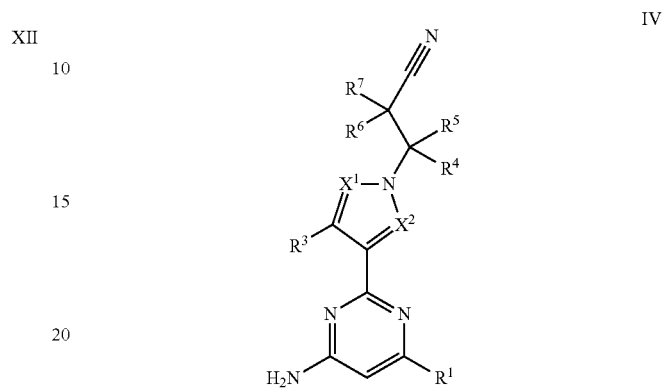

with 2-chloro-2-fluoroacetaldehyde or 2-bromo-2-fluoro-acetaldehyde; and optionally removing any protecting groups and optionally preparing a salt thereof.

Referring to method (a), suitable palladium catalysts include Pd(PPh₃)₄, Pd₂(dba)₃, Pd(OAc)₂, and Pd(PPh₃)₂Cl₂. Suitable ligands include XPHOS, DIPHOS or rac-BINAP. The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C. The leaving atom L¹ can be a halogen atom, such as chloride.

Compounds of formula II can be prepared by treating the corresponding 5-hydroxy derivative II-a

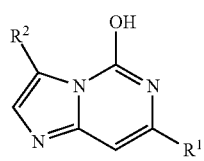

with a halogenating agent, such as POCl₃. Compounds of Formula II-a wherein R² is hydrogen and R¹ is as defined for Formula I can be formed by coupling the corresponding 7-chloro derivative with the appropriate boronic ester derivative in the presence of a palladium catalyst.

Compounds of formula III can be prepared by reacting the corresponding bromide derivative with a reagent having the formula B(ORᵃ)(ORᵇ). Examples of B(ORᵃ)(ORᵇ) include boronic acid (i.e., where Rᵃ and Rᵇ are both hydrogen), and boronic esters. Examples of boronic esters include dioxaborolanes (i.e., where Rᵃ and Rᵇ together with the atoms to which they are attached form an optionally substituted 5-membered ring) and dioxaborinanes (i.e., where Rᵃ and Rᵇ together with the atoms to which they are attached form an optionally substituted 6-membered ring). A particular example of a dioxoborinane is 4,4,4',4',5,5,5',5'-octamethyl-2,2'-bi(1,3,2-dioxaborolane) (also known as bis(pinacoloato)diboron), which can be prepared by reacting the corresponding bromide derivative with pinacol diborane in the presence of a palladium (II) catalyst (e.g., PdCl$_2$-dppf-DCM), and a base (e.g., an alkali metal carbonate, hydroxide, alkoxide or acetate), and optionally in the presence of a ligand, such as 1,1'-bis(diphenylphosphino)ferrocene (dppf).

Referring to method (b), the base may be, for example, an alkali metal acetate, carbonate, hydroxide, or alkoxide, such as for example potassium acetate, cesium carbonate, sodium carbonate, potassium carbonate, sodium hydroxide or sodium tert-butoxide. Suitable solvents include alcoholic solvents such as ethanol. The reaction is conveniently performed in the presence of a pH 7 buffer, such as a phosphate buffer. The reaction is conveniently performed at elevated temperatures, such as 90-100° C.

Compounds of Formula IV can be prepared by coupling the corresponding chloro derivative IV-a

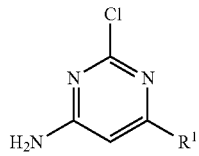

IV-a with the appropriate boronic ester derivative having the formula IV-b

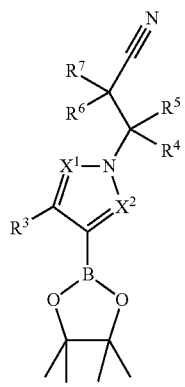

IV-b or other suitable boronic ester derivatives, in the presence of a palladium catalyst. Compound IV-a can be prepared by treating 2,6-dichloropyrimidin-4-amine with the appropriate boronic ester derivative when R$^1$ is as defined for Formula I (with the exception that R$^1$ is not C(=O)NR$^a$R$^b$).

Referring to method (c), suitable palladium catalysts include Pd(PPh$_3$)$_4$, Pd$_2$(dba)$_3$, Pd(OAc)$_2$ and Pd(PPh$_3$)$_2$Cl$_2$. Suitable ligands include XPHOS, DIPHOS or rac-BINAP. The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C.

Compounds of Formula V can be prepared by coupling a corresponding compound having the formula V-a

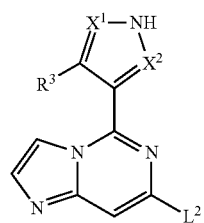

V-a with a corresponding acrylonitrile reagent having the formula

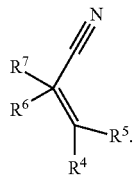

Compounds of formula V-a can be prepared by cyclizing corresponding compounds having formula V-b

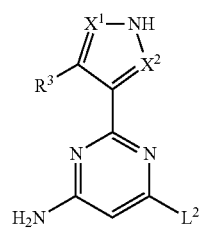

V-b with 2-chloroacetaldehyde in the presence of a base.

Referring to method (d), suitable bases include amine bases such as 1,8-diazabicyclo[5.4.0]undec-7-en (DBU) or alkali metal hydride bases such as sodium hydride. Suitable solvents include aprotic solvents such as ethers (for example tetrahydrofuran or p-dioxane) or DMF. The reaction is conveniently performed at temperatures between 0° C. and 50° C.

Compounds of Formula VII can be prepared by coupling a compound of Formula VII-a

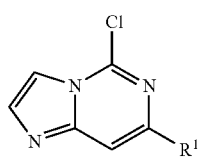

VII-a with the appropriate boronic ester derivative. Compounds of formula VII-a when R$^1$ is as defined for Formula I (with the exception that R$^1$ is not C(=O)NR$^a$R) can be prepared by coupling a compound having the formula VII-b

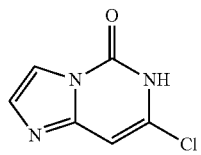

VII-b with the appropriate boronic ester derivative, followed by treatment with a chlorinating reagent such as POCl$_3$.

Referring to method (e), suitable bases include amine bases such as DBU or alkali metal hydride bases such as sodium hydride. Suitable solvents include aprotic solvents such as ethers (for example tetrahydrofuran or p-dioxane) or DMF. The reaction is conveniently performed at temperatures between 0° C. and 50° C.

Referring to method (f), suitable bases include amine bases, such as DIEA (diisopropylethylamine) or triethylamine, or alkali metal carbonates such as for example cesium carbonate, sodium carbonate, potassium carbonate. Suitable solvents include dichloromethane, dichloroethane, THF, acetonitrile and DMF. The reaction is conveniently performed at temperatures between 0° C. and ambient temperature. The leaving atom L$^3$ may be a halogen atom, for example chloro. Alternative, L$^3$ may be a leaving group, such as a triflate (OTf) or sulfonyl chloride (SO$_2$Cl).

Referring to methods (g) and (h), suitable bases include amine bases, such as DIEA (diisopropylethylamine) or triethylamine. Suitable reducing agents include Na(OAc)$_3$BH and NaCNBH$_3$. Suitable solvents include neutral solvents such as acetonitrile, THF and dichloroethane. The reaction is conveniently performed at ambient temperature.

Referring to methods (i) and (l), suitable coupling reagents include HATU, HBTU, TBTU, DCC, EDC and any other amide coupling reagents well known to persons skilled in the art. Suitable bases include amine bases, such as DIEA (diisopropylethylamine) or triethylamine. Suitable solvents include neutral solvents such as THF, DMF, dichloromethane and dichloroethane.

Referring to methods (j) and (k), suitable bases include amine bases, such as DIEA or triethylamine. Suitable solvents include neutral solvents such as dichloromethane and dichloroethane. The reaction is conveniently performed at temperatures between 0° C. and ambient temperature.

Referring to method (m), suitable solvents include dichloromethane and dichloroethane. The reaction is conveniently performed at temperatures between 0° C. and ambient temperature.

Referring to method (n), suitable solvents for the reaction with 1-iodopyrrolidine-2,5-dione include dichloromethane and dichloroethane. The reaction is conveniently performed at temperatures between 0° C. and ambient temperature. A suitable solvent for the reaction of the iodo intermediate with CuCN is DMF.

Referring to method (o), suitable dehydrating agents include 2,2,2-trichloroacetyl chloride, phosphorous oxychloride, and other suitable dehydrating agents known to persons skilled in the art. Compounds of Formula XII can be prepared by treating the corresponding acid having the formula XII-a

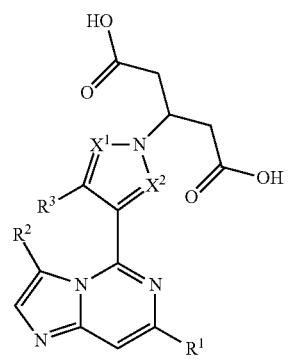

XII-a with ammonia in the presence of a coupling agent such as carbonyl diimidazole. The acid having formula XII-a can be prepared by treating a compound of formula VII-a

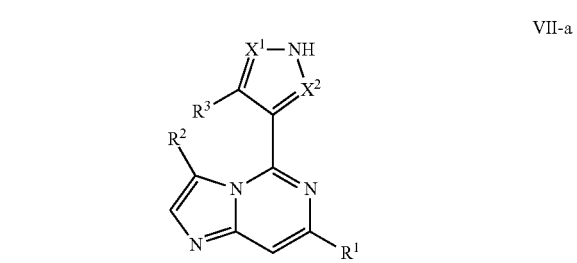

VII-a where R$^1$, R$^2$, R$^3$, X$^1$ and X$^2$ are as defined for Formula I, with (E)-dimethyl pent-2-enedioate, followed by saponification of the resulting diester.

Referring to methods (p) and (q), an example of an electrophilic fluorinating agent is 1-chloromethyl-4-fluoro-1,4-diazoniabicyclo[2.2.2]octane bis(tetrafluoroborate) (also known as Selectfluor). The reaction is conveniently performed at ambient temperature or at elevated temperatures in a suitable solvent such as acetonitrile for method (p) or an ether solvent for method (q).

Referring to method (r), the reaction is conveniently performed at ambient temperature or at elevated temperatures in a suitable solvent such as ether or alcohol solvents.

Amine groups in compounds described in any of the above methods may be protected with any convenient amine protecting group, for example as described in Greene & Wuts, eds., "Protecting Groups in Organic Synthesis", 2$^{nd}$ ed. New York; John Wiley & Sons, Inc., 1991. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", 2$^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", 2$^{nd}$ ed. New York; John Wiley & Sons, Inc., 1991. Examples of alcohol protecting groups include benzyl, trityl, silyl ethers, and the like.

The compounds of the formulas IV, V, VII, VII-a, IX, X, XI and XII are also believed to be novel and are provided as further aspects of the invention.

The compounds of Formula I represent novel inhibitors of one or more JAK kinases. In particular, the compounds are inhibitors of Tyk2, JAK1, JAK2, and/or JAK3, and are useful in the treatment of cytokine or JAK kinase-associated diseases such as autoimmune diseases, inflammatory diseases, rejection of transplanted organs, tissues and cells, as well as hematologic disorders and malignancies and their co-morbidities.

The ability of compounds of the invention to act as inhibitors of Tyk2 may be demonstrated by the assay described in Example A.

The ability of compounds of the invention to act as inhibitors of JAK1 may be demonstrated by the assay described in Example B.

The ability of compounds of the invention to act as inhibitors of JAK2 may be demonstrated by the assay described in Example C The ability of compounds of the invention to act as inhibitors of JAK3 may be demonstrated by the assay described in Example D.

Compounds of Formula I may be useful in the treatment of JAK kinase-associated diseases such as autoimmune diseases and inflammatory diseases.

Examples of autoimmune diseases and inflammatory diseases include, but are not limited to:

(i) arthritis, including rheumatoid arthritis, juvenile arthritis, psoriatic arthritis, reactive arthritis, ankylosing spondylitis, osteoarthritis, and seronegative arthopathies;

(ii) intestinal inflammations including Crohn's disease, ulcerative colitis, inflammatory bowel disease, celiac diseases, proctitis, and eosinophilic gastroenteritis;

(iii) airways diseases including asthma and other obstructive airway diseases, including severe refractory asthma, chronic asthma, airway hyper-responsiveness, bronchitis, allergic asthma, and chronic obstruction pulmonary disease;

(iv) allergic reactions including severe allergic reaction (including anaphylaxis);

(v) eye diseases, disorders or conditions including autoimmune diseases of the eye, uveitis including uveitis associated with Behcet's disease, lens-induced uveitis and optic neuritis;

(vi) skin diseases, conditions or disorders including psoriasis, atopic dermatitis, severe dermatitis, eczema, scleroderma, pruritus and other pruritic conditions, alopecia areata and mastocytosis;

(vii) sepsis, systemic inflammatory response syndrome, and neutropenic fever;

(viii) fibrosis, including hepatic fibrosis, idiopathic pulmonary fibrosis, myelofibrosis and scleroderma;

(ix) gout (resolution of tophi);

(x) lupus (also known as systemic lupus erythematosus), including manifestations such as cutaneous lupus, lupus nephritis, neuropsychiatric lupus and other manifestations;

(xi) neurodegenerative diseases including demyelinating diseases, such as multiple sclerosis, motor neuron disease, Alzheimer's disease, Parkinson's disease, amyotrophic lateral sclerosis, and ischemic reperfusion injury in stroke;

(xii) diabetes, including Type I diabetes and complications from diabetes, metabolic syndrome and obesity, and (xiii) axial spondyloarthorpathy (axial SpA).

Additional examples of autoimmune diseases and inflammatory diseases include nephropathy, sarcoidosis, pancreatitis, autoimmune thyroiditis, fibromyalgia, atherosclerosis, autoimmune hemolytic anemia, autoimmune atrophic gastritis of pernicious anemia, autoimmune encephalomyelitis, autoimmune orchitis, Goodpasture's disease, autoimmune myocarditis, autoimmune thrombocytopenia, sympathetic ophthalmia, myasthenia gravis, Graves' disease, primary biliary cirrhosis, chronic aggressive hepatitis, membranous glomerulopathy, Sjogren's syndrome, Reiter's syndrome, systemic sclerosis, polyarteritis nodosa, bullous pemphigoid, Cogan's syndrome, Wegener's granulomatosis, cystic fibrosis, mixed connective tissue disease, antiphospholipid syndrome, polymyositis, dermatomyositis, membranous nephritis, primary sclerosing cholangitis, severe chronic urticaria, giant cell arteritis, eosinophilic esophagitis, and eosinophilic gastritis.

Accordingly, this invention further provides a method of treating a disease or disorder selected from an autoimmune disease and an inflammatory disease in a mammal in need thereof, comprising administering to a mammal a therapeutically effective amount of at least one compound of Formula I or a pharmaceutically acceptable salt thereof.

In one embodiment, the autoimmune or inflammatory disease is selected from lupus, psoriasis, psoriatic arthritis, rheumatoid arthritis, multiple sclerosis and inflammatory bowel diseases.

Compounds of the present invention may also be useful for treating organ, tissue and cell transplants, including bone marrow transplant, and in the treatment of autoimmune and inflammatory diseases and of complications arising therefrom.

Accordingly, this invention further provides a method of treating organ, tissue or cell transplant rejection in a mammal in need thereof, comprising administering to a mammal a therapeutically effective amount of at least one compound of Formula I or a pharmaceutically acceptable salt thereof.

Compounds of the present invention may also be useful in treating certain malignancies, including solid tumors, skin cancer, and hematological malignancies such as lymphomas and leukemias, and further may be useful in treating the complications thereof, including sequelae of hematologic malignancies (for example, in the treatment of splenomegaly in myelofibrosis), as well as cachexia in patients with solid tumors.

Accordingly, this invention further provides a method of treating malignancies in a mammal, which comprises administering to said mammal a therapeutically effective amount of a compound of Formula I.

Compounds of Formula I may be administered alone as a sole therapy or can be administered in addition with one or more other substances and/or treatments that work by the same or a different mechanism of action. These agents may include but are not limited to cyclosporin A (e.g. Sandimmune® or Neoral®), rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®.), AtGam, aspirin, acetaminophen, ibuprofen, naproxen, piroxicam, antiinflammatory steroids (e.g. prednisolone or dexamethasone), methotrexate, statins, anti-TNF agents (e.g., Enbrel® (etanercept) or Humira® (adalimumab)), Orencia® (abatacept), cyclophosphamide, mycophenolic acid, hydroxychloroquine, and metformin. These agents may be administered with one or more compounds of Formula I as part of the same or separate dosage forms, via the same or different routes of administration, and on the same or different administration schedules according to standard pharmaceutical practice known to one skilled in the art.

In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonoal antibodies.

Accordingly, the compounds of Formula I may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors. These agents may be administered with one or more compounds of Formula I as part of the same or separate dosage forms, via the same or different routes of administration, and on the same or different administration schedules according to standard pharmaceutical practice known to one skilled in the art.

As used herein, terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

In one embodiment, the terms "treatment" or "treating" as used herein, mean an alleviation, in whole or in part, of symptoms associated with a disorder or condition (e.g., autoimmune diseases, inflammatory diseases, rejection of transplanted organs, tissues and cells, as well as hematologic disorders and malignancies and their co-morbidities as described herein), or slowing, or halting of further progression or worsening of those symptoms.

In one embodiment, the term "preventing" as used herein means the prevention of the onset, recurrence or spread, in whole or in part, of the disease or condition (e.g., autoimmune diseases, inflammatory diseases, rejection of transplanted organs, tissues and cells, as well as hematologic disorders and malignancies and their co-morbidities as described herein), or a symptom thereof.

The terms "effective amount" and "therapeutically effective amount" refer to an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

The present invention further provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g., a salt such sodium chloride, if desired. The solution is typically filtered, e.g., using a 0.2 micron filter, to remove impurities and contaminants.

The present invention further provides a compound of Formula I or a pharmaceutically acceptable salt thereof, for use in therapy. In one embodiment, the invention provides a compound of Formula I or a pharmaceutically acceptable salt thereof, for use in the treatment of cytokine or JAK kinase-associated diseases in a mammal.

In one embodiment, the invention provides a compound of Formula I or a pharmaceutically acceptable salt thereof, for use in the treatment of autoimmune diseases and inflammatory diseases in a mammal.

In one embodiment, the invention provides a compound of Formula I or a pharmaceutically acceptable salt thereof, for use in the treatment of transplant rejection in a mammal.

In one embodiment, the invention provides a compound of Formula I or a pharmaceutically acceptable salt thereof, for use in the treatment of hematologic disorders and malignancies in a mammal.

According to a further aspect, the present invention provides the use of a compound of Formula I or a pharmaceutically acceptable salt thereof, in the treatment of cytokine or JAK kinase-associated diseases in a mammal.

In one embodiment, the invention provides the use of a compound of Formula I or a pharmaceutically acceptable salt thereof, in the treatment of autoimmune diseases and inflammatory diseases.

In one embodiment, the invention provides the use of a compound of Formula I or a pharmaceutically acceptable salt thereof, in the treatment of organ, tissue or cell transplant rejection in a mammal.

In one embodiment, the invention provides the use of a compound of Formula I or a pharmaceutically acceptable salt thereof, in the treatment of malignancies in a mammal In one embodiment, the compound of Formula I is selected from:
3-(4-(7-(1-methyl-1H-pyrazol-4-yl)imidazo[1,2-c]pyrimidin-5-yl)-1H-pyrazol-1-yl)pentanedinitrile;
3-Cyclopropyl-3-(4-(7-(1-methyl-1H-pyrazol-4-yl)imidazo[1,2-c]pyrimidin-5-yl)-1H-pyrazol-1-yl)propanenitrile;
Enantiomer 1 of 3-cyclopropyl-3-(4-(7-(1-methyl-1H-pyrazol-4-yl)imidazo[1,2-c]pyrimidin-5-yl)-1H-pyrazol-1-yl)propanenitrile;
Enantiomer 2 of 3-cyclopropyl-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)pentanedinitrile;
3-(4-(7-(1-methyl-1H-pyrazol-4-yl)imidazo[1,2-c]pyrimidin-5-yl)-1H-pyrazol-1-yl)-3-(pyridin-2-yl)propanenitrile;
3-(4-(7-(1-methyl-1H-pyrazol-4-yl)imidazo[1,2-c]pyrimidin-5-yl)-1H-pyrazol-1-yl)-3-(pyridin-4-yl)propanenitrile;
3-(5-methoxypyridin-3-yl)-3-(4-(7-(1-methyl-1H-pyrazol-4-yl)imidazo[1,2-c]pyrimidin-5-yl)-1H-pyrazol-1-yl)propanenitrile;
3-(5-bromopyridin-3-yl)-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)-3-phenylpropanenitrile;
3-(2-chlorophenyl)-3-(4-(7-(1-methyl-1H-pyrazol-4-yl)imidazo[1,2-c]pyrimidin-5-yl)-1H-pyrazol-1-yl)propanenitrile;
3-(3-chlorophenyl)-3-(4-(7-(1-methyl-1H-pyrazol-4-yl)imidazo[1,2-c]pyrimidin-5-yl)-1H-pyrazol-1-yl)propanenitrile;
3-(4-chlorophenyl)-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)-3-(3-(trifluoromethyl)phenyl)propanenitrile;
3-(4-(7-(1-methyl-1H-pyrazol-4-yl)imidazo[1,2-c]pyrimidin-5-yl)-1H-pyrazol-1-yl)-3-phenylbutanenitrile;
3-cyclopentyl-3-(4-(7-(1-methyl-1H-pyrazol-4-yl)imidazo[1,2-c]pyrimidin-5-yl)-1H-pyrazol-1-yl)propanenitrile;
4,4-dimethyl-3-(4-(7-(1-methyl-1H-pyrazol-4-yl)imidazo[1,2-c]pyrimidin-5-yl)-1H-pyrazol-1-yl)pentanenitrile;
3-(4-(7-(1-methyl-1H-pyrazol-4-yl)imidazo[1,2-c]pyrimidin-5-yl)-1H-pyrazol-1-yl)propanenitrile;
3-cyclobutyl-3-(4-(7-(1-methyl-1H-pyrazol-4-yl)imidazo[1,2-c]pyrimidin-5-yl)-1H-pyrazol-1-yl)propanenitrile;
tert-butyl 4-(cyanomethyl)-4-(4-(7-(1-methyl-1H-pyrazol-4-yl)imidazo[1,2-c]pyrimidin-5-yl)-1H-pyrazol-1-yl)piperidine-1-carboxylate;
2-(1-(4-(7-(1-methyl-1H-pyrazol-4-yl)imidazo[1,2-c]pyrimidin-5-yl)-1H-pyrazol-1-yl)cyclohexyl)acetonitrile;
2-(1-(4-(7-(1-methyl-1H-pyrazol-4-yl)imidazo[1,2-c]pyrimidin-5-yl)-1H-pyrazol-1-yl)cyclopentyl)acetonitrile;
2-(3-(4-(7-(1-methyl-1H-pyrazol-4-yl)imidazo[1,2-c]pyrimidin-5-yl)-1H-pyrazol-1-yl)oxetan-3-yl)acetonitrile;
3-(4-(3-chloro-7-(1-methyl-1H-pyrazol-4-yl)imidazo[1,2-c]pyrimidin-5-yl)-1H-pyrazol-1-yl)-3-cyclopropylpropanenitrile;
5-(1-(2-cyano-1-cyclopropylethyl)-1H-pyrazol-4-yl)-7-(1-methyl-1H-pyrazol-4-yl)imidazo[1,2-c]pyrimidine-3-carbonitrile;
3-(1-acetylpiperidin-4-yl)-3-(4-(7-(1-methyl-1H-pyrazol-4-yl)imidazo[1,2-c]pyrimidin-5-yl)-1H-pyrazol-1-yl)propanenitrile;
2-(1-methyl-4-(4-(7-(1-methyl-1H-pyrazol-4-yl)imidazo[1,2-c]pyrimidin-5-yl)-1H-pyrazol-1-yl)piperidin-4-yl)acetonitrile;
2-(1-ethyl-4-(4-(7-(1-methyl-1H-pyrazol-4-yl)imidazo[1,2-c]pyrimidin-5-yl)-1H-pyrazol-1-yl)piperidin-4-yl)acetonitrile;
2-(4-(4-(7-(1-methyl-1H-pyrazol-4-yl)imidazo[1,2-c]pyrimidin-5-yl)-1H-pyrazol-1-yl)-1-propylpiperidin-4-yl)acetonitrile;
2-(4-(4-(7-(1-methyl-1H-pyrazol-4-yl)imidazo[1,2-c]pyrimidin-5-yl)-1H-pyrazol-1-yl)-1-(2,2,2-trifluoroethyl)piperidin-4-yl)acetonitrile;
3-cyclopropyl-3-(4-(7-(1-((2-(trimethylsilyl)ethoxy)methyl)-1H-pyrazol-4-yl)imidazo[1,2-c]pyrimidin-5-yl)-1H-pyrazol-1-yl)propanenitrile;
3-(4-(7-(1H-pyrazol-4-yl)imidazo[1,2-c]pyrimidin-5-yl)-1H-pyrazol-1-yl)-3-cyclopropylpropanenitrile;
3-Cyclopropyl-3-(4-(7-(1-isopropyl-1H-pyrazol-4-yl)imidazo[1,2-c]pyrimidin-5-yl)-1H-pyrazol-1-yl)propanenitrile;
3-cyclopropyl-3-(4-(7-(1-(pyridin-3-ylmethyl)-1H-pyrazol-4-yl)imidazo[1,2-c]pyrimidin-5-yl)-1H-pyrazol-1-yl)propanenitrile;
3-cyclopropyl-3-(4-(7-(1-(tetrahydro-2H-pyran-4-yl)-1H-pyrazol-4-yl)imidazo[1,2-c]pyrimidin-5-yl)-1H-pyrazol-1-yl)propanenitrile;
3-cyclopropyl-3-(4-(7-(1-isobutyl-1H-pyrazol-4-yl)imidazo[1,2-c]pyrimidin-5-yl)-1H-pyrazol-1-yl)propanenitrile;
3-Cyclopropyl-3-(4-(7-(1-(oxetan-3-yl)-1H-pyrazol-4-yl)imidazo[1,2-c]pyrimidin-5-yl)-1H-pyrazol-1-yl)propanenitrile;
3-cyclopropyl-3-(4-(7-(1-(2,2,2-trifluoroethyl)-1H-pyrazol-4-yl)imidazo[1,2-c]pyrimidin-5-yl)-1H-pyrazol-1-yl)propanenitrile;
3-cyclopropyl-3-(4-(7-(1-ethyl-1H-pyrazol-4-yl)imidazo[1,2-c]pyrimidin-5-yl)-1H-pyrazol-1-yl)propanenitrile;
3-cyclopropyl-3-(4-(7-(1-(2-isopropoxyethyl)-1H-pyrazol-4-yl)imidazo[1,2-c]pyrimidin-5-yl)-1H-pyrazol-1-yl)propanenitrile;
3-(4-(7-(1-cyclobutyl-1H-pyrazol-4-yl)imidazo[1,2-c]pyrimidin-5-yl)-1H-pyrazol-1-yl)-3-cyclopropylpropanenitrile;
3-cyclopropyl-3-(4-(7-(oxazol-5-yl)imidazo[1,2-c]pyrimidin-5-yl)-1H-pyrazol-1-yl)propanenitrile;
3-cyclopropyl-3-(4-(7-(1-(2-(4-methylpiperazin-1-yl)ethyl)-1H-pyrazol-4-yl)imidazo[1,2-c]pyrimidin-5-yl)-1H-pyrazol-1-yl)propanenitrile;
3-Cyclopropyl-3-(4-(7-(5-methyl-1,3,4-thiadiazol-2-yl)imidazo[1,2-c]pyrimidin-5-yl)-1H-pyrazol-1-yl)propanenitrile;
3-Cyclopropyl-3-(4-(7-(4-methyl-1H-imidazol-1-yl)imidazo[1,2-c]pyrimidin-5-yl)-1H-pyrazol-1-yl)propanenitrile;
3-Cyclopropyl-3-(4-(7-(thiazol-5-yl)imidazo[1,2-c]pyrimidin-5-yl)-1H-pyrazol-1-yl)propanenitrile;
3-cyclopropyl-3-(4-(7-(2-methylthiazol-5-yl)imidazo[1,2-c]pyrimidin-5-yl)-1H-pyrazol-1-yl)propanenitrile;
3-Cyclopropyl-3-(4-(7-(6-methylpyridin-3-yl)imidazo[1,2-c]pyrimidin-5-yl)-1H-pyrazol-1-yl)propanenitrile;
3-cyclopropyl-3-(4-(7-(2-methylpyridin-4-yl)imidazo[1,2-c]pyrimidin-5-yl)-1H-pyrazol-1-yl)propanenitrile;
3-cyclopropyl-3-(4-(7-(6-(4-methylpiperazin-1-yl)pyridin-3-yl)imidazo[1,2-c]pyrimidin-5-yl)-1H-pyrazol-1-yl)propanenitrile;

3-Cyclopropyl-3-(4-(7-(1,2,3,4-tetrahydroisoquinolin-6-yl) imidazo[1,2-c]pyrimidin-5-yl)-1H-pyrazol-1-yl)propanenitrile;

3-Cyclopropyl-3-(4-(7-(2-methyl-1,2,3,4-tetrahydroisoquinolin-6-yl)imidazo[1,2-c]pyrimidin-5-yl)-1H-pyrazol-1-yl)propanenitrile;

3-Cyclopropyl-3-(4-(7-(1,2,3,4-tetrahydroisoquinolin-7-yl) imidazo[1,2-c]pyrimidin-5-yl)-1H-pyrazol-1-yl)propanenitrile;

3-Cyclopropyl-3-(4-(7-(2-methyl-1,2,3,4-tetrahydroisoquinolin-7-yl)imidazo[1,2-c]pyrimidin-5-yl)-1H-pyrazol-1-yl)propanenitrile;

3-Cyclopropyl-3-(4-(7-(5,6,7,8-tetrahydroimidazo[1,2-a]pyrazin-3-yl)imidazo[1,2-c]pyrimidin-5-yl)-1H-pyrazol-1-yl)propanenitrile;

3-cyclopropyl-3-(4-(7-(7-methyl-5,6,7,8-tetrahydroimidazo[1,2-a]pyrazin-3-yl)imidazo[1,2-c]pyrimidin-5-yl)-1H-pyrazol-1-yl)propanenitrile;

3-(4-(7-(4-(8-Oxa-3-azabicyclo[3.2.1]octan-3-yl)phenyl) imidazo[1,2-c]pyrimidin-5-yl)-1H-pyrazol-1-yl)-3-cyclopropylpropanenitrile;

3-Cyclopropyl-3-(4-(7-(4-(4-methylpiperazin-1-yl)phenyl) imidazo[1,2-c]pyrimidin-5-yl)-1H-pyrazol-1-yl)propanenitrile;

Tert-butyl 3-(cyanomethyl)-3-(4-(7-(1-methyl-1H-pyrazol-4-yl)imidazo[1,2-c]pyrimidin-5-yl)-1H-pyrazol-1-yl)azetidine-1-carboxylate;

2-(3-(4-(7-(1-Methyl-1H-pyrazol-4-yl)imidazo[1,2-c]pyrimidin-5-yl)-1H-pyrazol-1-yl)azetidin-3-yl)acetonitrile;

2-(1-Acetyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(3,3,3-trifluoropropanoyl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(1-(trifluoromethyl)cyclopropanecarbonyl)azetidin-3-yl)acetonitrile;

2-(1-Cyclopropyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(oxetan-3-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(pyrimidin-2-yl)azetidin-3-yl)acetonitrile;

2-(1-(2,2-dDifluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,2-trifluoro ethyl) azetidin-3-yl)acetonitrile;

2-(1-ethyl-3-(4-(7-(1-methyl-1H-pyrazol-4-yl)imidazo[1,2-c]pyrimidin-5-yl)-1H-pyrazol-1-yl)azetidin-3-yl)acetonitrile;

2,2'-(3-(4-(7-(1-methyl-1H-pyrazol-4-yl)imidazo[1,2-c]pyrimidin-5-yl)-1H-pyrazol-1-yl)azetidine-1,3-diyl)diacetonitrile;

2-(1-(3-fluoropropyl)-3-(4-(7-(1-methyl-1H-pyrazol-4-yl) imidazo[1,2-c]pyrimidin-5-yl)-1H-pyrazol-1-yl)azetidin-3-yl)acetonitrile;

2-(1-(but-2-ynyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(prop-2-ynyl)azetidin-3-yl)acetonitrile;

2-(1-(2-fluoroethyl)-3-(4-(7-(1-methyl-1H-pyrazol-4-yl) imidazo[1,2-c]pyrimidin-5-yl)-1H-pyrazol-1-yl)azetidin-3-yl)acetonitrile;

3-(3-(cyanomethyl)-3-(4-(7-(1-methyl-1H-pyrazol-4-yl) imidazo[1,2-c]pyrimidin-5-yl)-1H-pyrazol-1-yl)azetidin-1-yl)propanenitrile;

2-(1-(1,3-difluoropropan-2-yl)-3-(4-(7-(1-methyl-1H-pyrazol-4-yl)imidazo[1,2-c]pyrimidin-5-yl)-1H-pyrazol-1-yl) azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,3,3-tetrafluoropropyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-propylazetidin-3-yl)acetonitrile;

2-(1-isopropyl-3-(4-(7-(1-methyl-1H-pyrazol-4-yl)imidazo [1,2-c]pyrimidin-5-yl)-1H-pyrazol-1-yl)azetidin-3-yl)acetonitrile;

2-(1-methyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-(cyclopropylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-isobutyl-3-(4-(7-(1-methyl-1H-pyrazol-4-yl)imidazo [1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(3,3,3-trifluoropropyl) azetidin-3-yl)acetonitrile;

2-(1-(cyclobutylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-benzyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-((tetrahydro-2H-pyran-4-yl)methyl)azetidin-3-yl)acetonitrile;

2-(3-(4-(3-Chloro-7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(1-(Isopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(methylsulfonyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(propylsulfonyl)azetidin-3-yl)acetonitrile;

2-(1-(cyclohexylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(trifluoromethylsulfonyl) azetidin-3-yl)acetonitrile;

2-(1-(ethylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(3,3,3-trifluoropropylsulfonyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(phenylsulfonyl)azetidin-3-yl)acetonitrile;

2-(3-(4-(7-(1-Isopropyl-1-H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-Isopropyl-1H-pyrazol-4-yl)imidazo[1,2-c]pyrimidin-5-yl)-1H-pyrazol-1-yl)-1-(trifluoromethylsulfonyl)azetidine-3-yl)acetonitrile;

2-(3-(4-(7-(2-Methylthiazol-5-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-Cyclobutyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-Ethyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-(Oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

3-(3-methyl-4-(7-(1-methyl-1H-pyrazol-4-yl)imidazo[1,2-c]pyrimidin-5-yl)-1H-pyrazol-1-yl)propanenitrile;

3-(5-methyl-4-(7-(1-methyl-1H-pyrazol-4-yl)imidazo[1,2-c]pyrimidin-5-yl)-1H-pyrazol-1-yl)propanenitrile;

2-(3-(3-methyl-4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

3-Cyclopropyl-3-(3-methyl-4-(7-(1-methyl-1H-pyrazol-4-yl)imidazo[1,2-c]pyrimidin-5-yl)-1H-pyrazol-1-yl)propanenitrile;

3-Cyclopentyl-3-(4-(7-(4-(1-methylpiperidin-4-yl)phenyl)imidazo[1,2-c]pyrimidin-5-yl)-1H-pyrazol-1-yl)propanenitrile;

Enantiomer 1 of 3-cyclopentyl-3-(4-(7-(4-(1-methylpiperidin-4-yl)phenyl)imidazo[1,2-c]pyrimidin-5-yl)-1H-pyrazol-1-yl)propanenitrile;

Enantiomer 2 of 3-cyclopentyl-3-(4-(7-(4-(1-methylpiperidin-4-yl)phenyl)imidazo[1,2-c]pyrimidin-5-yl)-1H-pyrazol-1-yl)propanenitrile;

3-Cyclopentyl-3-(4-(7-(4-morpholinophenyl)imidazo[1,2-c]pyrimidin-5-yl)-1H-pyrazol-1-yl)propanenitrile;

Enantiomer 1 of 3-cyclopentyl-3-(4-(7-(4-morpholinophenyl)imidazo[1,2-c]pyrimidin-5-yl)-1H-pyrazol-1-yl)propanenitrile;

Enantiomer 2 of 3-cyclopentyl-3-(4-(7-(4-morpholinophenyl)imidazo[1,2-c]pyrimidin-5-yl)-1H-pyrazol-1-yl)propanenitrile;

3-methyl-3-(4-(7-(4-morpholinophenyl)imidazo[1,2-c]pyrimidin-5-yl)-1H-pyrazol-1-yl)butanenitrile;

3-cyclopropyl-3-(4-(7-(4-morpholinophenyl)imidazo[1,2-c]pyrimidin-5-yl)-1H-pyrazol-1-yl)propanenitrile;

3-(4-(7-(4-morpholinophenyl)imidazo[1,2-c]pyrimidin-5-yl)-1H-pyrazol-1-yl)butanenitrile;

2-methyl-3-(4-(7-(4-morpholinophenyl)imidazo[1,2-c]pyrimidin-5-yl)-1H-pyrazol-1-yl)propanenitrile;

3-(4-(7-(4-morpholinophenyl)imidazo[1,2-c]pyrimidin-5-yl)-1H-pyrazol-1-yl)propanenitrile;

3-Cyclopentyl-3-(3-methyl-4-(7-(4-morpholinophenyl)imidazo[1,2-c]pyrimidin-5-yl)-1H-pyrazol-1-yl)propanenitrile;

N-tert-butyl-5-(1-(2-cyano-1-cyclopropylethyl)-1H-pyrazol-4-yl)imidazo[1,2-c]pyrimidine-7-carboxamide;

5-(1-(2-Cyano-1-cyclopropylethyl)-1H-pyrazol-4-yl)-N-cyclohexylimidazo[1,2-c]pyrimidine-7-carboxamide;

5-(1-(2-Cyano-1-cyclopropylethyl)-1H-pyrazol-4-yl)-N-cyclobutylimidazo[1,2-c]pyrimidine-7-carboxamide;

5-(1-(2-cyano-1-cyclopropylethyl)-1H-pyrazol-4-yl)-N-(pyridin-2-yl)imidazo[1,2-c]pyrimidine-7-carboxamide;

3-Cyclopropyl-3-(3-(7-(1-methyl-1H-pyrazol-4-yl)imidazo[1,2-c]pyrimidin-5-yl)-1H-pyrrol-1-yl)propanenitrile;

2-(3-(3-(7-(1-Methyl-1H-pyrazol-4-yl)imidazo[1,2-c]pyrimidin-5-yl)-1H-pyrrol-1-yl)azetidin-3-yl)acetonitrile;

2-(3-(3-(7-(1-Methyl-1H-pyrazol-4-yl)imidazo[1,2-c]pyrimidin-5-yl)-1H-pyrrol-1-yl)-1-(2,2,2-trifluoro ethyl)azetidin-3-yl)acetonitrile;

Tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate;

2-(3-(3-(7-(1-Methyl-1H-pyrazol-4-yl)imidazo[1,2-c]pyrimidin-5-yl)-1H-pyrazol-1-yl)azetidin-3-yl)acetonitrile;

2-(3-(3-(7-(1-Methyl-1H-pyrazol-4-yl)imidazo[1,2-c]pyrimidin-5-yl)-1H-pyrazol-1-yl)-1-(2,2,2-trifluoro ethyl)azetidin-3-yl)acetonitrile;

3-Cyclopropyl-3-(3-(7-(1-methyl-1H-pyrazol-4-yl)imidazo[1,2-c]pyrimidin-5-yl)-1H-pyrazol-1-yl)propanenitrile;

2-(3-(4-(7-(1-methyl-1H-pyrazol-4-yl)imidazo[1,2-c]pyrimidin-5-yl)-1H-pyrazol-1-yl)-1-(trifluoromethylsulfonyl)pyrrolidin-3-yl)acetonitrile;

2-(1-acetyl-3-(4-(7-(1-methyl-1H-pyrazol-4-yl)imidazo[1,2-c]pyrimidin-5-yl)-1H-pyrazol-1-yl)pyrrolidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,2-trifluoro ethyl)pyrrolidin-3-yl)acetonitrile;

2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(4-(4-methylpiperazin-1-yl)phenyl)imidazo[1,2-c]pyrimidin-5-yl)-1H-pyrazol-1-yl)-1-(2,2,2-trifluoroethyl)azetidin-3-yl)acetonitrile;

2-(3-(4-(7-(4-(4-methylpiperazin-1-yl)phenyl)imidazo[1,2-c]pyrimidin-5-yl)-1H-pyrazol-1-yl)-1-(trifluoromethylsulfonyl)azetidin-3-yl)acetonitrile;

2-(3-(4-(7-(2-methylthiazol-5-yl)imidazo[1,2-c]pyrimidin-5-yl)-1H-pyrazol-1-yl)-1-(trifluoromethylsulfonyl)azetidin-3-yl)acetonitrile;

2-(1-(cyclopropylsulfonyl)-3-(4-(7-(2-methylthiazol-5-yl)imidazo[1,2-c]pyrimidin-5-yl)-1H-pyrazol-1-yl)azetidin-3-yl)acetonitrile;

2-(1-(cyclopropylsulfonyl)-3-(4-(7-(2-methoxypyrimidin-5-yl)imidazo[1,2-c]pyrimidin-5-yl)-1H-pyrazol-1-yl)azetidin-3-yl)acetonitrile;

2-(3-(4-(7-(2-methoxypyrimidin-5-yl)imidazo[1,2-c]pyrimidin-5-yl)-1H-pyrazol-1-yl)-1-(trifluoromethylsulfonyl)azetidin-3-yl)acetonitrile;

2-(3-(3-(7-(1-(2-(methylsulfonyl)ethyl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(3-(7-(1-methyl-2-oxo-1,2-dihydropyridin-4-yl)imidazo[1,2-c]pyrimidin-5-yl)-1H-pyrazol-1-yl)-1-(2,2,2-trifluoroethyl)azetidin-3-yl)acetonitrile;

2-(3-(3-(7-(1-methyl-6-oxo-1,6-dihydropyridin-3-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(4-(trifluoromethyl)phenyl)imidazo[1,2-c]pyrimidin-5-yl)-1H-pyrazol-1-yl)-1-(trifluoromethylsulfonyl)azetidin-3-yl)acetonitrile;

3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

(S)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

R)-3-((S)-2,2-difluoro cyclopropyl)-3-(4-(7-(1-methyl-1H-pyrazol-4-yl)imidazo[1,2-c]pyrimidin-5-yl)-1H-pyrazol-1-yl)propanenitrile;

(S)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

(R)-3-((R)-2,2-difluoro cyclopropyl)-3-(4-(7-(1-methyl-1H-pyrazol-4-yl)imidazo[1,2-c]pyrimidin-5-yl)-1H-pyrazol-1-yl)propanenitrile;

2-(6-(4-(7-(1-methyl-1H-pyrazol-4-yl)imidazo[1,2-c]pyrimidin-5-yl)-1H-pyrazol-1-yl)-2-oxaspiro[3.3]heptan-6-yl)acetonitrile;

2-(3-(4-(7-cyclopropylimidazo[1,2-c]pyrimidin-5-yl)-1H-pyrazol-1-yl)-1-(2,2,2-trifluoroethyl)azetidin-3-yl)acetonitrile;

2-(2-(4-(7-(1-methyl-1H-pyrazol-4-yl)imidazo[1,2-c]pyrimidin-5-yl)-1H-pyrazol-1-yl)-7-oxaspiro[3.5]nonan-2-yl)acetonitrile;

3-cyclopropyl-3-(4-(3-fluoro-7-(1-methyl-1H-pyrazol-4-yl)imidazo[1,2-c]pyrimidin-5-yl)-1H-pyrazol-1-yl)propanenitrile;

2-(3-(4-(3-chloro-7-(1-(oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(3-fluoro-7-(1-methyl-1H-pyrazol-4-yl)imidazo[1,2-c]pyrimidin-5-yl)-1H-pyrazol-1-yl)-1-((trifluoromethyl)sulfonyl)azetidin-3-yl)acetonitrile;

2-(3-(4-(3-chloro-7-(1-methyl-1H-pyrazol-4-yl)imidazo[1,2-c]pyrimidin-5-yl)-1H-pyrazol-1-yl)-1-((trifluoromethyl)sulfonyl)azetidin-3-yl)acetonitrile;

2-(1-(2,2-difluoroethyl)-3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile;

2-(3-(4-(7-(1-(oxetan-3-yl)-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile;

2-(3-(4-(7-(4-methoxyphenyl)imidazo[1,2-c]pyrimidin-5-yl)-1H-pyrazol-1-yl)-1-(trifluoromethylsulfonyl)azetidin-3-yl)acetonitrile;

2-(1-(cyclopropylsulfonyl)-3-(4-(7-(4-methoxyphenyl)imidazo[1,2-c]pyrimidin-5-yl)-1H-pyrazol-1-yl)azetidin-3-yl)acetonitrile;

2-(2-(4-(7-(1-methyl-1H-pyrazol-4-yl)imidazo[1,2-c]pyrimidin-5-yl)-1H-pyrazol-1-yl)spiro[3.3]heptan-2-yl)acetonitrile;

2-(2-(4-(7-(1-methyl-1H-pyrazol-4-yl)imidazo[1,2-c]pyrimidin-5-yl)-1H-pyrazol-1-yl)spiro[3.4]octan-2-yl)acetonitrile;

2-(2-(4-(7-(1-(oxetan-3-yl)-1H-pyrazol-4-yl)imidazo[1,2-c]pyrimidin-5-yl)-1H-pyrazol-1-yl)spiro[3.3]heptan-2-yl)acetonitrile;

or a pharmaceutically acceptable salt or solvate thereof. In one embodiment, the salt is a hydrochloride or trifluoroacetate salt.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, or other suitable suppliers, and were used without further purification unless otherwise indicated. THF, DCM, toluene, DMF) and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried or dried under a stream of dry nitrogen.

Column chromatography was done on a Biotage system (Manufacturer: Dyax Corporation) having a silica gel or C-18 reverse phase column, or on a silica SepPak cartridge (Waters), or using conventional flash column chromatography on silica gel, unless otherwise specified.

Abbreviations used herein have the following meanings:

| | |
|---|---|
| APCI | Atmospheric Pressure Chemical Ionization |
| BINAP | 2,2'-bis(diphenylphosphino)-1,1'-binaphthyl |
| Boc | tert-butoxycarbonyl |
| $CDCl_3$ | Deuterated Chloroform |
| DBU | 2,3,4,6,7,8,9,10-Octahydropyrimido[1,2-a]azepine |
| DCC | N,N'-dicyclohexylcarbodiimide |
| DCE | 1,2-Dichloroethane |
| DCM | Dichloromethane |
| DIEA | Diisopropylethylamine |
| DIPHOS | 1,2-Bis(Diphenylphosphino)ethane |
| DME | 1,2-dimethoxyethane |
| DMF | N,N-Dimethylformamide |
| DMSO | dimethylsulfoxide |
| EDC | 1-(3-dimethylaminopropyl)-3-ethylcarboiimide |
| $Et_2O$ | Diethyl ether |
| HATU | (2-(7-Aza-1H-benzotriazole-1-yl)-1,1,3,3-tetramethyluronium hexafluorophosphate) |
| HBTU | O-Benzotriazole-N,N,N',N'-tetramethyl-uronium-hexafluoro-phosphate |
| IPA | Isopropyl alcohol |
| iPrOH | Isopropyl alcohol |
| LAH | Lithium Aluminum Hydride |
| LHMDS | Lithium bis(trimethylsilyl)amide (also known as lithium hexamethyldisilazide) |
| MTBE | tert-butyl-methylether |
| $NaBH(OAc)_3$ | Sodium triacetoxyborohydride |
| $Pd(PPh_3)_4$ | Tetrakis(triphenylphosphine)palladium(0) |
| $PdCl_2(dppf)*dcm$ | 1,1'-Bis(diphenylphosphino)ferrocene-palladium(II) dichloride dichloromethane complex |
| $Pd_2dba_3$ | Tris(dibenzylideneacetone)dipalladium(0) |
| $SiO_2$ | Silicon dioxide |
| S-Phos | 2-Dicyclohexylphosphino-2',6'-dimethoxybiphenyl |
| TBTU | O-(Benzotriazol-1-yl)-N,N,N',N'-tetramethyluronium tetrafluoroborate |
| TEA | triethylamine |
| TFA | Trifluoroacetic acid |
| THF | Tetrahydrofuran |
| TLC | Thin layer chromatography |
| XPHOS | 2-Dicyclohexylphosphino-2',4',6'-triisopropylbiphenyl |

General Enzyme Inhibition Assay Method

The assays described in Examples A, B, C and D for the determination of Tyk2, JAK1, JAK2 and JAK3 kinase activity, respectively, utilized the Omnia® Kinase fluorescence peptide substrate-based technology (Invitrogen). The specific components of the assay mixture are described in Examples A, B, C and D. In these assays, $Mg^{2+}$ is chelated upon phosphorylation of the Omnia peptide by the kinase to form a bridge between the chelation-enhanced fluorophore Sox and the phosphate, resulting in an increase in fluorescence emission at 485 nM when excited at 360 nM. The reactions were therefore read at excitation 360 nm and emission was measured at 485 nm every 50 seconds for 45 minutes using a PerkinElmer EnVision Multilabel Plate Reader.

The final buffer conditions for Tyk2, JAK1, JAK2, and JAK3 assays were as follows: 25 mM HEPES, pH 7.4, 10 mM MgCl$_2$, 0.01% Triton X-100 and 1 mM DTT.

IC$_{50}$ Determinations

Compounds were prepared at 50× the final concentration in DMSO by conducting 3-fold serial dilutions from a 500-µM intermediate dilution to give a 10-point dosing curve having a high dose of 10 µM. Two-µL aliquots of these were transferred to a fresh plate for a ten-fold intermediate dilution with assay buffer. Five-µL aliquots of the diluted compounds were then transferred to 20-µL of assay mixtures described in Examples A, B, C and D for a final concentration of DMSO of 2%. A standard or reference compound was typically included on each assay plate to validate that plate. For each plate, percent of control (POC) values were calculated for each well according to the following equation:

$$POC = \frac{\text{Sample} - \overline{X}_{min}}{\overline{X}_{max} - \overline{X}_{min}} \times 100,$$

where $\overline{X}_{max}$=Average Uninhibited Controls
$\overline{X}_{min}$=Average Background
IC$_{50}$'s were estimated from the POC's using a standard 4-parameter logistic model:

$$Y = A + \frac{B - A}{1 + \left(\frac{C}{X}\right)^D},$$

where
A=Minimum Y (Bottom Asymptote)
B=Maximum Y (Top Asymptote)
C=EC$_{50}$
D=Slope Factor
X=Compound Concentration (nM)
Y=POC
The IC$_{50}$ is defined as the concentration of inhibitor at which the POC equals 50 for the fitted curve.

Example A

Tyk2 Inhibition Assay

Compounds of Formula I were screened for their ability to inhibit Tyk2 using the general enzyme inhibition assay method, in which the assay mixture contained 10 µM (Km app) or 1 mM ATP, 8 µM Omnia® Y12 peptide (Catalog #IVGN KPZ3121C; Invitrogen Corporation, Carlsbad, Calif.) and 2 nM Tyk2 in a total volume of 20 µL. Human Tyk2 kinase domain, comprising amino acids 886 to 1187 with 10 additional histidine residues (histidine tag) on the carboxy terminus, was expressed and purified from bacculovirus in-house at Array BioPharma Inc. (Boulder, Colo.). The histidine tag was cleaved after purification using standard conditions.

Example B

JAK1 Inhibition Assay

Compounds of Formula I were screened for their ability to inhibit JAK1 using the general enzyme inhibition assay method, in which the assay mixture contained 40 µM (Km app) or 1 mM ATP, 8 µM Omnia® Y12 peptide (Catalog #IVGN KPZ3121C; Invitrogen Corporation, Carlsbad, Calif.) and 15 nM JAK1 in a total volume of 20 µL. JAK1 was purchased from Invitrogen Corporation, Carlsbad, Calif. (catalog #IVGN PV4775).

Example C

JAK2 Inhibition Assay

Compounds of Formula I were screened for their ability to inhibit JAK2 using the general enzyme inhibition assay method, in which the assay mixture contained 25 µM (Km app) or 1 mM ATP, 10 µM Omnia® Y7 peptide (Catalog #IVGN KNZ3071C, Invitrogen Corporation, Carlsbad, Calif.) and 5 nM JAK2 in a total volume of 20 µL. JAK2 was purchased from Invitrogen Corporation, Carlsbad, Calif. (catalog #IVGN PV4288).

Example D

JAK3 Inhibition Assay

Compounds of Formula I were screened for their ability to inhibit JAK3 using the general enzyme inhibition assay method, in which the assay mixture contained 10 µM (Km app) or 1 mM ATP, 10 µM Omnia® Y7 peptide (Catalog #IVGN KNZ3071C, Invitrogen Corporation, Carlsbad, Calif.) and 2.5 nM JAK3 in a total volume of 20 µL. JAK3 was purchased from Invitrogen Corporation, Carlsbad, Calif. (catalog #IVGN PV4080).

Compounds of Formula I are inhibitors of Tyk2, JAK1, JAK2 and/or JAK3. A compound is considered to be an inhibitor of Tyk2, JAK1, JAK2 and/or JAK3 if it has an IC$_{50}$ value equal to or less than 1000 nM when tested in the above assay of Example A, B, C or D, respectively.

Table A provides averaged IC$_{50}$ ranges for compounds described in the Examples when tested in the assays described in Examples A, B, C and D. For each IC$_{50}$ value shown in Table A, "A" represents an IC$_{50}$ value of less than 10 nM, "B" represents an IC$_{50}$ value of between 10 nM and 100 nM, "C" represents an IC$_{50}$ value of greater than 100 nM and less than 1000 nM, and "D" represents an IC$_{50}$ value of greater than 1000 nM.

TABLE A

| Example # | Tyk2 IC$_{50}$ | JAK1 IC$_{50}$ | JAK2 IC$_{50}$ | JAK3 IC$_{50}$ |
|---|---|---|---|---|
| 1 | A | B | B | C |
| 2 | A | C | B | D |
| 3 | B | C | C | C |
| 4 | A | B | B | C |
| 5 | B | C | C | D |
| 6 | B | C | B | D |
| 7 | A | B | B | C |
| 8 | B | C | B | D |
| 9 | B | C | B | D |
| 10 | A | B | B | C |
| 11 | A | B | B | C |
| 12 | B | B | B | C |
| 13 | A | B | A | C |
| 14 | B | B | B | C |
| 15 | A | B | B | C |
| 16 | C | D | C | D |
| 17 | A | B | B | D |
| 18 | B | C | C | D |
| 19 | B | C | C | D |
| 20 | A | B | B | D |

TABLE A-continued

| Example # | Tyk2 IC$_{50}$ | JAK1 IC$_{50}$ | JAK2 IC$_{50}$ | JAK3 IC$_{50}$ |
|---|---|---|---|---|
| 21 | C | D | D | D |
| 22 | B | C | C | D |
| 23 | B | C | C | D |
| 24 | B | B | B | D |
| 25 | A | B | B | C |
| 26 | C | D | C | D |
| 27 | C | C | C | D |
| 28 | B | D | C | D |
| 29 | C | D | D | D |
| 30 | C | D | D | D |
| 31 | B | C | C | D |
| 32 | B | C | B | C |
| 33 | B | C | C | D |
| 34 | A | C | B | C |
| 35 | A | C | B | C |
| 36 | A | C | B | C |
| 37 | B | C | B | D |
| 38 | A | C | B | C |
| 39 | A | B | B | C |
| 40 | A | C | B | C |
| 41 | B | C | B | D |
| 42 | A | B | B | C |
| 43 | B | D | C | D |
| 44 | B | C | B | C |
| 45 | C | D | D | D |
| 46 | B | D | C | D |
| 47 | B | C | C | D |
| 48 | B | C | B | C |
| 49 | B | C | C | D |
| 50 | B | C | C | D |
| 51 | A | C | B | C |
| 52 | B | B | B | C |
| 53 | B | B | B | C |
| 54 | A | B | B | C |
| 55 | B | B | B | C |
| 56 | C | D | C | D |
| 57 | B | C | C | D |
| 58 | A | B | B | C |
| 59 | A | B | B | C |
| 60 | A | B | B | C |
| 61 | C | D | C | D |
| 62 | C | D | D | D |
| 63 | C | D | D | D |
| 64 | B | C | B | C |
| 65 | B | B | B | C |
| 66 | B | C | C | D |
| 67 | B | D | C | D |
| 68 | C | D | D | D |
| 69 | A | C | B | D |
| 70 | A | B | B | C |
| 71 | A | C | B | D |
| 72 | B | D | C | D |
| 73 | A | C | B | D |
| 74 | A | C | C | D |
| 75 | C | D | D | D |
| 76 | B | C | C | D |
| 77 | A | C | B | D |
| 78 | B | C | C | D |
| 79 | B | D | C | D |
| 80 | A | C | B | D |
| 81 | B | C | C | D |
| 82 | B | D | C | D |
| 83 | B | D | C | D |
| 84 | A | C | B | D |
| 85 | B | C | C | D |
| 86 | B | C | C | D |
| 87 | B | D | C | D |
| 88 | C | D | C | D |
| 89 | C | D | D | D |
| 90 | A | C | B | C |
| 91 | B | C | C | D |
| 92 | A | C | B | D |
| 93 | A | C | C | D |
| 94 | B | D | C | D |
| 95 | A | B | B | D |
| 96 | A | A | A | C |
| 97 | A | C | B | D |
| 98 | A | C | B | D |
| 99 | B | C | C | D |
| 100 | A | C | B | D |
| 101 | A | A | A | C |
| 102 | B | C | C | D |
| 103 | A | B | B | C |
| 104 | A | C | B | D |
| 105 | A | C | B | D |
| 106 | C | D | C | D |
| 107 | C | D | D | D |
| 108 | B | D | C | D |
| 109 | B | D | C | D |
| 110 | A | B | B | C |
| 111 | B | C | C | C |
| 112 | A | B | B | C |
| 113 | A | B | B | C |
| 114 | A | C | B | C |
| 115 | A | A | A | C |
| 116 | B | C | C | D |
| 117 | A | B | B | C |
| 118 | A | B | B | C |
| 119 | B | B | B | C |
| 120 | A | B | B | D |
| 121 | A | C | B | D |
| 122 | C | D | D | D |
| 123 | C | D | D | D |
| 124 | C | D | D | D |
| 125 | C | C | D | D |
| 126 | A | B | B | C |
| 127 | B | C | C | D |
| 128 | A | C | B | D |
| 129 | C | D | D | D |
| 130 | C | D | C | D |
| 131 | B | D | C | D |
| 132 | B | D | C | C |
| 133 | A | B | B | C |
| 134 | C | D | C | D |
| 135 | B | C | B | C |
| 136 | A | B | B | D |
| 137 | A | B | B | C |
| 138 | A | B | B | C |
| 139 | A | B | B | D |
| 140 | A | B | B | D |
| 141 | B | D | C | D |
| 142 | B | D | D | D |
| 143 | A | C | B | D |
| 144 | B | D | C | D |
| 145 | A | C | B | D |
| 146 | A | B | C | D |
| 147 | A | B | B | C |
| 148 | A | C | B | D |
| 149 | C | D | D | D |
| 150 | A | C | B | D |
| 151 | A | C | B | C |
| 152 | A | C | B | C |
| 153 | A | C | B | C |
| 154 | A | B | A | C |
| 155 | A | B | B | C |
| 156 | A | C | B | D |
| 157 | B | C | B | D |
| 158 | A | A | B | C |
| 159 | A | B | B | D |
| 160 | A | C | B | C |
| 161 | A | C | B | D |
| 162 | A | C | B | C |

Preparation A

3-Methylbut-2-enenitrile

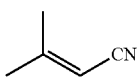

NaH (1.634 g, 40.86 mmol) was suspended in THF (100 mL) and cooled to 0° C. Diethyl cyanomethylphosphonate (6.856 mL, 43.58 mmol) was added drop-wise while maintaining the temperature below 5° C. The reaction mixture was stirred at 0° C. for 1 hour and then propan-2-one (2.000 mL, 27.24 mmol) added slowly. The reaction mixture was heated at reflux for 5 hours and then cooled to ambient temperature. The reaction mixture was partitioned between saturated aqueous NH₄Cl and EtOAc. The organics were washed with brine, dried, MgSO₄ and concentrated under reduced pressure to afford the crude material. The crude product was purified by flash column chromatography (eluant: 100% DCM) to furnish 3-methylbut-2-enenitrile (0.755 g, 9.31 mmol). $^1$H NMR (CDCl$_3$) δ 5.13-5.09 (m, 1H), 2.06 (s, 3H), 1.93 (s, 3H).

Preparation B

3-Cyclopropylacrylonitrile

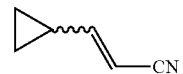

Diethyl cyanomethylphosphonate (1.914 mL, 11.92 mmol) and cyclopropanecarbaldehyde (1.000 ml, 13.12 mmol) were suspended in THF (20 mL) and cooled to 0° C. KOtBu (1.605 g, 14.31 mmol) was added in portion-wise (reaction became hot). The reaction mixture became very thick and hard to stir. The reaction mixture was stirred at ambient temperature overnight. The reaction mixture was partitioned between saturated aqueous NH₄Cl and EtOAc. The organic layer was washed with saturated aqueous NaHCO₃, water and brine, dried over MgSO₄ and concentrated under reduced pressure to afford the crude 3-cyclopropylacrylonitrile (1.055 g, 11.33 mmol, 95.02% yield) as a mixture of cis and trans isomers, which was used without further purification. $^1$H NMR (CDCl$_3$) (about a 1:1 ratio of E/Z) δ 6.13 (dd, 1H), 5.79 (t, 1H), 5.35 (d, 1H), 5.17 (d, 1H), 2.06-1.96 (m, 1H), 1.64-1.53 (m, 1H), 1.11-1.04 (m, 2H), 1.04-0.97 (m, 2H), 0.70-0.63 (m, 4H).

The compounds of Table 1 were prepared according to the method of Preparation B using the appropriate starting materials.

TABLE 1

| Compound | Structure | Name | Data |
|---|---|---|---|
| a | MeO-pyridine-CH=CH-CN | 3-(5-methoxy-pyridin-3-yl)acrylonitrile | MS(apci) m/z = 161.1 (M + H) |
| b | pyridin-4-yl-CH=CH-CN | 3-(pyridin-4-yl)acrylonitrile | $^1$H NMR (CDCl$_3$) (about a 4:1 ratio of E/Z) δ 8.76-8.73 (m, 0.5H), 8.72-8.68 (m, 2H), 7.64-7.61 (m, 0.5H), 7.36 (d, 1H), 7.33-7.28 (m, 2H), 7.12 (d, 0.25H), 6.09 (d, 1H), 5.70 (d, 0.25H). |
| c | pyridin-2-yl-CH=CH-CN | 3-(pyridin-2-yl)acrylonitrile | $^1$H NMR (CDCl$_3$) (about a 5:1 ratio of E/Z) δ 8.76-8.72 (m, 0.2H), 8.66-8.61 (m, 1H), 7.86-7.82 (m, 0.2H), 7.82-7.77 (m, 0.2H), 7.77-7.71 (m, 1H), 7.40 (d, 1H), 7.35-7.29 (m, 2.2H), 7.25 (d, 0.2H) 6.60 (d, 1H), 5.67 (d, 0.2H). |
| d | tBu-CH=CH-CN | 4,4-dimethylpent-2-enenitrile | $^1$H NMR (CDCl$_3$) (about a 1.7:1 ratio of E/Z) δ 6.72 (d, 0.6H), 6.35 (d, 1H), 5.23 (d, 0.6H), 5.22 (d, 1H), 1.25 (s, 9H), 1.08 (s, 5.3H). |
| e | Br-pyridine-CH=CH-CN | 3-(5-bromo-pyridin-3-yl)acrylonitrile | $^1$H NMR (CDCl$_3$) (ca. 5:1 ratio of E/Z) δ 8.76-8.69 (m, 1.4H), 8.60 (d, 1H), 8.44 (t, 0.2H), 7.92 (t, 1H), 7.35 (d, 1H), 7.10 (d, 0.2H), 5.99 (d, 1H), 5.67 (d, 0.2H). |

TABLE 1-continued

| Compound | Name | Data |
|---|---|---|
| f | 3-(3-chlorophenyl)acrylonitrile | $^1$H NMR (CDCl$_3$) (about a 4.4:1 ratio of E/Z) δ 7.77-7.75 (m, 0.23H), 1.12-7.69 (m, 0.23H), 7.46-7.30 (m, 5.5H), 7.08 (d, 0.23H), 5.89 (d, 1H), 5.52 (d, 0.23H). |
| g | 3-cyclopentylacrylonitrile | $^1$H NMR (CDCl$_3$) (about a 2:1 ratio of E/Z) δ 6.74-6.65 (m, 0.5H), 6.37 (t, 1H), 5.29 (dd, 0.5H), 5.21 (t, 1H), 3.09-2.96 (m, 1H), 2.65-2.53 (m, 0.5H), 1.99-1.80 (m, 3H), 1.78-1.56 (m, 6H), 1.44-1.29 (m, 3H). |
| h | 3-(3-(trifluoromethyl)phenyl)acrylonitrile | $^1$H NMR (CDCl$_3$) (about a 5:1 ratio of E/Z) δ 8.12 (d, 0.2H), 7.91 (s, 0.2H), 7.74-7.52 (m, 5H), 7.44 (d, 1H), 7.18 (d, 0.2H), 5.98 (d, 1H), 5.59 (d, 0.2H). |
| i | 3-phenylbut-2-enenitrile | $^1$H NMR (CDCl$_3$) E-major signals δ 7.49-7.37 (m, 5H), 5.62 (s, 1H), 2.47 (s, 3H) |
| J | 3-cyclobutylacrylonitrile | $^1$H NMR (CDCl$_3$) (about a 1:1 ratio of E/Z) δ 6.81 (dd, 1H), 6.55 (dd, 1H), 5.31-5.12 (m, 2H), 3.49 (m, 1H), 3.09 (m, 1H), 2.37-2.13 (m, 4H), 2.07-1.80 (m, 8H) |
| k | 5,5-dimethylhex-2-enenitrile | $^1$H NMR (CDCl$_3$) (about a 1:1 ratio of E/Z) δ 6.77-6.70 (m, 1H), 6.59-6.52 (m, 1H), 5.40 (d, 1H), 5.32 (d, 1H), 2.33 (d, 2H), 2.11 (d, 2H), 0.98 (s, 9H), 0.94 (s, 9H) |
| l | tert-butyl 4-(2-cyanovinyl)piperidine-1-carboxylate | MS(apci) m/z = 137.1 (M + H-Boc). |
| m | tert-butyl 4-(cyanomethylene)piperidine-1-carboxylate | MS(apci) m/z = 123.1 (M + H-Boc). |
| n | 2-cyclohexylideneacetonitrile | $^1$H NMR (CDCl$_3$) δ 5.04 (s, 1H), 2.49 (m, 2H), 2.25 (m, 2H), 1.58-1.71 (m, 6H). |
| o | 2-cyclopentylideneacetonitrile | $^1$H NMR (CDCl$_3$) δ 5.23 (m, 1H), 2.60 (m, 2H), 2.46 (m, 2H), 1.74-1.84 (m, 4H). |
| p | 2-(oxetan-3-ylidene)acetonitrile | $^1$H NMR (CDCl$_3$) δ 5.39 (m, 2H), 5.30 (m, 2H), 5.25 (m, 1H). |

Preparation C

1-(tetrahydro-2H-pyran-4-yl)-4-(4,4,5,5-tetramethyl-1,3,2-dioxaborolan-2-yl)-1H-pyrazole

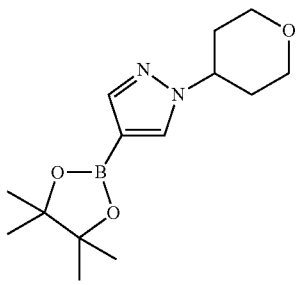 [SMILES: CC1(C)OB(c2cnn(C3CCOCC3)c2)OC1(C)C]

Step A: Preparation of tetrahydro-2H-pyran-4-yl methanesulfonate

To a solution of tetrahydro-2H-pyran-4-ol (2.5 g, 24.5 mmol) in DCM (40 mL) was added DIEA (6.40 mL, 36.7 mmol) at 0° C. and allowed to stir under nitrogen for 10 minutes. Methane sulfonyl chloride (2.18 mL, 28.1 mmol) was added slowly. The reaction was allowed to proceed for 1 hour at 0° C. The reaction was partitioned between 100 mL of DCM and 50 mL of 0.5 M hydrochloric acid. The layers were separated and the organic layer was then washed sequentially with water, saturated sodium bicarbonate, and brine. The organic layer was dried over MgSO$_4$, filtered, and concentrated under reduced pressure and dried on high vacuum to afford tetrahydro-2H-pyran-4-yl methanesulfonate (4.4 g, 24.4 mmol, 99.7% yield).

Step B: Preparation of 1-(tetrahydro-2H-pyran-4-yl)-4-(4,4,5,5-tetramethyl-1,3,2-dioxaborolan-2-yl)-1H-pyrazole In 8 mL of N,N-dimethylformamide were combined 4-(4,4,5,5-tetramethyl-1,3,2-dioxaborolan-2-yl)-1H-pyrazole (0.75 g, 3.87 mmol), tetrahydro-2H-pyran-4-yl methanesulfonate (1.04 g, 5.80 mmol), and Cs$_2$CO$_3$ (2.01 g, 6.18 mmol) in a glass bomb and then sealed under nitrogen and heated to 100° C. After one hour the reaction was cooled and water was added to dissolve all solids. The solution was diluted with water and then extracted with EtOAc (250 mL). The organic layer was then washed with water and brine. The combined aqueous layer was then extracted with EtOAc (200 mL). The organic layers were combined, dried over MgSO$_4$, filtered, and concentrated under reduced pressure. The crude material was dried overnight on high vacuum. The crude was purified by way of silica gel chromatography eluting with a gradient of 15-25% EtOAc in DCM to afford 1-(tetrahydro-2H-pyran-4-yl)-4-(4,4,5,5-tetramethyl-1,3,2-dioxaborolan-2-yl)-1H-pyrazole (0.176 g, 0.633 mmol, 16.4% yield). MS (apci) m/z=279.2 (M+H).

The compounds of Table 2 were prepared according to the method of Preparation C using the appropriate starting materials.

TABLE 2

| Compound | Structure | Name | Data |
| --- | --- | --- | --- |
| a | 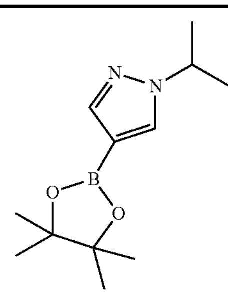 | 1-isopropyl-4-(4,4,5,5-tetramethyl-1,3,2-dioxaborolan-2-yl)-1H-pyrazole | MS(apci) m/z = 237.2 (M + H) |
| b | 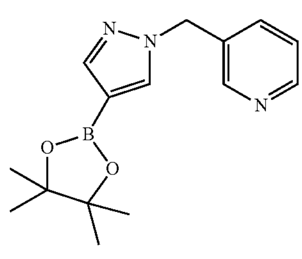 [SMILES: CC1(C)OB(c2cnn(Cc3cccnc3)c2)OC1(C)C] | 3-((4-(4,4,5,5-tetramethyl-1,3,2-dioxaborolan-2-yl)-1H-pyrazol-1-yl)methyl)pyridine | MS(apci) m/z = 286.2 (M + H) |
| c | 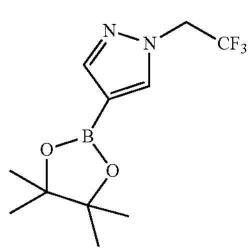 [SMILES: CC1(C)OB(c2cnn(CC(F)(F)F)c2)OC1(C)C] | 4-(4,4,5,5-tetramethyl-1,3,2-dioxaborolan-2-yl)-1-(2,2,2-trifluoroethyl)-1H-pyrazole | MS(apci) m/z = 277.1 (M + H) |

TABLE 2-continued

| Compound | Structure | Name | Data |
|---|---|---|---|
| d | 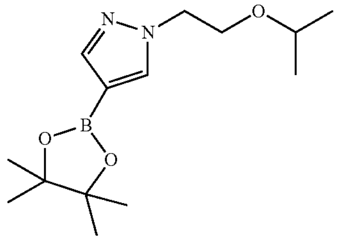 [SMILES: CC(C)OCCn1cc(B2OC(C)(C)C(C)(C)O2)cn1] | 1-(2-isopropoxyethyl)-4-(4,4,5,5-tetramethyl-1,3,2-dioxaborolan-2-yl)-1H-pyrazole | MS(apci) m/z = 281.2 (M + H) |
| e | 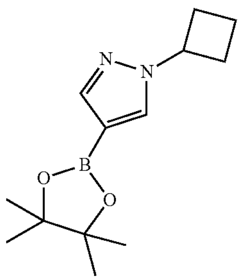 [SMILES: CC1(C)OB(c2cnn(C3CCC3)c2)OC1(C)C] | 1-cyclobutyl-4-(4,4,5,5-tetramethyl-1,3,2-dioxaborolan-2-yl)-1H-pyrazole | MS(apci) m/z = 249.2 (M + H) |
| f | 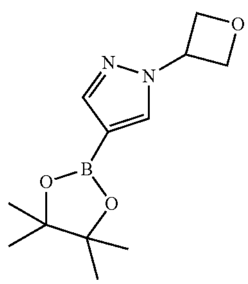 [SMILES: CC1(C)OB(c2cnn(C3COC3)c2)OC1(C)C] | 1-(oxetan-3-yl)-4-(4,4,5,5-tetramethyl-1,3,2-dioxaborolan-2-yl)-1H-pyrazole | MS(apci) m/z = 251.2 (M + H) |

Preparation D 1-(2-(4-methylpiperazin-1-yl)ethyl)-1H-pyrazol-4-ylboronic acid

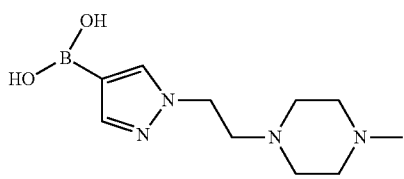 [SMILES: CN1CCN(CCn2cc(B(O)O)cn2)CC1]

Step A: Preparation of 2-(4-(4,4,5,5-tetramethyl-1,3,2-dioxaborolan-2-yl)-1H-pyrazol-1-yl)ethanol To a flask charged with 4-(4,4,5,5-tetramethyl-1,3,2-dioxaborolan-2-yl)-1H-pyrazole (1.000 g, 5.154 mmol), $Cs_2CO_3$ (2.687 g, 8.246 mmol), and 2-bromoethanol (0.5479 mL, 7.730 mmol) was added 10 mL of DMF and the flask was sealed under nitrogen and heated to 100° C. for 48 hours. The reaction was diluted with ethyl acetate (100 mL) and stirred for 30 minutes before it was passed through a glass microfiber filter and the cake was washed with ethyl acetate. The organic was concentrated under reduced pressure. The crude was then purified by silica gel chromatography eluting with a gradient of 75-100% ethyl acetate in Hexanes to afford 2-(4-(4,4,5,5-tetramethyl-1,3,2-dioxaborolan-2-yl)-1H-pyrazol-1-yl)ethanol (0.4290 g, 1.622 mmol, 31.47% yield). MS (apci) m/z=239.2 (M+H).

Step B: Preparation of 2-(4-(4,4,5,5-tetramethyl-1,3,2-dioxaborolan-2-yl)-1H-pyrazol-1-yl)ethyl methanesulfonate To a solution of 2-(4-(4,4,5,5-tetramethyl-1,3,2-dioxaborolan-2-yl)-1H-pyrazol-1-yl)ethanol (0.150 g, 0.630 mmol) and TEA (0.132 mL, 0.945 mmol) in 5 mL of DCM was added methansulfonyl chloride (0.0536 mL, 0.693 mmol) with stirring at 0° C. The reaction was allowed to proceed at 0° C. for 30 minutes. The reaction was loaded directly onto a silica gel column pre-pre-wetted with and eluted with 50% ethyl acetate in hexanes to afford 2-(4-(4,4,5,5-tetramethyl-1,3,2-dioxaborolan-2-yl)-1H-pyrazol-1-yl)ethyl methanesulfonate (0.169 g, 0.513 mmol, 81.4% yield) MS (apci) m/z=317.1 (M+H).

Step C: Preparation of 1-(2-(4-methylpiperazin-1-yl)ethyl)-1H-pyrazol-4-ylboronic acid To a solution of 2-(4-(4,4,5,5-tetramethyl-1,3,2-dioxaborolan-2-yl)-1H-pyrazol-1-yl)ethyl methanesulfonate (0.080 g, 0.253 mmol) in 0.5 mL N,N-dimethylformamide was added 1-methylpiperazine (0.281 mL, 2.53 mmol) and the reaction was sealed under nitrogen and heated to 50° C. for 2.5 hours. The reaction mixture was diluted with dichloromethane (3 mL) and then loaded directly onto a silica gel column pre-wetted and eluted with 15% methanol in dichloromethane containing 1% ammonium hydroxide to afford 1-(2-(4-methylpiperazin-1-yl)ethyl)-1H-pyrazol-4-ylboronic acid (0.038 g, 0.160 mmol, 63% yield) as a result of hydrolysis on silica in the presence of methanol and ammonium hydroxide. MS (apci) m/z=239.1 (M+H).

Preparation E 4-(4,4,5,5-tetramethyl-1,3,2-dioxaborolan-2-yl)-1-((2-(trimethylsilyl)ethoxy)methyl)-1H-pyrazole

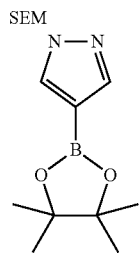

A solution of 4-(4,4,5,5-tetramethyl-1,3,2-dioxaborolan-2-yl)-1H-pyrazole (10.00 g, 51.54 mmol) in DMF (100 mL) was cooled to 0° C. in an ice bath and treated with sodium hydride (60% dispersion in oil) (3.092 g, 77.30 mmol) in one portion. The reaction mixture was stirred at 0° C. for 2 minutes, then at ambient temperature for 30 minutes. The reaction mixture was cooled to 0° C. and (2-(chloromethoxy)ethyl)trimethylsilane (11.82 mL, 67.00 mmol) was added. The reaction mixture was warmed to ambient temperature and allowed to stir overnight. The reaction mixture was poured into aqueous saturated ammonium chloride (100 mL) containing ice (approximately 100 mL) and stirred until the ice melted. After the ice melted, the cold mixture was extracted with ethyl acetate. The combined organic extracts were washed with water, brine, dried over MgSO₄, and concentrated under reduced pressure to afford the title compound (14.45 g, 44.56 mmol, 86.46% yield). MS (apci) m/z=325.0 (M+H).

Preparation F

Tert-butyl 3-(cyanomethyl)-3-(4-(4,4,5,5-tetramethyl-1,3,2-dioxaborolan-2-yl)-1H-pyrazol-1-yl)azetidine-1-carboxylate

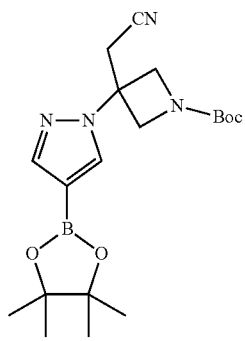 [SMILES: CC(C)(C)OC(=O)N1CC(CC#N)(n2cc(B3OC(C)(C)C(C)(C)O3)cn2)C1]

Step A: Preparation of tert-butyl 3-(cyanomethylene)azetidine-1-carboxylate

In a 5 L flask, a suspension of NaH (24.531 g, 613.34 mmol) in 500 mL of THF was cooled in an ice bath. A solution of diethyl cyanomethylphosphonate (104.08 mL, 648.39 mmol) in THF (200 mL) was added dropwise. After addition, another 120 mL of THF was added to aid stirring. The reaction was warmed to ambient temperature for 1 hour then cooled back to 0° C. for 1 hour to give a milky yellow solution. Then a solution of tert-butyl 3-oxoazetidine-1-carboxylate (100.00 g, 584.13 mmol) in THF (400 mL) was added dropwise over an hour. The resultant reaction mixture was stirred for 15 hours, then quenched with water and concentrated to remove THF. The resultant aqueous solution was extracted with EtOAc. The combined organic layers were washed with brine and dried with MgSO₄. The filtrate was concentrated down to a yellow oil, which precipitated out a yellow solid after sitting overnight. This solid was diluted in cold EtOAc, sonicated, filtered and washed with cold EtOAc and hexanes to afford 82.09 g of a cream colored solid (80%). Additional product was isolated by concentrating the filtrate in vacuo and purifying by silica chromatography using a gradient of 20-30% EtOAc/Hexanes to afford an additional 18.6 g (18%) of tert-butyl 3-(cyanomethylene)azetidine-1-carboxylate. $^1$H NMR (CDCl₃) δ 5.38 (m, 1H), 4.69-4.72 (m, 2H), 4.60-4.63 (m, 2H), 1.46 (s, 9H).

Step B: Preparation of tert-butyl 3-(cyanomethyl)-3-(4-(4,4,5,5-tetramethyl-1,3,2-dioxaborolan-2-yl)-1H-pyrazol-1-yl)azetidine-1-carboxylate In a 5 L flask, tert-butyl 3-(cyanomethylene)azetidine-1-carboxylate (Preparation F, Step A; 94.2 g, 485 mmol) and 4-(4,4,5,5-tetramethyl-1,3,2-dioxaborolan-2-yl)-1H-pyrazole (85.6 g, 441 mmol) were dissolved in acetonitrile (882 mL). To this was then added DBU (33.0 mL, 220 mmol). The resulting clear orange brown mixture was stirred at ambient temperature for 15 hours. The reaction mixture was concentrated down to remove solvents and afforded a dark reddish-orange oil. Solid crystals formed within a few hours at ambient temperature. This was isolated by washing with cold Et₂O and cold EtOAc (carefully to prevent dissolution) to afford 110 g (64% yield) of the title compound. The recrystallization was repeated to give another 13.7 g (8% yield). Additional compound was isolated by purification of the filtrate from the above recrystallization. This was purified by silica chromatography eluting with a 20-50% EtOAc/Hexanes gradient to afford an additional 22.7 g (13%) of the title compound. MS (apci) m/z=289.2 (M+H-Boc).

Preparation G 7-chloro-5-(1-((2-(trimethylsilyl)ethoxy)methyl)-1H-pyrazol-4-yl)imidazo[1,2-c]pyrimidine

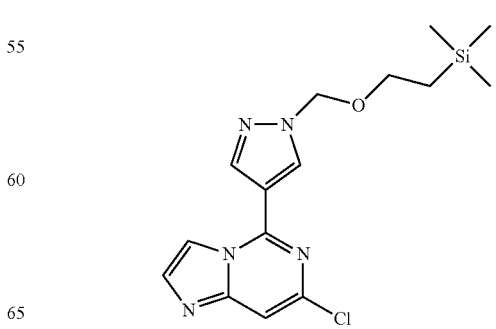

Step A: Preparation of 6-chloro-2-(1-((2-(trimethyl-silyl)ethoxy)methyl)-1H-pyrazol-4-yl)pyrimidin-4-amine A flask was charged with 2,6-dichloropyrimidin-4-amine (10.0 g, 61.0 mmol), 4-(4,4,5,5-tetramethyl-1,3,2-dioxaborolan-2-yl)-1-((2-(trimethylsilyl)ethoxy)methyl)-1H-pyrazole (Preparation E; 29.7 g, 91.5 mmol), and $K_2CO_3$ (25.3 g, 183 mmol) in dioxane (40 mL) before 300 mL of dioxane and 11 mL of water were added to the reaction mixture. The reaction mixture was then purged with argon for 30 minutes before tetrakis(triphenylphosphine)palladium (0) (3.52 g, 3.05 mmol) was added in one portion to the reaction which was then purged with argon for another 30 minutes. The reaction mixture was then sealed and heated at 50° C. overnight. The reaction mixture was cooled to ambient temperature and partitioned between ethyl acetate (300 mL) and aqueous saturated sodium bicarbonate (300 mL). The aqueous layer was then extracted with ethyl acetate twice more and separated. The organic layers were combined, dried over $MgSO_4$, filtered, and concentrated under reduced pressure. The resulting residue was purified by silica gel column chromatography eluting with 20-100% ethyl acetate in hexanes to afford 6-chloro-2-(1-((2-(trimethylsilyl)ethoxy)methyl)-1H-pyrazol-4-yl)pyrimidin-4-amine (5.00 g, 15.3 mmol, 25.2% yield). MS (apci) m/z=326.1 (M+H). Structure and regioisomer confirmed by observed nOe.

Step B: Preparation of 7-chloro-5-(1-((2(trimethylsilyl)ethoxy)methyl)-1H-pyrazol-4-yl)imidazo[1,2-c]pyrimidine To a solution of 6-chloro-2-(1-((2-(trimethylsilyl)ethoxy)methyl)-1H-pyrazol-4-yl)pyrimidin-4-amine (2.750 g, 8.439 mmol) in 60 mL of 1:1 absolute ethanol: pH=7 phosphate buffer were added sodium acetate (1.385 g, 16.88 mmol) and 2-chloroacetaldehyde (1.905 mL, 14.77 mmol) and the reaction mixture was then fitted with a condenser and heated to 95° C. overnight. The reaction was not complete so sodium acetate (1.385 g, 16.88 mmol) and 2-chloroacetaldehyde (1.905 mL, 14.77 mmol) were added and the reaction mixture was heated to 95° C. for four hours. After this time the reaction was allowed to cool to ambient temperature and was then diluted with aqueous saturated sodium bicarbonate (50 mL) and extracted with ethyl acetate. The organic layers were combined, dried over $MgSO_4$, filtered, and concentrated under reduced pressure. The resulting residue was purified by silica gel chromatography eluting with 30-45% ethyl acetate in hexanes (1 L) to afford the title compound (1.16 g, 3.315 mmol, 39.29% yield). MS (apci) m/z=350.1 (M+H).

Preparation H

7-Chloroimidazo[1,2-c]pyrimidin-5(6H)-one

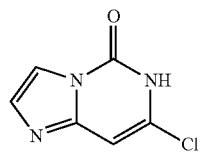 [SMILES: O=c1[nH]c(Cl)cc2nccn12]

Step A: Preparation of 7-chloro-5-(methylthio)imidazo[1,2-c]pyrimidine hydrochloride A solution of 6-chloro-2-(methylthio)pyrimidin-4-amine (25.17 g, 143.3 mmol) and 2-chloroacetaldehyde (27.73 mL, 215.0 mmol) (50% aqueous) in 1,4-dioxane (50 mL) was heated at 95° C. for 14 hours. The reaction mixture was allowed to cool to ambient temperature and then cooled in an ice bath. The reaction mixture was filtered and the solids washed with dioxane to afford 7-chloro-5-(methylthio)imidazo[1,2-c]pyrimidine hydrochloride (24.01 g, 101.7 mmol, 70.96% yield) as a tan powder. MS (apci) m/z=200.0 (M+H).

Step B: Preparation of 7-Chloroimidazo[1,2-c]pyrimidin-5(6H)-one

7-Chloro-5-(methylthio)imidazo[1,2-c]pyrimidine hydrochloride (10.5 g, 44.5 mmol) was partially dissolved in MeOH (40 mL) and then a solution of potassium hydroxide (11.2 g, 200 mmol) in water (100 mL) was slowly added and the reaction was heated to reflux. The reaction generates methane thiol, so caution was taken to contain this noxious gas in the hood. After 2 hours the reaction was cooled and then neutralized with a solution of 1N HCl to reach a pH of between 6 and 7. The reaction was filtered and the solid was washed with MeOH. The solids were dried on the filter cake and then dried on a high vacuum pump to provide 7-chloroimidazo[1,2-c]pyrimidin-5(6H)-one (6.6 g, 87% yield) as a white solid. MS (apci) m/z=170.1 (M+H).

Preparation I 7-(1-methyl-1H-pyrazol-4-yl)imidazo[1,2-c]pyrimidin-5(6H)-one

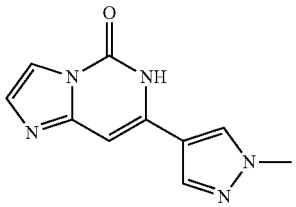 [SMILES: Cn1cc(-c2cc3nccn3c(=O)[nH]2)cn1]

To a mixture of 7-chloroimidazo[1,2-c]pyrimidin-5(6H)-one (Preparation H, 10.0 g, 59.0 mmol), 1-methyl-4-(4,4,5,5-tetramethyl-1,3,2-dioxaborolan-2-yl)-1H-pyrazole (19.0 g, 88.5 mmol) and XPHOS (2.81 g, 5.90 mmol) in isopropyl alcohol (400 mL) was added 2M $K_3PO_4$ (88.5 mL, 177 mmol). The mixture was purged with $N_2$ for 15 minutes with vigorous mixing and $Pd_2dba_3$ (2.70 g, 2.95 mmol) was added. The mixture was heated at reflux under a $N_2$ atmosphere for 20 hours. The mixture was charged additional 1-methyl-4-(4,4,5,5-tetramethyl-1,3,2-dioxaborolan-2-yl)-1H-pyrazole (6.00 g) and $Pd_2dba_3$ (1.00 g) and heated at reflux for an additional 20 hours. The mixture was cooled to ambient temperature and concentrated to an aqueous syrup. The syrup was partitioned into $H_2O$ (500 mL) and 50% EtOAc-hexanes (250 mL) and mixed. The mixture was filtered through filter paper and the orange organic layer was removed. The aqueous layer was washed with 50% EtOAc/hexanes and was cooled on an ice bath. The solution was treated with concentrated HCl to pH 6 with stirring and the resulting fine precipitate was collected, washed with $H_2O$ and $Et_2O$ and dried under vacuum to provide the title compound (9.65 g, 76% yield) as faint grey solid. MS (apci) m/z=216.2 (M+H).

Preparation J 5-chloro-7-(1-methyl-1H-pyrazol-4-yl)imidazo[1,2-c]pyrimidine

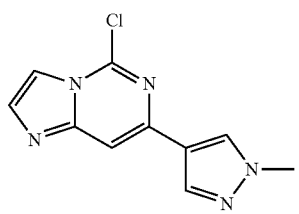 [SMILES: Cn1cc(-c2cc3nccn3c(Cl)n2)cn1]

To a suspension of 7-(1-methyl-1H-pyrazol-4-yl)imidazo[1,2-c]pyrimidin-5(6H)-one (Preparation I; 9.60 g, 44.6 mmol) in dry DCM (90 mL) was added DIEA and the suspension stirred at ambient temperature for 5 minutes. The mixture was cooled to 0° C. and POCl$_3$ (12.3 mL, 134 mmol) was added over 5 minutes. The mixture was allowed to reach ambient temperature and the resulting thick slurry was treated with dry DCM (50 mL). The mixture was vigorously stirred at ambient temperature for 23 hours. The resulting light tan suspension was diluted with hexanes (90 mL) and collected by vacuum filtration. The collected solid was washed with Et$_2$O and dried in vacuum to give the crude product salt. The salt was suspended in 5:20:75 MeOH/DIEA/EtOAc (200 mL) and stirred for 30 minutes at ambient temperature. The mixture was filtered through a SiO$_2$ plug capped with a Celite layer eluting with 5% MeOH/EtOAc. The filtrate was concentrated and the residual solid dried in vacuum to provide the title compound (5.65 g, 54% yield) as a light cream colored solid. MS (apci) m/z=234.2 (M+H).

Preparation K-1

7-(1-methyl-1H-pyrazol-4-yl)-5-(1H-pyrazol-4-yl)imidazo[1,2-c]pyrimidine (Method 1)

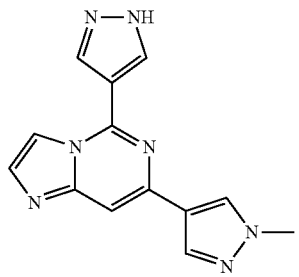 [SMILES: Cn1cc(-c2cc3nccn3c(-c3cn[nH]c3)n2)cn1]

To a mixture of 5-chloro-7-(1-methyl-1H-pyrazol-4-yl)imidazo[1,2-c]pyrimidine (Preparation J, 132 mg, 0.565 mmol) and 4-(4,4,5,5-tetramethyl-1,3,2-dioxaborolan-2-yl)-1H-pyrazole (164 mg, 0.847 mmol) in DME (4 mL) was added 1M K$_2$CO$_3$ (1.69 mL, 1.69 mmol) and the resulting solution was purged with N$_2$ for 15 minutes. Pd(PPh$_3$)$_4$ (65.3 mg, 0.0565 mmol) was added, the flask sealed, and the mixture stirred at 90° C. for 15 hours. The reaction mixture was cooled to ambient temperature and diluted with H$_2$O (10 mL). The aqueous mixture was extracted with EtOAc, the extracts were combined and diluted with hexanes (1 vol). After standing for 15 minutes, the resulting precipitate was collected by vacuum filtration and washed with 50% EtOAc-hexanes to afford desired product. The EtOAc filtrate was extracted with 1M NaOH and the extracts were combined with the previous aqueous portion. The aqueous mixture was treated with 6M HCl to pH 4 then with NaCl to saturation. The mixture was extracted with DCM and the combined extracts were dried over Na$_2$SO$_4$, filtered through a Celite pad and concentrated. The residual product was combined with the previous batch and dried in vacuum to provide the title compound (133 mg, 89% yield) as a light yellow solid. MS (apci) m/z=266.2 (M+H).

Preparation K-2

7-(1-methyl-1H-pyrazol-4-yl)-5-(1H-pyrazol-4-yl)imidazo[1,2-c]pyrimidine hydrochloride (Method 2)

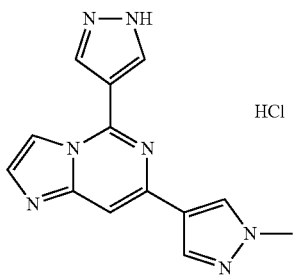 [SMILES: Cn1cc(-c2cc3nccn3c(-c3cn[nH]c3)n2)cn1 ; Cl]

Step A: Preparation of 6-chloro-2-(1-((2-(trimethylsilyl)ethoxy)methyl)-1H-pyrazol-4-yl)pyrimidin-4-amine and 2-chloro-6-(1-((2-(trimethylsilyl)ethoxy)methyl)-1H-pyrazol-4-yl)pyrimidin-4-amine 2,6-Dichloropyrimidin-4-amine (4.00 g, 24.4 mmol), 4-(4,4,5,5-tetramethyl-1,3,2-dioxaborolan-2-yl)-1-((2-(trimethylsilyl)ethoxy)methyl)-1H-pyrazole (Preparation E; 14.0 g, 36.6 mmol) and K$_3$PO$_4$ (15.5 g, 73.2 mmol) were suspended in dioxane (120 mL, 24.4 mmol) and H$_2$O (4.39 mL, 244 mmol). After degassing under nitrogen, Pd(PPh$_3$)$_4$ (1.41 g, 1.22 mmol) was added and the reaction sealed and stirred at 50° C. for 15 hours. After cooling, the reaction mixture was partitioned between saturated aqueous NaHCO$_3$ and EtOAc. The organics were washed with water, brine, dried with MgSO$_4$, filtered and concentrated under reduced pressure to afford the crude material as a thick yellow orange oil. The crude mixture was purified by silica chromatography using a 20-100% EtOAc/Hexanes gradient to afford 6-chloro-2-(1-((2-(trimethylsilyl)ethoxy)methyl)-1H-pyrazol-4-yl)pyrimidin-4-amine (4.00 g, 50.3%) and 2-chloro-6-(1-((2-(trimethylsilyl)ethoxy)methyl)-1H-pyrazol-4-yl)pyrimidin-4-amine (2.96 g, 37.2% yield). MS (apci) m/z=326.1 (M+H). The structure and regioisomer of products were confirmed by observed nOe.

Step B: Preparation of 6-(1-methyl-1H-pyrazol-4-yl)-2-(1-((2-(trimethylsilyl)ethoxy)-methyl)-1H-pyrazol-4-yl)pyrimidin-4-amine 6-Chloro-2-(1-((2-(trimethylsilyl)ethoxy)methyl)-1H-pyrazol-4-yl)pyrimidin-4-amine (1.00 g, 3.07 mmol), 1-methyl-4-(4,4,5,5-tetramethyl-1,3,2-dioxaborolan-2-yl)-1H-pyrazole (0.958 g, 4.60 mmol), K$_3$PO$_4$ (1.95 g, 9.21 mmol), and Pd(PPh$_3$)$_4$ (0.355 g, 0.307 mmol) were suspended in dioxane (15.3 mL) and H$_2$O (0.829 mL). After de-gassing with nitrogen, the reaction mixture was heated to 100° C. overnight. After cooling, the reaction mixture was diluted in EtOAc and washed with water and brine. The organics were dried with MgSO$_4$, filtered and concentrated down to an orange oil. Purification of the resulting crude material by silica chromatography using a gradient of 0-10% MeOH/EtOAc afforded 6-(1-methyl-1H-pyrazol-4-yl)-2-(1-((2-(trimethylsilyl)ethoxy)methyl)-1H-pyrazol-4-yl)pyrimidin-4-amine (0.623 g, 1.68 mmol, 54.7% yield) as a thick yellow oil. MS (apci) m/z=372.4 (M+H).

Step C: Preparation of 7-(1-methyl-1H-pyrazol-4-yl)-5-(1-((2-(trimethylsilyl)ethoxy)-methyl)-1H-pyrazol-4-yl)imidazo[1,2-c]pyrimidine 6-(1-methyl-1H-pyrazol-4-yl)-2-(1-((2-(trimethylsilyl)ethoxy)methyl)-1H-pyrazol-4-yl)pyrimidin-4-amine (2.0 g, 5.4 mmol) was suspended in a mixture of 40 mL of pH 7 phosphate buffer and 16 mL of EtOH. To the milky white mixture was added NaOAc (0.79 g, 9.7 mmol) followed by 2-chloroacetaldehyde (1.0 mL, 8.1 mmol). The reaction mixture was then heated to 95° C. After 5 hours, the reaction was incomplete and another portion of 2-chloroacetaldehyde (0.10 mL, 0.81 mmol) was added and stirred for another 1 hour. After cooling, the reaction mixture was diluted in EtOAc and saturated NaHCO$_3$. After separation, the organic layer was washed with brine, dried with MgSO$_4$, filtered and concentrated in vacuo. The residue was diluted in diethyl ether, sonicated, and filtered to afford 0.88 g of 7-(1-methyl-1H-pyrazol-4-yl)-5-(1-((2-(trimethylsilyl)ethoxy)-methyl)-1H-pyrazol-4-yl)imidazo[1,2-c]pyrimidine as an off-white solid. Additional product was obtained by concentration of the filtrate and purification by silica chromatography using 0-10% MeOH/EtOAc. This afforded another 0.80 g of the intermediate. MS (apci) m/z=396.2 (M+H).

Step D: Preparation of 7-(1-methyl-1H-pyrazol-4-yl)-5-(1H-pyrazol-4-yl)imidazo[1,2-c]pyrimidine hydrochloride 7-(1-Methyl-1H-pyrazol-4-yl)-5-(1-((2-(trimethylsilyl)ethoxy)methyl)-1H-pyrazol-4-yl)imidazo[1,2-c]pyrimidine (75 mg, 0.19 mmol) was dissolved in DCM (950 µL, 0.19 mmol). To this was added 4N HCl in dioxane (950 µL, 0.95 mmol) and stirred at ambient temperature for 1 hour, and the mixture was concentrated down to dryness to provide the title compound. MS (apci) m/z=266.2 (M+H).

Preparation L 7-(4-bromophenyl)-5-(1-((2-(trimethylsilyl)ethoxy)methyl)-1H-pyrazol-4-yl)imidazo[1,2-c]pyrimidine

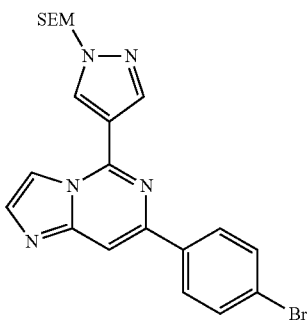 [SMILES: C[Si](C)(C)CCOCn1cc(-c2nc(-c3ccc(Br)cc3)cc3nccn23)cn1]

Step A: Preparation of 3-amino-3-(4-bromophenyl)acrylonitrile

An oven dried flask was charged with 300 mL of tetrahydrofuran and diisopropylamine (31.4 mL, 223 mmol) and cooled to 0° C. under nitrogen. To the reaction mixture was then added butyl lithium (2.5 M in hexanes) (79.1 mL, 198 mmol) slowly by syringe over 10 minutes. The reaction mixture was then allowed to stir at 0° C. for 20 minutes. The reaction mixture was then cooled to −78° C. and acetonitrile (10.8 mL, 206 mmol) was added slowly over 5 minutes. The reaction mixture was allowed to stir for 10 minutes before 4-bromobenzonitrile (30.0 g, 165 mmol) was added as a solution in 100 mL of tetrahydrofuran over 10 minutes. The reaction mixture was allowed to proceed at −78° C. for an additional 10 minutes before being allowed to slowly warm to ambient temperature and proceed overnight. The reaction mixture was cooled to 0° C. and 200 mL of water was slowly added. The reaction mixture was stirred for 10 minutes and the solids were collected by means of vacuum filtration and dried under high vacuum. The solids were suspended in dichloromethane and the resulting solids were collected by means of vacuum filtration to obtain 3-amino-3-(4-bromophenyl)acrylonitrile (34.2 g, 153 mmol, 93.0% yield). MS (apci) m/z=222.0 (M−H).

Step B: Preparation of 6-amino-4-(4-bromophenyl)pyrimidine-2(1H)-thione

To a flask charged with 600 mL of absolute ethanol was dissolved sodium (14.86 g, 646.5 mmol) with a catalytic amount of copper(II)sulfate (10 mg). The reaction volume was reduced by half under reduced pressure and thiourea (49.22 g, 646.5 mmol) and 3-amino-3-(4-bromophenyl)acrylonitrile (38.46 g, 172.4 mmol) were added at ambient temperature and the reaction mixture was fitted with a condenser and heated to reflux over the weekend. Water (400 mL) was added and the mixture was made acidic with concentrated aqueous hydrochloric acid to a pH=7. The reaction mixture was allowed to stir for 5 minutes and the resulting solids were collected by means of vacuum filtration and afforded 6-amino-4-(4-bromophenyl)pyrimidine-2(1H)-thione (53.90 g, 191.0 mmol, 110.8% yield). MS (apci) m/z=282.0 (M+H).

Step C: Preparation of 6-(4-bromophenyl)-2-(ethylthio)pyrimidin-4-amine

To a solution of 4-amino-6-(4-bromophenyl)pyrimidine-2 (1H)-thione (53.90 g, 191.0 mmol) and iodoethane (16.96 mL, 210.1 mmol) in 200 mL of DMSO was slowly added 200 mL of aqueous saturated sodium bicarbonate at ambient temperature with stirring. The reaction was allowed to stir for 1 hour before iodoethane (8.0 mL, 99.1 mmol) was added. The reaction mixture was stirred at ambient temperature overnight. The reaction mixture was poured into 500 mL of water and stirred for 20 minutes. The solid was collected by means of vacuum filtration and was dried under high vacuum overnight to afford 6-(4-bromophenyl)-2-(ethylthio)pyrimidin-4-amine (51.0 g, 156.2 mmol, 81.76% yield). MS (apci) m/z=310.0 (M+H).

Step D: Preparation of 7-(4-bromophenyl)-5-(ethylthio)imidazo[1,2-c]pyrimidine

To a slurry of 6-(4-bromophenyl)-2-(ethylthio)pyrimidin-4-amine (35.00 g, 112.8 mmol) in 20 mL of THF and 200 mL of water was added 2-bromo-1,1-dimethoxyethane (38.14 g, 225.7 mmol) at ambient temperature. The reaction flask was fitted with a condenser and the mixture was allowed to proceed with stirring at reflux overnight. After 24 hours, the reaction mixture was cooled and poured into 400 mL of water. The solid was collected by vacuum filtration. The wet solid was suspended in 500 mL of aqueous saturated sodium bicarbonate and gas evolution was observed. The mixture was stirred at ambient temperature for 10 minutes before it was extracted with DCM (8×500 mL). The organic layers were combined, dried over MgSO$_4$, filtered, and concentrated under reduced pressure. The crude was then dried under high vacuum overnight to afford 7-(4-bromophenyl)-5-(ethylthio) imidazo[1,2-c]pyrimidine (31 g, 87.18 mmol, 77.27% yield). MS (apci) m/z=334.0 (M+H).

Step E: Preparation of
7-(4-bromophenyl)imidazo[1,2-c]pyrimidin-5(6H)-one

To a flask charged with 7-(4-bromophenyl)-5-(ethylthio) imidazo[1,2-c]pyrimidine (62.34 g, 186.5 mmol), methanol (250 mL), and potassium hydroxide (52.32 g, 932.6 mmol) was added water (250 mL) and the reaction was fitted with a condenser and heated to reflux for 4 hours. The reaction mixture was diluted with water (500 mL) and acidified with concentrated hydrochloric acid to a pH=5. The solids were collected by vacuum filtration and then washed with water (3×500 mL) and the cake was dried. The semi dry solids were placed in a vacuum desiccator under high vacuum for two days to afford 7-(4-bromophenyl)imidazo[1,2-c]pyrimidin-5 (6H)-one (51.25 g, 176.7 mmol, 94.71% yield). MS (apci) m/z=290.0 (M+H).

Step F: Preparation of
7-(4-bromophenyl)-5-chloroimidazo[1,2-c]pyrimidine

To a flask charged with 7-(4-bromophenyl)imidazo[1,2-c] pyrimidin-5(6H)-one (25.00 g, 86.173 mmol), phosphoryl trichloride (31.554 mL, 344.69 mmol), and N,N-diethylaniline (27.420 mL, 172.35 mmol) was added acetonitrile (200 mL) and the mixture was heated to 50° C. overnight. The reaction mixture was concentrated under reduced pressure and the residue diluted with water and DCM. The aqueous was neutralized with potassium carbonate and the bi-phasic mixture passed through a pad of celite to remove the insoluble material. The layers were separated and the aqueous extracted with DCM. The combined organic layers were dried over MgSO$_4$ and concentrated under reduced pressure. The crude material was triturated with hexanes and the solids were collected by filtration to afford 7-(4-bromophenyl)-5-chloroimidazo[1,2-c]pyrimidine (10.369 g, 33.604 mmol, 38.997% yield). MS (apci) m/z=310.0 (M+H).

Step G: Preparation of 7-(4-bromophenyl)-5-(1-((2-(trimethylsilyl)ethoxy)methyl)-1H-pyrazol-4-yl) imidazo[1,2-c]pyrimidine To a flask charged with 7-(4-bromophenyl)-5-chloroimidazo[1,2-c]pyrimidine (2.68 g, 8.685 mmol), potassium carbonate (3.601 g, 26.06 mmol), and 4-(4,4,5,5-tetramethyl-1,3,2-dioxaborolan-2-yl)-1-((2-(trimethylsilyl)ethoxy) methyl)-1H-pyrazole (Preparation E; 6.628 g, 17.37 mmol) were combined in a glass bomb and the vessel was evacuated and backfilled with argon. To the reaction was added 100 mL of DME and then water (1.252 mL, 69.48 mmol) and argon was bubbled through the reaction for 20 minutes before tetrakis(triphenylphosphine)palladium (0) (1.004 g, 0.8685 mmol) was added in one portion. The reaction was fitted with a septum and argon was bubbled through for 10 minutes before the reaction was sealed and heated to 70° C. for 4 hours 4-(4,4,5,5-Tetramethyl-1,3,2-dioxaborolan-2-yl)-1-((2-(trimethylsilyl)ethoxy)methyl)-1H-pyrazole (Preparation E; 3.3 g, 8.6 mmol) was added. Argon was bubbled through for 10 minutes before the reaction was sealed and heated to 70° C. for 3 hours. The reaction was diluted with 10% methanol in DCM (300 mL), dried with MgSO$_4$, filtered, and then concentration under reduced pressure. The resultant crude was purified by silica gel chromatography eluting with a gradient of 30-75% ethyl acetate in hexanes to afford the title compound (1.625 g, 3.454 mmol, 39.77% yield). MS (apci) m/z=470.1 (M+H).

Preparation M 3-(4-(7-Chloroimidazo[1,2-c]pyrimidin-5-yl)-1H-pyrazol-1-yl)-3-cyclopropylpropanenitrile

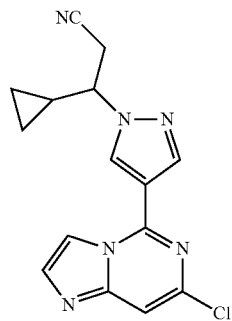 [SMILES: N#CCC(C1CC1)n1cc(-c2nc(Cl)cc3nccn23)cn1]

Step A: Preparation of 7-chloro-5-(1H-pyrazol-4-yl) imidazo[1,2-c]pyrimidine

To a solution of 7-chloro-5-(1-((2-(trimethylsilyl)ethoxy) methyl)-1H-pyrazol-4-yl)imidazo[1,2-c]pyrimidine (Preparation G; 0.250 g, 0.715 mmol) in 3.5 mL of DCM was added 2,2,2,-trifluoroacetic acid (2.2 mL, 28.6 mmol) and allowed to stir at ambient temperature for 1 hour before the reaction mixture was diluted with 5 mL of toluene and then concentrated under reduced pressure. The resulting residue was dissolved in 2 mL of 7M ammonia in methanol and stirred at ambient temperature for 30 minutes. The reaction mixture was concentrated under reduced pressure and the resulting residue was purified by silica gel chromatography eluting with a gradient of 2-5% methanol in DCM with 1% ammonium hydroxide to afford 7-chloro-5-(1H-pyrazol-4-yl)imidazo[1,2-c]pyrimidine (0.107 g, 0.468 mmol, 65.5% yield). MS (apci) m/z=220.1 (M+H).

Step B: Preparation of 3-(4-(7-chloroimidazo[1,2-c] pyrimidin-5-yl)-1H-pyrazol-1-yl)-3-cyclopropylpropanenitrile To a solution of 7-chloro-5-(1H-pyrazol-4-yl)imidazo[1,2-c]pyrimidine (0.107 g, 0.4872 mmol) and 3-cyclopropylacrylonitrile (Preparation B; 0.3403 g, 3.654 mmol) in 2 mL of acetonitrile was added DBU (0.1457 mL, 0.9744 mmol). The reaction mixture was sealed and heated to 50° C. and stirred overnight. To the reaction mixture was added more 3-cyclopropylacrylonitrile (0.100 g, 0.107 mmol) and DBU (0.072 mL, 0.448 mmol) and the reaction mixture was sealed and heated to 60° C. for 4 hours. The reaction mixture was loaded onto directly onto a column of silica gel and eluted with a gradient of 50-75% ethyl acetate in hexanes with 0.5% ammonium hydroxide to afford the title compound (0.119 g, 0.3729 mmol, 76.54% yield). MS (apci) m/z=313.1 (M+H).

Preparation N tert-Butyl 3-(4-(7-chloroimidazo[1,2-c]pyrimidin-5-yl)-1H-pyrazol-1-yl)-3-(cyanomethyl)azetidine-1-carboxylate

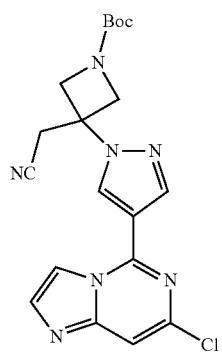 [SMILES: CC(C)(C)OC(=O)N1CC(CC#N)(n2cc(-c3nc(Cl)cc4nccn34)cn2)C1]

Prepared in the same manner as Preparation M replacing 3-cyclopropylacrylonitrile with tert-butyl 3-(cyanomethylene)azetidine-1-carboxylate (Preparation F, Step A) to obtain the title compound (0.050 g, 0.1208 mmol, 71.71% yield). MS (apci) m/z=414.1 (M+H).

Preparation O

Tert-butyl 3-(cyanomethyl)-3-(3-(7-(1-methyl-1H-pyrazol-4-yl)imidazo[1,2-c]pyrimidin-5-yl)-1H-pyrrol-1-yl)azetidine-1-carboxylate

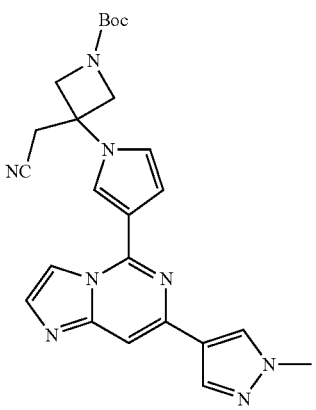 [SMILES: Cn1cc(-c2cc3nccn3c(-c3ccn(C4(CC#N)CN(C(=O)OC(C)(C)C)C4)c3)n2)cn1]

Step A: Preparation of 7-(1-methyl-1H-pyrazol-4-yl)-5-(1H-pyrrol-3-yl)imidazo[1,2-c]pyrimidine To a flask charged with 5-chloro-7-(1-methyl-1H-pyrazol-4-yl)imidazo[1,2-c]pyrimidine (Preparation J; 0.150 g, 0.642 mmol), 1-(triisopropylsilyl)-1H-pyrrol-3-ylboronic acid (0.257 g, 0.963 mmol), and potassium phosphate (0.321 mL, 0.642 mmol) was added 6 mL of dioxane and argon was bubbled through the mixture for 15 minutes. Tetrakis(triphenylphosphine)palladium (0) (0.0742 g, 0.0642 mmol) was added and argon was bubbled through the reaction for 15 minutes. The flask was sealed under argon and the mixture was heated at 75° C. with stirring overnight. The reaction was then concentrated under reduced pressure and then taken up in DCM (5 mL). A precipitate was formed and collected by means of vacuum filtration and washed with DCM (10 mL). The solid contained product without the triisopropylsilyl protection as well as inorganic salts. Further purification was not attempted and so was obtained 7-(1-methyl-1H-pyrazol-4-yl)-5-(1H-pyrrol-3-yl)imidazo[1,2-c]pyrimidine (0.220 g, 0.832 mmol, 130% yield). MS (apci) m/z=265.1 (M+H).

Step B: Preparation of tert-butyl 3-(cyanomethyl)-3-(3-(7-(1-methyl-1H-pyrazol-4-yl)imidazo[1,2-c]pyrimidin-5-yl)-1H-pyrrol-1-yl)azetidine-1-carboxylate To a flask charged with 7-(1-methyl-1H-pyrazol-4-yl)-5-(1H-pyrrol-3-yl)imidazo[1,2-c]pyrimidine (0.0500 g, 0.189 mmol), tert-butyl 3-(cyanomethylene)azetidine-1-carboxylate (Preparation F, Step A; 0.0459 g, 0.237 mmol), and DBU (0.0283 mL, 0.189 mmol) was added 1 mL of acetonitrile at ambient temperature. The suspension was then stirred and heated to 50° C. overnight. The reaction was loaded directly onto silica gel and eluted with a mixture of ethyl acetate and 0.5% ammonium hydroxide to afford the title compound (0.0860 g, 0.188 mmol, 99.14% yield) in high purity. MS (apci) m/z=459.2 (M+H).

Preparation P 3-cyclopropyl-3-(4-(4,4,5,5-tetramethyl-1,3,2-dioxaborolan-2-yl)-1H-pyrazol-1-yl)propanenitrile

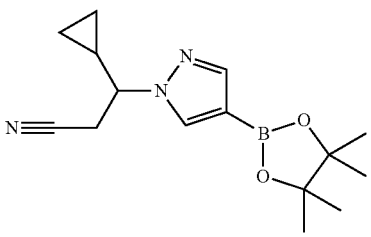 [SMILES: CC1(C)OB(c2cnn(C(CC#N)C3CC3)c2)OC1(C)C]

4-(4,4,5,5-Tetramethyl-1,3,2-dioxaborolan-2-yl)-1H-pyrazole (2.44 g, 12.6 mmol), 3-cyclopropylacrylonitrile (Preparation B; 2.34 g, 25.1 mmol) (as a mixture of isomers) and DBU (1.88 mL, 12.6 mmol) were suspended in MeCN (10 mL) and stirred at 40° C. for 3 days. The reaction mixture was cooled to ambient temperature and concentrated under reduced pressure to afford the crude material, which was purified by flash column chromatography (eluant: 25-35% EtOAc/Hexanes) to furnish 3-cyclopropyl-3-(4-(4,4,5,5-tetramethyl-1,3,2-dioxaborolan-2-yl)-1H-pyrazol-1-yl)propanenitrile (2.48 g, 8.64 mmol, 68.8% yield). MS (apci) m/z=288.2 (M+H).

Example 1

3-(4-(7-(1-methyl-1H-pyrazol-4-yl)imidazo[1,2-c]pyrimidin-5-yl)-1H-pyrazol-1-yl)pentanedinitrile

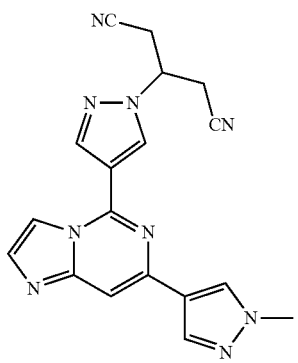 [SMILES: Cn1cc(-c2cc3nccn3c(-c3cnn(C(CC#N)CC#N)c3)n2)cn1]

Step A: Preparation of dimethyl 3-(4-(7-(1-methyl-1H-pyrazol-4-yl)imidazo[1,2-c]pyrimidin-5-yl)-1H-pyrazol-1-yl)pentanedioate 7-(1-Methyl-1H-pyrazol-4-yl)-5-(1H-pyrazol-4-yl)imidazo[1,2-c]pyrimidine (Preparation K; 0.165 g, 0.622 mmol) was suspended in CH$_3$CN (5 mL) and (E)-dimethyl pent-2-enedioate (0.295 g, 1.87 mmol) was added followed by DBU (0.0947 g, 0.622 mmol). The reaction was warmed to 55° C. and heated for 9 hours. The reaction was then cooled and concentrated. The residue was purified on silica gel (1-4% methanol in DCM) to afford dimethyl 3-(4-(7-(1-methyl-1H-pyrazol-4-yl)imidazo[1,2-c]pyrimidin-5-yl)-1H-pyrazol-1-yl)pentanedioate (205 mg, 78% yield). MS (apci) m/z=424.2 (M+H).

Step B: Preparation of 3-(4-(7-(1-methyl-1H-pyrazol-4-yl)imidazo[1,2-c]pyrimidin-5-yl)-1H-pyrazol-1-yl)pentanedioic acid Lithium hydroxide hydrate (0.0813 g, 1.94 mmol) was dissolved in water (2 mL) and was added to a solution of dimethyl 3-(4-(7-(1-methyl-1H-pyrazol-4-yl)imidazo[1,2-c]pyrimidin-5-yl)-1H-pyrazol-1-yl)pentanedioate (0.205 g, 0.484 mmol) in MeOH (4 mL). After stirring 3 days the reaction was concentrated to remove the MeOH and was then acidified to pH 4 with 1 N HCl (approximately 2 mL). Cooling resulted in a solid which was filtered and washed with MeOH. The filtrate was slightly concentrated to provide a second crop of product which was combined to provide 3-(4-(7-(1-methyl-1H-pyrazol-4-yl)imidazo[1,2-c]pyrimidin-5-yl)-1H-pyrazol-1-yl)pentanedioic acid (125 mg, 65% yield). MS (apci) m/z=396.2 (M+H).

Step C: Preparation of 3-(4-(7-(1-methyl-1H-pyrazol-4-yl)imidazo[1,2-c]pyrimidin-5-yl)-1H-pyrazol-1-yl)pentanediamide 3-(4-(7-(1-Methyl-1H-pyrazol-4-yl)imidazo[1,2-c]pyrimidin-5-yl)-1H-pyrazol-1-yl)pentanedioic acid (60 mg, 0.15 mmol) was dissolved in DMF (1 mL) and cooled to 0° C. Carbonyldiimidazole (69 mg, 0.42 mmol) was added and after 5 minutes, the reaction was warmed to ambient temperature. After stirring 2 hours NH$_3$ gas was bubbled for about 10 minutes. Approximately 2 mL of CH$_3$CN was added to the reaction to rinse the sides of the flask and the reaction was stirred for an additional 14 hours. The reaction was then diluted with water (11 mL) and washed with EtOAc (3×15 mL). The aqueous phase was concentrated and azeotroped with MeOH to provide the desired product 3-(4-(7-(1-methyl-1H-pyrazol-4-yl)imidazo[1,2-c]pyrimidin-5-yl)-1H-pyrazol-1-yl)pentanediamide (60 mg, 101% yield) which was used in the next step without further purification. MS (apci) m/z=394.1 (M+H).

Step D: Preparation of 3-(4-(7-(1-methyl-1H-pyrazol-4-yl)imidazo[1,2-c]pyrimidin-5-yl)-1H-pyrazol-1-yl)pentanedinitrile 3-(4-(7-(1-Methyl-1H-pyrazol-4-yl)imidazo[1,2-c]pyrimidin-5-yl)-1H-pyrazol-1-yl)pentanediamide (0.047 g, 0.12 mmol) was partially dissolved in DMF (0.3 mL) and DCM (0.5 mL) and triethylamine (0.08 g, 0.79 mmol) was added. 2,2,2-trichloroacetyl chloride (0.08 g, 0.44 mmol) was added at 0° C., and the reaction was stirred for 1 hour. Additional reagents (40 mg Et$_3$N and 30 mg acid chloride) were added and the reaction was complete. The reaction was concentrated and pumped to dryness. A minimum amount of water was added (1.5 mL) to dissolve the crude product. Excess sodium chloride was added to the aqueous layer and this mixture was extracted with EtOAc (10×10 mL) to recover the desired product. The organic phase was dried using MgSO$_4$ and concentrated to provide 3-(4-(7-(1-methyl-1H-pyrazol-4-yl)imidazo[1,2-c]pyrimidin-5-yl)-1H-pyrazol-1-yl)pentanedinitrile (42 mg, 98% yield). MS (apci) m/z=358.1 (M+H). $^1$H NMR (d$_6$-DMSO) δ 9.12 (s, 1H), 8.59 (s, 1H), 8.41 (s, 1H), 8.25 (s, 1H), 8.17 (s, 1H), 7.78 (s, 1H), 7.76 (s, 1H), 5.30-5.29 (m, 1H), 3.91 (s, 3H), 1.22-1.10 (m, 4H).

Example 2

3-Cyclopropyl-3-(4-(7-(1-methyl-1H-pyrazol-4-yl)imidazo[1,2-c]pyrimidin-5-yl)-1H-pyrazol-1-yl)propanenitrile

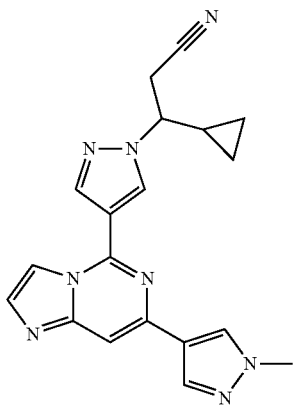 [SMILES: Cn1cc(-c2cc3nccn3c(-c3cnn(C(CC#N)C4CC4)c3)n2)cn1]

To a solution of 7-(1-methyl-1H-pyrazol-4-yl)-5-(1H-pyrazol-4-yl)imidazo[1,2-c]pyrimidine (Preparation; K-1; 0.130 g, 0.490 mmol) in dry DMF (2 mL) was added DBU (89.5 mg, 0.588 mmol) and 3-cyclopropylacrylonitrile (Preparation B; 0.183 g, 1.96 mmol). The reaction mixture was stirred at ambient temperature for 24 hours. Additional 3-cyclopropylacrylonitrile (0.046 g, 0.49 mmol) was added and the reaction mixture was stirred at ambient temperature for 72 hours. The reaction mixture was added to H$_2$O (8 mL), mixed and extracted with EtOAc. The combined EtOAc extracts were washed with saturated NaCl and dried over MgSO$_4$/activated carbon. The solution was eluted through a short SiO$_2$ column (15 mL course frit funnel, ½ full of SiO$_2$) eluting first with EtOAc, then with 10% MeOH/EtOAc. The 10% MeOH/EtOAc fraction was concentrated and the resulting residue treated with Et$_2$O and sonicated to give a granular suspension. The precipitate was allowed to settle, Et$_2$O decanted off, solid washed with Et$_2$O and then dried under vacuum to provide a 3-cyclopropyl-3-(4-(7-(1-methyl-1H-pyrazol-4-yl)imidazo[1,2-c]pyrimidin-5-yl)-1H-pyrazol-1-yl)propanenitrile (40 mg, 23% yield) as a white powder. MS (apci) m/z=359.2 (M+H).

Example 3

Enantiomer 1 of 3-cyclopropyl-3-(4-(7-(1-methyl-1H-pyrazol-4-yl)imidazo[1,2-c]pyrimidin-5-yl)-1H-pyrazol-1-yl)propanenitrile (Peak 1)

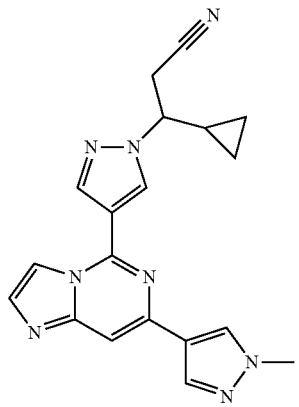 [SMILES: Cn1cc(-c2cc3nccn3c(-c3cnn(C(CC#N)C4CC4)c3)n2)cn1]

3-Cyclopropyl-3-(4-(7-(1-methyl-1H-pyrazol-4-yl)imidazo[1,2-c]pyrimidin-5-yl)-1H-pyrazol-1-yl)propanenitrile (Example 2; 0.010 g, 0.028 mmol) was separated by chiral HPLC (Chiral Tech. OD-H; 1 cm×250 mm; 220 nm, 5 mL/min; 20% Ethanol:80% Hexanes). Peak 1 was isolated to afford Enantiomer 1 of 3-cyclopropyl-3-(4-(7-(1-methyl-1H-pyrazol-4-yl)imidazo[1,2-c]pyrimidin-5-yl)-1H-pyrazol-1-yl)propanenitrile (3.0 mg, 30% yield) peak 1. MS (apci) m/z=359.2 (M+H). [α]20/D=+56.5° in chloroform (10 mg/mL).

Example 4

Enantiomer 2 of 3-cyclopropyl-3-(4-(7-(1-methyl-1H-pyrazol-4-yl)imidazo[1,2-c]pyrimidin-5-yl)-1H-pyrazol-1-yl)propanenitrile (Peak 2)

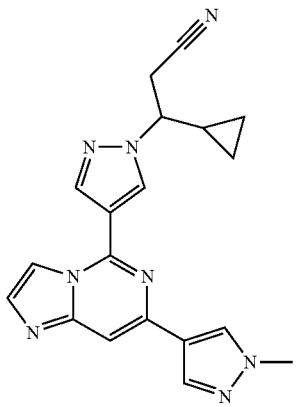 [SMILES: Cn1cc(-c2cc3nccn3c(-c3cnn(C(CC#N)C4CC4)c3)n2)cn1]

3-Cyclopropyl-3-(4-(7-(1-methyl-1H-pyrazol-4-yl)imidazo[1,2-c]pyrimidin-5-yl)-1H-pyrazol-1-yl)propanenitrile (Example 2; 0.010 g, 0.028 mmol) was separated by chiral HPLC (Chiral Tech. OD-H; 1 cm×250 mm; 220 nm, 5 mL/min; 20% Ethanol:80% Hexanes). Peak 2 was isolated to afford Enantiomer 2 of 3-cyclopropyl-3-(4-(7-(1-methyl-1H-pyrazol-4-yl)imidazo[1,2-c]pyrimidin-5-yl)-1H-pyrazol-1-yl)propanenitrile (2.5 mg, 25% yield). MS (apci) m/z=359.2 (M+H). [α]20/D=−58.5° in chloroform (10 mg/mL).

Example 5

3-(4-(7-(1-methyl-1H-pyrazol-4-yl)imidazo[1,2-c]pyrimidin-5-yl)-1H-pyrazol-1-yl)pentanedinitrile

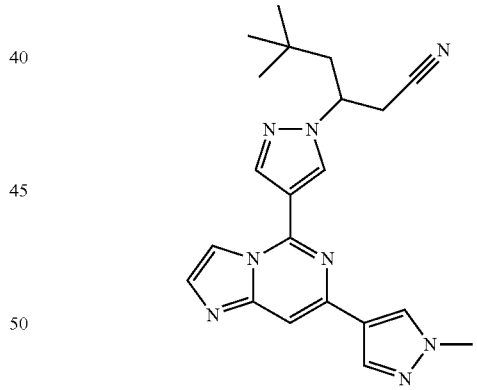

7-(1-Methyl-1H-pyrazol-4-yl)-5-(1H-pyrazol-4-yl)imidazo[1,2-c]pyrimidine (Preparation K; 0.040 mg, 0.15 mmol) was dissolved in dimethylformamide (0.6 mL) and 5,5-dimethylhex-2-enenitrile (Table 1, compound k; 56 mg, 0.045 mmol) and 2,3,4,6,7,8,9,10-octahydropyrimido[1,2-a]azepine (34 mg, 0.23 mmol) were added and the reaction was heated at 50° C. for 7 hours. The reaction was then cooled and the solvent was removed. The crude reaction was purified by silica gel chromatography using a gradient (1 to 4% MeOH/DCM) to provide 3-(4-(7-(1-methyl-1H-pyrazol-4-yl)imidazo[1,2-c]pyrimidin-5-yl)-1H-pyrazol-1-yl)pentanedinitrile (37 mg, 63% yield) as a solid. MS (apci) m/z=389.2 (M+H).

The compounds of Table 3 were prepared according to the method of Example 5 using the appropriate starting materials.

TABLE 3

| Ex. # | Structure | Name | MS |
|---|---|---|---|
| 6 | 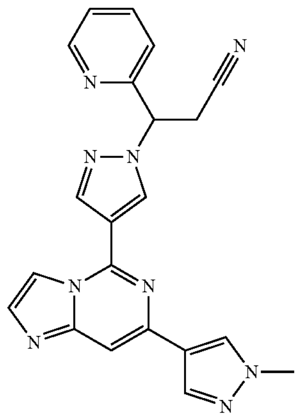 | 3-(4-(7-(1-methyl-1H-pyrazol-4-yl)imidazo[1,2-c]pyrimidin-5-yl)-1H-pyrazol-1-yl)-3-(pyridin-2-yl)propanenitrile | (apci) m/z = 396.1 (M + H) |
| 7 | 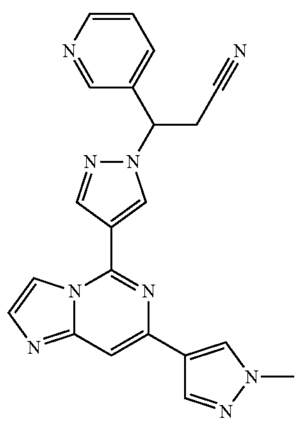 | 3-(4-(7-(1-methyl-1H-pyrazol-4-yl)imidazo[1,2-c]pyrimidin-5-yl)-1H-pyrazol-1-yl)-3-(pyridin-3-yl)propanenitrile | (apci) m/z = 396.2 (M + H) |
| 8 | 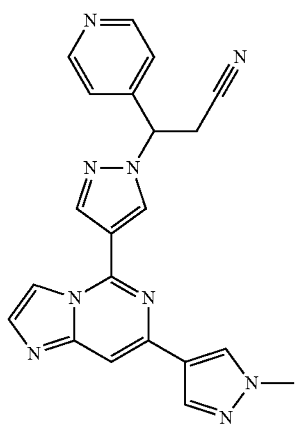 [SMILES: Cn1cc(-c2cc3nccn3c(-c3cnn(C(CC#N)c4ccncc4)c3)n2)cn1] | 3-(4-(7-(1-methyl-1H-pyrazol-4-yl)imidazo[1,2-c]pyrimidin-5-yl)-1H-pyrazol-1-yl)-3-(pyridin-4-yl)propanenitrile | (apci) m/z = 396.1 (M + H) |

TABLE 3-continued

| Ex. # | Structure | Name | MS |
|---|---|---|---|
| 9 | 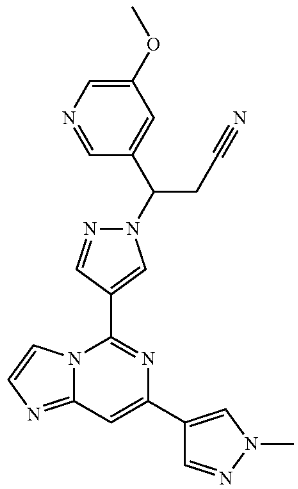 [SMILES: COc1cncc(C(CC#N)n2cc(-c3nc(-c4cnn(C)c4)cc4nccn34)cn2)c1] | 3-(5-methoxypyridin-3-yl)-3-(4-(7-(1-methyl-1H-pyrazol-4-yl)imidazo[1,2-c]pyrimidin-5-yl)-1H-pyrazol-1-yl)propanenitrile | (apci) m/z = 426.1 (M + H) |
| 10 | 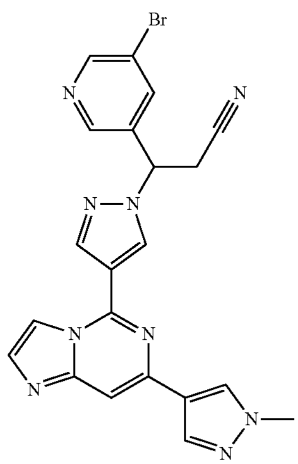 [SMILES: Cn1cc(-c2cc3nccn3c(-c3cnn(C(CC#N)c4cncc(Br)c4)c3)n2)cn1] | 3-(5-bromopyridin-3-yl)-3-(4-(7-(1-methyl-1H-pyrazol-4-yl)imidazo[1,2-c]pyrimidin-5-yl)-1H-pyrazol-1-yl)propanenitrile | (apci) m/z = 474/476 (M + H) |
| 11 | 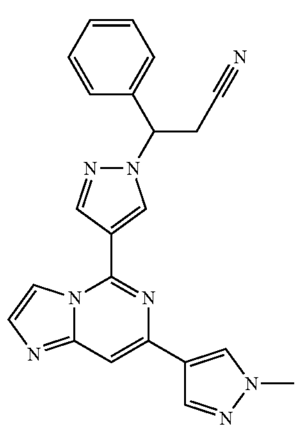 [SMILES: Cn1cc(-c2cc3nccn3c(-c3cnn(C(CC#N)c4ccccc4)c3)n2)cn1] | 3-(4-(7-(1-methyl-1H-pyrazol-4-yl)imidazo[1,2-c]pyrimidin-5-yl)-1H-pyrazol-1-yl)-3-phenylpropanenitrile | (apci) m/z = 395.1 (M + H) |

TABLE 3-continued

| Ex. # | Structure | Name | MS |
|---|---|---|---|
| 12 | 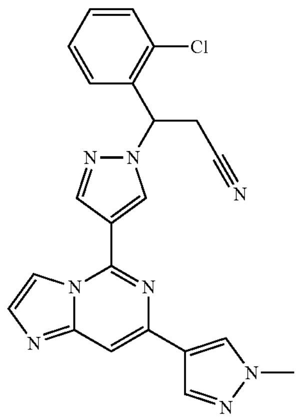 [SMILES: Cn1cc(-c2cc3nccn3c(-c3cnn(C(CC#N)c4ccccc4Cl)c3)n2)cn1] | 3-(2-chlorophenyl)-3-(4-(7-(1-methyl-1H-pyrazol-4-yl)imidazo[1,2-c]pyrimidin-5-yl)-1H-pyrazol-1-yl)propanenitrile | (apci) m/z = 429.1 (M + H) |
| 13 | 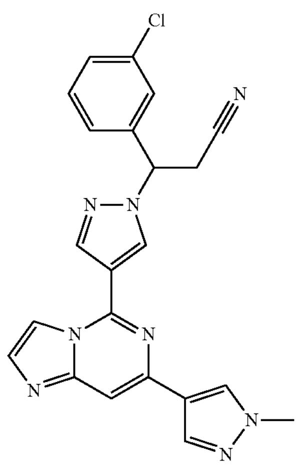 | 3-(3-chlorophenyl)-3-(4-(7-(1-methyl-1H-pyrazol-4-yl)imidazo[1,2-c]pyrimidin-5-yl)-1H-pyrazol-1-yl)propanenitrile | (apci) m/z = 429.1 (M + H) |
| 14 | 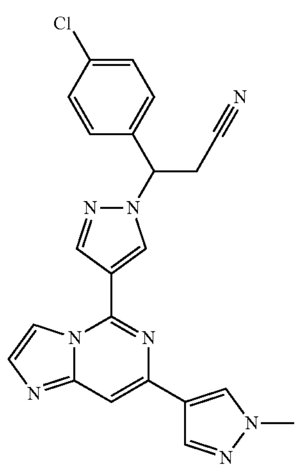 | 3-(4-chlorophenyl)-3-(4-(7-(1-methyl-1H-pyrazol-4-yl)imidazo[1,2-c]pyrimidin-5-yl)-1H-pyrazol-1-yl)propanenitrile | (apci) m/z = 429.1 (M + H) |

TABLE 3-continued
| Ex. # | Structure | Name | MS |
|---|---|---|---|
| 15 | 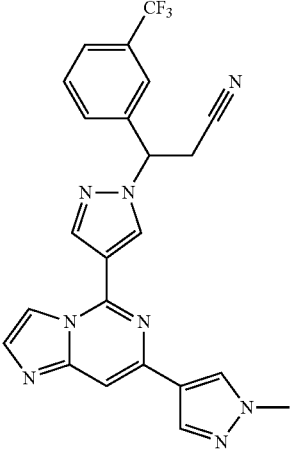 [SMILES: Cn1cc(-c2cc3nccn3c(-c3cnn(C(CC#N)c4cccc(Cl)c4)c3)n2)cn1] | 3-(4-(7-(1-methyl-1H-pyrazol-4-yl)imidazo[1,2-c]pyrimidin-5-yl)-1H-pyrazol-1-yl)-3-(3-(trifluoromethyl)phenyl)propanenitrile | (apci) m/z = 463.1 (M + H) |
| 16 | 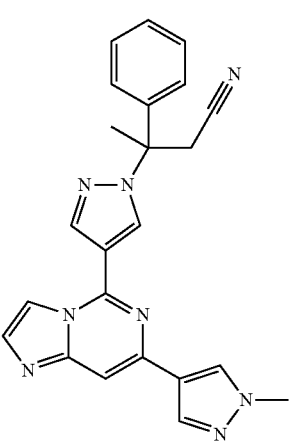 [SMILES: Cn1cc(-c2cc3nccn3c(-c3cnn(C(C)(CC#N)c4ccccc4)c3)n2)cn1] | 3-(4-(7-(1-methyl-1H-pyrazol-4-yl)imidazo[1,2-c]pyrimidin-5-yl)-1H-pyrazol-1-yl)-3-phenylbutanenitrile | (apci) m/z = 409.2 (M+H) |
| 17 | 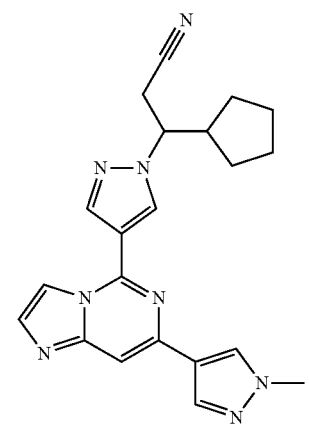 [SMILES: Cn1cc(-c2cc3nccn3c(-c3cnn(C(CC#N)C4CCCC4)c3)n2)cn1] | 3-cyclopentyl-3-(4-(7-(1-methyl-1H-pyrazol-4-yl)imidazo[1,2-c]pyrimidin-5-yl)-1H-pyrazol-1-yl)propanenitrile | (apci) m/z = 387.2 (M + H) |

TABLE 3-continued

| Ex. # | Structure | Name | MS |
|---|---|---|---|
| 18 | 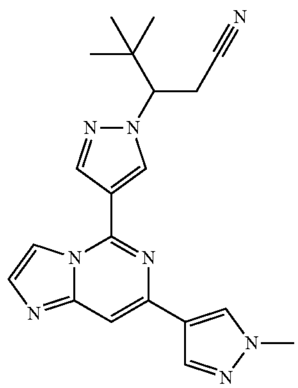 [SMILES: Cn1cc(-c2cc3nccn3c(-c3cnn(C(CC#N)C(C)(C)C)c3)n2)cn1] | 4,4-dimethyl-3-(4-(7-(1-methyl-1H-pyrazol-4-yl)imidazo[1,2-c]pyrimidin-5-yl)-1H-pyrazol-1-yl)pentanenitrile | (apci) m/z = 375.2 (M + H) |
| 19 | 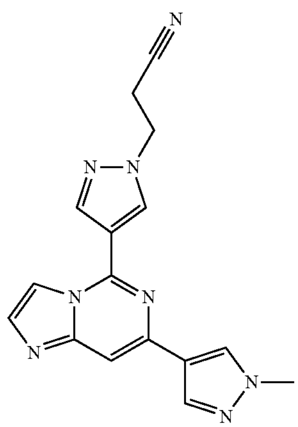 [SMILES: Cn1cc(-c2cc3nccn3c(-c3cnn(CCC#N)c3)n2)cn1] | 3-(4-(7-(1-methyl-1H-pyrazol-4-yl)imidazo[1,2-c]pyrimidin-5-yl)-1H-pyrazol-1-yl)propanenitrile | (apci) m/z = 319.1 (M + H) |
| 20 | 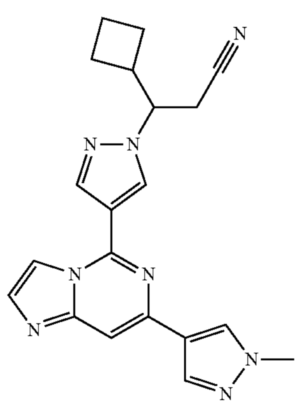 [SMILES: Cn1cc(-c2cc3nccn3c(-c3cnn(C(CC#N)C4CCC4)c3)n2)cn1] | 3-cyclobutyl-3-(4-(7-(1-methyl-1H-pyrazol-4-yl)imidazo[1,2-c]pyrimidin-5-yl)-1H-pyrazol-1-yl)propanenitrile | (apci) m/z = 373.2 (M + H) |

TABLE 3-continued

| Ex. # | Structure | Name | MS |
|---|---|---|---|
| 21 | 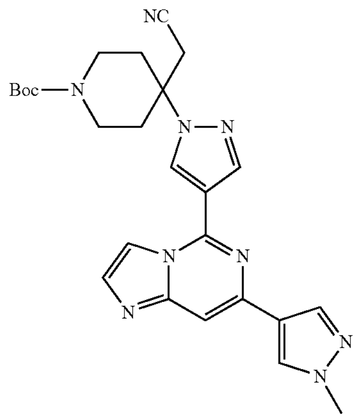 [SMILES: Cn1cc(-c2cc3nccn3c(-c3cnn(C4(CC#N)CCN(C(=O)OC(C)(C)C)CC4)c3)n2)cn1] | tert-butyl 4-(cyanomethyl)-4-(4-(7-(1-methyl-1H-pyrazol-4-yl)imidazo[1,2-c]pyrimidin-5-yl)-1H-pyrazol-1-yl)piperidine-1-carboxylate | (apci) m/z = 488.2 (M + H) |
| 22 | 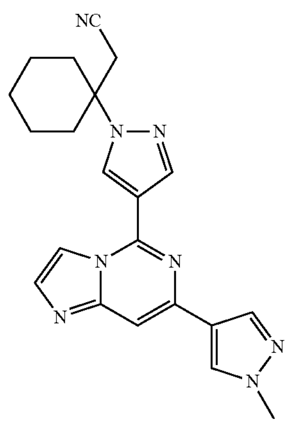 [SMILES: Cn1cc(-c2cc3nccn3c(-c3cnn(C4(CC#N)CCCCC4)c3)n2)cn1] | 2-(1-(4-(7-(1-methyl-1H-pyrazol-4-yl)imidazo[1,2-c]pyrimidin-5-yl)-1H-pyrazol-1-yl)cyclohexyl)acetonitrile | (apci) m/z = 387.3 (M + H) |
| 23 | 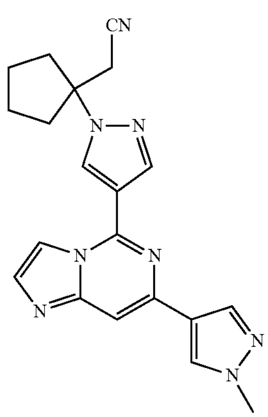 [SMILES: Cn1cc(-c2cc3nccn3c(-c3cnn(C4(CC#N)CCCC4)c3)n2)cn1] | 2-(1-(4-(7-(1-methyl-1H-pyrazol-4-yl)imidazo[1,2-c]pyrimidin-5-yl)-1H-pyrazol-1-yl)cyclopentyl)acetonitrile | (apci) m/z = 373.2 (M + H) |

TABLE 3-continued

| Ex. # | Structure | Name | MS |
|---|---|---|---|
| 24 | 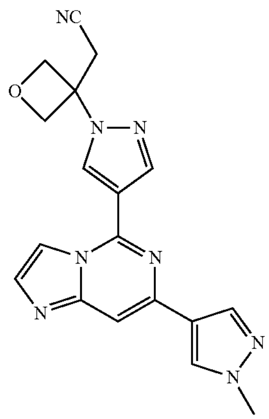 [SMILES: Cn1cc(-c2cc3nccn3c(-c3cnn(C4(CC#N)COC4)c3)n2)cn1] | 2-(3-(4-(7-(1-methyl-1H-pyrazol-4-yl)imidazo[1,2-c]pyrimidin-5-yl)-1H-pyrazol-1-yl)oxetan-3-yl)acetonitrile | (apci) m/z = 361.2 (M + H) |

Example 25

3-(4-(3-chloro-7-(1-methyl-1H-pyrazol-4-yl)imidazo[1,2-c]pyrimidin-5-yl)-1H-pyrazol-1-yl)-3-cyclopropylpropanenitrile

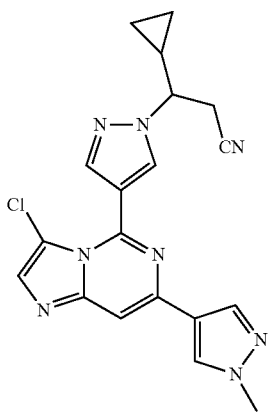 [SMILES: Cn1cc(-c2cc3ncc(Cl)n3c(-c3cnn(C(CC#N)C4CC4)c3)n2)cn1]

3-Cyclopropyl-3-(4-(7-(1-methyl-1H-pyrazol-4-yl)imidazo[1,2-c]pyrimidin-5-yl)-1H-pyrazol-1-yl)propanenitrile (Example 2) (46 mg, 0.13 mmol) and 1-chloropyrrolidine-2,5-dione (26 mg, 0.19 mmol) were suspended in DCM (1.3 mL, 0.13 mmol) and stirred at ambient temperature for 1 hour. This was immediately purified by silica chromatography using a 0-10% MeOH/EtOAc gradient to afford the title compound (18 mg, 34% yield) as a light yellow solid. MS (apci) m/z=393.2 (M+H).

Example 26

5-(1-(2-cyano-1-cyclopropylethyl)-1H-pyrazol-4-yl)-7-(1-methyl-1H-pyrazol-4-yl)imidazo[1,2-c]pyrimidine-3-carbonitrile

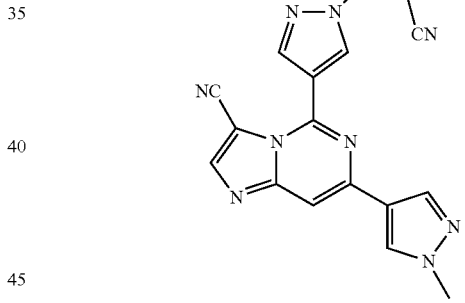

Step A: Preparation of 3-cyclopropyl-3-(4-(3-iodo-7-(1-methyl-1H-pyrazol-4-yl)imidazo[1,2-c]pyrimidin-5-yl)-1H-pyrazol-1-yl)propanenitrile 3-cyclopropyl-3-(4-(7-(1-methyl-1H-pyrazol-4-yl)imidazo[1,2-c]pyrimidin-5-yl)-1H-pyrazol-1-yl)propanenitrile (Example 2; 84.6 mg, 0.236 mmol) and 1-iodopyrrolidine-2,5-dione (79.7 mg, 0.354 mmol) were suspended in DCM (2.36 mL, 0.236 mmol) and stirred at ambient temperature for 15 hours. The reaction mixture was diluted in EtOAc and washed with saturated sodium bicarbonate and brine. The organic layer was dried with MgSO₄, filtered and concentrated in vacuo. Purification of the resulting crude material by silica chromatography using 0-5% MeOH/EtOAc gradient afforded 3-cyclopropyl-3-(4-(3-iodo-7-(1-methyl-1H-pyrazol-4-yl)imidazo[1,2-c]pyrimidin-5-yl)-1H-pyrazol-1-yl)propanenitrile (86.5 mg, 75.7% yield). MS (apci) m/z=485.2 (M+H).

Step B: Preparation of 5-(1-(2-cyano-1-cyclopropylethyl)-1H-pyrazol-4-yl)-7-(1-methyl-1H-pyrazol-4-yl)imidazo[1,2-c]pyrimidine-3-carbonitrile In a microwave safe flask, 3-cyclopropyl-3-(4-(3-iodo-7-(1-methyl-1H-pyrazol-4-yl)imidazo[1,2-c]pyrimidin-5-yl)-1H-pyrazol-1-yl)propanenitrile (22.4 mg, 0.0463 mmol) and cyanocopper (4.56 mg, 0.0509 mmol) were suspended in DMF (463 μL, 0.0463 mmol). The reaction mixture was heated at 160° C. for 1 hour. The reaction mixture was cooled and diluted in EtOAc and 10% NH₄OH (10 mL). The mixture was separated and the aqueous layer extracted with EtOAc. The combined organic layers were washed with brine, dried with MgSO₄, filtered and concentrated in vacuo. Purification using preparative TLC in 15% MeOH/EtOAc afforded 5-(1-(2-cyano-1-cyclopropylethyl)-1H-pyrazol-4-yl)-7-(1-methyl-1H-pyrazol-4-yl)imidazo[1,2-c]pyrimidine-3-carbonitrile (11.0 mg, 62.0% yield). MS (apci) m/z=384.4 (M+H).

Example 27

3-(1-acetylpiperidin-4-yl)-3-(4-(7-(1-methyl-1H-pyrazol-4-yl)imidazo[1,2-c]pyrimidin-5-yl)-1H-pyrazol-1-yl)propanenitrile

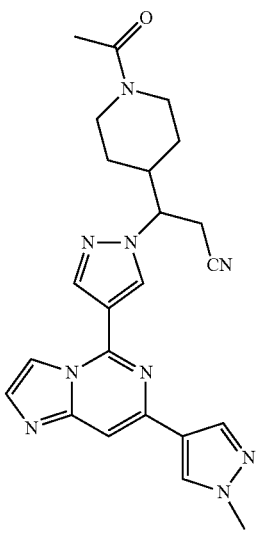 [SMILES: CC(=O)N1CCC(C(CC#N)n2cc(-c3nc(-c4cnn(C)c4)cc4nccn34)cn2)CC1]

Step A: Preparation of tert-butyl 4-(2-cyano-1-(4-(7-(1-methyl-1H-pyrazol-4-yl)imidazo[1,2-c]pyrimidin-5-yl)-1H-pyrazol-1-yl)ethyl)piperidine-1-carboxylate To 7-(1-methyl-1H-pyrazol-4-yl)-5-(1H-pyrazol-4-yl)imidazo[1,2-c]pyrimidine (Preparation K; 50 mg, 0.19 mmol) was added DMF (950 μL, 0.19 mmol), tert-butyl 4-(2-cyanovinyl)piperidine-1-carboxylate (Table 1, compound 1; 67 mg, 0.28 mmol) and DBU (185 μL, 1.3 mmol). The reaction mixture was heated to 45° C. for 8 hours, then diluted in EtOAc and washed with water and brine. The organic layer was dried with MgSO₄, filtered and concentrated down to a yellow oil. Purification of the resulting crude material by reverse phase HPLC using a 0-100% acetonitrile/water gradient afforded tert-butyl 4-(2-cyano-1-(4-(7-(1-methyl-1H-pyrazol-4-yl)imidazo[1,2-c]pyrimidin-5-yl)-1H-pyrazol-1-yl)ethyl)piperidine-1-carboxylate (59 mg, 62% yield). MS (apci) m/z=502.2 (M+H).

Step B: Preparation of 3-(4-(7-(1-methyl-1H-pyrazol-4-yl)imidazo[1,2-c]pyrimidin-5-yl)-1H-pyrazol-1-yl)-3-(piperidin-4-yl)propanenitrile hydrochloride Tert-butyl 4-(2-cyano-1-(4-(7-(1-methyl-1H-pyrazol-4-yl)imidazo[1,2-c]pyrimidin-5-yl)-1H-pyrazol-1-yl)ethyl)piperidine-1-carboxylate (59.4 mg, 0.118 mmol) was dissolved in DCM (592 μL, 0.118 mmol). To this was added 4N HCl in dioxane (296 μL, 1.18 mmol) and stirred at ambient temperature for 1 hour. Complete conversion was observed after 1 hour and the reaction mixture was concentrated to dryness to afford the HCl salt of 3-(4-(7-(1-methyl-1H-pyrazol-4-yl)imidazo[1,2-c]pyrimidin-5-yl)-1H-pyrazol-1-yl)-3-(piperidin-4-yl)propanenitrile (56.0 mg, 99.7% yield). MS (apci) m/z=402.3 (M+H).

Step C: Preparation of 3-(1-acetylpiperidin-4-yl)-3-(4-(7-(1-methyl-1H-pyrazol-4-yl)imidazo[1,2-c]pyrimidin-5-yl)-1H-pyrazol-1-yl)propanenitrile 3-(4-(7-(1-methyl-1H-pyrazol-4-yl)imidazo[1,2-c]pyrimidin-5-yl)-1H-pyrazol-1-yl)-3-(piperidin-4-yl)propanenitrile hydrochloride (10.0 mg, 0.021 mmol) was suspended in THF (211 μL, 0.0211 mmol). To this was added triethylamine (8.81 DIPHOS, 0.0632 mmol) to free-base. Acetic anhydride (2.38 μL, 0.0253 mmol) was added and the reaction mixture stirred at ambient temperature for 30 minutes. The reaction mixture was then diluted in saturated sodium bicarbonate and EtOAc. The layers were separated and the aqueous layer was extracted with EtOAc. The combined organic layers were washed with brine, dried with MgSO₄, filtered and concentrated in vacuo. Purification of the resulting crude material by reverse phase HPLC using 0-100% acetonitrile/water gradient afforded the title compound (7.2 mg, 77% yield). MS (apci) m/z=444.3 (M+H).

Example 28

2-(1-methyl-4-(4-(7-(1-methyl-1H-pyrazol-4-yl)imidazo[1,2-c]pyrimidin-5-yl)-1H-pyrazol-1-yl)piperidin-4-yl)acetonitrile

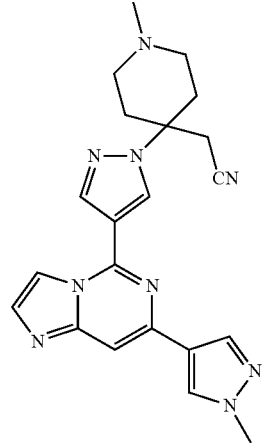 [SMILES: CN1CCC(CC#N)(n2cc(-c3nc(-c4cnn(C)c4)cc4nccn34)cn2)CC1]

Step A: Preparation of 2-(4-(4-(7-(1-Methyl-1H-pyrazol-4-yl)imidazo[1,2-c]pyrimidin-5-yl)-1H-pyrazol-1-yl)piperidin-4-yl)acetonitrile hydrochloride Tert-butyl 4-(cyanomethyl)-4-(4-(7-(1-methyl-1H-pyrazol-4-yl)imidazo[1,2-c]pyrimidin-5-yl)-1H-pyrazol-1-yl)piperidine-1-carboxylate (Example 21; 17 mg, 0.035 mmol) was dissolved in DCM (170 μL, 0.035 mmol) and treated with 4N HCl in dioxane (170 μL, 0.70 mmol). After 90 minutes, the reaction mixture was concentrated in vacuo to afford 2-(4-(4-(7-(1-methyl-1H-pyrazol-4-yl)imidazo[1,2-c]pyrimidin-5-yl)-1H-pyrazol-1-yl)piperidin-4-yl)acetonitrile hydrochloride (16 mg, 98% yield). MS (apci) m/z=388.3 (M+H).

Step B: Preparation of 2-(1-methyl-4-(4-(7-(1-methyl-1H-pyrazol-4-yl)imidazo[1,2-c]pyrimidin-5-yl)-1H-pyrazol-1-yl)piperidin-4-yl)acetonitrile 2-(4-(4-(7-(1-methyl-1H-pyrazol-4-yl)imidazo[1,2-c]pyrimidin-5-yl)-1H-pyrazol-1-yl)piperidin-4-yl)acetonitrile hydrochloride (15.8 mg, 0.0318 mmol) was suspended in acetonitrile (318 μL, 0.0318 mmol). To this was added triethylamine (17.7 μL, 0.127 mmol) to freebase, followed by formaldehyde (25.8 mg, 0.318 mmol). After 30 minutes, NaBH(OAc)₃ (33.7 mg, 0.159 mmol) was added. After stirring for 30 minutes, the reaction mixture was diluted in saturated sodium bicarbonate and EtOAc. The aqueous layer was back-extracted with DCM. The combined organic layer was washed with brine, dried with MgSO₄, filtered and concentrated. Purification of the resulting crude material by reverse phase HPLC using a 0-100% acetonitrile/water gradient afforded 2-(1-methyl-4-(4-(7-(1-methyl-1H-pyrazol-4-yl)imidazo[1,2-c]pyrimidin-5-yl)-1H-pyrazol-1-yl)piperidin-4-yl)acetonitrile (2.0 mg, 16% yield). MS (apci) m/z=402.1 (M+H).

Example 29

2-(1-ethyl-4-(4-(7-(1-methyl-1H-pyrazol-4-yl)imidazo[1,2-c]pyrimidin-5-yl)-1H-pyrazol-1-yl)piperidin-4-yl)acetonitrile

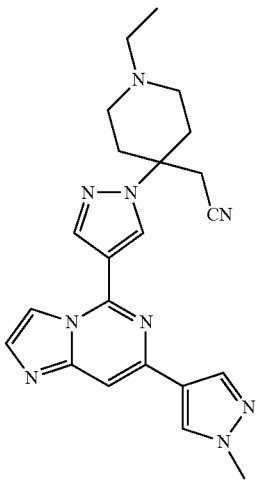 [SMILES: CCN1CCC(CC#N)(n2cc(-c3nc(-c4cnn(C)c4)cc4nccn34)cn2)CC1]

2-(4-(4-(7-(1-Methyl-1H-pyrazol-4-yl)imidazo[1,2-c]pyrimidin-5-yl)-1H-pyrazol-1-yl)piperidin-4-yl)acetonitrile hydrochloride (Example 28, Step A; 27.0 mg, 0.0543 mmol) was suspended in acetonitrile (543 μL, 0.0543 mmol). To this was added triethylamine (30.3 μL, 0.217 mmol) to freebase, followed by acetaldehyde (30.5 μL, 0.543 mmol). After 30 minutes, NaBH(OAc)₃ (57.6 mg, 0.272 mmol) was added to reduce. After stirring for 30 minutes, the reaction mixture was diluted in saturated bicarbonate and EtOAc. The aqueous layer was back-extracted with DCM. The combined organic layer was washed with brine, dried with MgSO₄, filtered and concentrated. Purification of the resulting crude material by reverse phase HPLC using a 0-100% acetonitrile/water gradient afforded afford 2-(1-ethyl-4-(4-(7-(1-methyl-1H-pyrazol-4-yl)imidazo[1,2-c]pyrimidin-5-yl)-1H-pyrazol-1-yl)piperidin-4-yl)acetonitrile (5.9 mg, 26% yield). MS (apci) m/z=416.2 (M+H).

Example 30

2-(4-(4-(7-(1-methyl-1H-pyrazol-4-yl)imidazo[1,2-c]pyrimidin-5-yl)-1H-pyrazol-1-yl)-1-propylpiperidin-4-yl)acetonitrile

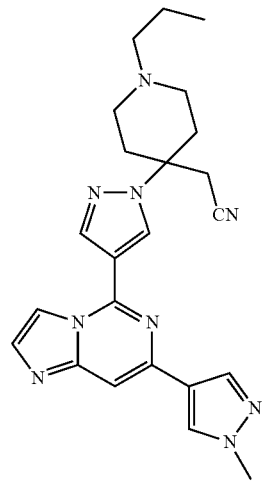 [SMILES: CCCN1CCC(CC#N)(n2cc(-c3nc(-c4cnn(C)c4)cc4nccn34)cn2)CC1]

2-(4-(4-(7-(1-Methyl-1H-pyrazol-4-yl)imidazo[1,2-c]pyrimidin-5-yl)-1H-pyrazol-1-yl)piperidin-4-yl)acetonitrile hydrochloride (Example 28, Step A; 30.0 mg, 0.0604 mmol) was suspended in acetonitrile (604 μL, 0.0604 mmol). To this was added triethylamine (33.7 μA, 0.242 mmol), followed by propionaldehyde (43.6 μL, 0.6043 mmol). After 30 minutes, NaBH(OAc)₃ (64.0 mg, 0.302 mmol) was added. After stirring for 30 minutes, the reaction mixture was diluted in saturated sodium bicarbonate and EtOAc. The aqueous layer was back-extracted with DCM. The combined organic layers were washed with brine, dried with MgSO₄, filtered and concentrated. Purification of the resulting crude material by reverse phase HPLC using a 0-100% acetonitrile/water gradient afforded afford 2-(4-(4-(7-(1-methyl-1H-pyrazol-4-yl)imidazo[1,2-c]pyrimidin-5-yl)-1H-pyrazol-1-yl)-1-propylpiperidin-4-yl)acetonitrile (7.0 mg, 23% yield). MS (apci) m/z=430.3 (M+H).

Example 31

2-(4-(4-(7-(1-methyl-1H-pyrazol-4-yl)imidazo[1,2-c]pyrimidin-5-yl)-1H-pyrazol-1-yl)-1-(2,2,2-trifluoroethyl)piperidin-4-yl)acetonitrile

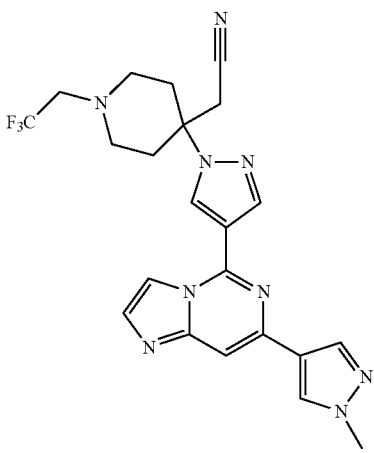 [SMILES: Cn1cc(-c2cc3nccn3c(-c3cnn(C4(CC#N)CCN(CC(F)(F)F)CC4)c3)n2)cn1]

2-(4-(4-(7-(1-Methyl-1H-pyrazol-4-yl)imidazo[1,2-c]pyrimidin-5-yl)-1H-pyrazol-1-yl)piperidin-4-yl)acetonitrile hydrochloride (Example 28, Step A; 0.050 g, 0.11 mmol) was dissolved in DIEA (0.12 mL, 0.70 mmol) and DMF (0.2 mL) with sonication. 2,2,2-Trifluoroethyl trifluoromethanesulfonate (0.025 g, 0.11 mmol) was added and the reaction was stirred at ambient temperature. After four hours the reaction was applied to a silica caplet and pumped to dryness. The caplet was applied to a silica column and eluted with 0.5-2% MeOH/DCM. The purified product was isolated to provide 2-(4-(4-(7-(1-methyl-1H-pyrazol-4-yl)imidazo[1,2-c]pyrimidin-5-yl)-1H-pyrazol-1-yl)-1-(2,2,2-trifluoroethyl)piperidin-4-yl)acetonitrile (5.0 mg, 10% yield) as a solid. MS (apci) m/z=470.2 (M+H).

Example 32

3-cyclopropyl-3-(4-(7-(1-((2-(trimethylsilyl)ethoxy)methyl)-1H-pyrazol-4-yl)imidazo[1,2-c]pyrimidin-5-yl)-1H-pyrazol-1-yl)propanenitrile

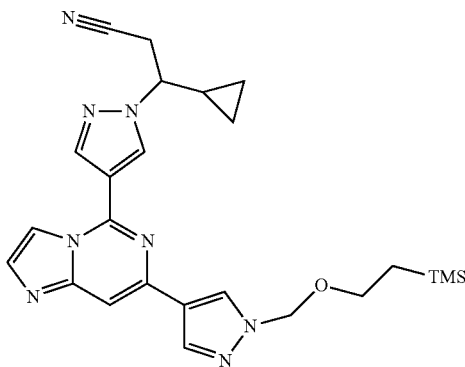 [SMILES: C[Si](C)(C)CCOCn1cc(-c2cc3nccn3c(-c3cnn(C(CC#N)C4CC4)c3)n2)cn1]

Step A: Preparation of 7-(1-((2-(trimethylsilyl)ethoxy)methyl)-1H-pyrazol-4-yl)imidazo[1,2-c]pyrimidin-5(6H)-one A flask was charged with 7-chloroimidazo[1,2-c]pyrimidin-5(6H)-one (Preparation H, 1.02 g, 6.00 mmol), 4-(4,4,5,5-tetramethyl-1,3,2-dioxaborolan-2-yl)-1-((2-(trimethylsilyl)ethoxy)methyl)-1H-pyrazole (Preparation E, 3.24 g, 9.00 mmol), K₃PO₄ (2.55 g, 12.0 mmol) and XPHOS (0.572 g, 1.20 mmol). Degassed iPrOH (24 mL) and degassed H₂O (2 mL) were added and the suspension was sonicated for 1-2 minutes. The mixture was purged with N₂ for 10 minutes with vigorous mixing and Pd₂dba₃ (0.549 g, 0.600 mmol) was added. The mixture was heated at reflux under an N₂ atmosphere for 24 hours and was cooled to ambient temperature. The mixture was diluted with EtOAc (20 mL) and was sonicated for 5 minutes. The suspension was filtered through a packed Celite plug (EtOAc elution) and concentrated to give an orange, oily solid. The solid was treated with Et₂O and was stirred until a granular suspension formed. The solid was collected, washed with Et₂O and H₂O and dried in vacuum to give the title compound (1.51 g, 76% yield) as a light tan powder. MS (apci) m/z=332.3 (M+H).

Step B: Preparation of 5-chloro-7-(1-((2-(trimethylsilyl)ethoxy)methyl)-1H-pyrazol-4-yl)imidazo[1,2-c]pyrimidine To a solution of 7-(1-((2-(trimethylsilyl)ethoxy)methyl)-1H-pyrazol-4-yl)imidazo[1,2-c]pyrimidin-5(6H)-one (Step B, 772 mg, 2.33 mmol) in dry DCM (15 mL) was added DIEA (1.22 mL, 6.99 mmol) and the mixture was stirred at ambient temperature for 5 minutes. The mixture was cooled to 0° C. and POCl₃ (855 µL, 9.32 mmol) was added. The mixture was stirred for 1 hour at 0° C. then at ambient temperature for 18 hours. The reaction mixture was concentrated and the residual syrup was dissolved in EtOAc (15 mL). The solution was added dropwise to stirred 1M K₂CO₃ (20 mL) cooled to 0° C. and stirred for 30 minutes. The mixture was allowed to reach ambient temperature and the EtOAc layer was removed. The remaining aqueous layer was extracted with EtOAc (2×) and the combined EtOAc fractions were washed with saturated NaCl. The EtOAc solution was dried over MgSO₄/activated carbon, filtered through a packed Celite plug (EtOAc elution) and concentrated. The residual dark syrup was dissolved in Et₂O, treated with activated carbon and filtered through a packed Celite pug (Et₂O elution). The Et₂O solution was concentrated to give a brittle tan foam that was pulverized to a flowing solid and dried in vacuum. This afforded the title compound (416 mg, 51.0% yield) as a light tan solid. MS (apci) m/z=350.1 (M+H).

Step C: Preparation of 3-cyclopropyl-3-(4-(7-(1-((2-(trimethylsilyl)ethoxy)methyl)-1H-pyrazol-4-yl)imidazo[1,2-c]pyrimidin-5-yl)-1H-pyrazol-1-yl)propanenitrile A flask was charged with 5-chloro-7-(1-((2-(trimethylsilyl)ethoxy)methyl)-1H-pyrazol-4-yl)imidazo[1,2-c]pyrimidine (Step C, 150 mg, 0.429 mmol), 3-cyclopropyl-3-(4-(4,4,5,5-tetramethyl-1,3,2-dioxaborolan-2-yl)-1H-pyrazol-1-yl)propanenitrile (Preparation P; 185 mg, 0.643 mmol) and K₃PO₄ (273 mg, 1.29 mmol). DME (2.5 mL) and H₂O (1.5 mL) were added and the resulting solution was purged with N₂ for 15 minutes. Pd(PPh₃)₄ (49.5 mg, 0.0429 mmol) was added, the flask sealed, and the mixture stirred at 80° C. for 3.5 hours. The mixture was cooled to ambient temperature and was diluted with H₂O (5 mL). The mixture was extracted with 50% EtOAc/hexanes and the combined extracts were washed with saturated NaCl and dried over MgSO₄/activated carbon. The dried solution was eluted through a SiO₂ column eluting with 50% EtOAc/hexanes, EtOAc and 10% MeOH/EtOAc. The EtOAc and 10% MeOH/EtOAc pools were combined and concentrated to give a gold syrup. The syrup was dissolved in Et₂O and concentrated to give the title compound (153 mg, 75.0% yield) as a brittle, light beige foam. MS (apci) m/z=475.3 (M+H).

Example 33

3-(4-(7-(1H-pyrazol-4-yl)imidazo[1,2-c]pyrimidin-5-yl)-1H-pyrazol-1-yl)-3-cyclopropylpropanenitrile

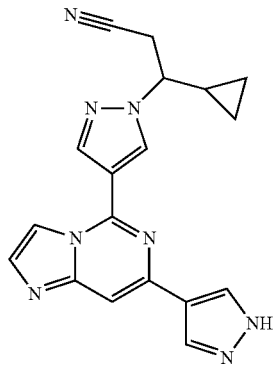 [SMILES: N#CCC(C1CC1)n1cc(-c2nc(-c3cn[nH]c3)cc3nccn23)cn1]

To a solution of 3-cyclopropyl-3-(4-(7-(1-((2-(trimethylsilyl)ethoxy)methyl)-1H-pyrazol-4-yl)imidazo[1,2-c]pyrimidin-5-yl)-1H-pyrazol-1-yl)propanenitrile (Example 32, 65.0 mg, 0.137 mmol) in DCM (2 mL) was added trifluoroacetic acid (2 mL) and the mixture was stirred at ambient temperature for 1.5 hours. The mixture was concentrated and the residue was partitioned into EtOAc (3 mL) and saturated NaHCO$_3$ (3 mL). The biphasic mixture was stirred for 15 minutes and NaCl was added until saturated. The EtOAc layer was removed and the remaining aqueous portion was extracted with EtOAc. The combined EtOAc extracts were dried over MgSO$_4$, filtered through a Celite plug and concentrated. The residual solid was dissolved in 10% MeOH/EtOAc and eluted through a SiO$_2$ column using 10% MeOH/EtOAc for elution. The solution was concentrated to give the title compound (46 mg, 98% yield) as a white solid. MS (apci) m/z=345.2 (M+H).

Example 34

3-Cyclopropyl-3-(4-(7-(1-isopropyl-1H-pyrazol-4-yl)imidazo[1,2-c]pyrimidin-5-yl)-1H-pyrazol-1-yl)propanenitrile

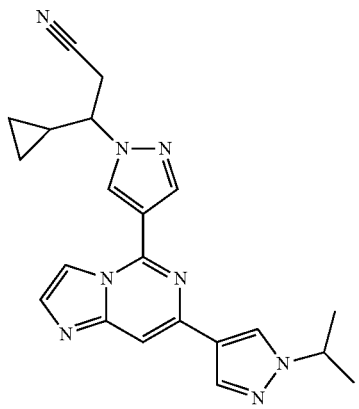 [SMILES: CC(C)n1cc(-c2cc3nccn3c(-c3cnn(C(CC#N)C4CC4)c3)n2)cn1]

Step A: Preparation of 7-(1-isopropyl-1H-pyrazol-4-yl)-5-(1-((2-(trimethylsilyl)ethoxy)methyl)-1H-pyrazol-4-yl)imidazo[1,2-c]pyrimidine To a flask charged with 7-chloro-5-(1-((2-(trimethylsilyl)ethoxy)methyl)-1H-pyrazol-4-yl)imidazo[1,2-c]pyrimidine (Preparation G; 0.200 g, 0.572 mmol), 1-isopropyl-4-(4,4,5,5-tetramethyl-1,3,2-dioxaborolan-2-yl)-1H-pyrazole (0.202 g, 0.857 mmol) (Table 2, compound a), and potassium phosphate (0.857 mL, 1.71 mmol) was added 5 mL of Dioxane and argon was bubbled through for 10 minutes before dicyclohexyl(2',4',6'-triisopropylbiphenyl-2-yl)phosphine (0.0545 g, 0.114 mmol) and tris(dibenzylideneacetone)dipalladium (0.0523 g, 0.0572 mmol) were added quickly and argon was bubbled through the reaction for 10 minutes before it was sealed and heated to 65° C. overnight. The reaction was diluted with ethyl acetate (100 mL) and washed with aqueous saturated sodium bicarbonate (40 mL) and brine (40 mL). The organic layer was dried over MgSO$_4$, filtered, and concentrated under reduced pressure. The crude was purified by silica gel column chromatography, eluting with a mixture of ethyl acetate and 0.5% ammonium hydroxide to afford 7-(1-isopropyl-1H-pyrazol-4-yl)-5-(1-((2-(trimethylsilyl)ethoxy)methyl)-1H-pyrazol-4-yl)imidazo[1,2-c]pyrimidine (0.191 g, 0.446 mmol, 78.1% yield). MS (apci) m/z=424.2 (M+H).

Step B: Preparation of 7-(1-isopropyl-1H-pyrazol-4-yl)-5-(1H-pyrazol-4-yl)imidazo[1,2-c]pyrimidine To a solution of 7-(1-isopropyl-1H-pyrazol-4-yl)-5-(1-((2-(trimethylsilyl)ethoxy)methyl)-1H-pyrazol-4-yl)imidazo[1,2-c]pyrimidine (0.191 g, 0.451 mmol) in 2.5 mL of DCM was added 2,2,2-trifluoroacetic acid (1.5 mL, 19.5 mmol) slowly at ambient temperature with stirring under an inert atmosphere. After 4 hours the reaction mixture was concentrated under reduced pressure and then allowed to dry on high vacuum over the weekend. The crude residue was taken up in 5 mL of 1M NaOH and stirred for 10 minutes before solid sodium chloride was added in sufficient amount to saturate the aqueous. The aqueous was then extracted with chloroform and then extracted with 10% MeOH in DCM (50 mL). The organic layers were combined, dried over MgSO$_4$, filtered, and concentrated under reduced pressure. The crude was dissolved in DCM in preparation for silica gel chromatography and a short time later a large amount of precipitate was observed. This solid was collected by means of vacuum filtration and the solid was rinsed with DCM to afford 7-(1-isopropyl-1H-pyrazol-4-yl)-5-(1H-pyrazol-4-yl)imidazo[1,2-c]pyrimidine (0.070 g, 0.239 mmol, 52.9% yield). MS (apci) m/z=294.1 (M+H).

Step C: Preparation of 3-cyclopropyl-3-(4-(7-(1-isopropyl-1H-pyrazol-4-yl)imidazo[1,2-c]pyrimidin-5-yl)-1H-pyrazol-1-yl)propanenitrile To a flask charged with 7-(1-isopropyl-1H-pyrazol-4-yl)-5-(1H-pyrazol-4-yl)imidazo[1,2-c]pyrimidine (0.0600 g, 0.2046 mmol) and 3-cyclopropylacrylonitrile (Preparation B; 0.1048 g, 1.125 mmol) was added 1 mL of acetonitrile and DBU (0.04588 mL, 0.3068 mmol) at ambient temperature with stirring. The flask was then sealed and heated to 50° C. overnight. The reaction mixture was diluted with dichloromethane and loaded directly onto a silica gel column and eluted with ethyl acetate with 0.5% ammonium hydroxide to afford the title compound (0.047 g, 0.1204 mmol, 58.86% yield). MS (apci) m/z=387.2 (M+H).

The compounds of Table 4 were prepared according to the procedures of Example 34 Steps A-C, replacing 1-isopropyl-4-(4,4,5,5-tetramethyl-1,3,2-dioxaborolan-2-yl)-1H-pyrazole in Step A with the appropriate boronate ester from Table 2.

TABLE 4

| Ex. # | Structure | Name | MS |
|---|---|---|---|
| 35 | 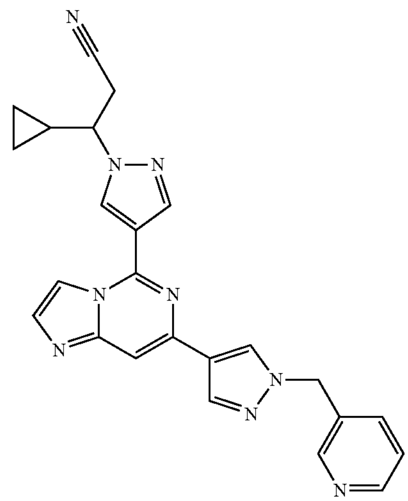 [SMILES: N#CCC(C1CC1)n1cc(-c2nc(-c3cnn(Cc4cccnc4)c3)cc3nccn23)cn1] | 3-cyclopropyl-3-(4-(7-(1-(pyridin-3-ylmethyl)-1H-pyrazol-4-yl)imidazo[1,2-c]pyrimidin-5-yl)-1H-pyrazol-1-yl)propanenitrile | (apci) m/z = 436.2 (M + H) |
| 36 | 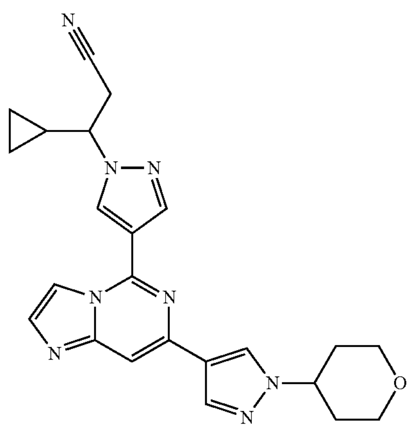 [SMILES: N#CCC(C1CC1)n1cc(-c2nc(-c3cnn(C4CCOCC4)c3)cc3nccn23)cn1] | 3-cyclopropyl-3-(4-(7-(1-(tetrahydro-2H-pyran-4-yl)-1H-pyrazol-4-yl)imidazo[1,2-c]pyrimidin-5-yl)-1H-pyrazol-1-yl)propanenitrile | (apci) m/z = 429.2 (M + H) |
| 37 | 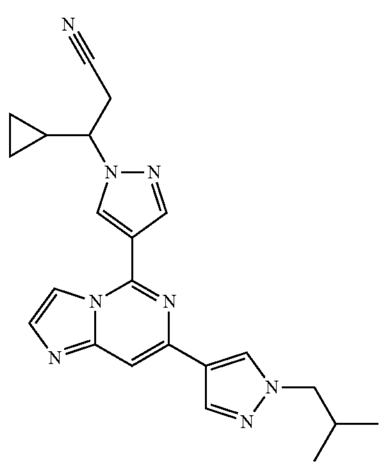 [SMILES: CC(C)Cn1cc(-c2cc3nccn3c(-c3cnn(C(CC#N)C4CC4)c3)n2)cn1] | 3-cyclopropyl-3-(4-(7-(1-isobutyl-1H-pyrazol-4-yl)imidazo[1,2-c]pyrimidin-5-yl)-1H-pyrazol-1-yl)propanenitrile | (apci) m/z = 401.2 (M + H) |

Example 38

3-Cyclopropyl-3-(4-(7-(1-(oxetan-3-yl)-1H-pyrazol-4-yl)imidazo[1,2-c]pyrimidin-5-yl)-1H-pyrazol-1-yl)propanenitrile

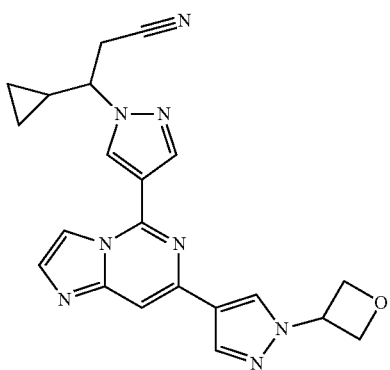 [SMILES: N#CCC(C1CC1)n1cc(-c2nc(-c3cnn(C4COC4)c3)cc3nccn23)cn1]

To a flask charged with 3-(4-(7-chloroimidazo[1,2-c]pyrimidin-5-yl)-1H-pyrazol-1-yl)-3-cyclopropylpropanenitrile (Preparation M; 0.050 g, 0.16 mmol), 1-(oxetan-3-yl)-4-(4,4,5,5-tetramethyl-1,3,2-dioxaborolan-2-yl)-1H-pyrazole (Table 2, compound f; 0.078 g, 0.21 mmol), and potassium phosphate (0.24 mL, 0.48 mmol) was added 2 mL of dioxane and argon was bubbled through for 5 minutes before dicyclohexyl(2',4',6'-triisopropylbiphenyl-2-yl)phosphine (0.015 g, 0.032 mmol) and tris(dibenzylideneacetone)dipalladium (0.015 g, 0.016 mmol) were added. The reaction was fitted with a septum and argon was bubbled through for 10 minutes before it was sealed and then heated to 75° C. for 2 hours. The reaction mixture was diluted with dichloromethane and loaded directly onto a silica gel column pre-wetted and eluted with ethyl acetate containing 0.5% ammonium hydroxide to afford the title compound (0.034 g, 0.081 mmol, 50% yield). MS (apci) m/z=401.2 (M+H).

The compounds of Table 5 were prepared according to the procedure of Example 38, replacing 1-(oxetan-3-yl)-4-(4,4,5,5-tetramethyl-1,3,2-dioxaborolan-2-yl)-1H-pyrazole with the appropriate boronate ester or boronic acid.

TABLE 5

| Ex. # | Structure | Name | MS |
|---|---|---|---|
| 39 | 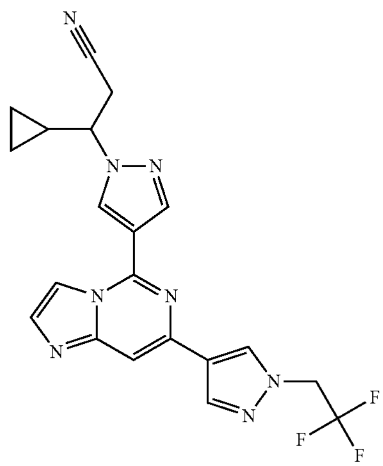 [SMILES: N#CCC(C1CC1)n1cc(-c2nc(-c3cnn(CC(F)(F)F)c3)cc3nccn23)cn1] | 3-cyclopropyl-3-(4-(7-(1-(2,2,2-trifluoroethyl)-1H-pyrazol-4-yl)imidazo[1,2-c]pyrimidin-5-yl)-1H-pyrazol-1-yl)propanenitrile | (apci) m/z = 427.1 (M + H) |
| 40 | 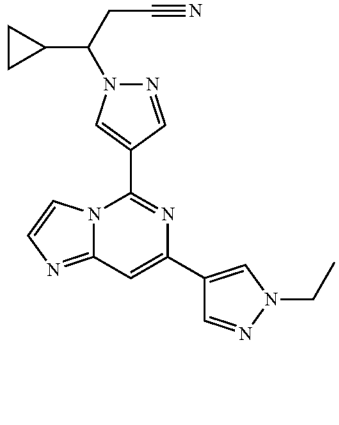 [SMILES: CCn1cc(-c2cc3nccn3c(-c3cnn(C(CC#N)C4CC4)c3)n2)cn1] | 3-cyclopropyl-3-(4-(7-(1-ethyl-1H-pyrazol-4-yl)imidazo[1,2-c]pyrimidin-5-yl)-1H-pyrazol-1-yl)propanenitrile | (apci) m/z = 373.2 (M + H) |

TABLE 5-continued

| Ex. # | Structure | Name | MS |
|---|---|---|---|
| 41 | 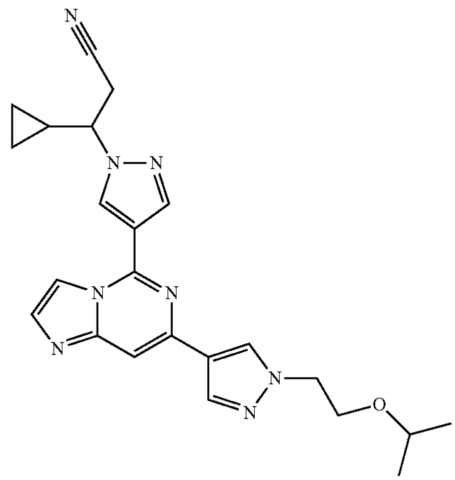 [SMILES: CC(C)OCCn1cc(-c2cc3nccn3c(-c3cnn(C(CC#N)C4CC4)c3)n2)cn1] | 3-cyclopropyl-3-(4-(7-(1-(2-isopropoxyethyl)-1H-pyrazol-4-yl)imidazo[1,2-c]pyrimidin-5-yl)-1H-pyrazol-1-yl]propanenitrile | (apci) m/z = 331.2 (M + H) |
| 42 | 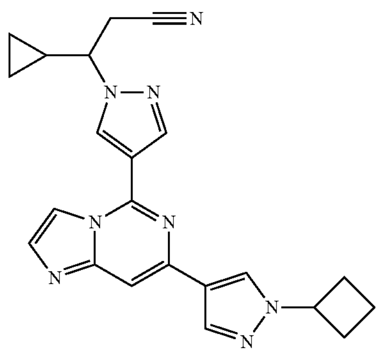 [SMILES: N#CCC(C1CC1)n1cc(-c2nc(-c3cnn(C4CCC4)c3)cc3nccn23)cn1] | 3-(4-(7-(1-cyclobutyl-1H-pyrazol-4-yl)imidazo[1,2-c]pyrimidin-5-yl)-1H-pyrazol-1-yl)-3-cyclopropylpropanenitrile | (apci) m/z = 399.2 (M + H) |
| 43 | 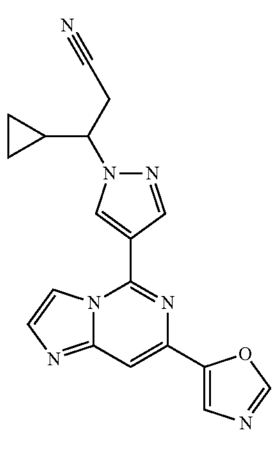 [SMILES: N#CCC(C1CC1)n1cc(-c2nc(-c3cnco3)cc3nccn23)cn1] | 3-cyclopropyl-3-(4-(7-(oxazol-5-yl)imidazo[1,2-c]pyrimidin-5-yl)-1H-pyrazol-1-yl)propanenitrile | (apci) m/z = 346.1 (M + H) |

TABLE 5-continued

| Ex. # | Structure | Name | MS |
|---|---|---|---|
| 44 | 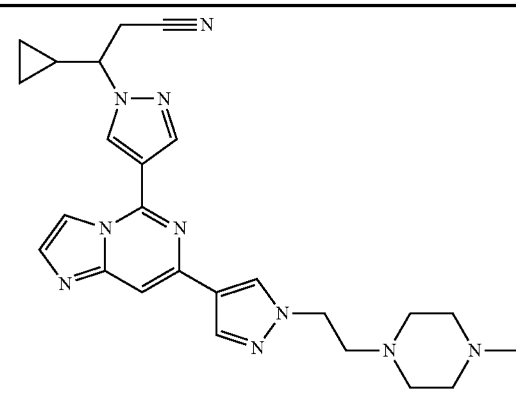 | 3-cyclopropyl-3-(4-(7-(1-(2-(4-methylpiperazin-1-yl)ethyl)-1H-pyrazol-4-yl)imidazo[1,2-c]pyrimidin-5-yl)-1H-pyrazol-1-yl)propanenitrile | (apci) m/z = 471.3 (M + H) |

Example 45

3-Cyclopropyl-3-(4-(7-(5-methyl-1,3,4-thiadiazol-2-yl)imidazo[1,2-c]pyrimidin-5-yl)-1H-pyrazol-1-yl)propanenitrile

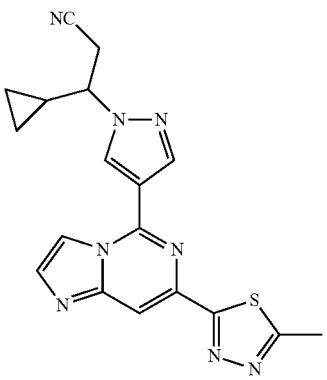 [SMILES: Cc1nnc(-c2cc3nccn3c(-c3cnn(C(CC#N)C4CC4)c3)n2)s1]

Step A: Preparation of methyl 5-hydroxyimidazo[1,2-c]pyrimidine-7-carboxylate 7-chloroimidazo[1,2-c]pyrimidin-5(6H)-one (Preparation H, 3.56 g, 21.0 mmol), 1,1'-bis(diphenylphosphino) ferrocene-dichloropalladium (0.864 g, 1.05 mmol) and triethylamine (8.78 mL, 63.0 mmol) were suspended in MeOH (70 mL) in a stainless steel bomb. The system was sealed and then charged with 150 psi of carbon monoxide (CO). The system was purged and then re-charged with CO, followed by heating at 120° C. for 15 hours. The system was cooled to 30° C., and then carefully vented to remove CO(g) and purged with nitrogen to remove any excess. The reaction mixture was transferred to a 500 mL flask and concentrated to afford the crude title compound (4.00 g, 98.0% yield). MS (apci) m/z=194.1 (M+H).

Step B: Preparation of methyl 5-chloroimidazo[1,2-c]pyrimidine-7-carboxylate Methyl 5-hydroxyimidazo[1,2-c]pyrimidine-7-carboxylate (4.0 g, 21 mmol) and N,N-diethylaniline (6.6 mL, 41 mmol) were suspended in POCl₃ (80 mL, 870 mmol) and heated at 50° C. for 30 minutes. The reaction mixture remained heterogeneous, so the temperature was raised to 100° C. After 30 minutes, LCMS analysis showed mostly the title compound, along with 5,7-dichloroimidazo[1,2-c]pyrimidine (which was presumably formed from 7-chloroimidazo[1,2-c]pyrimidin-5-ol carried through from the previous step). The reaction mixture was cooled to ambient temperature and concentrated down to remove the POCl₃. The residue was cooled in an ice bath and quenched carefully with water. Solid K₂CO₃ was added to neutralize the solution to pH 7, which was then extracted with DCM. The combined organic layers were filtered through a Biotage phase separator cartridge and washed with DCM. The filtrate was concentrated down to a thick dark greenish brown residue. While sitting overnight, a precipitate formed. The resultant solid was triturated in DCM and Et₂O to give afford methyl 5-chloroimidazo[1,2-c]pyrimidine-7-carboxylate (6.4 g, 21 mmol, 100% yield) as a brick-red solid. The solid was 70% pure, but could not be purified at this stage due to its insolubility. The crude material was used directly in the next step. MS (apci) m/z=212.2 (M+H).

Step C: Preparation of methyl 5-(1-((2-(trimethylsilyl)ethoxy)methyl)-1H-pyrazol-4-yl)imidazo[1,2-c]pyrimidine-7-carboxylate Methyl 5-chloroimidazo[1,2-c]pyrimidine-7-carboxylate (1.00 g, 4.73 mmol), 4-(4,4,5,5-tetramethyl-1,3,2-dioxaborolan-2-yl)-1-((2-(trimethylsilyl)ethoxy)methyl)-1H-pyrazole (Preparation E; 1.53 g, 4.73 mmol), K₃PO₄ (2.01 g, 9.45 mmol), Pd₂dba₃ (0.433 g, 0.473 mmol), and XPHOS (0.563 g, 1.18 mmol) were combined dry. To this was added isopropanol (20 mL) and water (0.34 mL, 19 mmol). After degassing for 10 minutes, the flask was sealed and heated to 80° C. for 15 hours. The reaction mixture was diluted in EtOAc and undissolved solid was removed by filtration. The filtrate was concentrated down and purified by silica chromatography using 50-100% EtOAc/Hexanes gradient to afford methyl 5-(1-((2-(trimethylsilyl)ethoxy)methyl)-1H-pyrazol-4-yl)imidazo[1,2-c]pyrimidine-7-carboxylate (0.477 g, 1.28 mmol, 27.0% yield) as an orange brown solid. MS (apci) m/z=374.1 (M+H).

Step D: Preparation of 5-(1-((2-(trimethylsilyl)ethoxy)methyl)-1H-pyrazol-4-yl)imidazo-[1,2-c]pyrimidine-7-carbohydrazide In a 20 mL flask, methyl 5-(1-((2-(trimethylsilyl)-ethoxy)methyl)-1H-pyrazol-4-yl)imidazo[1,2-c]pyrimidine-7-carboxylate (Example 122; Step C) (50 mg, 0.13 mmol) was dissolved in EtOH (540 µL, 0.13 mmol). To this was added a large excess of hydrazine hydrate (104 µL, 3.3 mmol). The reaction mixture was refluxed for 1 hour, and then concentrated down to dryness. The residue was diluted in EtOAc and washed with water and brine. The organic layer was dried with MgSO$_4$, filtered and concentrated in vacuo to afford 5-(1-((2-(trimethylsilyl)ethoxy)methyl)-1H-pyrazol-4-yl)imidazo[1,2-c]pyrimidine-7-carbohydrazide (45 mg, 90% yield) as a yellow oil. MS (apci) m/z=374.4 (M+H).

Step E: Preparation of N'-acetyl-5-(1-((2-(trimethylsilyl)ethoxy)methyl)-1H-pyrazol-4-yl)imidazo[1,2-c]pyrimidine-7-carbohydrazide In a 20 mL flask, 5-(1-((2-(trimethylsilyl)-ethoxy)methyl)-1H-pyrazol-4-yl)imidazo[1,2-c]pyrimidine-7-carbohydrazide (45.1 mg, 0.121 mmol) was dissolved in DCM (604 µL, 0.121 mmol). After cooling to 0° C., triethylamine (20.2 µL, 0.145 mmol) and acetyl chloride (9.45 µL, 0.133 mmol) were added. The reaction mixture was allowed to warm to ambient temperature for 15 hours. This was then diluted in EtOAc and washed with water and brine. The organic layer was then dried with MgSO$_4$, filtered and concentrated down to afford N'-acetyl-5-(1-((2-(trimethylsilyl)ethoxy)methyl)-1H-pyrazol-4-yl)imidazo[1,2-c]pyrimidine-7-carbohydrazide (40.9 mg, 81.5% yield) as a light yellow solid. MS (apci) m/z=416.2 (M+H).

Step F: Preparation of 2-(5-(1H-pyrazol-4-yl)imidazo[1,2-c]pyrimidin-7-yl)-5-methyl-1,3,4-thiadiazole In a 20 mL flask, N'-acetyl-5-(1-((2-(trimethylsilyl)ethoxy)methyl)-1H-pyrazol-4-yl)imidazo[1,2-c]pyrimidine-7-carbohydrazide (40.9 mg, 0.0984 mmol) was dissolved in dioxane (984 µL, 0.0984 mmol). To this was added di-Phosphorus pentasulfide (21.9 mg, 0.0492 mmol) and Bis(trimethylsilyl)ether (32.0 mg, 0.197 mmol). The reaction mixture was heated to 100° C. for 72 hours. After cooling, the reaction mixture was quenched with a solution of K$_2$CO$_3$ (45.5 mg) in H$_2$O (1 mL). The mixture was stirred for 20 minutes, then concentrated in vacuo to remove solvents. The residue was diluted in water and extracted with DCM. The combined organic layers were dried with MgSO$_4$, filtered and concentrated in vacuo to afford the thiadiazole (17.4 mg, 62.4% yield) as a yellow solid. The crude material was taken onto the next step. MS (apci) m/z=284.2 (M+H).

Step G: Preparation of 3-cyclopropyl-3-(4-(7-(5-methyl-1,3,4-thiadiazol-2-yl)imidazo-[1,2-c]pyrimidin-5-yl)-1H-pyrazol-1-yl)propanenitrile In a 20 mL flask, 2-(5-(1H-pyrazol-4-yl)imidazo[1,2-c]pyrimidin-7-yl)-5-methyl-1,3,4-thiadiazole (17.4 mg, 0.0614 mmol) and 3-cyclopropylacrylonitrile (Preparation B; 17.2 mg, 0.184 mmol) were dissolved in DMF (614 µL, 0.0614 mmol). To this was added DBU (23.0 µA, 0.154 mmol) and stirred at ambient temperature for 40 h. The reaction was incomplete, so another portion of DBU (23.0 µA, 0.154 mmol) and 3-cyclopropylacrylonitrile (17.2 mg, 0.184 mmol) were added. After 4 hours, the reaction mixture was diluted in EtOAc, and washed with water and brine. The organic layer was dried with MgSO$_4$, filtered and concentrated down to a yellow oil. The crude material was purified by silica chromatography using a 0-10% MeOH/EtOAc gradient to afford 3-cyclopropyl-3-(4-(7-(5-methyl-1,3,4-thiadiazol-2-yl)imidazo[1,2-c]pyrimidin-5-yl)-1H-pyrazol-1-yl)propanenitrile (7.2 mg, 31% yield). MS (apci) m/z=377.2 (M+H).

Example 46

3-Cyclopropyl-3-(4-(7-(4-methyl-1H-imidazol-1-yl)imidazo[1,2-c]pyrimidin-5-yl)-1H-pyrazol-1-yl)propanenitrile

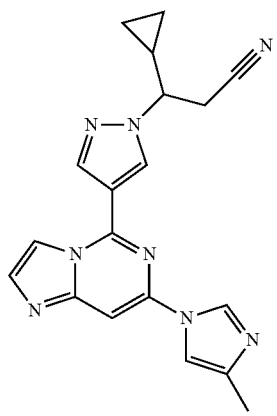 [SMILES: Cc1cn(-c2cc3nccn3c(-c3cnn(C(CC#N)C4CC4)c3)n2)cn1]

Step A: Preparation of 7-(4-methyl-1H-imidazol-1-yl)-5-(1-((2-(trimethylsilyl)ethoxy)methyl)-1H-pyrazol-4-yl)imidazo[1,2-c]pyrimidine To a flask charged with 4-methyl-1H-imidazole (0.117 g, 1.43 mmol) and 1 mL of N,N-dimethylformamide was added sodium hydride (60% in oil dispersion) (0.0514 g, 1.29 mmol) at 0° C. with stirring. The reaction mixture was then placed under nitrogen and allowed to warm to ambient temperature and stirred for 30 minutes. To the reaction was added 7-chloro-5-(1-((2-(trimethylsilyl)ethoxy)methyl)-1H-pyrazol-4-yl)imidazo[1,2-c]pyrimidine (Preparation G; 0.100 g, 0.286 mmol) and argon was bubbled through the reaction for 5 minutes. The reaction was sealed and heated to 100° C. The reaction was diluted with dichloromethane (50 mL) and 5 mL of aqueous saturated sodium bicarbonate was added. The reaction mixture was stirred for 20 minutes, then concentrated to dryness under reduced pressure at 50° C. and dried on high vacuum overnight. The crude material was taken up in 1:1 ethyl acetate: dichloromethane with 5% methanol (100 mL) and sonicated for 1 hour. This suspension was filtered, the cake was washed with EtOAc (50 mL) and the rinse was then concentrated under reduced pressure. The resulting residue was purified by silica gel chromatography eluting with 1% methanol in dichloromethane containing 0.5% ammonium hydroxide to obtain 7-(4-methyl-1H-imidazol-1-yl)-5-(1-((2-(trimethylsilyl)ethoxy)methyl)-1H-pyrazol-4-yl)imidazo[1,2-c]pyrimidine (0.053 g, 0.077 mmol, 27% yield). MS (apci) m/z=396.2 (M+H).

Step B: Preparation of 3-cyclopropyl-3-(4-(7-(4-methyl-1H-imidazol-1-yl)imidazo[1,2-c]pyrimidin-5-yl)-1H-pyrazol-1-yl)propanenitrile Prepared in the same manner as Example 34 Steps B and C, replacing 7-(1-isopropyl-1H-pyrazol-4-yl)-5-(1-((2-(trimethylsilyl)ethoxy)methyl)-1H-pyrazol-4-yl)imidazo[1,2-c]pyrimidine with 7-(4-methyl-1H-imidazol-1-yl)-5-(1-((2-(trimethylsilyl)ethoxy)methyl)-1H-pyrazol-4-yl)imidazo[1,2-c]pyrimidine to afford the title compound (0.010 g, 0.0163 mmol, 44% yield). MS (apci) m/z=359.1 (M+H).

Example 47

3-Cyclopropyl-3-(4-(7-(thiazol-5-yl)imidazo[1,2-c]pyrimidin-5-yl)-1H-pyrazol-1-yl)propanenitrile

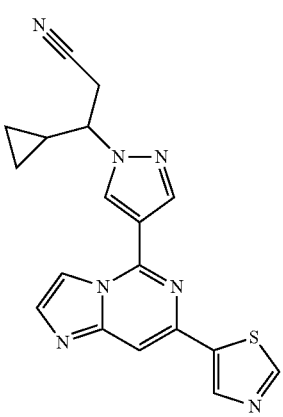 [SMILES: N#CCC(C1CC1)n1cc(-c2nc(-c3cncs3)cc3nccn23)cn1]

To a flask charged with 3-(4-(7-chloroimidazo[1,2-c]pyrimidin-5-yl)-1H-pyrazol-1-yl)-3-cyclopropylpropanenitrile (Preparation M; 0.020 g, 0.064 mmol), 5-(tributylstannyl)thiazole (0.029 g, 0.077 mmol), dicyclohexyl(2',4',6'-triisopropylbiphenyl-2-yl)phosphine (0.0061 g, 0.013 mmol), and tris(dibenzylideneacetone)dipalladium (0.0059 g, 0.0064 mmol), evacuated and backfilled with argon, was added 1.5 mL of dioxane. Argon was bubbled through the reaction for 5 minutes and the flask was sealed and heated to 100° C. for 3 hours. The reaction mixture was loaded onto a silica gel column pre-wetted and eluted with ethyl acetate containing 0.5% ammonium hydroxide to afford the title compound (0.018 g, 0.050 mmol, 78% yield). MS (apci) m/z=362.1 (M+H).

Example 48

3-cyclopropyl-3-(4-(7-(2-methylthiazol-5-yl)imidazo[1,2-c]pyrimidin-5-yl)-1H-pyrazol-1-yl))propanenitrile

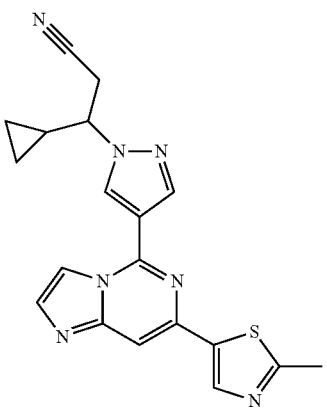 [SMILES: Cc1ncc(-c2cc3nccn3c(-c3cnn(C(CC#N)C4CC4)c3)n2)s1]

Prepared in the same manner as Example 47 replacing 5-(tributylstannyl) thiazole with 2-methyl-5-(trimethylstannyl)thiazole to afford title compound (0.021 g, 0.056 mmol, 70% yield). MS (apci) m/z=376.1 (M+H).

Example 49

3-Cyclopropyl-3-(4-(7-(6-methylpyridin-3-yl)imidazo[1,2-c]pyrimidin-5-yl)-1H-pyrazol-1-yl)propanenitrile

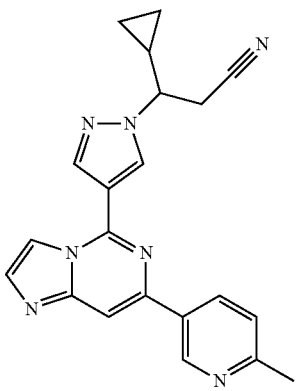 [SMILES: Cc1ccc(-c2cc3nccn3c(-c3cnn(C(CC#N)C4CC4)c3)n2)cn1]

To 3-(4-(7-chloroimidazo[1,2-c]pyrimidin-5-yl)-1H-pyrazol-1-yl)-3-cyclopropyl-propanenitrile (Preparation M; 50 mg, 0.16 mmol) in dioxane (5 mL) was added K$_2$CO$_3$ (66 mg, 0.48 mmol), diacetoxypalladium (1.8 mg, 0.0080 mmol), 6-methylpyridin-3-ylboronic acid (44 mg, 0.32 mmol) and sodium 2'-(dicyclohexylphosphino)-2,6-dimethoxybiphenyl-3-sulfonate (8.2 mg, 0.016 mmol). The reaction mixture was degassed with argon, sealed and heated to 80° C. for 5 hours. The reaction was cooled to ambient temperature and concentrated under reduced pressure. The residue was purified by silica gel chromatography (DCM/MeOH 10:1) to give the final product (20 mg, 34% yield). MS (apci) m/z=370.2 (M+H).

The compounds of Table 6 were prepared according to the procedure of Example 49, replacing 6-methylpyridin-3-ylboronic acid with the appropriate commercially available boronate ester.

TABLE 6

| Ex. # | Structure | Name | MS |
|---|---|---|---|
| 50 | 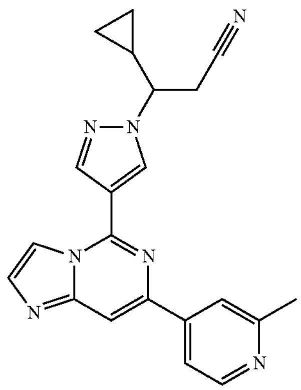 [SMILES: Cc1cc(-c2cc3nccn3c(-c3cnn(C(CC#N)C4CC4)c3)n2)ccn1] | 3-cyclopropyl-3-(4-(7-(2-methylpyridin-4-yl)imidazo[1,2-c]pyrimidin-5-yl)-1H-pyrazol-1-yl)propanenitrile | (apci) m/z = 370.3 (M + H) |
| 51 | 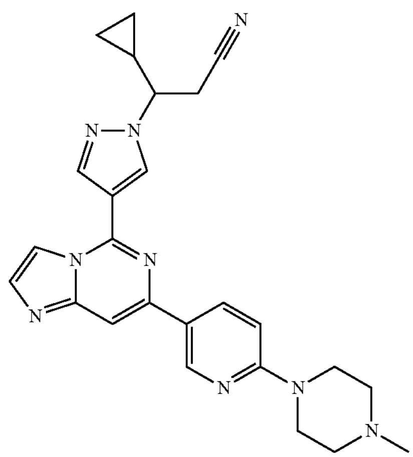 [SMILES: CN1CCN(c2ccc(-c3cc4nccn4c(-c4cnn(C(CC#N)C5CC5)c4)n3)cn2)CC1] | 3-cyclopropyl-3-(4-(7-(6-(4-methylpiperazin-1-yl)pyridin-3-yl)imidazo[1,2-c]pyrimidin-5-yl)-1H-pyrazol-1-yl)propanenitrile | (apci) m/z = 454.2 (M + H) |

Example 52

3-Cyclopropyl-3-(4-(7-(1,2,3,4-tetrahydroisoquinolin-6-yl)imidazo[1,2-c]pyrimidin-5-yl)-1H-pyrazol-1-yl)propanenitrile

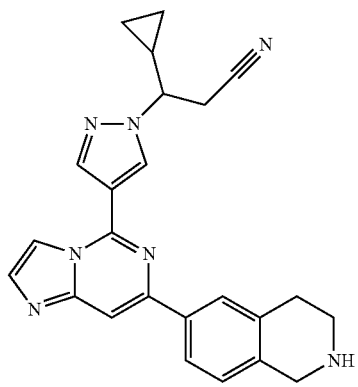 [SMILES: N#CCC(C1CC1)n1cc(-c2nc(-c3ccc4c(c3)CCNC4)cc3nccn23)cn1]

To 3-(4-(7-chloroimidazo[1,2-c]pyrimidin-5-yl)-1H-pyrazol-1-yl)-3-cyclopropyl-propanenitrile (Preparation M; 50 mg, 0.16 mmol) in dioxane (5 mL) was added K₂CO₃ (66 mg, 0.48 mmol), diacetoxypalladium (1.8 mg, 0.0080 mmol), 2-(tert-butoxycarbonyl)-1,2,3,4-tetrahydroisoquinolin-6-yl-boronic acid (89 mg, 0.32 mmol) and sodium 2'-(dicyclohexylphosphino)-2,6-dimethoxybiphenyl-3-sulfonate (8.2 mg, 0.016 mmol). The reaction mixture was degassed with argon, sealed and heated to 80° C. for 5 hours. The reaction was cooled to ambient temperature and concentrated under reduced pressure. The residue was purified by silica gel chromatography (DCM/MeOH 10:1) to give the intermediate product, to which was added DCM/TFA (1 mL/1 mL). The reaction mixture was stirred for 30 minutes and concentrated under reduced pressure. The residue was purified by silica gel chromatography (DCM/MeOH/NH₄OH 10:1:0.1) to give the final product (20 mg, 31% yield). MS (apci) m/z=410.3 (M+H).

Example 53

3-Cyclopropyl-3-(4-(7-(2-methyl-1,2,3,4-tetrahydroisoquinolin-6-yl)imidazo[1,2-c]pyrimidin-5-yl)-1H-pyrazol-1-yl)propanenitrile

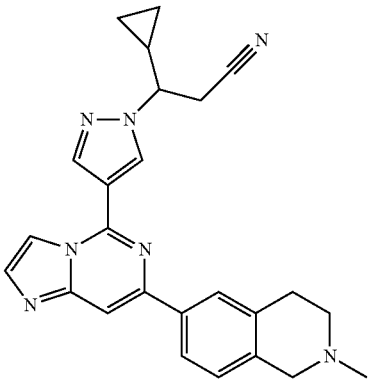 [SMILES: CN1CCc2cc(-c3cc4nccn4c(-c4cnn(C(CC#N)C5CC5)c4)n3)ccc2C1]

To 3-cyclopropyl-3-(4-(7-(1,2,3,4-tetrahydroisoquinolin-6-yl)imidazo[1,2-c]pyrimidin-5-yl)-1H-pyrazol-1-yl)propanenitrile (Example 52; 10 mg, 0.024 mmol) in DCM/MeOH (1 mL/1 mL) was added formaldehyde (49 mg, 0.49 mmol) and sodium triacetoxyborohydride (16 mg, 0.073 mmol). The reaction mixture was stirred at ambient temperature for 30 minutes and concentrated under reduced pressure. The residue was purified by silica gel chromatography (DCM/MeOH/NH$_4$OH 10:1:0.1) to give the final product (5.0 mg, 48% yield). MS (apci) m/z=424.3 (M+H).

Example 54

3-Cyclopropyl-3-(4-(7-(1,2,3,4-tetrahydroisoquinolin-7-yl)imidazo[1,2-c]pyrimidin-5-yl)-1H-pyrazol-1-yl)propanenitrile

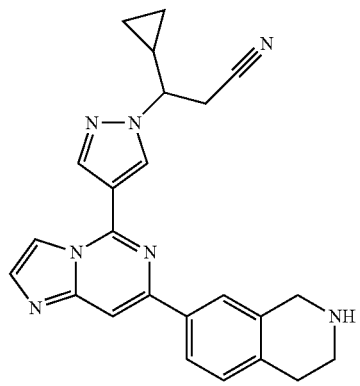 [SMILES: N#CCC(C1CC1)n1cc(-c2nc(-c3ccc4c(c3)CNCC4)cc3nccn23)cn1]

Prepared in the same manner as Example 52 replacing 2-(tert-butoxycarbonyl)-1,2,3,4-tetrahydroisoquinolin-6-ylboronic acid with 2-(tert-butoxycarbonyl)-1,2,3,4-tetrahydroisoquinolin-7-ylboronic acid to afford the title compound (20 mg, 31% yield). MS (apci) m/z=410.3 (M+H).

Example 55

3-Cyclopropyl-3-(4-(7-(2-methyl-1,2,3,4-tetrahydroisoquinolin-7-yl)imidazo[1,2-c]pyrimidin-5-yl)-1H-pyrazol-1-yl)propanenitrile

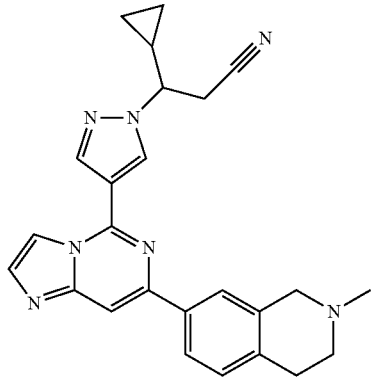 [SMILES: CN1CCc2ccc(-c3cc4nccn4c(-c4cnn(C(CC#N)C5CC5)c4)n3)cc2C1]

To 3-cyclopropyl-3-(4-(7-(1,2,3,4-tetrahydroisoquinolin-7-yl)imidazo[1,2-c]pyrimidin-5-yl)-1H-pyrazol-1-yl)propanenitrile (Example 54; 10 mg, 0.024 mmol) in DCM/MeOH (1 mL/1 mL) was added formaldehyde (49 mg, 0.49 mmol) and sodium triacetoxyborohydride (16 mg, 0.073 mmol). The reaction mixture was stirred at ambient temperature for 30 minutes and concentrated under reduced pressure. The residue was purified by silica gel chromatography (DCM/MeOH/NH$_4$OH 10:1:0.1) to give the final product (5.0 mg, 48% yield). MS (apci) m/z=424.3 (M+H).

Example 56

3-Cyclopropyl-3-(4-(7-(5,6,7,8-tetrahydroimidazo[1,2-a]pyrazin-3-yl)imidazo[1,2-c]pyrimidin-5-yl)-1H-pyrazol-1-yl)propanenitrile

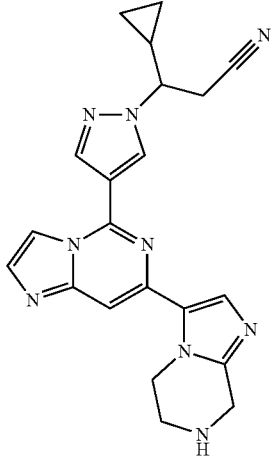 [SMILES: N#CCC(C1CC1)n1cc(-c2nc(-c3cnc4n3CCNC4)cc3nccn23)cn1]

To 3-(4-(7-chloroimidazo[1,2-c]pyrimidin-5-yl)-1H-pyrazol-1-yl)-3-cyclopropyl-propanenitrile (Preparation M; 100 mg, 0.320 mmol) in dioxane (10 mL) was added K$_2$CO$_3$ (88.4 mg, 0.639 mmol), diacetoxypalladium (7.18 mg, 0.0320 mmol), triphenylphosphine (16.8 mg, 0.0639 mmol) and tert-butyl 5,6-dihydroimidazo[1,2-a]pyrazine-7(8H)-carboxylate (107 mg, 0.480 mmol). The reaction was sealed and heated to 95° C. for 5 hours. The reaction was cooled to ambient temperature and concentrated under reduced pressure. The residue was purified by silica gel chromatography (DCM/MeOH/NH$_4$OH 10:1:0.1) to give the final product (33 mg, 26% yield). MS (apci) m/z=400.4 (M+H).

Example 57

3-cyclopropyl-3-(4-(7-(7-methyl-5,6,7,8-tetrahydroimidazo[1,2-a]pyrazin-3-yl)imidazo[1,2-c]pyrimidin-5-yl)-1H-pyrazol-1-yl)propanenitrile

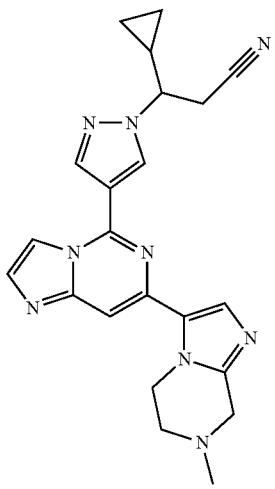 [SMILES: CN1CCn2c(-c3cc4nccn4c(-c4cnn(C(CC#N)C5CC5)c4)n3)cnc2C1]

To 3-cyclopropyl-3-(4-(7-(5,6,7,8-tetrahydroimidazo[1,2-a]pyrazin-3-yl)imidazo[1,2-c]pyrimidin-5-yl)-1H-pyrazol-1-yl)propanenitrile (Example 56; 10 mg, 0.025 mmol) in DCM/MeOH (1 mL/1 mL) was added formaldehyde (50 mg, 0.50 mmol) and sodium triacetoxyborohydride (16 mg, 0.075 mmol). The reaction mixture was stirred at ambient temperature for 30 minutes and concentrated under reduced pressure. The residue was purified by silica gel chromatography (DCM/MeOH/NH₄OH 10:1:0.1) to give the final product (5.0 mg, 48% yield). MS (apci) m/z=414.4 (M+H).

Example 58

3-(4-(7-(4-(8-Oxa-3-azabicyclo[3.2.1]octan-3-yl)phenyl)imidazo[1,2-c]pyrimidin-5-yl)-1H-pyrazol-1-yl)-3-cyclopropylpropanenitrile

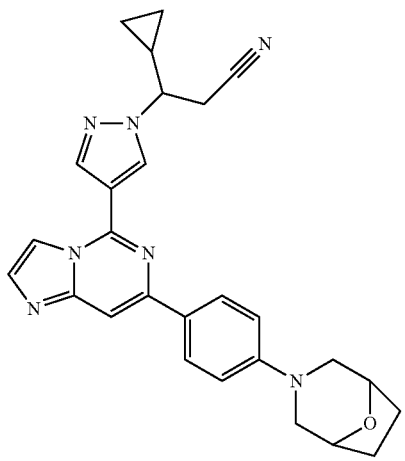 [SMILES: N#CCC(C1CC1)n1cc(-c2nc(-c3ccc(N4CC5CCC(C4)O5)cc3)cc3nccn23)cn1]

Step A: Preparation of 3-(4-(5-(1-((2-(trimethylsilyl)ethoxy)methyl)-1H-pyrazol-4-yl)imidazo[1,2-c]pyrimidin-7-yl)phenyl)-8-oxa-3-azabicyclo[3.2.1]octane To a flask charged with 7-(4-bromophenyl)-5-(1-((2-(trimethylsilyl)ethoxy)methyl)-1H-pyrazol-4-yl)imidazo[1,2-c]pyrimidine (Preparation L; 0.250 g, 0.531 mmol), 8-oxa-3-azabicyclo[3.2.1]octane (0.430 g, 3.80 mmol), and potassium 2-methylpropan-2-olate (0.119 g, 1.06 mmol) was added 6 mL of THF at ambient temperature with stirring. Argon was bubbled through the reaction for 10 minutes before dicyclohexyl(2',6'-dimethoxybiphenyl-2-yl)phosphine (0.0436 g, 0.106 mmol) and tris(dibenzylideneacetone)dipalladium (0.0487 g, 0.0531 mmol) were added. Argon was bubbled through the reaction for 15 minutes before the reaction was sealed and allowed to proceed at 40° C. for 4 hours. The reaction was charged with more tris(dibenzylideneacetone)dipalladium (0.0487 g, 0.0531 mmol) and purged with argon for 5 minutes before it was sealed and allowed to proceed at 40° C. for 7 hours. The reaction mixture was diluted with DCM and aqueous saturated sodium bicarbonate (2 mL) and stirred for 30 minutes. The layers were separated and the organic layer was dried over MgSO₄, filtered, and concentrated under reduced pressure. The crude residue was purified by silica gel chromatography eluting with 1% methanol in DCM to afford 3-(4-(5-(1-((2-(trimethylsilyl)ethoxy)methyl)-1H-pyrazol-4-yl)imidazo[1,2-c]pyrimidin-7-yl)phenyl)-8-oxa-3-azabicyclo[3.2.1]octane (0.133 g, 0.265 mmol, 49.0% yield). MS (apci) m/z=503.2 (M+H).

Step B: Preparation of 3-(4-(7-(4-(8-oxa-3-azabicyclo[3.2.1]octan-3-yl)phenyl)imidazo[1,2-c]pyrimidin-5-yl)-1H-pyrazol-1-yl)-3-cyclopropylpropanenitrile Prepared in the same manner as Example 34 Steps B and C replacing 7-(1-isopropyl-1H-pyrazol-4-yl)-5-(1-((2-(trimethylsilyl)ethoxy)methyl)-1H-pyrazol-4-yl)imidazo[1,2-c]pyrimidine with 3-(4-(5-(1-((2-(trimethylsilyl)ethoxy)methyl)-1H-pyrazol-4-yl)imidazo[1,2-c]pyrimidin-7-yl)phenyl)-8-oxa-3-azabicyclo[3.2.1]octane to afford the title compound (0.042 g, 0.08751 mmol, 52% yield) MS (apci) m/z=466.2 (M+H).

Example 59

3-Cyclopropyl-3-(4-(7-(4-(4-methylpiperazin-1-yl)phenyl)imidazo[1,2-c]pyrimidin-5-yl)-1H-pyrazol-1-yl)propanenitrile

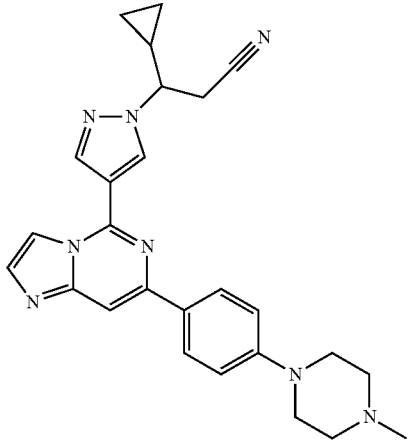 [SMILES: CN1CCN(c2ccc(-c3cc4nccn4c(-c4cnn(C(CC#N)C5CC5)c4)n3)cc2)CC1]

Prepared in the same manner as Example 58 Steps A to C replacing 8-oxa-3-azabicyclo[3.2.1]octane in Step A with 1-methylpiperazine to afford the title compound (0.030 g, 0.06298 mmol, 44% yield). MS (apci) m/z=453.2 (M+H).

Example 60

3-Cyclopropyl-3 (4 (7 (4 (1 methyl-1H-pyrazol-4-yl)phenyl)imidazo[1,2-c]pyrimidin-5-yl)-1H-pyrazol-1-yl)propanenitrile

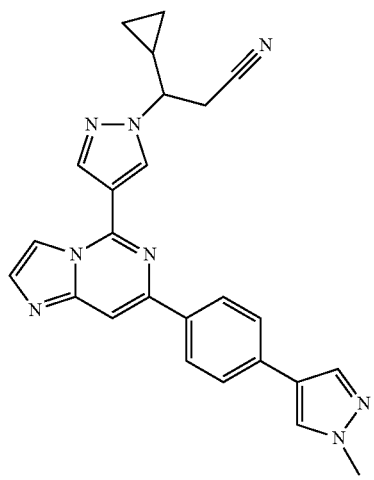 [SMILES: Cn1cc(-c2ccc(-c3cc4nccn4c(-c4cnn(C(CC#N)C5CC5)c4)n3)cc2)cn1]

Step A: Preparation of 7-(4-(1-methyl-1H-pyrazol-4-yl)phenyl)-5-(1-((2-(trimethylsilyl)ethoxy)methyl)-1H-pyrazol-4-yl)imidazo[1,2-c]pyrimidine A flask charged with 7-(4-bromophenyl)-5-(1-((2-(trimethylsilyl)ethoxy)methyl)-1H-pyrazol-4-yl)imidazo[1,2-c]pyrimidine (Preparation L; 0.200 g, 0.425 mmol), 1-methyl-4-(4,4,5,5-tetramethyl-1,3,2-dioxaborolan-2-yl)-1H-pyrazole (0.195 g, 0.935 mmol), potassium phosphate (0.271 g, 1.28 mmol), dicyclohexyl(2',4',6'-triisopropylbiphenyl-2-yl)phosphine (0.0507 g, 0.106 mmol), and tris(dibenzylideneacetone)dipalladium (0.0389 g, 0.0425 mmol) was evacuated and backfilled with argon. To the reaction was added 4 mL of isopropanol (degassed with argon for 30 minutes) and water (0.0460 mL, 2.55 mmol). The reaction was sealed and allowed to proceed at 100° C. for 4 hours. The reaction was then diluted with DCM (100 mL), dried over MgSO$_4$, filtered, and concentrated under reduced pressure. The resulting crude was then purified by means of silica gel chromatography eluting with a linear gradient of 1-5% methanol in DCM to afford 7-(4-(1-methyl-1H-pyrazol-4-yl)phenyl)-5-(1-((2-(trimethylsilyl)ethoxy)methyl)-1H-pyrazol-4-yl)imidazo[1,2-c]pyrimidine (0.174 g, 0.365 mmol, 85.9% yield). MS (apci) m/z=472.2 (M+H).

Step B: Preparation of 3-cyclopropyl-3-(4-(7-(4-(1-methyl-1H-pyrazol-4-yl)phenyl)imidazo[1,2-c]pyrimidin-5-yl)-1H-pyrazol-1-yl)propanenitrile Prepared in the same manner as Example 34 Steps B and C, replacing 7-(1-isopropyl-1H-pyrazol-4-yl)-5-(1-((2-(trimethylsilyl)ethoxy)methyl)-1H-pyrazol-4-yl)imidazo[1,2-c]pyrimidine with 7-(4-(1-methyl-1H-pyrazol-4-yl)phenyl)-5-(1-((2-(trimethylsilyl)ethoxy)methyl)-1H-pyrazol-4-yl)imidazo[1,2-c]pyrimidine to afford the title compound (0.036 g, 0.08120 mmol; 73% yield). MS (apci) m/z=435.2 (M+H).

Example 61

Tert-butyl 3-(cyanomethyl)-3-(4-(7-(1-methyl-1H-pyrazol-4-yl)imidazo[1,2-c]pyrimidin-5-yl)-1H-pyrazol-1-yl)azetidine-1-carboxylate

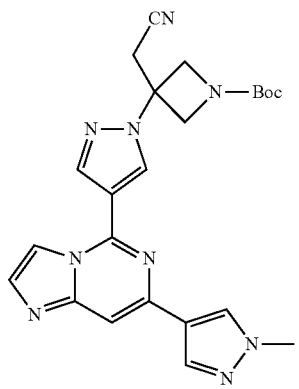 [SMILES: Cn1cc(-c2cc3nccn3c(-c3cnn(C4(CC#N)CN(C(=O)OC(C)(C)C)C4)c3)n2)cn1]

In a 5 L 4-necked flask with an overhead mechanical stirrer was added 5-chloro-7-(1-methyl-1H-pyrazol-4-yl)imidazo[1,2-c]pyrimidine (Preparation J; 34.83 g, 149.1 mmol), tert-butyl 3-(cyanomethyl)-3-(4-(4,4,5,5-tetramethyl-1,3,2-dioxaborolan-2-yl)-1H-Pyrazol-1-yl)azetidine-1-carboxylate (Preparation F; 86.82 g, 223.6 mmol), and K$_3$PO$_4$ (94.92 g, 447.2 mmol) by powder funnel. Dioxane (745.3 mL, 149.1 mmol) was added to rinse down funnel. Pd(PPh$_3$)$_4$ (17.23 g, 14.91 mmol) was added, followed by 74.5 mL of water. The reaction mixture was slowly heated to 70° C. as measured by an internal temperature probe. After heating for 6 hours, the reaction mixture was cooled to ambient temperature. The reaction mixture was diluted in EtOAc (500 mL) and water (100 mL), and then the resultant solids were filtered out. The solids were washed with EtOAc (2×500 mL) to afford a grey-white solid, which was re-introduced back to the 5 L 4-neck flask and diluted with 1 L of water and 300 mL of EtOAc. This was stirred for 3 hours, and then the solids were isolated by filtration. After washing with EtOAc (2×500 mL), the solids were dried to afford tert-butyl 3-(cyanomethyl)-3-(4-(7-(1-methyl-1H-pyrazol-4-yl)imidazo[1,2-c]pyrimidin-5-yl)-1H-pyrazol-1-yl)azetidine-1-carboxylate (60.83 g, 132.4 mmol, 88.81% yield). MS (apci) m/z=460.1 (M+H).

Example 62

2-(3-(4-(7-(1-Methyl-1H-pyrazol-4-yl)imidazo[1,2-c]pyrimidin-5-yl)-1H-pyrazol-1-yl)azetidin-3-yl)acetonitrile hydrochloride

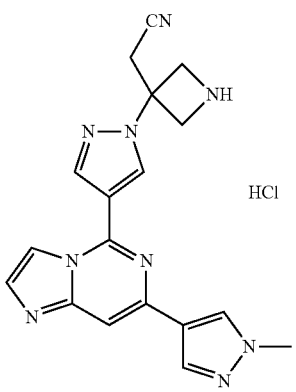 [SMILES: Cn1cc(-c2cc3nccn3c(-c3cnn(C4(CC#N)CNC4)c3)n2)cn1 ; Cl]

A 5 L 4-neck flask was equipped with an overhead stirrer and purged with N$_2$. To this was added tert-butyl 3-(cyanomethyl)-3-(4-(7-(1-methyl-1H-pyrazol-4-yl)imidazo[1,2-c]pyrimidin-5-yl)-1H-pyrazol-1-yl)azetidine-1-carboxylate (Example 61; 60.83 g, 132.4 mmol) and dioxane (661.9 mL, 132.4 mmol) and the flask was placed in a cool water bath. 4N HCl in dioxane (661.9 mL, 2648 mmol) was added in a fast stream. An additional 50 mL of dioxane was added to wash down the sides. The reaction stalled after 2 hours, so another 140 mL of HCl in dioxane was added. After 4 hours, another 50 mL of HCl in dioxane was added to drive to completion. The solids were filtered, washed with dioxane, and then washed with Et$_2$O. The resultant solids were dried under high vacuum to afford 76 g (77% by weight, 103% yield) of the title compound as a powdery white solid. MS (apci) m/z=360.2 (M+H).

Example 63

2-(1-Acetyl-3-(4-(7-(1-methyl-1H-pyrazol-4-yl)imidazo[1,2-c]pyrimidin-5-yl)-1H-pyrazol-1-yl)azetidin-3-yl)acetonitrile

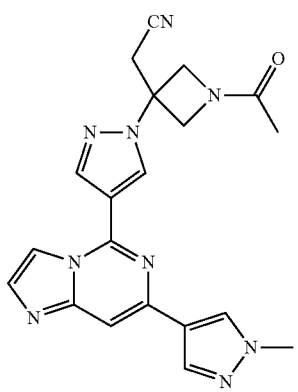 [SMILES: CC(=O)N1CC(CC#N)(n2cc(-c3nc(-c4cnn(C)c4)cc4nccn34)cn2)C1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 20 mg, 0.046 mmol) in THF (460 µL, 0.046 mmol) was added triethylamine (19 µL, 0.14 mmol) and acetic anhydride (5.7 mg, 0.056 mmol). After stirring at ambient temperature for 30 minutes, the reaction mixture was diluted in water. The reaction mixture was directly purified by reverse phase HPLC using a 0-100% acetonitrile/water gradient to afford 2-(1-acetyl-3-(4-(7-(1-methyl-1H-pyrazol-4-yl)imidazo[1,2-c]pyrimidin-5-yl)-1H-pyrazol-1-yl)azetidin-3-yl)acetonitrile (15 mg, 0.038 mmol, 82% yield) as a fluffy white solid. MS (apci) m/z=402.2 (M+H).

Example 64

2-(3-(4-(7-(1-Methyl-1H-pyrazol-4-yl)imidazo[1,2-c]pyrimidin-5-yl)-1H-pyrazol-1-yl)-1-(3,3,3-trifluoropropanoyl)azetidin-3-yl)acetonitrile

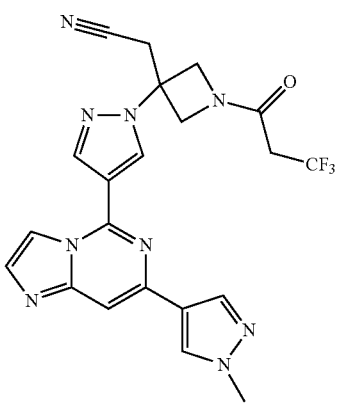 [SMILES: Cn1cc(-c2cc3nccn3c(-c3cnn(C4(CC#N)CN(C(=O)CC(F)(F)F)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62, 50.0 mg, 0.116 mmol) and HATU (52.8, 0.139 mmol) in dry DMF (0.50 mL) was added 3,3,3-trifluoropropanoic acid (19.3 mg, 0.150 mmol) and the mixture was stirred at ambient temperature for 2 minutes. DIEA (80.6 µL, 0.463 mmol) was added and the resulting homogeneous solution was stirred at ambient temperature for 18 hours. The reaction mixture was added to $H_2O$ (5.0 mL) and extracted with EtOAc. The combined extracts were washed with $H_2O$, saturated aqueous $NaHCO_3$ and dried over $MgSO_4$. The solution was eluted through a silica gel column eluting with EtOAc then with 10% MeOH/EtOAc. The 10% MeOH/EtOAc pool was concentrated to give the title compound (32 mg, 59% yield) as a white solid. MS (apci) m/z=470.2 (M+H).

Example 65

2-(3-(4-(7-(1-Methyl-1H-pyrazol-4-yl)imidazo[1,2-c]pyrimidin-5-yl)-1H-pyrazol-1-yl)-1-(1-(trifluoromethyl)cyclopropanecarbonyl)azetidin-3-yl)acetonitrile

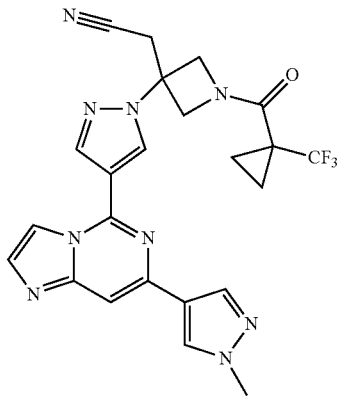 [SMILES: Cn1cc(-c2cc3nccn3c(-c3cnn(C4(CC#N)CN(C(=O)C5(C(F)(F)F)CC5)C4)c3)n2)cn1]

The title compound was prepared according to the method of Example 64, replacing 3,3,3-trifluoropropanoic acid with 1-(trifluoromethyl)cyclopropane carboxylic acid. The compound was obtained as a white solid (25 mg, 44% yield). MS (apci) m/z=496.3 (M+H).

Example 66

2-(1-Cyclopropyl-3-(4-(7-(1-methyl-1H-pyrazol-4-yl)imidazo[1,2-c]pyrimidin-5-yl)-1H-pyrazol-1-yl)azetidin-3-yl)acetonitrile

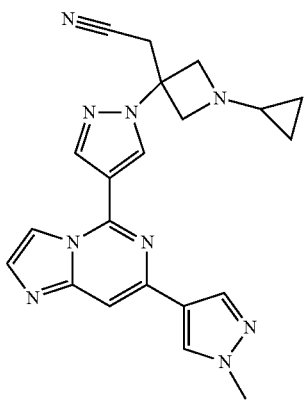 [SMILES: Cn1cc(-c2cc3nccn3c(-c3cnn(C4(CC#N)CN(C5CC5)C4)c3)n2)cn1]

To a fine suspension of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62, 50.2 mg, 0.107 mmol) in 2:1 MeOH/acetic acid (0.60 mL) was added (1-ethoxycyclopropoxy)trimethylsilane (94.2 mg, 0.535 mmol) and the mixture was stirred at ambient temperature for 5 minutes. Sodium cyanoborohydride (42.5 mg, 0.642 mmol) was added in one portion and the mixture was stirred at 50° C. for 3 hours. The mixture was cooled to ambient temperature and concentrated to dryness. The residual white solid was partitioned into DCM and 1M $K_2CO_3$ (3 mL each) and the mixture was stirred until both layers were homogeneous. The DCM layer was removed and the aqueous layer was extracted with DCM. The combined DCM extracts were dried over $Na_2SO_4$, filtered through a Celite pad and concentrated to give a colorless glass. The glass was purified on a silica gel column eluting with a step gradient of EtOAc, 5% MeOH/EtOAc, and 10% MeOH/EtOAc to furnish the title compound (35 mg, 82% yield) as a white solid. MS (apci) m/z=400.2 (M+H).

Example 67

2-(3-(4-(7-(1-Methyl-1H-pyrazol-4-yl)imidazo[1,2-c]pyrimidin-5-yl)-1H-pyrazol-1-yl)-1-(oxetan-3-yl)azetidin-3-yl)acetonitrile

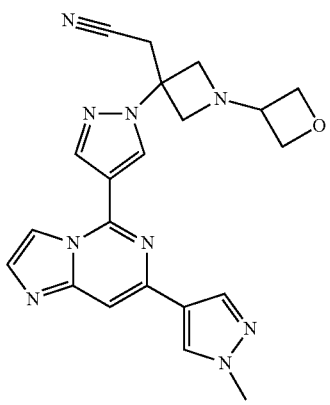 [SMILES: Cn1cc(-c2cc3nccn3c(-c3cnn(C4(CC#N)CN(C5COC5)C4)c3)n2)cn1]

To a suspension of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62, 78.4 mg, 0.181 mmol) in dry MeOH (1.0 mL) was sequentially added 3-oxetanone (39.2 mg, 0.544 mmol) and acetic acid (0.30 mL). The mixture was stirred at ambient temperature for 5 minutes and sodium cyanoborohydride (72.0 mg, 1.29 mmol) was added slowly in portions over 5 minutes. The mixture was stirred at ambient temperature for 16 hours and additional 3-oxetanone (2.0 equivalents) was added. Stirring was continued for 4 hours and the mixture concentrated to dryness. The residual solids were partitioned into DCM and 1M $K_2CO_3$ (3 mL each) and 1M NaOH was added to adjust the pH to 13. The mixture was stirred until both layers were homogeneous, the DCM layer was removed and the aqueous layer was extracted with DCM. The DCM extracts were combined and dried over $Na_2SO_4$. The solution was eluted through a silica gel plug eluting with DCM, 10% MeOH/EtOAc, and then 20% (9:1 MeOH/$NH_4OH$)/EtOAc. The 20% pool was concentrated to give a colorless glass. The glass was dissolved in minimal DCM and treated with hexanes to give a granular white precipitate. The suspension was concentrated to afford the title compound (54 mg, 72% yield) as a white solid. MS (apci) m/z=416.2 (M+H).

Example 68

2-(3-(4-(7-(1-Methyl-1H-pyrazol-4-yl)imidazo[1,2-c]pyrimidin-5-yl)-1H-pyrazol-1-yl)-1-(pyrimidin-2-yl)azetidin-3-yl)acetonitrile

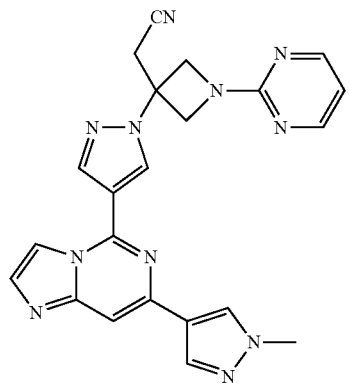 [SMILES: Cn1cc(-c2cc3nccn3c(-c3cnn(C4(CC#N)CN(c5ncccn5)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 30 mg, 0.069 mmol) in acetonitrile (690 μL, 0.069 mmol) was added $K_2CO_3$ (38 mg, 0.28 mmol) and 2-bromopyrimidine (12 mg, 0.076 mmol). The reaction mixture was heated to 45° C. for 3 days. After diluting in EtOAc, the mixture was washed with water and brine. The organic layer was dried with $MgSO_4$, filtered and concentrated in vacuo to a clear colorless oil. The oil was purified by reverse phase HPLC using 0-100% acetonitrile/water gradient to afford 2-(3-(4-(7-(1-methyl-1H-pyrazol-4-yl)imidazo[1,2-c]pyrimidin-5-yl)-1H-pyrazol-1-yl)-1-(pyrimidin-2-yl)azetidin-3-yl)acetonitrile (6.1 mg, 20% yield) as a white solid. MS (apci) m/z=438.2 (M+H).

Example 69

2-(1-(2,2-dDifluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile

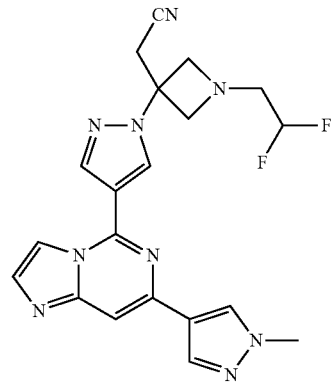 [SMILES: Cn1cc(-c2cc3nccn3c(-c3cnn(C4(CC#N)CN(CC(F)F)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 30.0 mg, 0.0694 mmol) in acetonitrile (694 µL, 0.0694 mmol) was added K$_2$CO$_3$ (38.4 mg, 0.278 mmol) and 2,2-difluoroethyl trifluoromethanesulfonate (29.7 mg, 0.139 mmol). After heating to 45° C. for 2 hours, the reaction was incomplete and another portion of 2,2-difluoroethyl trifluoromethanesulfonate (20.0 mg, 0.0936 mmol) was added to drive to completion. Purification of the crude reaction mixture by reverse phase HPLC afforded 2-(1-(2,2-difluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile (13.2 mg, 45% yield). MS (apci) m/z=424.2 (M+1-1).

Example 70

2-(3-(4-(7-(1-Methyl-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile

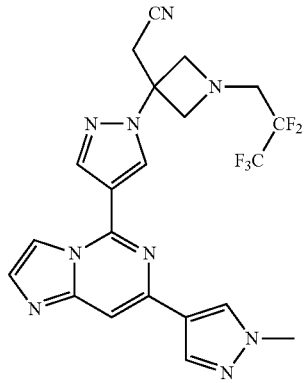 [SMILES: Cn1cc(-c2cc3nccn3c(-c3cnn(C4(CC#N)CN(CC(F)(F)C(F)(F)F)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 30.0 mg, 0.0694 mmol) in acetonitrile (694 µL, 0.0694 mmol) was added triethylamine (38.7 µL, 0.278 mmol) and 2,2,3,3,3-pentafluoropropyl trifluoromethanesulfonate (39.1 mg, 0.139 mmol). The reaction mixture was heated to 45° C. for 2 hours. The crude reaction mixture was purified by reverse phase HPLC to afford 2-(3-(4-(7-(1-methyl-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile (2.0 mg, 5.9% yield). MS (apci) m/z=492.2 (M+H).

Example 71

2-(3-(4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile

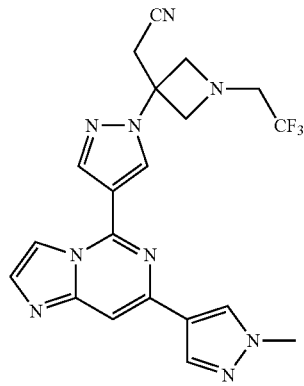 [SMILES: Cn1cc(-c2cc3nccn3c(-c3cnn(C4(CC#N)CN(CC(F)(F)F)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 50 mg, 0.12 mmol) in acetonitrile (1.2 mL, 0.12 mmol) was added K$_2$CO$_3$ (48 mg, 0.35 mmol) and 2,2,2-trifluoroethyl trifluoromethanesulfonate (30 mg, 0.13 mmol). The reaction mixture was heated to 45° C. for 15 hours, then cooled. After diluting in water, the mixture was extracted with EtOAc. The combined organic layers were dried over MgSO$_4$, filtered and concentrated in vacuo. Purification of the crude material by reverse phase HPLC using a 0-100% acetonitrile/water gradient afforded 2-(3-(4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile (24 mg, 48.0% yield). MS (apci) m/z=442.2 (M+H).

The compounds of Table 7 were prepared according to the method of Example 71 (alkylation) using the appropriate starting materials.

TABLE 7

| Ex. # | Structure | Name | MS |
|---|---|---|---|
| 72 | 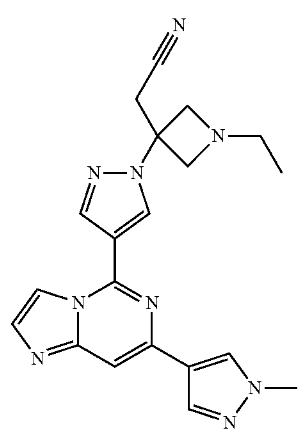 [SMILES: CCN1CC(CC#N)(n2cc(-c3nc(-c4cnn(C)c4)cc4nccn34)cn2)C1] | 2-(1-ethyl-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 388.2 (M + H) |

TABLE 7-continued

| Ex. # | Structure | Name | MS |
|---|---|---|---|
| 73 | 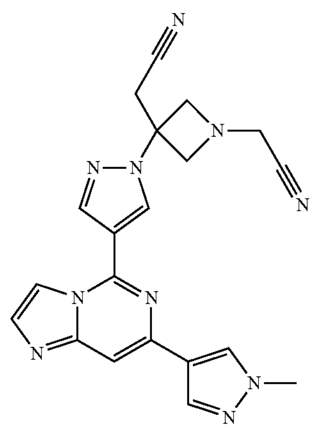 [SMILES: Cn1cc(-c2cc3nccn3c(-c3cnn(C4(CC#N)CN(CC#N)C4)c3)n2)cn1] | 2,2'-(3-(4-(7-(1-methyl-1H-pyrazol-4-yl)imidazo[1,2-c]pyrimidin-5-yl)-1H-pyrazol-1-yl)azetidine-1,3-diyl)diacetonitrile | (apci) m/z = 399.5 (M + H) |
| 74 | 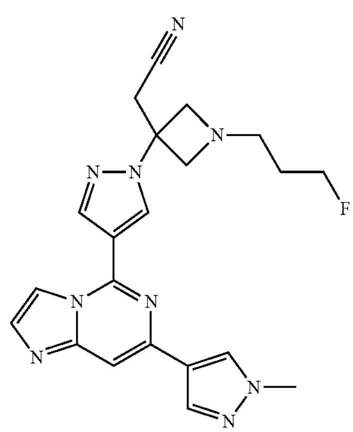 [SMILES: Cn1cc(-c2cc3nccn3c(-c3cnn(C4(CC#N)CN(CCCF)C4)c3)n2)cn1] | 2-(1-(3-fluoropropyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 420.2 (M + H) |
| 75 | 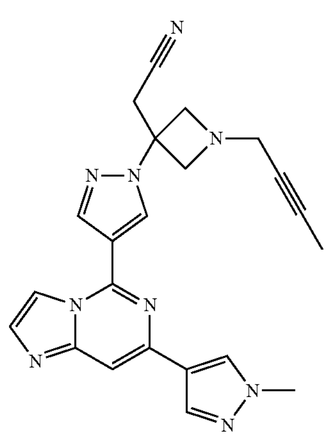 [SMILES: CC#CCN1CC(CC#N)(n2cc(-c3nc(-c4cnn(C)c4)cc4nccn34)cn2)C1] | 2-(1-(but-2-ynyl)-3-(4-(7-(1-methyl-1H-pyrazol-4-yl)imidazo[1,2-c]pyrimidin-5-yl)-1H-pyrdzol-1-yl)azetidin-3-yl)acetonitrile | (apci) m/z = 412.2 (M + H) |

TABLE 7-continued

| Ex. # | Structure | Name | MS |
|---|---|---|---|
| 76 | 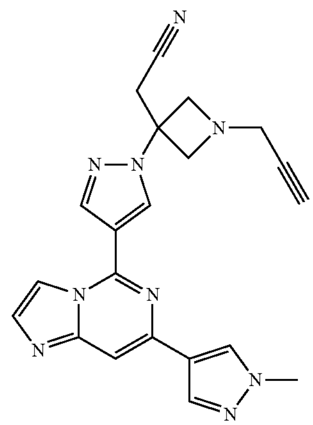 [SMILES: C#CCN1CC(CC#N)(n2cc(-c3nc(-c4cnn(C)c4)cc4nccn34)cn2)C1] | 2-(3-(4-(7-(1-methyl-1H-pyrazol-4-yl)imidazo[1,2-c]pyrimidin-5-yl)-1H-pyrazol-1-yl)-1-(prop-2-ynyl)azetidin-3-yl)acetonitrile | (apci) m/z = 398.2 (M + H) |
| 77 | 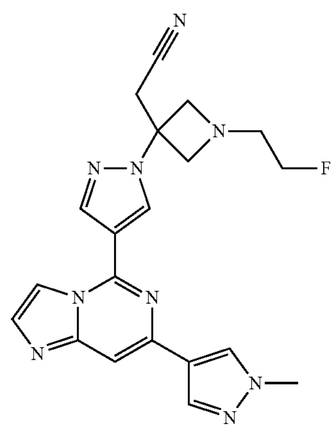 [SMILES: Cn1cc(-c2cc3nccn3c(-c3cnn(C4(CC#N)CN(CCF)C4)c3)n2)cn1] | 2-(1-(2-fluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 406.2 (M + H) |
| 78 | 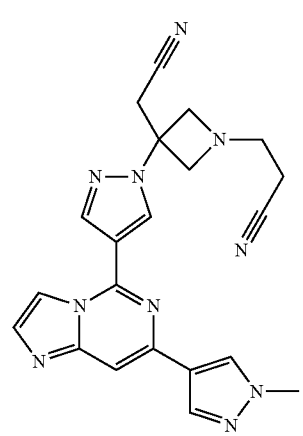 [SMILES: Cn1cc(-c2cc3nccn3c(-c3cnn(C4(CC#N)CN(CCC#N)C4)c3)n2)cn1] | 3-(3-(cyanomethyl)-3-(4-(7-(1-methyl-1H-pyrazol-4-yl)imidazo[1,2-c]pyrimidin-5-yl)-1H-pyrazol-1-yl)azetidin-1-yl)propanenitrile | (apci) m/z = 413.2 (M + H) |

TABLE 7-continued

| Ex. # | Structure | Name | MS |
|---|---|---|---|
| 79 | 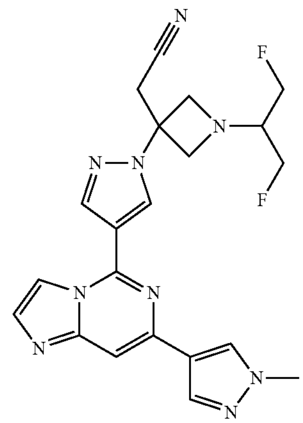 [SMILES: Cn1cc(-c2cc3nccn3c(-c3cnn(C4(CC#N)CN(C(CF)CF)C4)c3)n2)cn1] | 2-(1-(1,3-difluoropropan-2-yl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 438.3 (M + H) |
| 80 | 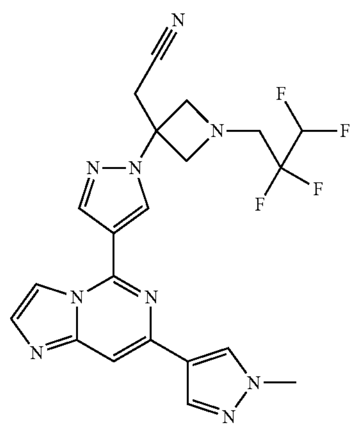 [SMILES: Cn1cc(-c2cc3nccn3c(-c3cnn(C4(CC#N)CN(CC(F)(F)C(F)F)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(2,2,3,3-tetrafluoropropyl)azetidin-3-yl)acetonitrile | (apci) m/z = 474.2 (M + H) |

Example 81

2-(3-(4-(7-(1-methyl-1H-pyrazol-4-yl)imidazo[1,2-c]pyrimidin-5-yl)-1H-pyrazol-1-yl)-1-propylazetidin-3-yl)acetonitrile

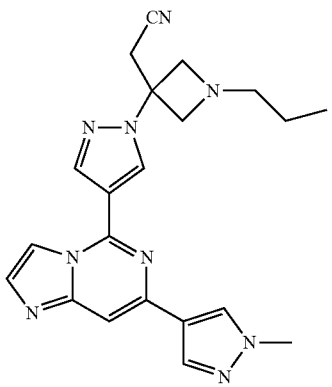 [SMILES: CCCN1CC(CC#N)(n2cc(-c3nc(-c4cnn(C)c4)cc4nccn34)cn2)C1]

In a 2 mL flask, 2-(3-(4-(7-(1-methyl-1H-pyrazol-4-yl)imidazo[1,2-c]pyrimidin-5-yl)-1H-pyrazol-1-yl)azetidin-3-yl)acetonitrile hydrochloride (Example 62; 15 mg, 0.035 mmol) was suspended in acetonitrile (350 µL, 0.035 mmol). To this was added triethylamine (19 µL, 0.14 mmol), followed by propionaldehyde (25 µL, 0.35 mmol). After stirring for 30 minutes, NaBH(OAc)₃ (37 mg, 0.17 mmol) was added. After the reaction was complete, it was quenched with saturated bicarbonate solution and extracted with EtOAc. The organic layer was washed with brine, dried with MgSO₄, filtered and concentrated in vacuo. The residue was purified by reverse phase HPLC using a 0-100% acetonitrile/water gradient to afford 2-(3-(4-(7-(1-methyl-1H-pyrazol-4-yl)imidazo-[1,2-c]pyrimidin-5-yl)-1H-pyrazol-1-yl)-1-propylazetidin-3-yl)acetonitrile (7.1 mg, 51% yield) as a white solid. MS (apci) m/z=402.2 (M+H).

The compounds of Table 8 were prepared according to the method of Example 81 (reductive amination) using the appropriate starting materials.

TABLE 8

| Ex. # | Structure | Name | MS |
|---|---|---|---|
| 82 | 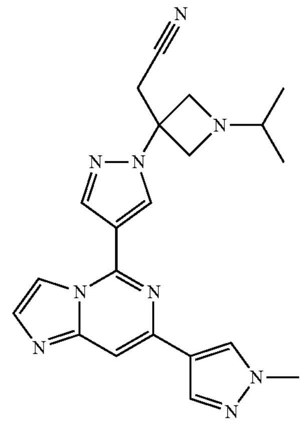 [SMILES: CC(C)N1CC(CC#N)(n2cc(-c3nc(-c4cnn(C)c4)cc4nccn34)cn2)C1] | 2-(1-isopropyl-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 402.2 (M + H) |
| 83 | 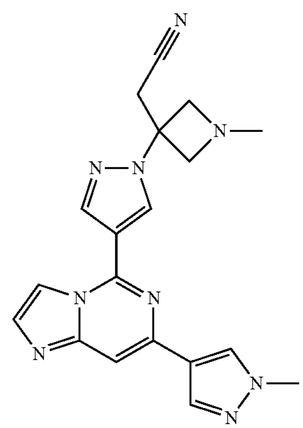 [SMILES: CN1CC(CC#N)(n2cc(-c3nc(-c4cnn(C)c4)cc4nccn34)cn2)C1] | 2-(1-methyl-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 374.2 (M + H) |
| 84 | 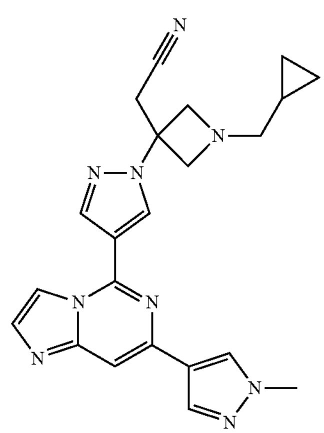 [SMILES: Cn1cc(-c2cc3nccn3c(-c3cnn(C4(CC#N)CN(CC5CC5)C4)c3)n2)cn1] | 2-(1-(cyclopropylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 414.2 (M + H) |

TABLE 8-continued

| Ex. # | Structure | Name | MS |
|---|---|---|---|
| 85 | 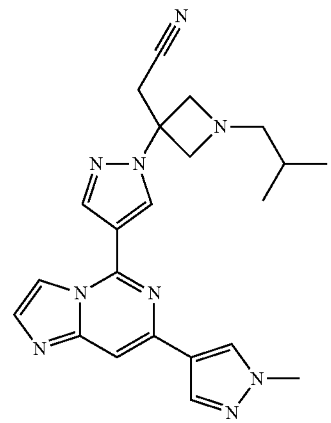 [SMILES: CC(C)CN1CC(CC#N)(n2cc(-c3nc(-c4cnn(C)c4)cc4nccn34)cn2)C1] | 2-(1-isobutyl-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 416.2 (M + H) |
| 86 | 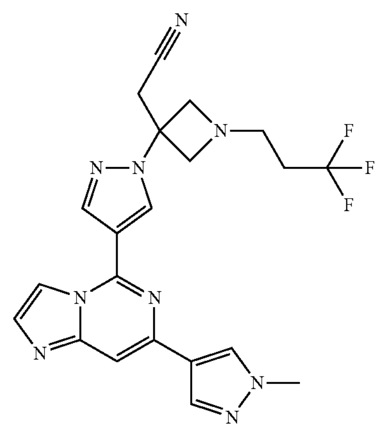 [SMILES: Cn1cc(-c2cc3nccn3c(-c3cnn(C4(CC#N)CN(CCC(F)(F)F)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(3,3,3-trifluoropropyl)azetidin-3-yl)acetonitrile | (apci) m/z = 456.2 (M + H) |
| 87 | 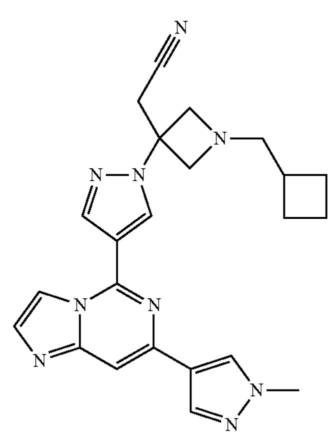 [SMILES: Cn1cc(-c2cc3nccn3c(-c3cnn(C4(CC#N)CN(CC5CCC5)C4)c3)n2)cn1] | 2-(1-(cyclobutylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 428.2 (M + H) |

TABLE 8-continued

| Ex. # | Structure | Name | MS |
|---|---|---|---|
| 88 | 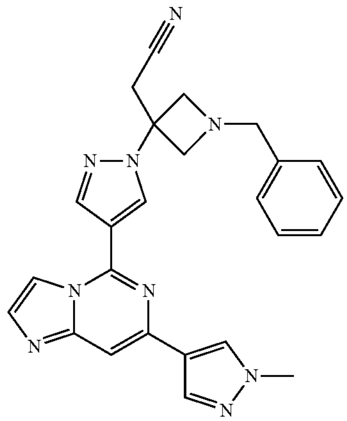 [SMILES: Cn1cc(-c2cc3nccn3c(-c3cnn(C4(CC#N)CN(Cc5ccccc5)C4)c3)n2)cn1] | 2-(1-benzyl-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 450.2 (M + H) |
| 89 | 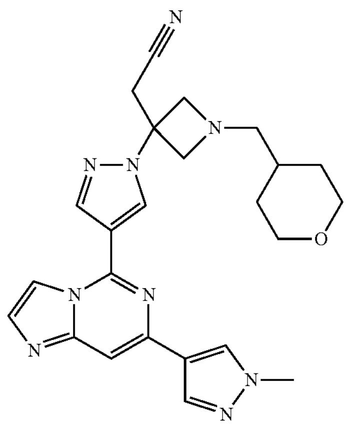 [SMILES: Cn1cc(-c2cc3nccn3c(-c3cnn(C4(CC#N)CN(CC5CCOCC5)C4)c3)n2)cn1] | 2-(3-(4-(7-(1-methyl-1H-pyrazol-4-yl)imidazo[1,2-c]pyrimidin-5-yl)-1H-pyrazol-1-yl)-1-((tetrahydro-2H-pyran-4-yl)methyl)azetidin-3-yl)acetonitrile | (apci) m/z = 458.3 (M + H) |

Example 90

2-(3-(4-(3-Chloro-7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile

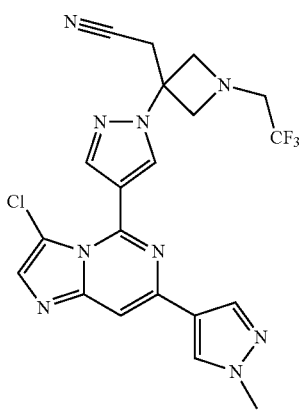 [SMILES: Cn1cc(-c2cc3ncc(Cl)n3c(-c3cnn(C4(CC#N)CN(CC(F)(F)F)C4)c3)n2)cn1]

To a solution of 2-(3-(4-(7-(1-methyl-1H-pyrazol-4-yl)imidazo[1,2-c]pyrimidin-5-yl)-1H-pyrazol-1-yl)-1-(2,2,2-trifluoro ethyl)azetidin-3-yl)acetonitrile (Example 71, 100 mg, 0.227 mmol) in DCM (1.5 mL) was added saturated NaHCO₃ (1.0 mL) followed by N-chlorosuccinimide (46.3 mg, 0.340 mmol) in one portion. The biphasic mixture was vigorously stirred at ambient temperature for 17 hours and was diluted with DCM (2 mL). The solution was washed with H₂O, dried over Na₂SO₄ and eluted through a silica gel plug (EtOAc elution). The solution was concentrated, the residual glass was dissolved in minimal DCM and hexane was added to afford a granular suspension. The suspension was concentrated and the residual solid was washed with warm 25% EtOAc/hexanes and dried in vacuum to afford the title compound (22 mg, 20% yield) as an ivory white powder. MS (apci) m/z=476.1 (M+H).

Example 91

2-(1-(Isopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile

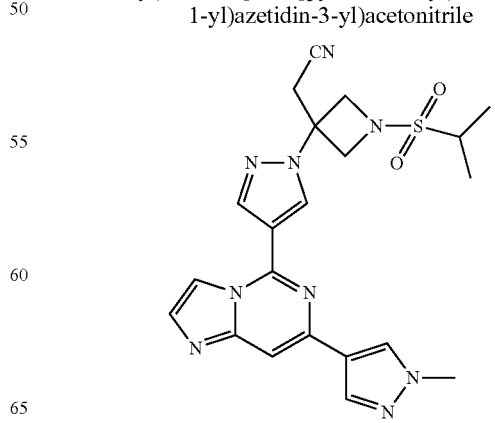

2-(3-(4-(7-(1-Methyl-1H-pyrazol-4-yl)imidazo[1,2-c]pyrimidin-5-yl)-1H-pyrazol-1-yl)azetidin-3-yl)acetonitrile hydrochloride (Example 62; 7.1 mg, 0.016 mmol) was suspended in DCM (90 µL, 0.018 mmol) and cooled in an ice bath. To this was added triethylamine (7.5 µL, 0.054 mmol) followed by propane-2-sulfonyl chloride (2.7 mg, 0.019 mmol). The reaction mixture was allowed to warm to ambient temperature. After 15 hours, the reaction mixture was diluted in EtOAc and washed with water and brine. The organic layer was dried with MgSO$_4$, filtered and concentrated down to afford 2-(1-(isopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile (4.8 mg, 0.010 mmol, 58% yield) as a light yellow oil. MS (apci) m/z=466.6 (M+H).

The compounds of Table 9 were prepared according to the method of Example 91 using the appropriate starting materials.

TABLE 9

| Ex. # | Structure | Name | MS |
|---|---|---|---|
| 92 | 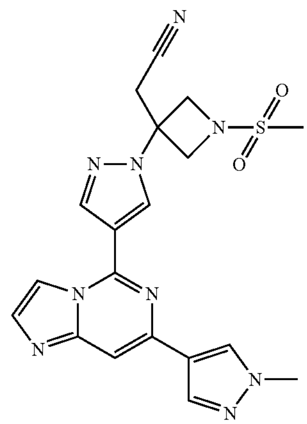 [SMILES: Cn1cc(-c2cc3nccn3c(-c3cnn(C4(CC#N)CN(S(C)(=O)=O)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(methylsulfonyl)azetidin-3-yl)acetonitrile | (apci) m/z = 438.2 (M + H) |
| 93 | 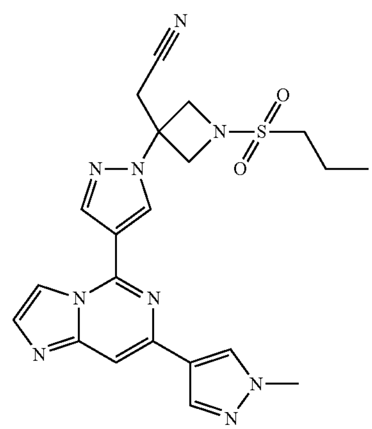 [SMILES: CCCS(=O)(=O)N1CC(CC#N)(n2cc(-c3nc(-c4cnn(C)c4)cc4nccn34)cn2)C1] | 2-(3-(4-(7-(1-methyl-1H-pyrazol-4-yl)imidazo[1,2-c]pyrimidin-5-yl)-1H-pyrazol-1-yl)-1-(propylsulfonyl)azetidin-3-yl)acetonitrile | (apci) m/z = 466.2 (M + H) |
| 94 | 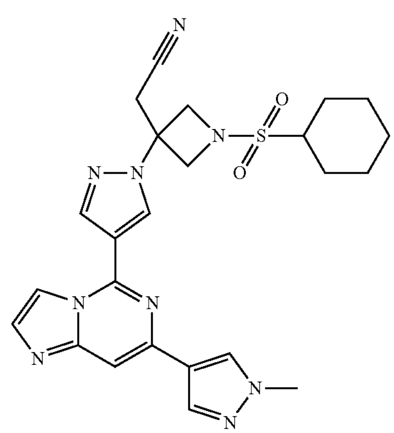 [SMILES: Cn1cc(-c2cc3nccn3c(-c3cnn(C4(CC#N)CN(S(=O)(=O)C5CCCCC5)C4)c3)n2)cn1] | 2-(1-(cyclohexylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 506.2 (M + H) |

TABLE 9-continued

| Ex. # | Structure | Name | MS |
|---|---|---|---|
| 95 | 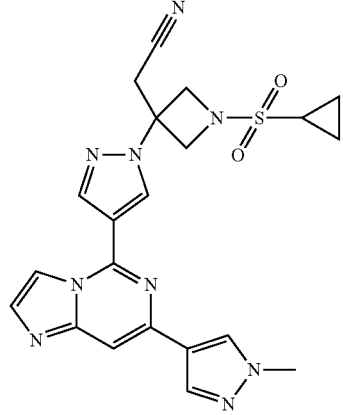 [SMILES: Cn1cc(-c2cc3nccn3c(-c3cnn(C4(CC#N)CN(S(=O)(=O)C5CC5)C4)c3)n2)cn1] | 2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 464.2 (M + H) |
| 96 | 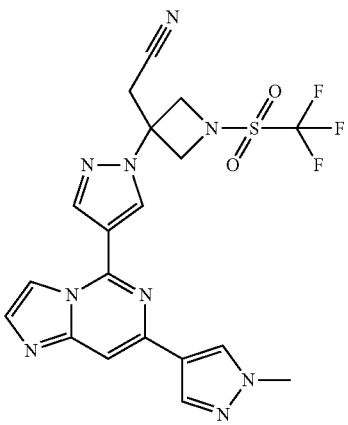 [SMILES: Cn1cc(-c2cc3nccn3c(-c3cnn(C4(CC#N)CN(S(=O)(=O)C(F)(F)F)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile | (apci) m/z = 492.2 (M + H) |
| 97 | 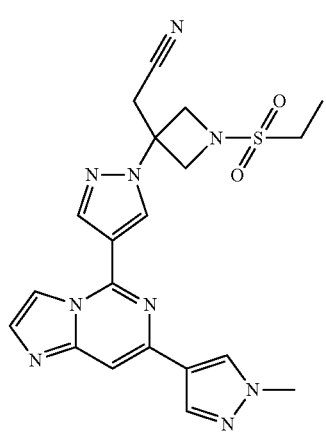 [SMILES: CCS(=O)(=O)N1CC(CC#N)(n2cc(-c3nc(-c4cnn(C)c4)cc4nccn34)cn2)C1] | 2-(1-(ethylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile | (apci) m/z = 452.2 (M + H) |

TABLE 9-continued

| Ex. # | Structure | Name | MS |
|---|---|---|---|
| 98 | 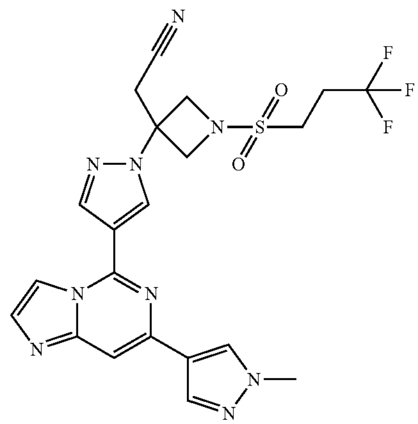 [SMILES: Cn1cc(-c2cc3nccn3c(-c3cnn(C4(CC#N)CN(S(=O)(=O)CCC(F)(F)F)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(3,3,3-trifluoropropylsulfonyl)azetidin-3-yl)acetonitrile | (apci) m/z = 520.2 (M + H) |
| 99 | 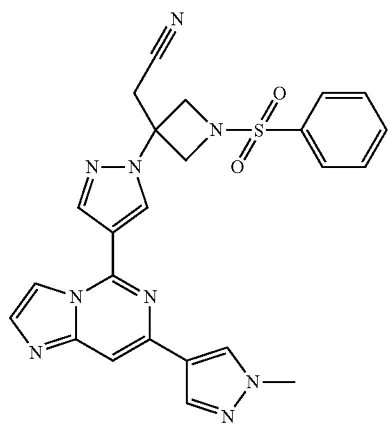 [SMILES: Cn1cc(-c2cc3nccn3c(-c3cnn(C4(CC#N)CN(S(=O)(=O)c5ccccc5)C4)c3)n2)cn1] | 2-(3-(4-(7-(1-methyl-1H-pyrazol-4-yl)imidazo[1,2-c]pyrimidin-5-yl)-1H-pyrazol-1-yl)-1-(phenylsulfonyl)azetidin-3-yl)acetonitrile | (apci) m/z = 500.2 (M + H) |

Example 100

2-(3-(4-(7-(1-Isopropyl-1-H-pyrazol-4-yl)imidazo[1,2-c]pyrimidin-5-yl)-1H-pyrazol-1-yl)-1-(2,2,2-trifluoro ethyl)azetidin-3-yl)acetonitrile

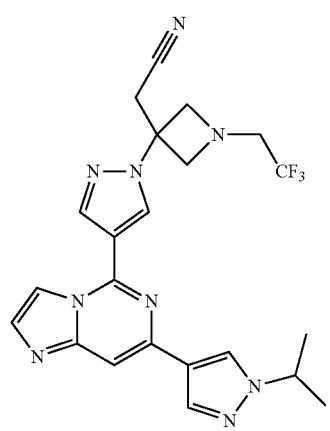 [SMILES: CC(C)n1cc(-c2cc3nccn3c(-c3cnn(C4(CC#N)CN(CC(F)(F)F)C4)c3)n2)cn1]

Step A: Preparation of tert-butyl 3-(cyanomethyl)-3-(4-(7-(1-isopropyl-1H-pyrazol-4-yl)imidazo[1,2-c]imidazo[1,2-c]pyrimidin-5-yl)-1H-pyrazol-1-yl)azetidine-1-carboxylate 7-(1-isopropyl-1H-pyrazol-4-yl)-5-(1H-pyrazol-4-yl)imidazo[1,2-c]pyrimidine (Example 34, Step B) was reacted in the same manner as Example 34, Step C, replacing 3-cyclopropylacrylonitrile with tert-butyl 3-(cyanomethylene)azetidine-1-carboxylate (Preparation F, Step A) to obtain tert-butyl 3-(cyanomethyl)-3-(4-(7-(1-isopropyl-1H-pyrazol-4-yl)imidazo[1,2-c]pyrimidin-5-yl)-1H-pyrazol-1-yl)azetidine-1-carboxylate (0.090 g, 0.1846 mmol, 64% yield). MS (apci) m/z=488.3 (M+H).

Step B: Preparation of 2-(3-(4-(7-(1-isopropyl-1H-pyrazol-4-yl)imidazo[1,2-c]pyrimidin-5-yl)-1H-pyrazol-1-yl)azetidin-3-yl)acetonitrile hydrochloride To a suspension of tert-butyl 3-(cyanomethyl)-3-(4-(7-(1-isopropyl-1H-pyrazol-4-yl)imidazo[1,2-c]pyrimidin-5-yl)-1H-pyrazol-1-yl)azetidine-1-carboxylate (0.090 g, 0.185 mmol) in 1.5 mL of dioxane was added hydrogen chloride (1.8 mL, 7.20 mmol) in dioxane at ambient temperature with stirring. After 2 hours, 0.5 mL of methanol was added to dissolve all solids and the reaction was concentrated under reduced pressure. The crude was suspended in DCM, sonicated, and concentrated three times and the resulting crude was dried on high vacuum for 3 hours to afford 2-(3-(4-(7-

(1-isopropyl-1H-pyrazol-4-yl)imidazo[1,2-c]pyrimidin-5-yl)-1H-pyrazol-1-yl)azetidin-3-yl)acetonitrile hydrochloride (0.116 g, 0.217 mmol, 93% yield). MS (apci) m/z=388.2 (M+H).

Step C: Preparation of 2-(3-(4-(7-(1-isopropyl-1-H-pyrazol-4-yl)imidazo[1,2-c]pyrimidin-5-yl)-1H-pyrazol-1-yl)-1-(2,2,2-trifluoro ethyl)azetidin-3-yl)acetonitrile To a flask charged with 2-(3-(4-(7-(1-isopropyl-1H-pyrazol-4-yl)imidazo[1,2-c]pyrimidin-5-yl)-1H-pyrazol-1-yl)azetidin-3-yl)acetonitrile hydrochloride (0.050 g, 0.10 mmol) was added 1 mL of acetonitrile, potassium carbonate (0.10 g, 0.75 mmol), and 2,2,2-trifluoroethyl trifluoromethanesulfonate (0.040 g, 0.17 mmol) at ambient temperature with stirring. The reaction flask was then sealed and allowed to proceed at ambient temperature over the weekend. The reaction was diluted with DCM and the suspension was loaded directly onto a silica gel column pre-wetted and eluted with 75% ethyl acetate in Hexanes with 1% ammonium hydroxide to afford the title compound (0.022 g, 0.047 mmol, 47% yield). MS (apci) m/z=470.2 (M+H).

Example 101

2-(3-(4-(7-(1-Isopropyl-1H-pyrazol-4-yl)imidazo[1,2-c]pyrimidin-5-yl)-1H-pyrazol-1-yl)-1-(trifluoromethylsulfonyl)azetidine-3-yl)acetonitrile

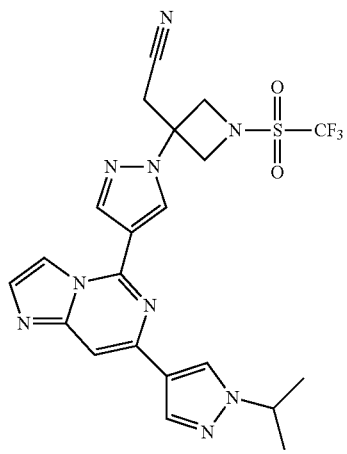 [SMILES: CC(C)n1cc(-c2cc3nccn3c(-c3cnn(C4(CC#N)CN(S(=O)(=O)C(F)(F)F)C4)c3)n2)cn1]

To a flask charged with 2-(3-(4-(7-(1-isopropyl-1H-pyrazol-4-yl)imidazo[1,2-c]pyrimidin-5-yl)-1H-pyrazol-1-yl)azetidin-3-yl)acetonitrile hydrochloride (Example 100 Step B; 0.050 g, 0.1006 mmol) and TEA (0.08416 mL, 0.6038 mmol) and 1 mL of DCM was added trifluoroacetic anhydride (0.01862 mL, 0.1107 mmol) at 0° C. with stirring. The reaction was allowed to warm to ambient temperature and stirred overnight. The reaction was diluted with DCM (2 mL) and then loaded directly onto silica and eluted with 75% ethyl acetate in hexanes with 1% ammonium hydroxide to afford the title compound (0.018 g, 0.03465 mmol, 34.43% yield). MS (apci) m/z=520.1 (M+H).

Example 102

2-(3-(4-(7-(2-Methylthiazol-5-yl)imidazo[1,2-c]pyrimidin-5-yl)-1H-pyrazol-1-yl)-1-(2,2,2-trifluoroethyl)azetidin-3-yl)acetonitrile

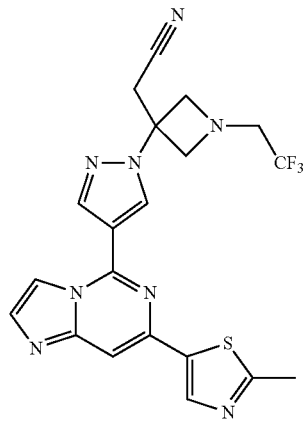 [SMILES: Cc1ncc(-c2cc3nccn3c(-c3cnn(C4(CC#N)CN(CC(F)(F)F)C4)c3)n2)s1]

Step A: Preparation of 2-methyl-5-(5-(1-((2-(trimethylsilyl)ethoxy)methyl)-1H-pyrazol-4-yl)imidazo[1,2-c]pyrimidin-7-yl)thiazole A flask charged with 7-chloro-5-(1-((2-(trimethylsilyl)ethoxy)methyl)-1H-pyrazol-4-yl)imidazo[1,2-c]pyrimidine (Preparation G; 0.200 g, 0.572 mmol) and 2-methyl-5-(trimethylstannyl)thiazole (0.165 g, 0.629 mmol) was evacuated and backfilled with argon before 4 mL of dioxane were added and argon was bubbled through for 5 minutes. Tris(dibenzylideneacetone)dipalladium (0.0523 g, 0.0572 mmol) and dicyclohexyl(2',4',6'-triisopropylbiphenyl-2-yl)phosphine (0.0545 g, 0.114 mmol) were added, argon was bubbled through the reaction for 10 minutes. The reaction flask was sealed and heated to 100° C. with stirring for 2 hours. The reaction mixture was loaded directly onto a silica gel column pre-wetted and eluted with a gradient of 25-100% ethyl acetate with 1% ammonium hydroxide to afford 2-methyl-5-(5-(1-((2-(trimethylsilyl)ethoxy)methyl)-1H-pyrazol-4-yl)imidazo[1,2-c]pyrimidin-7-yl)thiazole (0.196 g, 0.475 mmol, 83.1% yield). MS (apci) m/z=413.1 (M+H).

Step B: Preparation of 5-(5-(1H-pyrazol-4-yl)imidazo[1,2-c]pyrimidin-7-yl)-2-methylthiazole 2-methyl-5-(5-(1-((2-(trimethylsilyl)ethoxy)methyl)-1H-pyrazol-4-yl)imidazo[1,2-c]pyrimidin-7-yl)thiazole (0.196 g, 0.475 mmol) was dissolved in 3 mL of DCM before TFA (2.0 mL, 26.0 mmol) was added slowly at room temperature. The reaction was allowed to stir at room temperature for 8 hours. The reaction mixture was concentrated under reduced pressure to afford the crude material. The crude material was purified via column chromatography, eluting with 5% MeOH in DCM with 1% $NH_4OH$ to afford the title compound (0.087 g, 64.9% yield). MS (apci) m/z=283.1 (M+H).

Step C: Preparation of tert-butyl 3-(cyanomethyl)-3-(4-(7-(2-methylthiazol-5-yl)imidazo[1,2-c]pyrimidin-5-yl)-1H-pyrazol-1-yl)azetidine-1-carboxylate 2-Methyl-5-(5-(1-((2-(trimethylsilyl)ethoxy)methyl)-1H-pyrazol-4-yl)imidazo[1,2-c]pyrimidin-7-yl)thiazole (14 mg, 0.50 mmol) was reacted in the same manner as Example 34, Step C replacing 3-cyclopropylacrylonitrile with tert-butyl 3-(cyanomethylene)azetidine-1-carboxylate (Preparation F, Step A; 0.0096 g, 0.050 mmol) to afford tert-butyl 3-(cyanomethyl)-3-(4-(7-(2-methylthiazol-5-yl)imidazo[1,2-c]pyrimidin-5-yl)-1H-pyrazol-1-yl)azetidine-1-carboxylate (0.018 g, 0.03702 mmol, 75% yield). MS (apci) m/z=477.1 (M+H).

Step D: Preparation of 2-(3-(4-(7-(2-methylthiazol-5-yl)imidazo[1,2-c]pyrimidin-5-yl)-1H-pyrazol-1-yl)-1-(2,2,2-trifluoro ethyl)azetidin-3-yl)acetonitrile Prepared in the same manner as Example 100, Steps B and C replacing tert-butyl 3-(cyanomethyl)-3-(4-(7-(1-isopropyl-H-pyrazol-4-yl)imidazo[1,2-c]pyrimidin-5-yl)-1H-pyrazol-1-yl)azetidine-1-carboxylate with tert-butyl 3-(cyanomethyl)-3-(4-(7-(2-methylthiazol-5-yl)imidazo[1,2-c]pyrimidin-5-yl)-1H-pyrazol-1-yl)azetidine-1-carboxylate to afford the title compound (0.012 g, 0.022 mmol, 54% yield). MS (apci) m/z=459.1 (M+H).

Example 103

2-(3-(4-(7-(1-Cyclobutyl-1H-pyrazol-4-yl)imidazo[1,2-c]pyrimidin-5-yl)-1H-pyrazol-1-yl)-1-(2,2,2-trifluoro ethyl)azetidin-3-yl)acetonitrile

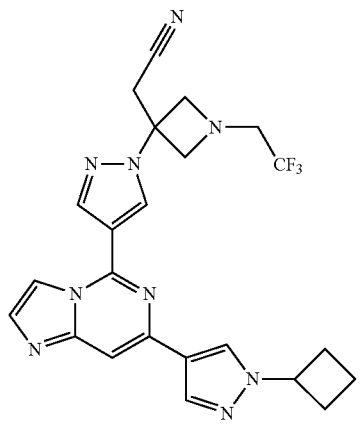 [SMILES: N#CCC1(n2cc(-c3nc(-c4cnn(C5CCC5)c4)cc4nccn34)cn2)CN(CC(F)(F)F)C1]

Step A: Preparation of tert-butyl 3-(cyanomethyl)-3-(4-(7-(1-cyclobutyl-1H-pyrazol-4-yl)imidazo[1,2-c]pyrimidin-5-yl)-1H-pyrazol-1-yl)azetidine-1-carboxylate The tert-butyl 3-(4-(7-chloroimidazo[1,2-c]pyrimidin-5-yl)-1H-pyrazol-1-yl)-3-(cyanomethyl) azetidine-1-carboxylate (0.080 g, 0.19 mmol) (Preparation N), 1-cyclobutyl-4-(4,4,5,5-tetramethyl-1,3,2-dioxaborolan-2-yl)-1H-pyrazole (Table 2, compound e; 0.072 g, 0.29 mmol), and potassium phosphate (0.29 mL, 0.58 mmol) were combined in 3 mL of dioxane and argon was bubbled through for 10 minutes before dicyclohexyl(2',4',6-triisopropylbiphenyl-2-yl)phosphine (0.018 g, 0.039 mmol) and $Pd_2dba_3$ (0.018 g, 0.019 mmol) were added. Argon was bubbled through the reaction for 15 minutes. The reaction flask was sealed and heated to 75° C. with stirring for 2.5 hours and then at ambient temperature overnight. The reaction was concentrated under reduced pressure and the crude was purified by silica gel chromatography eluting with EtOAc containing 0.5% $NH_4OH$ to afford tert-butyl 3-(cyanomethyl)-3-(4-(7-(1-cyclobutyl-1H-pyrazol-4-yl)imidazo[1,2-c]pyrimidin-5-yl)-1H-pyrazol-1-yl)azetidine-1-carboxylate (0.094 g, 0.19 mmol, 97% yield). MS (apci) m/z=500.3 (M+H).

Step B: Preparation of 2-(3-(4-(7-(1-cyclobutyl-1H-pyrazol-4-yl)imidazo[1,2-c]pyrimidin-5-yl)-1H-pyrazol-1-yl)-1-(2,2,2-trifluoro ethyl)azetidin-3-yl)acetonitrile Prepared in the same manner as Example 100 Steps B and C replacing tert-butyl 3-(cyanomethyl)-3-(4-(7-(1-isopropyl-H-pyrazol-4-yl)imidazo[1,2-c]pyrimidin-5-yl)-1H-pyrazol-1-yl)azetidine-1-carboxylate with tert-butyl 3-(cyanomethyl)-3-(4-(7-(1-cyclobutyl-1H-pyrazol-4-yl)imidazo[1,2-c]pyrimidin-5-yl)-1H-pyrazol-1-yl)azetidine-1-carboxylate to afford the title compound (0.023 g, 0.044 mmol, 45% yield). MS (apci) m/z=482.2 (M+H).

Example 104

2-(3-(4-(7-(1-Ethyl-1H-pyrazol-4-yl)imidazo[1,2-c]pyrimidin-5-yl)-1H-pyrazol-1-yl)-1-(2,2,2-trifluoro-ethyl)azetidin-3-yl)acetonitrile

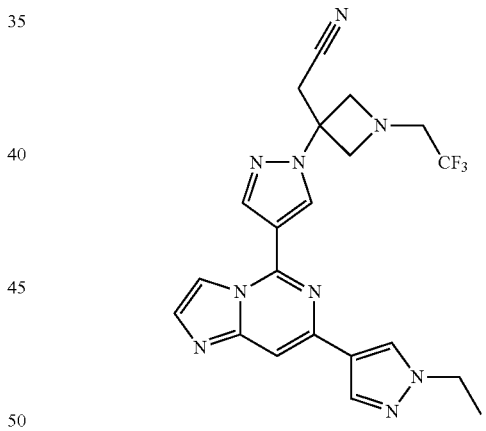

Step A: Preparation of 2-(3-(4-(7-chloroimidazo[1,2-c]pyrimidin-5-yl)-1H-pyrazol-1-yl)azetidin-3-yl)acetonitrile hydrochloride To a suspension of tert-butyl 3-(4-(7-chloroimidazo[1,2-c]pyrimidin-5-yl)-1H-pyrazol-1-yl)-3-(cyanomethyl)azetidine-1-carboxylate (Preparation N; 0.050 g, 0.12 mmol) in 1 mL of dioxane was added hydrogen chloride (0.5 mL, 2.0 mmol) as a 4M solution in dioxane at ambient temperature. The reaction mixture was stirred for 2.5 hours. The solvent was then removed under a stream of nitrogen at ambient temperature overnight. About 5% of the starting material was observed, so the crude material was subjected to the reaction conditions outlined above for 1 hour and the solvent was again removed under a stream of nitrogen to afford 2-(3-(4-

(7-chloroimidazo[1,2-c]pyrimidin-5-yl)-1H-pyrazol-1-yl) azetidin-3-yl)acetonitrile hydrochloride (0.059 g, 0.13 mmol, 106% yield). MS (apci) m/z=314.1 (M+H).

Step B: Preparation of 2-(3-(4-(7-chloroimidazo[1,2-c]pyrimidin-5-yl)-1H-pyrazol-1-yl)-1-(2,2,2-trifluoroethyl)azetidin-3-yl)acetonitrile In 1.5 mL of DMF were combined 2-(3-(4-(7-chloroimidazo[1,2-c]pyrimidin-5-yl)-1H-pyrazol-1-yl)azetidin-3-yl) acetonitrile hydrochloride (0.059 g, 0.14 mmol), DIEA (0.15 mL, 0.84 mmol), and 2,2,2-trifluoroethyl trifluoromethanesulfonate (0.049 g, 0.21 mmol) and allowed to proceed at ambient temperature with stirring. After 2 hours the DMF was removed under reduced pressure with heating and the crude was purified by means of silica gel chromatography eluting with 1:1 EtOAc/hexanes containing 0.25% NH₄OH to afford 2-(3-(4-(7-chloroimidazo[1,2-c]pyrimidin-5-yl)-1H-pyrazol-1-yl)-1-(2,2,2-trifluoro ethyl)azetidin-3-yl)acetonitrile (0.034 g, 0.086 mmol, 62% yield). MS (apci) m/z=396.1 (M+H).

Step C: Preparation of 2-(3-(4-(7-(1-ethyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile In a flask containing 2-(3-(4-(7-chloroimidazo[1,2-c]pyrimidin-5-yl)-1H-pyrazol-1-yl)-1-(2,2,2-trifluoroethyl)azetidin-3-yl)acetonitrile (0.015 g, 0.038 mmol), 1-ethyl-1H-pyrazol-4-ylboronic acid (0.0080 g, 0.057 mmol), and K₃PO₄ (0.057 mL, 0.11 mmol) was added 1 mL of dioxane and argon was bubbled through for 10 minutes before dicyclohexyl(2',4',6'-triisopropylbiphenyl-2-yl)phosphine (0.0036 g, 0.0076 mmol) and tris(dibenzylideneacetone)dipalladium (0.0035 g, 0.0038 mmol) were added and the reaction was then sealed and heated to 80° C. for 6 hours. The reaction mixture was loaded directly onto a silica gel column and eluted with EtOAc containing 0.5% NH₄OH to afford the title compound (0.015 g, 0.031 mmol, 83% yield). MS (apci) m/z=456.2 (M+H).

Example 105

2-(3-(4-(7-(1-(Oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile

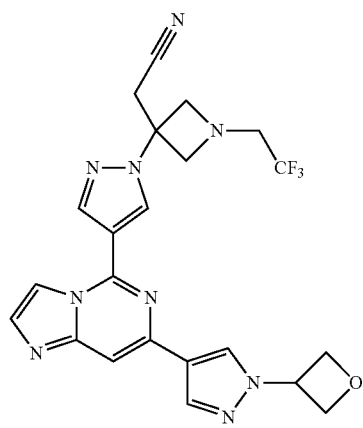 [SMILES: N#CCC1(n2cc(-c3nc(-c4cnn(C5COC5)c4)cc4nccn34)cn2)CN(CC(F)(F)F)C1]

Prepared in the same manner as Example 104, Step C replacing 1-ethyl-1H-pyrazol-4-ylboronic acid with 1-(oxetan-3-yl)-4-(4,4,5,5-tetramethyl-1,3,2-dioxaborolan-2-yl)-1H-pyrazole (Table 2, compound f) to afford the title compound 2-(3-(4-(7-(1-(oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile (0.010 g, 0.021 mmol, 55% yield). MS (apci) m/z=484.0 (M+H).

Example 106

3-(3-methyl-4-(7-(1-methyl-1H-pyrazol-4-yl)imidazo[1,2-c]pyrimidin-5-yl)-1H-pyrazol-1-yl)propanenitrile

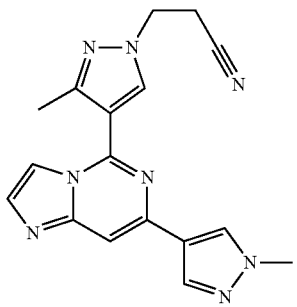 [SMILES: Cc1nn(CCC#N)cc1-c1nc(-c2cnn(C)c2)cc2nccn12]

Step A: Preparation of 7-(1-methyl-1H-pyrazol-4-yl)-5-(3-methyl-1H-pyrazol-4-yl)imidazo[1,2-c]pyrimidine To a flask charged with 5-chloro-7-(1-methyl-1H-pyrazol-4-yl)imidazo[1,2-c]pyrimidine (Preparation J; 0.650 g, 2.78 mmol), 3-methyl-4-(4,4,5,5-tetramethyl-1,3,2-dioxaborolan-2-yl)-1H-pyrazole (0.868 g, 4.17 mmol), and 2 M K₃PO₄ (4.17 mL, 8.35 mmol) was added 20 mL of DME and argon was bubbled through for 15 minutes before tetrakis(triphenylphosphine)palladium (0) (0.321 g, 0.278 mmol) was added. The flask was sealed and the reaction was heated to 100° C. for 4 hours, then allowed to cool to ambient temperature and stirred overnight. The reaction mixture was diluted with EtOAc (300 mL) and washed with aqueous saturated sodium bicarbonate (50 mL). The organic layer was washed with brine (50 mL), dried over MgSO₄, filtered, and concentrated under reduced pressure. The crude material was taken up in DCM in preparation for chromatography when a precipitate began to form and continued to thicken over time. The addition of minimal MeOH (0.5 mL) did not dissolve the precipitate. The solid was collected by vacuum filtration and retained. The rinse was purified by means of silica gel chromatography eluting with a gradient of 5-10% MeOH in EtOAc containing 1% NH₄OH. This was successful at generating material that was combined with the solid above to afford 7-(1-methyl-1H-pyrazol-4-yl)-5-(3-methyl-1H-pyrazol-4-yl)imidazo[1,2-c]pyrimidine (0.215 g, 0.770 mmol, 27.7% yield). MS (apci) m/z=280.1 (M+H).

Step B: Preparation of 3-(3-methyl-4-(7-(1-methyl-1H-pyrazol-4-yl)imidazo[1,2-c]pyrimidin-5-yl)-1H-pyrazol-1-yl)propanenitrile To a flask charged with 7-(1-methyl-1H-pyrazol-4-yl)-5-(3-methyl-1H-pyrazol-4-yl)imidazo[1,2-c]pyrimidine (0.025 g, 0.090 mmol) and acrylonitrile (0.032 mL, 0.49 mmol) was added 1 mL of acetonitrile and DBU (0.027 mL, 0.18 mmol) and the flask was sealed under nitrogen and allowed to proceed at ambient temperature overnight. The reaction was diluted with 3 mL of DCM, loaded directly onto a silica gel column and eluted with 1% MeOH in EtOAc containing 1% NH₄OH to afford a mixture of regioisomers from alkylation at N-1 and N-2. The mixture was purified by silica gel chromatography, eluting with a gradient of 1.0-5.0% MeOH in DCM with 0.5% NH₄OH to afford the title compound (5.0 mg, 0.0150 mmol, 17% yield). MS (apci) m/z=333.1 (M+H). The structure and regioisomer were confirmed by observed nOe signals.

Example 107

3-(5-methyl-4-(7-(1-methyl-1H-pyrazol-4-yl)imidazo[1,2-c]pyrimidin-5-yl)-1H-pyrazol-1-yl)propanenitrile

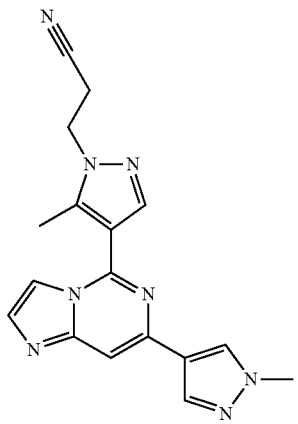 [SMILES: Cc1c(-c2nc(-c3cnn(C)c3)cc3nccn23)cnn1CCC#N]

The title compound was isolated from Example 106. This minor isomer was purified by means of preparative TLC, eluting with 10% MeOH in DCM containing 1% NH₄OH to afford the title compound (4.0 mg, 0.0120 mmol, 13% yield). MS (apci) m/z=333.2 (M+H).

Example 108

2-(3-(3-methyl-4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile

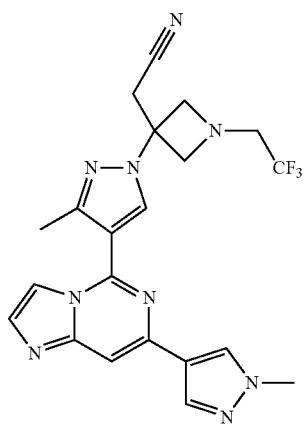 [SMILES: Cc1nn(C2(CC#N)CN(CC(F)(F)F)C2)cc1-c1nc(-c2cnn(C)c2)cc2nccn12]

Step A: Preparation of tert-butyl 3-(cyanomethyl)-3-(3-methyl-4-(7-(1-methyl-1H-pyrazol-4-yl)imidazo[1,2-c]pyrimidin-5-yl)-1H-pyrazol-1-yl)azetidine-1-carboxylate)

Prepared in the same manner as Example 106, Step B, replacing acrylonitrile with tert-butyl 3-(cyanomethylene)azetidine-1-carboxylate (Preparation F, Step A) to afford tert-butyl 3-(cyanomethyl)-3-(3-methyl-4-(7-(1-methyl-1H-pyrazol-4-yl)imidazo[1,2-c]pyrimidin-5-yl)-1H-pyrazol-1-yl)azetidine-1-carboxylate (0.064 g, 0.135 mmol, 76% yield). MS (apci) m/z=474.2 (M+H).

Step B: Preparation of 2-(3-(3-methyl-4-(7-(1-methyl-1H-pyrazol-4-yl)imidazo pyrimidin-5-yl)-1H-pyrazol-1-yl)-1-(2,2,2-trifluoroethyl)azetidin-3-yl)acetonitrile Prepared in the same manner as Example 100, Steps B and C, replacing tert-butyl 3-(cyanomethyl)-3-(4-(7-(1-isopropyl-H-pyrazol-4-yl)imidazo[1,2-c]pyrimidin-5-yl)-1H-pyrazol-1-yl)azetidine-1-carboxylate with tert-butyl 3-(cyanomethyl)-3-(3-methyl-4-(7-(1-methyl-1H-pyrazol-4-yl)imidazo[1,2-c]pyrimidin-5-yl)-1H-pyrazol-1-yl)azetidine-1-carboxylate to afford the title compound (0.018 g, 0.038 mmol, 53% yield). MS (apci) m/z=456.2 (M+H).

Example 109

3-Cyclopropyl-3-(3-methyl-4-(7-(1-methyl-1H-pyrazol-4-yl)imidazo[1,2-c]pyrimidin-5-yl)-1H-pyrazol-1-yl)propanenitrile

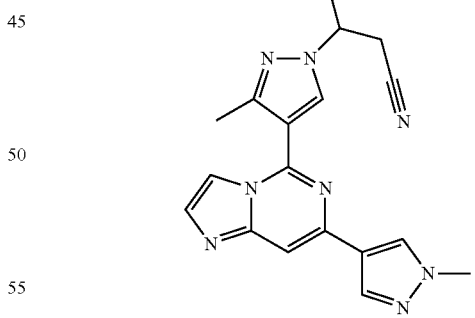

Prepared in the same manner as Example 106 Step B replacing acrylonitrile with 3-cyclopropylacrylonitrile (Preparation B) to afford the title compound (0.029 g, 0.0778 mmol, 87% yield). MS (apci) m/z=373.2 (M+H).

Example 110

3-Cyclopentyl-3-(4-(7-(4-(1-methylpiperidin-4-yl)phenyl)imidazo[1,2-c]pyrimidin-5-yl)-1H-pyrazol-1-yl)propanenitrile

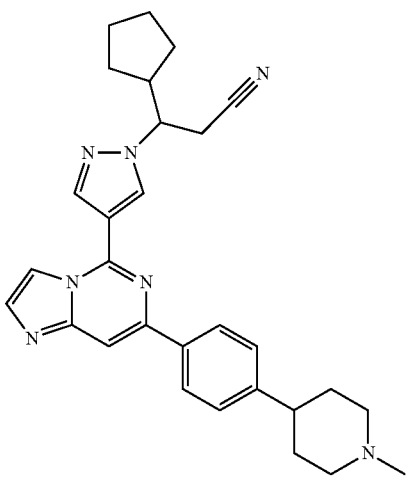 [SMILES: CN1CCC(c2ccc(-c3cc4nccn4c(-c4cnn(C(CC#N)C5CCCC5)c4)n3)cc2)CC1]

Step A: Preparation of tert-butyl 4-(4-(4,4,5,5-tetramethyl-1,3,2-dioxaborolan-2-yl)phenyl)piperidine-1-carboxylate To a solution of tert-butyl 4-(4-bromophenyl)piperidine-1-carboxylate (13.5 g, 39.7 mmol) in dioxane (40 mL) was added 4,4,5,5-tetramethyl-1,3,2-dioxaborolane (8.64 mL, 59.5 mmol) and triethylamine (16.6 mL, 119 mmol). The solution was purged with argon for 5 minutes. Dichlorobis(acetonitrile) palladium (0.309 g, 1.19 mmol) and 2-dicyclohexylphosphino-2',6'-dimethoxybiphenyl (1.95 g, 4.76 mmol) were then added, and the reaction mixture was again purged with argon for 5 minutes. The reaction mixture was then sealed and heated at 110° C. for 90 minutes. The reaction mixture was cooled to ambient temperature and filtered through a glass fiber filter paper. The filtrate was concentrated under reduced pressure and the residue purified by silica gel column chromatography, eluting with 5-10% EtOAc in hexanes to afford tert-butyl 4-(4-(4,4,5,5-tetramethyl-1,3,2-dioxaborolan-2-yl)phenyl)piperidine-1-carboxylate (9.13 g, 23.6 mmol, 59.4% yield) as a solid. MS (apci) m/z=288.3 (M+H-Boc).

Step B: Preparation of tert-butyl 4-(4-(5-hydroxyimidazo[1,2-c]pyrimidin-7-yl)phenyl)piperidine-1-carboxylate A flask charged with 7-chloroimidazo[1,2-c]pyrimidin-5(6H)-one (Preparation H, 1.75 g, 10.3 mmol), tert-butyl 4-(4-(4,4,5,5-tetramethyl-1,3,2-dioxaborolan-2-yl)phenyl)piperidine-1-carboxylate (4.00 g, 10.3 mmol), potassium phosphate (4.38 g, 20.6 mmol), dicyclohexyl(2',4',6'-triisopropylbiphenyl-2-yl)phosphine (0.738 g, 1.55 mmol), and tris(dibenzylideneacetone)dipalladium (0.473 g, 0.516 mmol) was evacuated and backfilled with argon. Isopropanol (50 mL) and water (0.744 mL, 41.3 mmol) were added. The reaction was fitted with a septum and argon was bubbled through the reaction for 20 minutes before it was sealed and allowed to proceed at 90° C. for 6 hours. The reaction was recharged with catalyst, argon was bubbled through for 10 minutes, and the reaction was sealed and allowed to react at 90° C. for two days. The solvent was concentrated under reduced pressure, 200 mL of 2:1 2.5M potassium hydroxide/methanol was added and the reaction was stirred for 1 hour. A large amount of solids were observed so another 200 mL of the above mentioned mixture was added and much of the solid was dissolved. The solid was collected by means of vacuum filtration through a pad of celite and was then washed with 200 mL of the above mentioned mixture. The rinse was isolated and the pH was adjusted with 1 M hydrochloric until pH=9. The resulting solids were collected by means of vacuum filtration. This solid was taken up in 300 mL of water and allowed to stir for 30 minutes before the solid was collected by means of vacuum filtration and washed with water. The solid was dried on high vacuum and triturated with methanol. The mixture was filtered and the solid was dried under high vacuum to afford tert-butyl 4-(4-(5-hydroxyimidazo[1,2-c]pyrimidin-7-yl)phenyl)piperidine-1-carboxylate (1.75 g, 4.44 mmol, 43.0% yield). MS (apci) m/z=395.2 (M+H).

Step C: Preparation of 7-(4-(piperidin-4-yl)phenyl)imidazo[1,2-c]pyrimidin-5-ol To a flask charged with tert-butyl 4-(4-(5-hydroxyimidazo[1,2-c]pyrimidin-7-yl)phenyl)piperidine-1-carboxylate (1.75 g, 4.44 mmol) in 40 mL of dichloromethane was added 2,2,2-trifluoroacetic acid (15 mL, 195 mmol) at ambient temperature for 3 hours. The solvent was concentrated under reduced pressure and the resulting crude was taken up in methanol (10 mL) and to it was added aqueous saturated sodium bicarbonate slowly. The resulting solid was collected by means of vacuum filtration and was dried overnight on high vacuum. This solid was triturated with water (50 mL) and solids were collected by means of vacuum filtration and dried on high vacuum to afford 7-(4-(piperidin-4-yl)phenyl)imidazo[1,2-c]pyrimidin-5-ol (1.03 g, 3.50 mmol, 78.9% yield). MS (apci) m/z=295.1 (M+H).

Step D: Preparation of 7-(4-(1-methylpiperidin-4-yl)phenyl)imidazo[1,2-c]pyrimidin-5(6H)-one To a suspension of 7-(4-(piperidin-4-yl)phenyl)imidazo[1,2-c]pyrimidin-5-ol (1.03 g, 3.50 mmol) in tetrahydrofuran (35 mL) and N,N-dimethylacetamide (2.5 mL) was added formaldehyde (5.21 mL, 70.0 mmol) followed by sodium triacetoxyborohydride (3.71 g, 17.5 mmol) and the reaction was allowed proceed at ambient temperature with stirring under nitrogen for 30 minutes. Aqueous saturated sodium bicarbonate was added slowly and gas evolution was observed. To the aqueous was added dichloromethane (100 mL) and a thick white precipitate was observed. The organic was collected and a second extraction with dichloromethane yielded a homogenous milky mixture. The biphasic mixture was filtered and the solid was washed with dichloromethane and retained. The biphasic mixture was separated and the aqueous was extracted with DCM. The organic layers were combined, dried over $Na_2SO_4$, filtered, and concentrated under reduced pressure. The resulting crude material was triturated with diethyl ether and the resulting solids were collected by means of vacuum filtration. The two crops of solids were combined to afford 7-(4-(1-methylpiperidin-4-yl)phenyl)imidazo[1,2-c]pyrimidin-5-ol (0.935 g, 3.03 mmol, 86.6% yield). MS (apci) m/z=309.2 (M+H).

Step E: Preparation of 5-chloro-7-(4-(1-methylpiperidin-4-yl)phenyl)imidazo[1,2-c]pyrimidine To a suspension of 7-(4-(1-methylpiperidin-4-yl)phenyl)imidazo[1,2-c]pyrimidin-5(6H)-one (0.728 g, 2.361 mmol) in phosphoryl trichloride (12 mL, 131.1 mmol) under nitrogen was added N,N-diethylaniline (0.9390 mL, 5.902 mmol). The reaction was then heated to 50° C. for 4 hours. The reaction was concentrated, and the residue obtained was treated with 15 mL of a 1:1 mixture of ice and saturated aqueous sodium bicarbonate. The resulting mixture was extracted with dichloromethane (4×30 mL). The combined organic layers were dried over $MgSO_4$, filtered, and concentrated under reduced pressure. The residue obtained was triturated with diethyl ether and the solid was collected by means of vacuum filtration. The solid was saved. The filtrate was concentrated and the resulting residue purified by silica gel column chromatography, eluting with 20% methanol in dichloromethane. The product-containing fractions were concentrated under reduced pressure and the material was combined with the triturated solid to afford 5-chloro-7-(4-(1-methylpiperidin-4-yl)phenyl)imidazo[1,2-c]pyrimidine (550 mg, 1.68 mmol, 63% yield). MS (apci) m/z=327.1 (M+H).

Step F: Preparation of 7-(4-(1-methylpiperidin-4-yl)phenyl)-5-(1H-pyrazol-4-yl)imidazo[1,2-c]pyrimidine 5-Chloro-7-(4-(1-methylpiperidin-4-yl)phenyl)imidazo[1,2-c]pyrimidine (0.120 g, 0.367 mmol), 4-(4,4,5,5-tetramethyl-1,3,2-dioxaborolan-2-yl)-1H-pyrazole (0.107 g, 0.551 mmol) and potassium carbonate (0.152 g, 1.10 mmol) were suspended in a mixture of DME (5 mL) and water (2 mL) and purged with argon for 5 minutes. Tetrakis(triphenylphosphine)palladium (0) (0.02121 g, 0.01836 mmol) was added and the reaction sealed and heated at 100° C. for 18 hours. The reaction mixture was cooled to ambient temperature and diluted with water and filtered. The solids were washed with acetone and then dried under high vacuum to afford 7-(4-(1-methylpiperidin-4-yl)phenyl)-5-(1H-pyrazol-4-yl)imidazo[1,2-c]pyrimidine (0.0310 g, 0.0865 mmol, 23.55% yield). MS (apci) m/z=359.2 (M+H).

Step G: Preparation of 3-cyclopentyl-3-(4-(7-(4-(1-methylpiperidin-4-yl)phenyl)imidazo[1,2-c]pyrimidin-5-yl)-1H-pyrazol-1-yl)propanenitrile 7-(4-(1-Methylpiperidin-4-yl)phenyl)-5-(1H-pyrazol-4-yl)imidazo[1,2-c]pyrimidine (0.130 g, 0.363 mmol) and 3-cyclopentylacrylonitrile (Table 1, compound g; 0.220 g, 1.81 mmol) were suspended in DMF (10 mL) and 2,3,4,6,7,8,9,10-octahydropyrimido[1,2-a]azepine (0.2169 mL, 1.451 mmol) added in one portion. The reaction mixture was stirred at ambient temperature for 66 hours. The reaction mixture was partitioned between saturated aqueous 1 N NaOH and EtOAc. The organics were washed with brine, dried over $MgSO_4$ and concentrated under reduced pressure to afford the crude material, which was purified by flash column chromatography (eluant: 2-6% (9:1, MeOH:$NH_4OH$)/DCM) to furnish 3-cyclopentyl-3-(4-(7-(4-(1-methylpiperidin-4-yl)phenyl)imidazo[1,2-c]pyrimidin-5-yl)-1H-pyrazol-1-yl)propanenitrile (0.096 g, 0.200 mmol, 55.19% yield). MS (apci) m/z=480.3 (M+H).

Example 111

Enantiomer 1 of 3-cyclopentyl-3 (4 (7 (4 (1 methylpiperidin-4-yl)phenyl)imidazo[1,2-c]pyrimidin-5-yl)-1H-pyrazol-1-yl)propanenitrile (Peak 1)

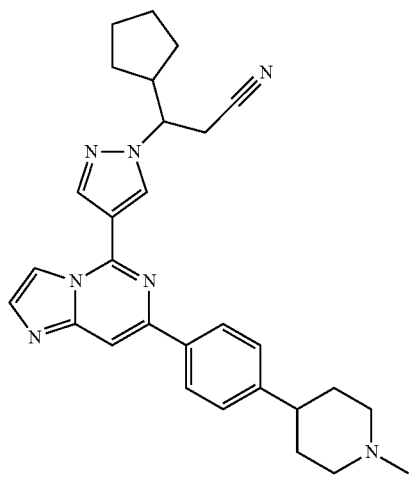 [SMILES: CN1CCC(c2ccc(-c3cc4nccn4c(-c4cnn(C(CC#N)C5CCCC5)c4)n3)cc2)CC1]

3-cyclopentyl-3-(4-(7-(4-(1-methylpiperidin-4-yl)phenyl)imidazo[1,2-c]pyrimidin-5-yl)-1H-pyrazol-1-yl)propanenitrile (Example 110; 0.010 g, 0.021 mmol) was separated by chiral HPLC (Chiral Tech. OD-H, 2.2 cm×250 mm; 220 nm, 12 mL/min; 40% Ethanol:60% Hexanes). Peak 1 was isolated to afford a single Enantiomer 1 of 3-cyclopentyl-3-(4-(7-(4-(1-methylpiperidin-4-yl)phenyl)imidazo[1,2-c]pyrimidin-5-yl)-1H-pyrazol-1-yl)propanenitrile (2.9 mg, 29% yield). MS (apci) m/z=480.3 (M+H).

Example 112

Enantiomer 2 of 3-cyclopentyl-3-(4-(7-(4-(1-methylpiperidin-4-yl)phenyl)imidazo[1,2-c]pyrimidin-5-yl)-1H-pyrazol-1-yl)propanenitrile (Peak 2)

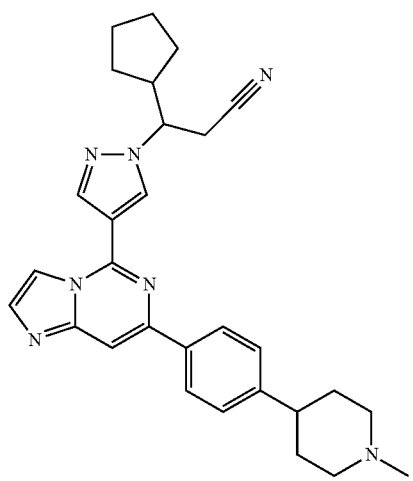 [SMILES: CN1CCC(c2ccc(-c3cc4nccn4c(-c4cnn(C(CC#N)C5CCCC5)c4)n3)cc2)CC1]

3-Cyclopentyl-3-(4-(7-(4-(1-methylpiperidin-4-yl)phenyl)imidazo[1,2-c]pyrimidin-5-yl)-1H-pyrazol-1-yl)propanenitrile (Example 110; 0.010 g, 0.021 mmol) was separated by chiral HPLC (Chiral Tech. OD-H, 2.2 cm×250 mm; 220 nm, 12 mL/min; 40% Ethanol:60% Hexanes). Peak 2 was isolated to afford a single Enantiomer 2 of 3-cyclopentyl-3-(4-(7-(4-(1-methylpiperidin-4-yl)phenyl)imidazo[1,2-c]pyrimidin-5-yl)-1H-pyrazol-1-yl)propanenitrile (3.6 mg, 36% yield). MS (apci) m/z=480.3 (M+H).

Example 113

3-Cyclopentyl-3-(4-(7-(4-morpholinophenyl)imidazo[1,2-c]pyrimidin-5-yl)-1H-pyrazol-1-yl)propanenitrile

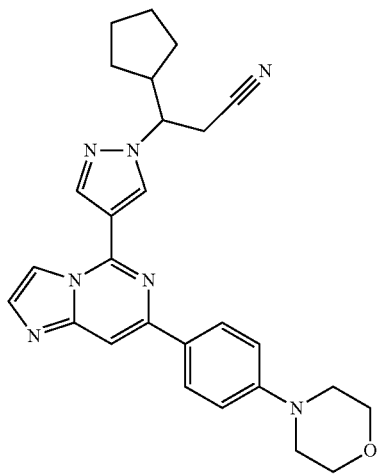 [SMILES: N#CCC(C1CCCC1)n1cc(-c2nc(-c3ccc(N4CCOCC4)cc3)cc3nccn23)cn1]

Step A: Preparation of 4-(4-(5-(methylthio)imidazo[1,2-c]pyrimidin-7-yl)phenyl)morpholine A suspension of 7-chloro-5-(methylthio)imidazo[1,2-c]pyrimidine hydrochloride (1.85 g, 7.83 mmol; Preparation H, Step A), 4-morpholinophenylboronic acid (1.78 g, 8.62 mmol) and potassium phosphate (3.33 g, 15.7 mmol) in isopropanol (25 mL) was purged with argon for 5 minutes, and then $Pd_2dba_3$ (0.717 g, 0.783 mmol) and XPHOS (1.49 g, 3.13 mmol) were added. The reaction was again purged for 5 minutes with argon before being sealed and heated to 90° C. for 18 hours. The reaction mixture was diluted with EtOAc (75 mL) and filtered. The filtrate was concentrated under reduced pressure, and the residue obtained was purified by silica gel column chromatography, eluting with 10-15-20% acetone in DCM to afford 4-(4-(5-(methylthio)imidazo[1,2-c]pyrimidin-7-yl)phenyl)morpholine (0.663 g, 25.9% yield) as a yellow solid. MS (apci) m/z=327.1 (M+H).

Step B: Preparation of 7-(4-morpholinophenyl)imidazo[1,2-c]pyrimidin-5(6H)-one 4-(4-(5-(methylthio)imidazo[1,2-c]pyrimidin-7-yl)phenyl)morpholine (0.4000 g, 1.225 mmol) and potassium hydroxide (1.021 mL, 6.127 mmol) were suspended in DMSO (3 mL) and heated at 100° C. for 1.5 hours in a microwave. The reaction mixture was diluted with water (40 mL) and acidified with acetic acid (1.052 mL, 18.38 mmol). The resulting solids were collected by filtration and dried under high vacuum to afford 7-(4-morpholinophenyl)imidazo[1,2-c]pyrimidin-5(6H)-one (0.3460 g, 95.28% yield). MS (apci) m/z=297.2 (M+H).

Step C: Preparation of 4-(4-(5-chloroimidazo[1,2-c]pyrimidin-7-yl)phenyl)morpholine A suspension of 7-(4-morpholinophenyl)imidazo[1,2-c]pyrimidin-5-ol (0.500 g, 1.69 mmol) in $POCl_3$ (1.54 mL, 16.9 mmol) was heated to 100° C. and allowed to proceed overnight. The reaction was transferred to a flask with dichloromethane and the organics were concentrated under reduced pressure. To the crude material was added water and the mixture was stirred for 20 minutes at ambient temperature before it was neutralized with 1N NaOH to a pH of 7. The solids were collected by vacuum filtration and washed with water. The solids were purified by silica gel column chromatography eluting with 15% acetone in dichloromethane to afford 4-(4-(5-chloroimidazo[1,2-c]pyrimidin-7-yl)phenyl)morpholine (0.0400 g, 0.127 mmol, 7.53% yield). MS (apci) m/z=315.1 (M+H).

Step D: Preparation of 4-(4-(5-(1H-pyrazol-4-yl)imidazo[1,2-c]pyrimidin-7-yl)phenyl)morpholine 4-(4-(5-Chloroimidazo[1,2-c]pyrimidin-7-yl)phenyl)morpholine (0.0400 g, 0.127 mmol), 4-(4,4,5,5-tetramethyl-1,3,2-dioxaborolan-2-yl)-1H-pyrazole (0.0370 g, 0.191 mmol) and potassium carbonate (0.0527 g, 0.381 mmol) were suspended in a mixture of DME (2 mL) and water (1 mL) and de-gassed with argon for 5 minutes. Tetrakis(triphenylphosphine)palladium (0) (0.00734 g, 0.00635 mmol) was added and the reaction sealed and heated at 100° C. for 2 hours. The reaction mixture was concentrated under reduced pressure. The residue was partitioned between saturated aqueous $NaHCO_3$ and EtOAc. The organics were washed with brine, dried, $MgSO_4$ and concentrated under reduced pressure to afford the crude material, which was purified by flash column chromatography (eluant: 0.5%-6% (9:1 MeOH:$NH_4OH$)/DCM) to furnish 4-(4-(5-(1H-pyrazol-4-yl)imidazo[1,2-c]pyrimidin-7-yl)phenyl)morpholine (0.0160 g, 0.046 mmol, 36.4% yield). MS (apci) m/z=347.1 (M+H).

Step E: Preparation of 3-cyclopentyl-3-(4-(7-(4-morpholinophenyl) imidazo[1,2-c]pyrimidin-5-yl)-1H-pyrazol-1-yl)propanenitrile 4-(4-(5-(1H-Pyrazol-4-yl)imidazo[1,2-c]pyrimidin-7-yl)phenyl)morpholine (0.0300 g, 0.0866 mmol) and 3-cyclopentylaerylonitrile (Table 1, compound g; 0.0175 g, 0.144 mmol) were suspended in DMF (3 mL) and 2,3,4,6,7,8,9,10-octahydropyrimido[1,2-a]azepine (0.0324 mL, 0.217 mmol) added in one portion. The reaction mixture was stirred at ambient temperature over the weekend. The reaction mixture was partitioned between saturated aqueous 1 N NaOH and EtOAc. The solids were isolated by filtration. The organics were washed with brine, dried over $MgSO_4$ and concentrated under reduced pressure to afford the crude material, which was purified by flash column chromatography (eluant: 0.5-3% (9:1, MeOH:$NH_4OH$)/DCM) to provide 3-cyclopentyl-3-(4-(7-(4-morpholinophenyl)imidazo[1,2-c]pyrimidin-5-yl)-1H-pyrazol-1-yl)propanenitrile (0.0190 g, 0.04064 mmol, 46.9% yield). MS (apci) m/z=468.2 (M+H).

Example 114

Enantiomer 1 of 3-cyclopentyl-3-(4-(7-(4-morpholinophenyl)imidazo[1,2-c]pyrimidin-5-yl)-1H-pyrazol-1-yl)propanenitrile (Peak 1)

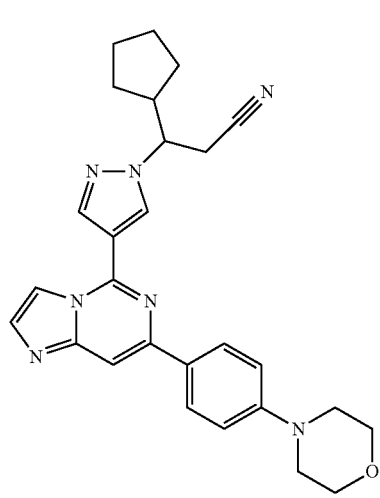 [SMILES: N#CCC(C1CCCC1)n1cc(-c2nc(-c3ccc(N4CCOCC4)cc3)cc3nccn23)cn1]

3-Cyclopentyl-3-(4-(7-(4-morpholinophenyl)imidazo[1,2-c]pyrimidin-5-yl)-1H-pyrazol-1-yl)propanenitrile (Example 113; 0.015 g, 0.032 mmol) was separated by chiral HPLC (Chiral Tech. OD-H, 2.2 cm×250 mm; 220 nm, 21 mL/min; 50% Ethanol: 50% Hexanes). Peak 1 was isolated to afford the single enantiomer 1 of 3-cyclopentyl-3-(4-(7-(4-(1-methylpiperidin-4-yl)phenyl)imidazo[1,2-c]pyrimidin-5-yl)-1H-pyrazol-1-yl)propanenitrile (6.0 mg, 40% yield). MS (apci) m/z=468.2 (M+H).

Example 115

Enantiomer 2 of 3-cyclopentyl-3-(4-(7-(4-morpholinophenyl)imidazo[1,2-c]pyrimidin-5-yl)-1H-pyrazol-1-yl)propanenitrile (Peak 2)

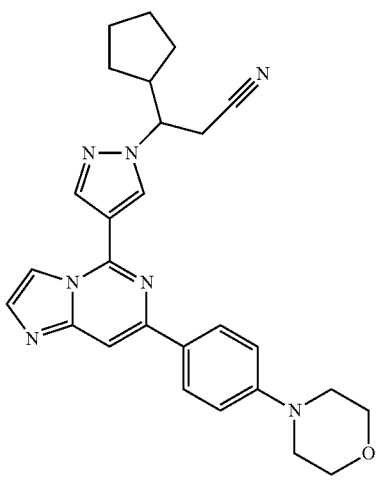 [SMILES: N#CCC(C1CCCC1)n1cc(-c2nc(-c3ccc(N4CCOCC4)cc3)cc3nccn23)cn1]

3-Cyclopentyl-3-(4-(7-(4-morpholinophenyl)imidazo[1,2-c]pyrimidin-5-yl)-1H-pyrazol-1-yl)propanenitrile (Example 113; 0.015 g, 0.032 mmol) was separated by chiral HPLC (Chiral Tech. OD-H, 2.2 cm×250 mm; 220 nm, 21 mL/min; 50% Ethanol: 50% Hexanes). Peak 2 was isolated to afford the single Enantiomer 2 of 3-cyclopentyl-3-(4-(7-(4-(1-methylpiperidin-4-yl)phenyl)imidazo[1,2-c]pyrimidin-5-yl)-1H-pyrazol-1-yl)propanenitrile (5.0 mg, 33% yield). MS (apci) m/z=468.2 (M+H).

The compounds of Table 9 were prepared according to the method of Example 113 using the appropriate starting materials.

TABLE 9

| Ex. # | Structure | Name | MS |
|---|---|---|---|
| 116 | 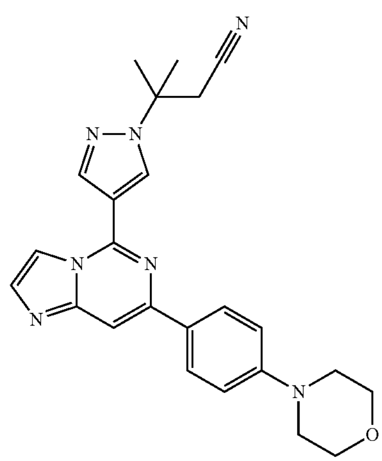 [SMILES: CC(C)(CC#N)n1cc(-c2nc(-c3ccc(N4CCOCC4)cc3)cc3nccn23)cn1] | 3-methyl-3-(4-(7-(4-morpholinophenyl)imidazo[1,2-c]pyrimidin-5-yl)-1H-pyrazol-1-yl)butanenitrile | (apci) m/z = 428.2 (M + H) |

TABLE 9-continued

| Ex. # | Structure | Name | MS |
|---|---|---|---|
| 117 | 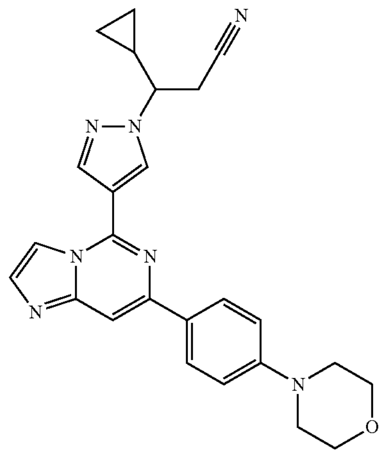 [SMILES: N#CCC(C1CC1)n1cc(-c2nc(-c3ccc(N4CCOCC4)cc3)cc3nccn23)cn1] | 3-cyclopropyl-3-(4-(7-(4-morpholinophenyl)imidazo[1,2-c]pyrimidin-5-yl)-1H-pyrazol-1-yl)propanenitrile | (apci) m/z = 440.2 (M + H) |
| 118 | 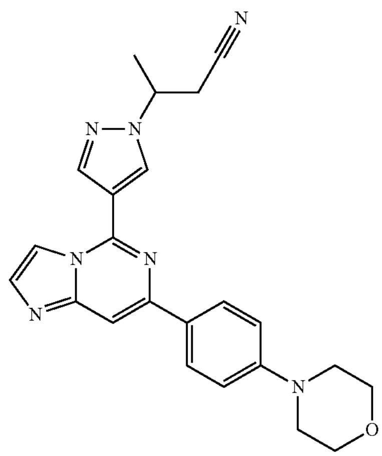 [SMILES: CC(CC#N)n1cc(-c2nc(-c3ccc(N4CCOCC4)cc3)cc3nccn23)cn1] | 3-(4-(7-(4-morpholinophenyl)imidazo[1,2-c]pyrimidin-5-yl)-1H-pyrazol-1-yl)butanenitrile | (apci) m/z = 414.2 (M + H) |
| 119 | 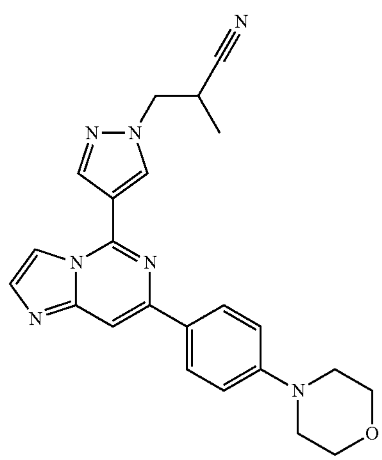 [SMILES: CC(C#N)Cn1cc(-c2nc(-c3ccc(N4CCOCC4)cc3)cc3nccn23)cn1] | 2-methyl-3-(4-(7-(4-morpholinophenyl)imidazo[1,2-c]pyrimidin-5-yl)-1H-pyrazol-1-yl)propanenitrile | (apci) m/z = 414.2 (M + H) |

TABLE 9-continued

| Ex. # | Structure | Name | MS |
|---|---|---|---|
| 120 | 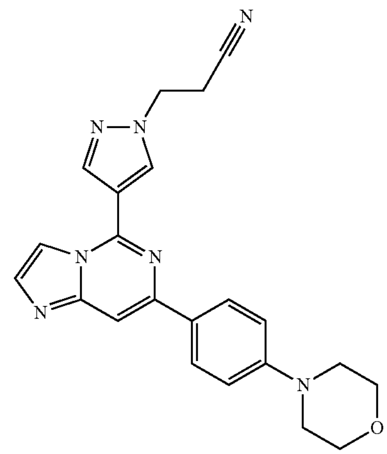 [SMILES: N#CCCn1cc(-c2nc(-c3ccc(N4CCOCC4)cc3)cc3nccn23)cn1] | 3-(4-(7-(4-morpholinophen-yl)imidazo[1,2-c]pyrimidin-5-yl)-1H-pyrazol-1-yl)propanenitrile | (apci) m/z = 400.2 (M + H) |

Example 121

3-Cyclopentyl-3-(3-methyl-4-(7-(4-morpholinophenyl)imidazo[1,2-c]pyrimidin-5-yl)-1H-pyrazol-1-yl)propanenitrile

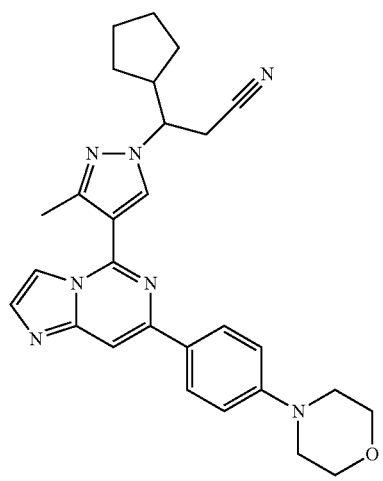 [SMILES: Cc1nn(C(CC#N)C2CCCC2)cc1-c1nc(-c2ccc(N3CCOCC3)cc2)cc2nccn12]

Step A: Preparation of 4-(4-(5-(3-methyl-1H-pyrazol-4-yl)imidazo[1,2-c]pyrimidin-7-yl)phenyl)morpholine 4-(4-(5-Chloroimidazo[1,2-c]pyrimidin-7-yl)phenyl)morpholine (Example 113, Step D) (0.120 g, 0.381 mmol), 5-methyl-4-(4,4,5,5-tetramethyl-1,3,2-dioxaborolan-2-yl)-1H-pyrazole (0.119 g, 0.572 mmol) and potassium carbonate (0.158 g, 1.144 mmol) were suspended in a mixture of DME (5 mL) and water (2 mL) and de-gassed with Ar(g). Tetrakis(triphenylphosphine)palladium (0) (0.0220 g, 0.0191 mmol) was added and the reaction sealed and heated at 100° C. for 4 hours. The reaction mixture was diluted with water and filtered. The solids were washed with acetone and dried under high vacuum to afford 4-(4-(5-(3-methyl-1H-pyrazol-4-yl)imidazo[1,2-c]pyrimidin-7-yl)phenyl)morpholine (0.0660 g, 0.1831 mmol, 48.0% yield). MS (apci) m/z=361.1 (M+H).

Step B: Preparation of 3-cyclopentyl-3-(3-methyl-4-(7-(4-morpholinophenyl) imidazo[1,2-c]pyrimidin-5-yl)-1H-pyrazol-1-yl)propanenitrile 4-(4-(5-(3-methyl-1H-pyrazol-4-yl)imidazo[1,2-c]pyrimidin-7-yl)phenyl)morpholine (0.0690 g, 0.191 mmol), 3-cyclopentylacrylonitrile (Table 1, compound g; 0.0696 g, 0.574 mmol) and DBU 0.0661 mL, 0.479 mmol) were suspended in DMF (3 mL) and stirred overnight. The reaction mixture was partitioned between saturated aqueous NaHCO₃ and EtOAc. The organics were washed with brine, dried, MgSO₄ and concentrated under reduced pressure to afford the crude material, which was purified by flash column chromatography (eluant: 0.5-2% (9:1, MeOH:NH₄OH)/DCM) to furnish 3-cyclopentyl-3-(3-methyl-4-(7-(4-morpholinophenyl) imidazo[1,2-c]pyrimidin-5-yl)-1H-pyrazol-1-yl)propanenitrile (0.0380 g, 0.078905 mmol, 41.2% yield). MS (apci) m/z=482.2 (M+H).

Example 122

N-tert-butyl-5-(1-(2-cyano-1-cyclopropylethyl)-1H-pyrazol-4-yl)imidazo[1,2-c]pyrimidine-7-carboxamide

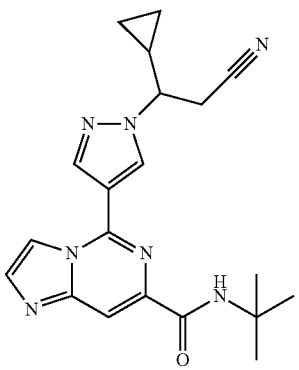 [SMILES: CC(C)(C)NC(=O)c1cc2nccn2c(-c2cnn(C(CC#N)C3CC3)c2)n1]

Step A: Preparation of methyl 5-(1H-pyrazol-4-yl) imidazo[1,2-c]pyrimidine-7-carboxylate hydrochloride In a 100 mL flask, methyl 5-(1-((2-(trimethylsilyl)ethoxy) methyl)-1H-pyrazol-4-yl)imidazo[1,2-c]pyrimidine-7-carboxylate (0.477 g, 1.28 mmol) (Example 45; Step C) was dissolved in DCM (12.8 mL, 1.28 mmol). To this was added 4N HCl in dioxane (4.79 mL, 19.2 mmol). After stirring at ambient temperature for 4 hours, the reaction mixture was concentrated down to remove solvents. The resultant solid was diluted in DCM, sonicated and filtered to afford 0.363 g (100% yield) of the HCl salt as a light yellow solid. MS (apci) m/z=244.3 (M+H).

Step B: Preparation of methyl 5-(1-(2-cyano-1-cyclopropylethyl)-1H-pyrazol-4-yl)imidazo[1,2-c]pyrimidine-7-carboxylate In a 100 mL flask, methyl 5-(1H-pyrazol-4-yl)imidazo[1, 2-c]pyrimidine-7-carboxylate hydrochloride (0.300 g, 1.07 mmol) and 3-cyclopropylacrylonitrile (Preparation B; 0.300 g, 3.22 mmol) were suspended in DMF (5.36 mL, 1.07 mmol) and DBU (0.722 mL, 4.83 mmol) added in one portion. The reaction mixture was stirred at ambient temperature for 15 hours. The reaction mixture was diluted in EtOAc and washed with water and brine. The combined organic layers were dried over MgSO₄, filtered, and concentrated down to a yellow oil. Purification of the crude material by silica chromatography using a gradient of 50-100% EtOAc afforded methyl 5-(1-(2-cyano-1-cyclopropylethyl)-1H-pyrazol-4-yl)imidazo[1,2-c] pyrimidine-7-carboxylate (0.127 g, 0.378 mmol, 35.2% yield) as a yellow oil. MS (apci) m/z=337.2 (M+H).

Step C: Preparation of 5-(1-(2-cyano-1-cyclopropylethyl)-1H-pyrazol-4-yl)imidazo[1,2-c]pyrimidine-7-carboxylic acid In a 20 mL flask, methyl 5-(1-(2-cyano-1-cyclopropylethyl)-1H-pyrazol-4-yl)imidazo[1,2-c]pyrimidine-7-carboxylate (0.127 g, 0.378 mmol) was dissolved in MeOH (1.89 mL, 0.378 mmol) and treated with LiOH (0.755 mL, 0.755 mmol). The reaction mixture was stirred at ambient temperature for 1 hour, then concentrated down to dryness and used directly in the next step. MS (apci) m/z=323.1 (M+H).

Step D: Preparation of N-tert-butyl-5-(1-(2-cyano-1-cyclopropylethyl)-1H-pyrazol-4-yl)imidazo[1,2-c] pyrimidine-7-carboxamide In a 2 mL flask, 5-(1-(2-cyano-1-cyclopropylethyl)-1H-pyrazol-4-yl)imidazo[1,2-c]pyrimidine-7-carboxylic acid (6.5 mg, 0.020 mmol) and HATU (9.2 mg, 0.024 mmol) were dissolved in DMF (101 µL, 0.020 mmol). After 5 minutes, 2-methylpropan-2-amine (4.4 mg, 0.061 mmol) and diisopropylethylamine (11 µL, 0.061 mmol) were added and the reaction mixture stirred at ambient temperature for 45 minutes. The reaction mixture was diluted in EtOAc and washed with water, saturated sodium bicarbonate, water and brine. The organic layer was dried over MgSO₄, filtered and concentrated in vacuo. The crude material was purified by reverse phase HPLC using a gradient of 40-100% acetonitrile/water to afford N-tert-butyl-5-(1-(2-cyano-1-cyclopropylethyl)-1H-pyrazol-4-yl)imidazo[1,2-c]pyrimidine-7-carboxamide (1.0 mg, 0.0026 mmol, 13% yield). MS (apci) m/z=378.3 (M+H).

Example 123

5-(1-(2-Cyano-1-cyclopropylethyl)-1H-pyrazol-4-yl)-N-cyclohexylimidazo[1,2-c]pyrimidine-7-carboxamide

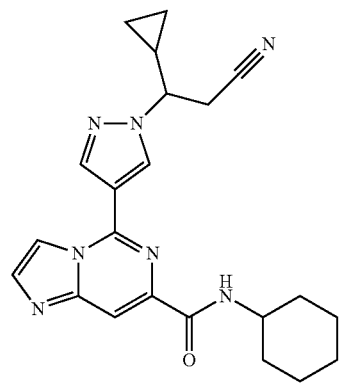 [SMILES: N#CCC(C1CC1)n1cc(-c2nc(C(=O)NC3CCCCC3)cc3nccn23)cn1]

Prepared according to the method of Example 122 Step G, replacing methylpropan-2-amine with cyclohexanamine (9.2 mg, 0.093 mmol) to afford 5.5 mg (44% yield). MS (apci) m/z=404.2 (M+H).

Example 124

5-(1-(2-Cyano-1-cyclopropylethyl)-1H-pyrazol-4-yl)-N-cyclobutylimidazo[1,2-c]pyrimidine-7-carboxamide

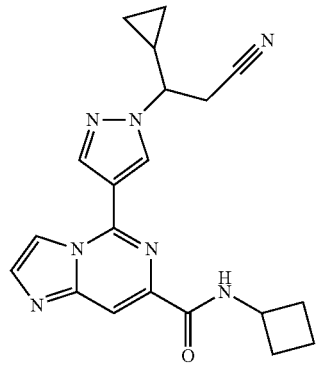 [SMILES: N#CCC(C1CC1)n1cc(-c2nc(C(=O)NC3CCC3)cc3nccn23)cn1]

Prepared according to the method of Example 122 Step G, replacing methylpropan-2-amine with cyclobutanamine (6.62 mg, 0.0931 mmol) to afford 7.8 mg (67% yield). MS (apci) m/z=376.3 (M+H).

Example 125

5-(1-(2-cyano-1-cyclopropylethyl)-1H-pyrazol-4-yl)-N-(pyridin-2-yl)imidazo[1,2-c]pyrimidine-7-carboxamide

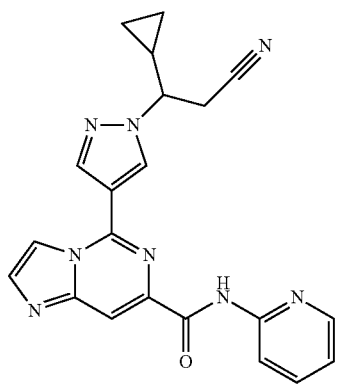 [SMILES: N#CCC(C1CC1)n1cc(-c2nc(C(=O)Nc3ccccn3)cc3nccn23)cn1]

Prepared according to the method of Example 122 Step G, replacing methylpropan-2-amine with pyridin-2-amine (10.5 mg, 0.112 mmol) and heating to 80° C. for 2 days to afford 3.2 mg (22% yield). MS (apci) m/z=399.2 (M+H).

Example 126

3-Cyclopropyl-3-(3-(7-(1-methyl-1H-pyrazol-4-yl)imidazo[1,2-c]pyrimidin-5-yl)-1H-pyrrol-1-yl)propanenitrile

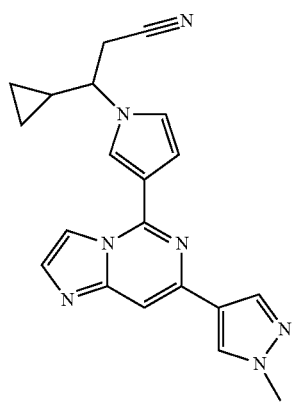 [SMILES: Cn1cc(-c2cc3nccn3c(-c3ccn(C(CC#N)C4CC4)c3)n2)cn1]

Prepared in the same manner as Preparation O, Step B, replacing tert-butyl 3-(cyanomethylene)azetidine-1-carboxylate with 3-cyclopropylacrylonitrile (Preparation B) to afford the title compound (0.010 g, 0.026 mmol, 23% yield). MS (apci) m/z=358.1 (M+H).

Example 127

2-(3-(3-(7-(1-Methyl-1H-pyrazol-4-yl)imidazo[1,2-c]pyrimidin-5-yl)-1H-pyrrol-1-yl)azetidin-3-yl)acetonitrile trifluoroacetate

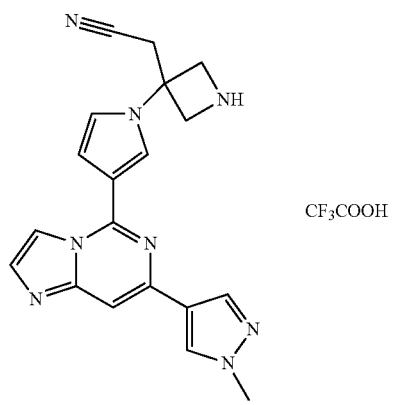 [SMILES: Cn1cc(-c2cc3nccn3c(-c3ccn(C4(CC#N)CNC4)c3)n2)cn1 ; "CF3COOH"]

To a solution of tert-butyl 3-(cyanomethyl)-3-(3-(7-(1-methyl-1H-pyrazol-4-yl)imidazo[1,2-c]pyrimidin-5-yl)-1H-pyrrol-1-yl)azetidine-1-carboxylate (Preparation O, 79.0 mg, 0.172 mmol) in dry DCM (1.5 mL) was added trifluoroacetic acid (2 mL) and the mixture stirred at ambient temperature for 3 hours. The mixture was concentrated and the residual gel was treated with EtOAc and sonicated until a white suspension. The EtOAc was decanted, the residual solid was washed with EtOAc and dried in vacuum to afford the title compound (trifluoroacetate salt, 100 mg, 99% yield) as an ivory white solid. MS (apci) m/z=359.2.

Example 128

2-(3-(3-(7-(1-Methyl-1H-pyrazol-4-yl)imidazo[1,2-c]pyrimidin-5-yl)-1H-pyrrol-1-yl)-1-(2,2,2-trifluoroethyl)azetidin-3-yl)acetonitrile

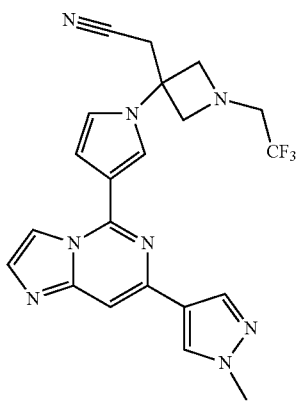 [SMILES: Cn1cc(-c2cc3nccn3c(-c3ccn(C4(CC#N)CN(CC(F)(F)F)C4)c3)n2)cn1]

A solution of 2-(3-(3-(7-(1-methyl-1H-pyrazol-4-yl)imidazo[1,2-c]pyrimidin-5-yl)-1H-pyrrol-1-yl)azetidin-3-yl)acetonitrile trifluoroacetate (Example 127, 100 mg, 0.182 mmol) in dry DMF (1.0 mL) was cooled on an ice bath and DIEA (191 µL, 1.09 mmol) and 2,2,2-trifluoroethyl trifluoromethanesulfonate (63.5 mg, 0.273 mmol) were added sequentially. The ice bath was removed and the reaction mixture was stirred at ambient temperature for 17 hours. The mixture was added to $H_2O$ (5 mL), mixed and extracted with DCM. The combined organic extracts were washed with 0.5M $Na_2CO_3$ and $H_2O$, and dried over $Na_2SO_4$. The crude material was eluted through a $SiO_2$ plug eluting first with DCM then 10% MeOH/EtOAc. The 10% MeOH/EtOAc pool was concentrated to give a colorless glass. The glass was dissolved in minimal DCM and treated with hexanes to afford a white suspension. The suspension was concentrated providing the title compound (25 mg, 31% yield) as a white solid. MS (apci) m/z=441.2.

Example 129

Tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate

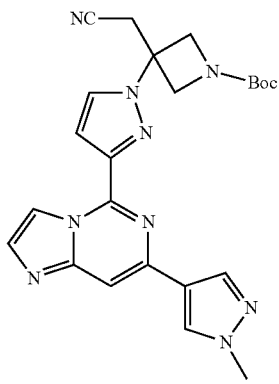 [SMILES: Cn1cc(-c2cc3nccn3c(-c3ccn(C4(CC#N)CN(C(=O)OC(C)(C)C)C4)n3)n2)cn1]

Step A: Preparation of 3-(4,4,5,5-tetramethyl-1,3,2-dioxaborolan-2-yl)-1-((2-(trimethylsilyl)ethoxy)methyl)-1H-pyrazole A solution of 3-(4,4,5,5-tetramethyl-1,3,2-dioxaborolan-2-yl)-1H-pyrazole (250 mg, 1.3 mmol) in dry DMF (2.6 mL) was cooled to 0° C. and NaH (77 mg, 1.9 mmol) was added in one portion. The mixture was warmed at ambient temperature for 30 minutes, then cooled to 0° C. and 2-(Trimethylsilyl) ethoxymethyl chloride (290 µL, 1.7 mmol) was added. The reaction mixture was allowed to warm to ambient temperature overnight. The next day, a mixture of 3-(4,4,5,5-tetramethyl-1,3,2-dioxaborolan-2-yl)-1-((2-(trimethylsilyl)ethoxy)methyl)-1H-pyrazole, 1-((2-(trimethylsilyl)ethoxy)methyl)-1H-pyrazol-3-ylboronic acid and 1-((2-(trimethylsilyl)ethoxy)methyl)-1H-pyrazole was observed. The reaction mixture was quenched with cold saturated ammonium chloride (5 mL) and diluted with $Et_2O$. The layers were separated and extracted with another portion of $Et_2O$. The combined organic layer was washed with brine, dried with $MgSO_4$, filtered and concentrated down to a clear oil. The crude mixture was taken onto the next step without purification. MS (apci) m/z=242.9 (M+H).

Step B: Preparation of 7-(1-methyl-1H-pyrazol-4-yl)-5-(1-((2-(trimethylsilyl)ethoxy)-methyl)-1H-pyrazol-3-yl)imidazo[1,2-c]pyrimidine and 7-(1-methyl-1H-pyrazol-4-yl)-5-(1-((2-(trimethylsilyl)ethoxy)methyl)-1H-pyrazol-5-yl)imidazo[1,2-c]pyrimidine 5-Chloro-7-(1-methyl-1H-pyrazol-4-yl)imidazo[1,2-c]pyrimidine (Preparation J; 100 mg, 0.428 mmol), 3-(4,4,5,5-tetramethyl-1,3,2-dioxaborolan-2-yl)-1-((2-(trimethylsilyl)ethoxy)methyl)-1H-pyrazole (Step A, 208 mg, 0.642 mmol; also containing some 1-((2-(trimethylsilyl)ethoxy)methyl)-1H-pyrazol-3-ylboronic acid), and $K_3PO_4$ (273 mg, 1.28 mmol) were suspended in dioxane (2.14 mL, 0.428 mmol). To this was added $Pd(PPh_3)_4$ (49.5 mg, 0.0428 mmol) followed by 0.21 mL of water. The reaction mixture was heated at 70° C. for 15 hours. The reaction mixture was then diluted in EtOAc and washed with water and brine. The organic layer was dried over $MgSO_4$, filtered and concentrated in vacuo. The resultant residue was purified by silica chromatography using a 0-10% MeOH/EtOAc gradient to afford the two title isomers (3:1 ratio, 0.120 g, 71% yield). MS (apci) m/z=396.2 (M+H).

Step C: Preparation of 7-(1-methyl-1H-pyrazol-4-yl)-5-(1H-pyrazol-3-yl)imidazo[1,2-c]pyrimidine hydrochloride The mixture of isomers (0.120 g, 0.302 mmol) from Step B were dissolved in DCM (1.51 mL, 0.302 mmol) and treated with 4N HCl in dioxane (1.51 mL, 6.04 mmol). After stirring at ambient temperature for 90 minutes, the reaction mixture was concentrated in vacuo to afford 7-(1-methyl-1H-pyrazol-4-yl)-5-(1H-pyrazol-3-yl)imidazo[1,2-c]pyrimidine hydrochloride (0.104 g, 0.307 mmol, 100% yield) as a yellow solid. MS (apci) m/z=266.2 (M+H).

Step D: Preparation of tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate 7-(1-Methyl-1H-pyrazol-4-yl)-5-(1H-pyrazol-3-yl)imidazo[1,2-c]pyrimidine hydrochloride (50.2 mg, 0.148 mmol) and tert-butyl 3-(cyanomethylene)azetidine-1-carboxylate (Preparation F, Step A; 31.7 mg, 0.163 mmol) were suspended in acetonitrile (742 µL, 0.148 mmol). DBU (88.8 µL, 0.594 mmol) was added to the reaction mixture and stirred at ambient temperature for 15 hours overnight. The reaction mixture was purified directly by reverse phase HPLC using a 0-100% acetonitrile/water gradient, followed by a second purification using silica chromatography (0-10% MeOH/EtOAc) to afford tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate (29.6 mg, 43.4% yield). MS (apci) m/z=460.1 (M+H).

Example 130

2-(3-(3-(7-(1-Methyl-1H-pyrazol-4-yl)imidazo[1,2-c]pyrimidin-5-yl)-1H-pyrazol-1-yl)azetidin-3-yl)acetonitrile hydrochloride

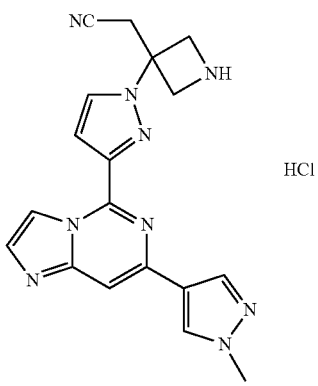 [SMILES: Cn1cc(-c2cc3nccn3c(-c3ccn(C4(CC#N)CNC4)n3)n2)cn1 ; Cl]

Tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate (Example 129; 28.3 mg, 0.0616 mmol) was dissolved in DCM (308 μL, 0.0616 mmol) and treated with 4N HCl in dioxane (308 μL, 1.23 mmol). The reaction mixture was stirred at ambient temperature for 1 hour, then concentrated in vacuo to afford 2-(3-(3-(7-(1-methyl-1H-pyrazol-4-yl)imidazo[1,2-c]pyrimidin-5-yl)-1H-pyrazol-1-yl)azetidin-3-yl)acetonitrile hydrochloride (14.3 mg, 53.7% yield) as a white solid. MS (apci) m/z=360.2 (M+H).

Example 131

2-(3-(3-(7-(1-Methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile

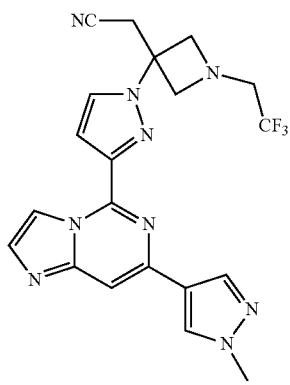 [SMILES: Cn1cc(-c2cc3nccn3c(-c3ccn(C4(CC#N)CN(CC(F)(F)F)C4)n3)n2)cn1]

2-(3-(3-(7-(1-Methyl-1H-pyrazol-4-yl)imidazo[1,2-c]pyrimidin-5-yl)-1H-pyrazol-1-yl)azetidin-3-yl)acetonitrile hydrochloride (Example 130; 13.0 mg, 0.0301 mmol) was suspended in DMF (301 μL, 0.0301 mmol) and treated with diisopropylethylamine (31.4 μL, 0.180 mmol) and 2,2,2-trifluoroethyl trifluoromethanesulfonate (9.07 mg, 0.0391 mmol). The reaction mixture was stirred at ambient temperature for 15 hours. Another portion of 2,2,2-trifluoroethyl trifluoromethanesulfonate (2.0 mg, 0.87 mmol) was added and stirred for another 24 hours. The reaction mixture was then purified by reverse phase HPLC using 0-100% acetonitrile/water gradient, followed by preparative TLC using 10% MeOH/EtOAc to afford 2-(3-(3-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile (9.6 mg, 72% yield). MS (apci) m/z=442.3 (M+H).

Example 132

3-Cyclopropyl-3-(3-(7-(1-methyl-1H-pyrazol-4-yl)imidazo[1,2-c]pyrimidin-5-yl)-1H-pyrazol-1-yl)propanenitrile

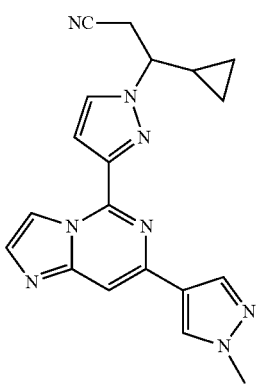 [SMILES: Cn1cc(-c2cc3nccn3c(-c3ccn(C(CC#N)C4CC4)n3)n2)cn1]

7-(1-Methyl-1H-pyrazol-4-yl)-5-(1H-pyrazol-3-yl)imidazo[1,2-c]pyrimidine hydrochloride (Example 129, Step C, 50.2 mg, 0.148 mmol) and 3-cyclopropylacrylonitrile (Preparation B; 69.1 mg, 0.742 mmol) were suspended in acetonitrile (742 μL, 0.148 mmol). DBU (88.8 μL, 0.594 mmol) was added to the reaction mixture and heated at 45° C. for 15 hours. The reaction mixture was purified by reverse phase HPLC using a 0-100% acetonitrile/water gradient. The resultant solid was diluted in Et₂O, sonicated, filtered and washed with Et₂O to afford the title compound as a light yellow solid (9.3 mg, 17% yield). MS (apci) m/z=359.2 (M+H).

Example 133

2-(3-(4-(7-(1-methyl-1H-pyrazol-4-yl)imidazo[1,2-c]pyrimidin-5-yl)-1H-pyrazol-1-yl)-1-(trifluoromethylsulfonyl)pyrrolidin-3-yl)acetonitrile

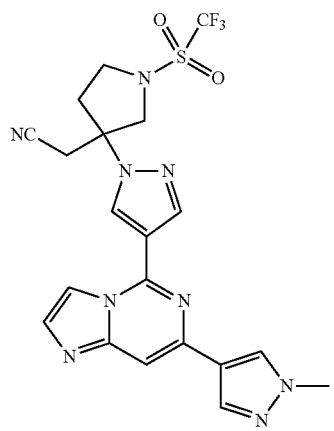 [SMILES: Cn1cc(-c2cc3nccn3c(-c3cnn(C4(CC#N)CCN(S(=O)(=O)C(F)(F)F)C4)c3)n2)cn1]

Step A: Preparation of Tert-butyl 3-(cyanomethylene)pyrrolidine-1-carboxylate Diethyl cyanomethylphosphonate (4.247 mL, 26.99 mmol) was suspended in THF (135.0 mL) and cooled to 0° C. Potassium 2-methylpropan-2-olate (32.39 mL, 32.39 mmol) was added portion-wise and stirred at 0° C. for 10 minutes. tert-Butyl 3-oxopyrrolidine-1-carboxylate (5 g, 26.99 mmol) was added dropwise as a solution in THF (25 mL). The resulting mixture was allowed to warm to ambient temperature overnight. The reaction mixture was concentrated under reduced pressure and the residue partitioned between saturated aqueous NH$_4$Cl and EtOAc. The organics were washed with brine, dried, MgSO$_4$ and concentrated under reduced pressure to afford the crude material, which was passed through a pad of Celite® and silica, eluting with DCM to furnish tert-butyl 3-(cyanomethylene)pyrrolidine-1-carboxylate (2.5 g, 12.00 mmol, 44.47% yield. $^1$H NMR (CDCl$_3$) δ 5.8 (s, 1H), 4.26 (t, 2H), 3.85 (s, 2H), 2.28 (t, 2H), 2.06-1.96 (m, 1H), 1.54 (s, 9H).

Step B: Preparation of Tert-butyl 3-(cyanomethyl)-3-(4-(7-(1-methyl-1H-pyrazol-4-yl)imidazo[1,2-c]pyrimidin-5-yl)-1H-pyrazol-1-yl)pyrrolidine-1-carboxylate Prepared according to Example 2, replacing 3-cyclopropylacrylonitrile with tert-butyl 3-(cyanomethylene)pyrrolidine-1-carboxylate_to afford the title compound 31.6% yield. MS (apci) m/z=474.2 (M+H).

Step C: Preparation of 2-(3-(4-(7-(1-methyl-1H-pyrazol-4-yl)imidazo[1,2-c]pyrimidin-5-yl)-1H-pyrazol-1-yl)-1-(trifluoromethylsulfonyl)pyrrolidin-3-yl)acetonitrile To a solution of tert-butyl 3-(cyanomethyl)-3-(4-(7-(1-methyl-1H-pyrazol-4-yl)imidazo[1,2-c]pyrimidin-5-yl)-1H-pyrazol-1-yl)pyrrolidine-1-carboxylate in MeOH was added 4M HCl/dioxane. After 20 minutes at ambient temperature, the resulting solution was concentrated to a solid. To the solid was added DCM and DIEA. The resulting solution was cooled to −70° C., and trifluoromethanesulfonic anhydride was added. The resulting mixture was allowed to warm to ambient temperature overnight. The reaction mixture was concentrated to an oil and the oil was chromatographed to yield the title compound in 82.7% yield MS (apci) m/z=406.2 (M+H).

Example 134

2-(1-acetyl-3-(4-(7-(1-methyl-1H-pyrazol-4-yl)imidazo[1,2-c]pyrimidin-5-yl)-1H-pyrazol-1-yl)pyrrolidin-3-yl)acetonitrile

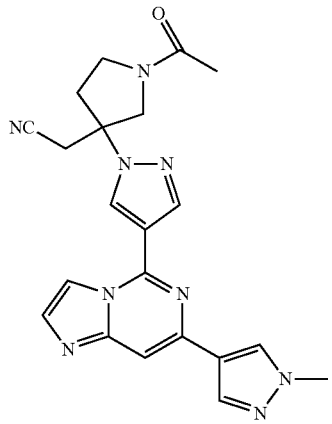 [SMILES: CC(=O)N1CCC(CC#N)(n2cc(-c3nc(-c4cnn(C)c4)cc4nccn34)cn2)C1]

Prepared in the same manner as Example 133, replacing trifluoromethanesulfonic anhydride with acetyl chloride to yield title compound in 26.2% yield. MS (apci) m/z=416.1 (M+H).

Example 135

2-(3-(4-(7-(1-methyl-1H-pyrazol-4-yl)imidazo[1,2-c]pyrimidin-5-yl)-1H-pyrazol-1-yl)-1-(2,2,2-trifluoroethyl)pyrrolidin-3-yl)acetonitrile

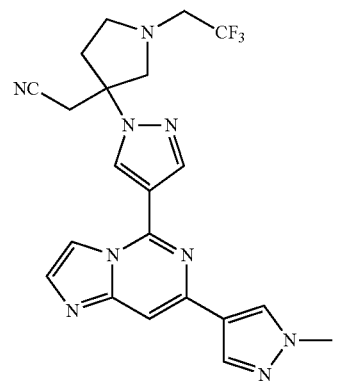 [SMILES: Cn1cc(-c2cc3nccn3c(-c3cnn(C4(CC#N)CCN(CC(F)(F)F)C4)c3)n2)cn1]

Prepared according to Example 133, replacing trifluoromethanesulfonic anhydride with 2,2,2-trifluoroethyl trifluoromethanesulfonate to yield title compound in 33.3% yield. MS (apci) m/z=456.1 (M+H).

Example 136

2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile

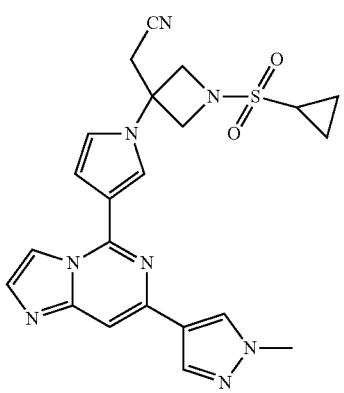 [SMILES: Cn1cc(-c2cc3nccn3c(-c3ccn(C4(CC#N)CN(S(=O)(=O)C5CC5)C4)c3)n2)cn1]

Prepared according to Example 128, replacing 2,2,2-trifluoroethyl trifluoromethanesulfonate with cyclopropanesulfonyl chloride to yield title compound in 9.5% yield. MS (apci) m/z=463.1 (M+H).

Example 137

2-(3-(4-(7-(4-(4-methylpiperazin-1-yl)phenyl)imidazo[1,2-c]pyrimidin-5-yl)-1H-pyrazol-1-yl)-1-(2,2,2-trifluoroethyl)azetidin-3-yl)acetonitrile

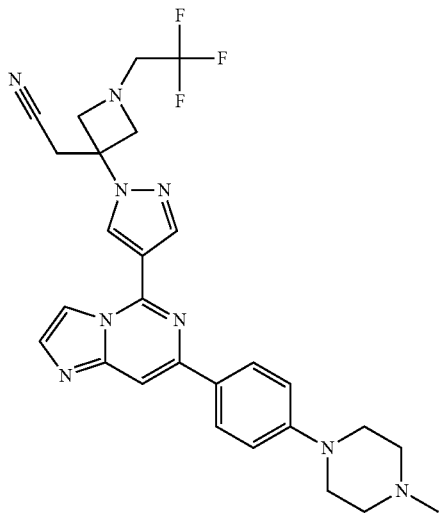 [SMILES: CN1CCN(c2ccc(-c3cc4nccn4c(-c4cnn(C5(CC#N)CN(CC(F)(F)F)C5)c4)n3)cc2)CC1]

Step A: Preparation of Tert-butyl 3-(cyanomethyl)-3-(4-(7-(4-(4-methylpiperazin-1-yl)phenyl)imidazo[1,2-c]pyrimidin-5-yl)-1H-pyrazol-1-yl)azetidine-1-carboxylate: Prepared according to Example 103 Step A, replacing 1-(oxetan-3-yl)-4-(4,4,5,5-tetramethyl-1,3,2-dioxaborolan-2-yl)-1H-pyrazole with 1-methyl-4-(4-(4,4,5,5-tetramethyl-1,3,2-dioxaborolan-2-yl)phenyl)piperazine to yield title compound in 58.2% yield. MS (apci) m/z=554.2 (M+H).

Step B: Preparation of 2-(3-(4-(7-(4-(4-methylpiperazin-1-yl)phenyl)imidazo[1,2-c]pyrimidin-5-yl)-1H-pyrazol-1-yl)-1-(2,2,2-trifluoro ethyl)azetidin-3-yl)acetonitrile: Tert-butyl 3-(cyanomethyl)-3-(4-(7-(4-(4-methylpiperazin-1-yl)phenyl)imidazo[1,2-c]pyrimidin-5-yl)-1H-pyrazol-1-yl)azetidine-1-carboxylate (250 mg, 0.4515 mmol) was dissolved in MeOH (5 mL) and a 4M HCl/dioxane solution (5 mL) was added. The resulting mixture was stirred for 20 minutes and then was concentrated to a solid. To the solid was added dichloromethane and diisopropyl ethylamine. (787 µL, 4.52 mmol). After 10 minutes, the resulting mixture was cooled to −40° C. and 2,2,2-trifluoroethyl trifluoromethanesulfonate (210 mg, 0.903 mmol) was added. The reaction mixture was allowed to warm to ambient temperature overnight. The resulting mixture was concentrated to an oil and the oil was chromatographed to yield 7.5 mg (3.1%) of the title compound. MS (apci) m/z=536.2.1 (M+H).

Example 138

2-(3-(4-(7-(4-(4-methylpiperazin-1-yl)phenyl)imidazo[1,2-c]pyrimidin-5-yl)-1H-pyrazol-1-yl)-1-(trifluoromethylsulfonyl)azetidin-3-yl)acetonitrile

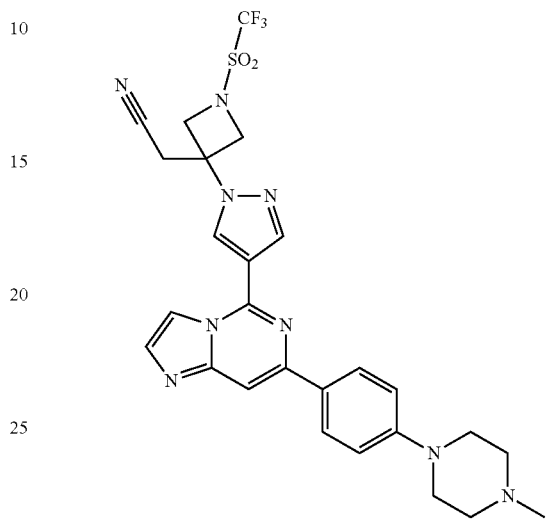

Prepared according to Example 137, replacing 2,2,2-trifluoroethyl trifluoromethanesulfonate with trifluoromethanesulfonic anhydride to yield title compound in 34% yield. MS (apci) m/z=586.1 (M+H).

Example 139

2-(3-(4-(7-(2-methylthiazol-5-yl)imidazo[1,2-c]pyrimidin-5-yl)-1H-pyrazol-1-yl)-1-(trifluoromethylsulfonyl)azetidin-3-yl)acetonitrile

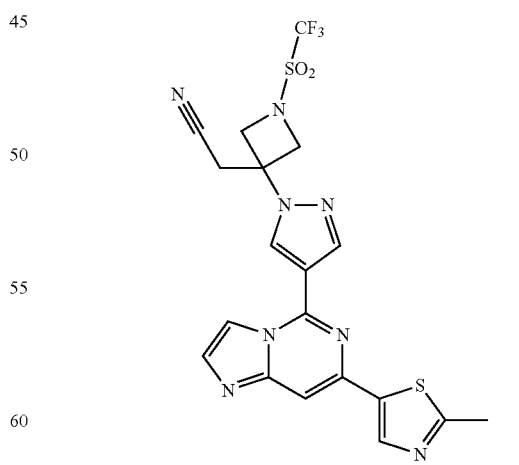

Step A: Preparation of tert-butyl 3-(cyanomethyl)-3-(4-(7-(2-methylthiazol-5-yl)imidazo[1,2-c]pyrimidin-5-yl)-1H-pyrazol-1-yl)azetidine-1-carboxylate: Prepared according to Example 103, Step A, replacing 1-(oxetan-3-yl)-4-(4,4,5,5- tetramethyl-1,3,2-dioxaborolan-2-yl)-1H-pyrazole with 2-methyl-5-(trimethylstannyl)thiazole to yield title compound in 46.8% yield. MS (apci) m/z=477.1 (M+H).

Step B: Preparation of 2-(3-(4-(7-(2-methylthiazol-5-yl)imidazo[1,2-c]pyrimidin-5-yl)-1H-pyrazol-1-yl)-1-(trifluoromethylsulfonyl)azetidin-3-yl)acetonitrile tert-Butyl 3-(cyanomethyl)-3-(4-(7-(2-methylthiazol-5-yl)imidazo[1,2-c]pyrimidin-5-yl)-1H-pyrazol-1-yl)azetidine-1-carboxylate (225 mg, 0.4515 mmol) was dissolved in MeOH (5 mL) and a 4 M HCl/dioxane solution (5 mL) was added. The resulting mixture was stirred for 20 minutes and then was concentrated to a solid. To the solid was added dichloromethane (15 mL) and diisopropyl ethylamine (787 µL, 4.52 mmol). After 10 minutes, the resulting mixture was cooled to −40° C. and trifluoromethanesulfonic anhydride (232 mg, 0.823 mmol) was added. The reaction mixture was allowed to come to ambient temperature over night. The resulting mixture was concentrated to an oil and the oil was chromatographed to yield 142.6 mg (68.1%) of the title compound. MS (apci) m/z=509.0 (M+H).

Example 140

2-(1-(cyclopropylsulfonyl)-3-(4-(7-(2-methylthiazol-5-yl)imidazo[1,2-c]pyrimidin-5-yl)-1H-pyrazol-1-yl)azetidin-3-yl)acetonitrile

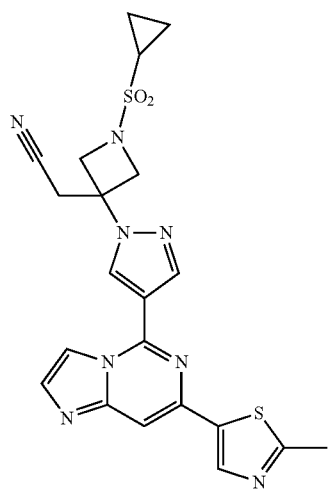 [SMILES: Cc1ncc(-c2cc3nccn3c(-c3cnn(C4(CC#N)CN(S(=O)(=O)C5CC5)C4)c3)n2)s1]

Prepared according to Example 139, replacing 2,2,2-trifluoroethyl trifluoromethanesulfonate with cyclopropanesulfonyl chloride to yield title compound in 36.8% yield. MS (apci) m/z=481.1 (M+H).

Example 141

2-(1-(cyclopropylsulfonyl)-3-(4-(7-(2-methoxypyrimidin-5-yl)imidazo[1,2-c]pyrimidin-5-yl)-1H-pyrazol-1-yl)azetidin-3-yl)acetonitrile

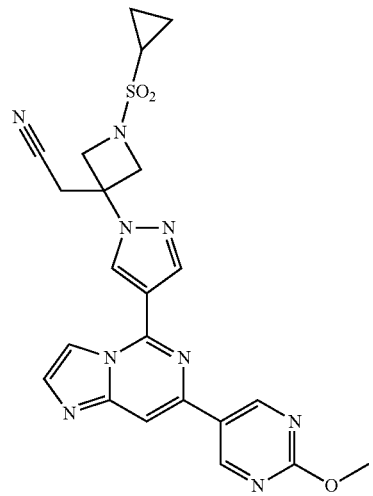 [SMILES: COc1ncc(-c2cc3nccn3c(-c3cnn(C4(CC#N)CN(S(=O)(=O)C5CC5)C4)c3)n2)cn1]

Step A: Preparation of tert-butyl 3-(cyanomethyl)-3-(4-(7-(2-methoxypyrimidin-5-yl)imidazo[1,2-c]pyrimidin-5-yl)-1H-pyrazol-1-yl)azetidine-1-carboxylate Prepared according to Example 103, Step A, replacing 1-(oxetan-3-yl)-4-(4,4,5,5-tetramethyl-1,3,2-dioxaborolan-2-yl)-1H-pyrazole with 2-methoxypyrimidin-5-ylboronic acid to yield title compound in 52% yield. MS (apci) m/z=488.1 (M+H).

Step B: Preparation of 2-(1-(cyclopropylsulfonyl)-3-(4-(7-(2-methoxypyrimidin-5-yl)imidazo[1,2-c]pyrimidin-5-yl)-1H-pyrazol-1-yl)azetidin-3-yl)acetonitrile tert-Butyl 3-(cyanomethyl)-3-(4-(7-(2-methoxypyrimidin-5-yl)imidazo[1,2-c]pyrimidin-5-yl)-1H-pyrazol-1-yl)azetidine-1-carboxylate (150 mg, 0.308 mmol) was dissolved in MeOH (5 ml) and a 4M HCl/dioxane solution (5 mL) was added. The resulting mixture was stirred for 20 minutes and then was concentrated to a solid. To the solid was added dichloromethane (15 mL) and diisopropyl ethylamine (787 µL, 4.52 mmol). After 10 minutes, the resulting mixture was cooled to −40° C. and cyclopropanesulfonyl chloride (43.3 mg, 0308 mmol) was added. The reaction mixture was allowed to come to ambient temperature overnight. The resulting mixture was concentrated to an oil and the oil was chromatographed to yield 70.8 mg (46.8%) of the title compound. MS (apci) m/z=509.0 (M+H).

Example 142

2-(3-(4-(7-(2-methoxypyrimidin-5-yl)imidazo[1,2-c]pyrimidin-5-yl)-1H-pyrazol-1-yl)-1-(trifluoromethylsulfonyl)azetidin-3-yl)acetonitrile

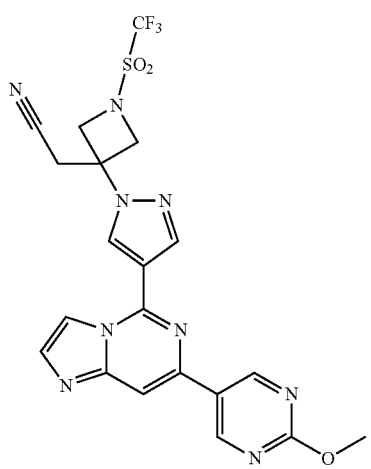 [SMILES: COc1ncc(-c2cc3nccn3c(-c3cnn(C4(CC#N)CN(S(=O)(=O)C(F)(F)F)C4)c3)n2)cn1]

Prepared according to Example 141, replacing cyclopropanesulfonyl chloride with trifluoromethanesulfonic anhydride to yield title compound in 91.7% yield. MS (apci) m/z=520.2 (M+H).

Example 143

2-(3-(3-(7-(1-(2-(methylsulfonyl)ethyl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile

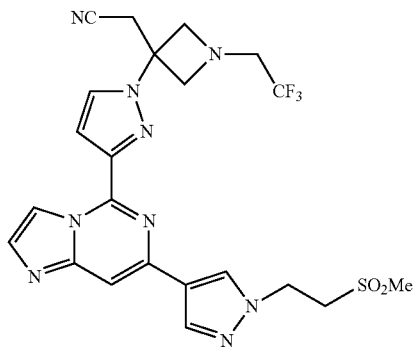 [SMILES: CS(=O)(=O)CCn1cc(-c2cc3nccn3c(-c3ccn(C4(CC#N)CN(CC(F)(F)F)C4)n3)n2)cn1]

Step A: Preparation of 1-(2-(methylsulfonyl)ethyl)-4-(4,4,5,5-tetramethyl-1,3,2-dioxaborolan-2-yl)-1H-pyrazole 4-(4,4,5,5-Tetramethyl-1,3,2-dioxaborolan-2-yl)-1H-pyrazole (5.3 g, 27.31 mmol), methylvinyl sulfone (4.349 g, 40.97 mmol) and DBU (2.042 mL, 13.66 mmol) were suspended in dry acetonitrile (54.63 mL) in a sealed glass bomb and heated in a sand bath at 90° C. overnight. The resulting reaction mixture was concentrated to a solid and the solids were washed with hexanes to yield 5.2 g (63.4%) of the title compound.

Step B: Preparation of tert-butyl 3-(cyanomethyl)-3-(4-(7-(1-(2-(methylsulfonyl)ethyl)-1H-pyrazol-4-yl)imidazo[1,2-c]pyrimidin-5-yl)-1H-pyrazol-1-yl)azetidine-1-carboxylate Prepared according to Example 103, Step A, replacing 1-(oxetan-3-yl)-4-(4,4,5,5-tetramethyl-1,3,2-dioxaborolan-2-yl)-1H-pyrazole with 2-methoxypyrimidin-5-ylboronic acid to yield title compound in 53% yield. MS (apci) m/z=552.2 (M+H).

Step C: Preparation of 2-(3-(3-(7-(1-(2-(methylsulfonyl)ethyl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile Tert-butyl 3-(cyanomethyl)-3-(4-(7-(1-(2-(methylsulfonyl)ethyl)-1H-pyrazol-4-yl)imidazo[1,2-c]pyrimidin-5-yl)-1H-pyrazol-1-yl)azetidine-1-carboxylate (150 mg, 0.2725 mmol) was dissolved in MeOH (5 mL) and a 4M HCl/dioxane solution (5 mL) was added. The resulting mixture was stirred for 20 minutes and then concentrated to a solid. To the solid was added dichloromethane and diisopropyl ethylamine. (474 µL, 4.52 mmol). After 10 minutes, the resulting mixture was cooled to −40° C. and 2,2,2-trifluoroethyl trifluoromethanesulfonate (126 mg, 0.543 mmol) was added. The reaction mixture was allowed to come to ambient temperature overnight. The resulting mixture was concentrated to an oil and the oil was chromatographed to yield 75 mg (51.7%) of the title compound. MS (apci) m/z=534.1 (M+H).

Example 144

2-(3-(3-(7-(1-methyl-2-oxo-1,2-dihydropyridin-4-yl)imidazo[1,2-c]pyrimidin-5-yl)-1H-pyrazol-1-yl)-1-(2,2,2-trifluoroethyl)azetidin-3-yl)acetonitrile

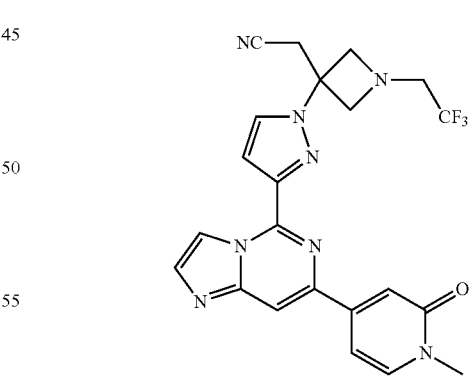

Step A: Preparation of tert-butyl 3-(cyanomethyl)-3-(3-(7-(1-methyl-2-oxo-1,2-dihydropyridin-4-yl)imidazo[1,2-c]pyrimidin-5-yl)-1H-pyrazol-1-yl)azetidine-1-carboxylate:

Prepared according to Example 103, Step A, replacing 1-(oxetan-3-yl)-4-(4,4,5,5-tetramethyl-1,3,2-dioxaborolan-2-yl)-1H-pyrazole with 1-methyl-4-(4,4,5,5-tetramethyl-1,3,2-dioxaborolan-2-yl)pyridin-2(1H)-one to yield title compound in 70.9% yield. MS (apci) m/z=487.1 (M+H).

Step B: Preparation of 2-(3-(3-(7-(1-methyl-2-oxo-1,2-dihydropyridin-4-yl)imidazo[1,2-c]pyrimidin-5-yl)-1H-pyrazol-1-yl)-1-(2,2,2-trifluoroethyl)azetidin-3-yl)acetonitrile: tert-Butyl 3-(cyanomethyl)-3-(3-(7-(1-methyl-2-oxo-1,2-dihydropyridin-4-yl)imidazo[1,2-c]pyrimidin-5-yl)-1H-pyrazol-1-yl)azetidine-1-carboxylate (250 mg, 0.514 mmol) was dissolved in MeOH (5 mL) and a 4M HCl/dioxane solution (5 mL) was added. The resulting mixture was stirred for 20 minutes and then was concentrated to a solid. To the solid was added dichloromethane and diisopropyl ethylamine (478 µL, 4.54 mmol). After 10 minutes, the resulting mixture was cooled to −40° C. and 2,2,2-trifluoroethyl trifluoromethanesulfonate (239 mg 1.03 mmol) was added. The reaction mixture was allowed to come to ambient temperature over night. The resulting mixture was concentrated to an oil and the oil was chromatographed to yield 54.7 mg (22.7%) of the title compound. MS (apci) m/z=469.1 (M+H).

Example 145

2-(3-(3-(7-(1-methyl-6-oxo-1,6-dihydropyridin-3-yl)imidazo[1,2-c]pyrimidin-5-yl)-1H-pyrazol-1-yl)-1-(2,2,2-trifluoroethyl)azetidin-3-yl)acetonitrile

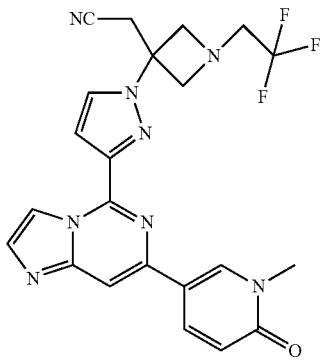 [SMILES: Cn1cc(-c2cc3nccn3c(-c3ccn(C4(CC#N)CN(CC(F)(F)F)C4)n3)n2)ccc1=O]

Prepared according to Example 144, replacing 1-methyl-4-(4,4,5,5-tetramethyl-1,3,2-dioxaborolan-2-yl)pyridin-2(1H)-one with 1-methyl-5-(4,4,5,5-tetramethyl-1,3,2-dioxaborolan-2-yl)pyridin-2(1H)-one to yield title compound in 22.7% yield. MS (apci) m/z=487.1 (M+H).

Example 146

2-(3-(4-(7-(4-(trifluoromethyl)phenyl)imidazo[1,2-c]pyrimidin-5-yl)-1H-pyrazol-1-yl)-1-(trifluoromethylsulfonyl)azetidin-3-yl)acetonitrile

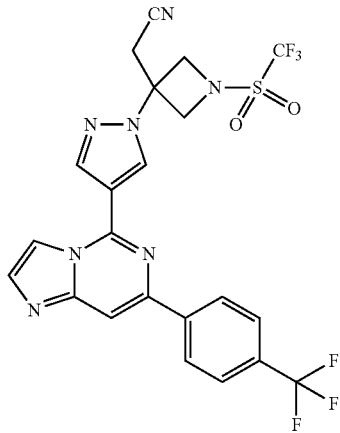 [SMILES: N#CCC1(n2cc(-c3nc(-c4ccc(C(F)(F)F)cc4)cc4nccn34)cn2)CN(S(=O)(=O)C(F)(F)F)C1]

Step A: Preparation of tert-butyl 3-(cyanomethyl)-3-(4-(7-(4-(trifluoromethyl)phenyl)imidazo[1,2-c]pyrimidin-5-yl)-1H-pyrazol-1-yl)azetidine-1-carboxylate: To a vial charged with tert-butyl 3-(4-(7-chloroimidazo[1,2-c]pyrimidin-5-yl)-1H-pyrazol-1-yl)-3-(cyanomethyl)azetidine-1-carboxylate (Preparation N; 490 mg; 1.18 mmol); 4-(trifluoromethyl)phenylboronic acid (337 mg; 1.78 mmol); Pd₂dba₃ (108 mg; 0.118 mmol); XPHOS (113 mg; 0.237 mmol) and potassium phosphate (3.55 mmol; 2M aqueous solution) was added 1,4-dioxane (10 mL). The mixture was sparged with nitrogen for 15 minutes. The vial was then sealed and heated for 3 hours at 75° C. with magnetic stirring. The mixture was diluted with methylene chloride (20 mL) and aqueous sodium bicarbonate solution (20 mL) was added. The mixture was extracted into methylene chloride (2×20 mL). The combined organic extracts were dried over magnesium sulfate, filtered and evaporated under reduced pressure. The resulting materiel was triturated with ether and the solids were collected and dried under vacuum to give the desired product as an off white solid (410 mg). MS (apci) m/z=524.2 (M+H).

Step B: Preparation of 2-(3-(4-(7-(4-(trifluoromethyl)phenyl)imidazo[1,2-c]pyrimidin-5-yl)-1H-pyrazol-1-yl)azetidin-3-yl)acetonitrile dihydro chloride To a solution of tert-butyl 3-(cyanomethyl)-3-(4-(7-(4-(trifluoromethyl)phenyl)imidazo[1,2-c]pyrimidin-5-yl)-1H-pyrazol-1-yl)azetidine-1-carboxylate (400 mg; 0.764 mmol) in 1,4-dioxane (5 mL) was added, in two equal portions, a solution of hydrogen chloride (31 mmol; 4M in 1,4-dioxane). The resulting suspension was stirred in a sealed vial for 2 days at ambient temperature. The solvent was evaporated under a stream of nitrogen and the resulting solid was dried under vacuum to give an off white solid (370 mg). MS (apci) m/z=424.1 (M+H).

Step C: Preparation of 2-(3-(4-(7-(4-(trifluoromethyl)phenyl)imidazo[1,2-c]pyrimidin-5-yl)-1H-pyrazol-1-yl)-1-(trifluoromethylsulfonyl)azetidin-3-yl)acetonitrile A solution of 2-(3-(4-(7-(4-(trifluoromethyl)phenyl)imidazo[1,2-c]pyrimidin-5-yl)-1H-pyrazol-1-yl)azetidin-3-yl)acetonitrile dihydrochloride (100 mg; 0.201 mmol) and 4-dimethylaminopyridine (1.2 mg; 0.01 mmol) in methylene chloride (3 mL) under nitrogen was cooled to 0° C. TEA (225 µL; 1.61 mmol) was added followed by trifluoromethanesulfonic anhydride (68 µL; 0.403 mmol). The mixture was stirred for 3 hours. The mixture was diluted with methylene chloride (20 mL) and washed with aqueous sodium bicarbonate (20 mL). The aqueous phase was extracted with methylene chloride (20 mL) and the combined organic phases were dried (sodium sulfate and magnesium sulfate), filtered and evaporated under reduced pressure. The material was purified by chromatography on silica gel, eluting with methylene chloride/6% ammonia in methanol (50:1) to give an off white solid (76 mg). MS (apci) m/z=556.1 (M+H).

Example 147

3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile

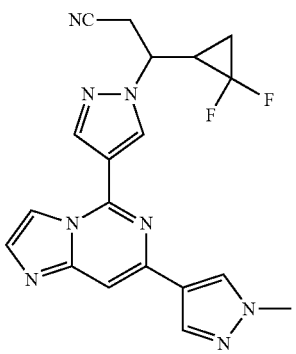 [SMILES: Cn1cc(-c2cc3nccn3c(-c3cnn(C(CC#N)C4CC4(F)F)c3)n2)cn1]

Step A: Preparation of 2,2-difluorocyclopropanecarbaldehyde

To a solution of 2-iodoxybenzoic acid (7.12 g; 25.4 mmol) in DMSO (50 mL) was added (2,2-difluorocyclopropyl)methanol (2.50 g; 23.1 mmol) and the mixture was stirred for 3 hours under nitrogen. Water (200 mL) was added. The white solids were removed by filtration and the filter cake was washed with ether, taking care not to evaporate the volatile product. A minimal quantity of ether was added to the filtrate and the aqueous phase was separated. The ether solution was washed with water and then dried (magnesium sulfate and sodium sulfate). The solution was filtered under nitrogen taking care not to use too much reduced pressure. The resulting ether solution (about 90 mL) was taken directly to the next step.

Step B: Preparation of 3-(2,2-difluorocyclopropyl)acrylonitrile

To a solution of diethyl cyanomethylphosphonate (4.09 g; 23.1 mmol) in dry THF (200 mL) at 0° C. under nitrogen was added potassium t-butoxide (23.1 mmol; 1M solution in THF). The mixture was stirred for 1 hour. The solution of 2,2-difluorocyclopropanecarbaldehyde from Step A was added and the mixture was stirred while allowing to warm to ambient temperature. A portion of the solvent was removed under reduced pressure and the remaining solution was diluted with ammonium chloride solution (50 mL). The mixture was extracted into ethyl acetate (2×50 mL). The combined extracts were dried (magnesium sulfate and sodium sulfate), filtered and evaporated under reduced pressure. The material was purified by chromatography on silica gel, eluting with hexane/ethyl acetate (3:1) to give 3-(2,2-difluorocyclopropyl)acrylonitrile (0.50 g) as a pale yellow oil (containing some ethyl acetate).

Step C: Preparation of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile To a mixture of 7-(1-methyl-1H-pyrazol-4-yl)-5-(1H-pyrazol-4-yl)imidazo[1,2-c]pyrimidine (200 mg; 0.754 mmol) and DBU (56 µL; 0.37 mmol) in acetonitrile (10 mL) was added 3-(2,2-difluorocyclopropyl)acrylonitrile (0.75 mmol). The mixture was stirred in a sealed vial at 50° C. for 24 hours. Further 3-(2,2-difluorocyclopropyl)acrylonitrile (0.4 mmol) was added and the mixture was stirred for a further 24 hours at 50° C. The solvent was removed under reduced pressure and the material was purified on silica gel, eluting with methylene chloride/6% ammonium hydroxide in methanol (50:1 to 15:1) to give 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile (160 mg) as a mixture of diastereoisomers. MS (apci) m/z=395.1 (M+H).

Example 147A

Isolation of (S)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile

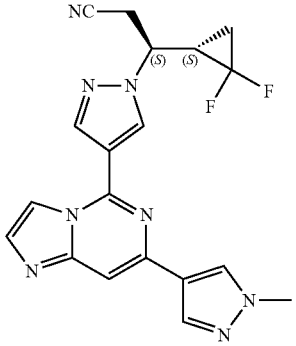

A mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile (prepared according to Example 147) is subjected to chiral chromatography to provide (S)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile as a single enantiomer. Alternatively a mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile is subjected to column chromatography to separate the two diastereomers. Each diastereomeric pair is then subjected to chiral chromatography to yield the two enantiomers and provide (S)-3-(S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile as a single enantiomer.

Example 147B

Isolation of (R)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile

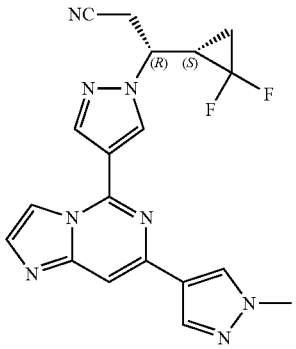

A mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile (prepared according to Example 147) is subjected to chiral chromatography to provide (R)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile. Alternatively a mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile is subjected to column chromatography to separate the two diastereomers. Each diastereomeric pair is then subjected to chiral chromatography to yield the two enantiomers and provide (R)-3-((S)-2,2-difluoro cyclopropyl)-3-(4-(7-(1-methyl-1H-pyrazol-4-yl)imidazo[1,2-c]pyrimidin-5-yl)-1H-pyrazol-1-yl)propanenitrile as a single enantiomer.

Example 147C

Isolation of (S)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile

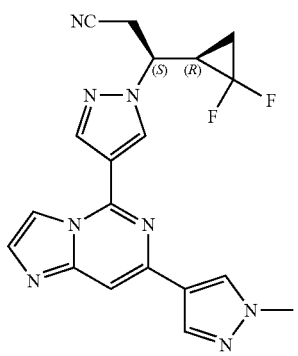

A mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile (prepared according to Example 147) is subjected to chiral chromatography to provide (S)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile. Alternatively a mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile is subjected to column chromatography to separate the two diastereomers. Each diastereomeric pair is then subjected to chiral chromatography to yield the two enantiomers and provide (S)-3-((R)-2,2-difluoro cyclopropyl)-3-(4-(7-(1-methyl-1H-pyrazol-4-yl)imidazo[1,2-c]pyrimidin-5-yl)-1H-pyrazol-1-yl)propanenitrile as a single enantiomer.

Example 147D

Isolation of (R)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile

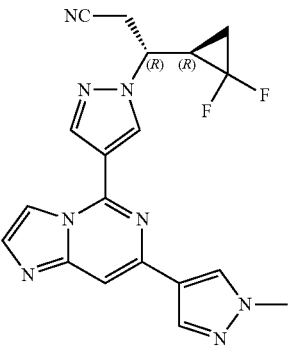

A mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile (prepared according to Example 147) is subjected to chiral chromatography to provide (R)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile. Alternatively a mixture of 3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile is subjected to column chromatography to separate the two diastereomers. Each diastereomeric pair is then subjected to chiral chromatography to yield the two enantiomers and provide (R)-3-((R)-2,2-difluoro cyclopropyl)-3-(4-(7-(1-methyl-1H-pyrazol-4-yl)imidazo[1,2-c]pyrimidin-5-yl)-1H-pyrazol-1-yl)propanenitrile as a single enantiomer.

Example 148

2-(6-(4-(7-(1-methyl-1H-pyrazol-4-yl)imidazo[1,2-c]pyrimidin-5-yl)-1H-pyrazol-1-yl)-2-oxaspiro[3.3]heptan-6-yl)acetonitrile

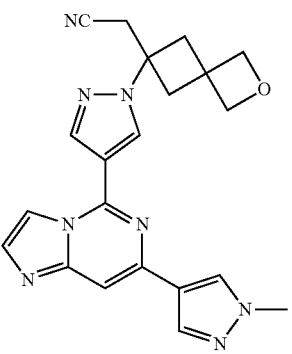 [SMILES: Cn1cc(-c2cc3nccn3c(-c3cnn(C4(CC#N)CC5(COC5)C4)c3)n2)cn1]

Step A: Preparation of
6-(phenylsulfonyl)-2-oxaspiro[3.3]heptane

To a solution of methylsulfonylbenzene (2.00 g; 12.8 mmol) in dry THF (40 mL) under nitrogen at 0° C. was added butyl lithium (25.6 mmol; 2.5M solution on hexane). The mixture was stirred for 1 hour and then cooled to −20° C. Tetramethylethylenediamine (1.93 mL; 12.8 mmol) was added followed by a solution of 3,3-bis(chloromethyl)oxetane (1.98 g; 12.8 mmol) in dry THF (10 mL). The mixture was allowed to warm to 0° C. and then slowly allowed to reach 15° C. over 12 hours. Water (100 mL) was added and the mixture was extracted into ethyl acetate (4×50 mL). The combined extracts were dried over sodium sulfate, filtered and concentrated under reduced pressure. The material was purified on silica gel (Biotage system, utilizing two 120 g columns in series) eluting with hexane/ethyl acetate (2:1 to 1:2 gradient). The desired product was obtained as an off white solid (700 mg).

Step B: Preparation of 2-oxaspiro[3.3]heptan-6-one

A solution of 6-(phenylsulfonyl)-2-oxaspiro[3.3]heptane (300 mg; 1.26 mmol) in dry THF (5 mL) was stirred under nitrogen at −78° C. Butyl lithium (1.38 mmol; 2.5M solution in hexane) was added and the mixture was stirred for 15 minutes. Peroxybis(trimethylsilane) (247 mg; 1.38 mmol) was added as a solution THF (2 mL) and the mixture was allowed to warm to ambient temperature with stirring over 12 hours. The mixture was added to aqueous sodium bicarbonate (50 mL) and extracted into ethyl acetate (5×25 mL). The combined extracts were dried over sodium sulfate, filtered and concentrated under reduced pressure. The material was purified by chromatography on silica gel, eluting with hexane/ethyl acetate (1:1) to give the product as an oil (52 mg).

Step C: Preparation of
2-(2-oxaspiro[3.3]heptan-6-ylidene)acetonitrile

To a solution of diethyl cyanomethylphosphonate (82 mg; 0.464 mmol) in THF (2 mL) at 0° C. under nitrogen was added potassium t-butoxide (0.51 mmol; 1M solution in THF) and the mixture was stirred at 0° C. for 1 hour. A solution of 2-oxaspiro[3.3]heptan-6-one (52 mg; 0.464 mmol) in THF (1 mL) was added. A precipitate formed and further THF (1 mL) was added to enhance the stirring. The reaction mixture was allowed to stir for 4 hours at ambient temperature. The reaction mixture was partitioned between saturated aqueous ammonium chloride (10 mL) and ethyl acetate (10 mL). The phases were separated and the aqueous phase was extracted with ethyl acetate (3×10 mL). The extracts were combined, dried (sodium sulfate), filtered and evaporated under reduced pressure. The material was purified by silica gel chromatography eluting with hexane/ethyl acetate (3:2) to give the product as a colorless oil (20 mg).

Step D: Preparation of 2-(6-(4-(7-(1-methyl-1H-pyrazol-4-yl)imidazo[1,2-c]pyrimidin-5-yl)-1H-pyrazol-1-yl)-2-oxaspiro[3.3]heptan-6-yl)acetonitrile A mixture of 7-(1-methyl-1H-pyrazol-4-yl)-5-(1H-pyrazol-4-yl)imidazo[1,2-c]pyrimidine (25 mg; 0.094 mmol), 2-(2-oxaspiro[3.3]heptan-6-ylidene)acetonitrile (19 mg; 0.14 mmol) and DBU (7.2 mg; 0.047 mmol) in acetonitrile (1 mL) was stirred in a sealed vial at 50° C. for 24 hours. The solvent was removed under reduced pressure and the material was purified by silica gel chromatography, eluting with (6% ammonium hydroxide in methanol)/methylene chloride (1:25 to 1:15 gradient) to provide pure desired product as a white solid (27.5 mg). MS (apci) m/z=401.1 (M+H).

Example 149

2-(3-(4-(7-cyclopropylimidazo[1,2-c]pyrimidin-5-yl)-1H-pyrazol-1-yl)-1-(2,2,2-trifluoroethyl)azetidin-3-yl)acetonitrile

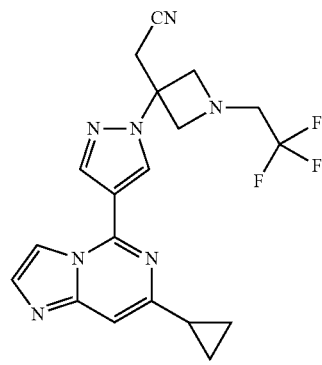 [SMILES: N#CCC1(n2cc(-c3nc(C4CC4)cc4nccn34)cn2)CN(CC(F)(F)F)C1]

Step A: Preparation of tert-butyl 3-(cyanomethyl)-3-(4-(7-cyclopropylimidazo[1,2-c]pyrimidin-5-yl)-1H-pyrazol-1-yl)azetidine-1-carboxylate: To a vial were added tert-butyl 3-(4-(7-chloroimidazo[1,2-c]pyrimidin-5-yl)-1H-pyrazol-1-yl)-3-(cyanomethyl)azetidine-1-carboxylate (Preparation N; 400 mg; 0.967 mmol), cyclopropylboronic acid (830 mg; 9.67 mmol), Pd₂dba₃ (177 mg; 0.193 mmol), XPHOS (92 mg; 0.913 mmol), S-Phos (79 mg; 0.913 mmol), potassium phosphate (3.87 mmol; 2M aqueous solution) and 1,4-dioxane (10 mL). The mixture was sparged with nitrogen for 15 minutes and the vial was sealed. The mixture was heated at 75° C. with stirring for 6 hours. The mixture was allowed to cool and diluted with methylene chloride (30 mL). Aqueous sodium bicarbonate solution (20 mL) was added. The phases were separated and the aqueous phase was extracted into methylene chloride (2×30 mL). The combined organic phases were dried (magnesium sulfate), filtered and concentrated under reduced pressure.

The material was purified by chromatography on silica gel, eluting with methylene chloride/6% ammonium hydroxide in methanol (98:2 to 96:4 gradient) to give the desired product (260 mg).

Step B: Preparation of 2-(3-(4-(7-cyclopropylimidazo[1,2-c]pyrimidin-5-yl)-1H-pyrazol-1-yl)azetidin-3-yl)acetonitrile trihydrochloride: To a solution of tert-butyl 3-(cyanomethyl)-3-(4-(7-cyclopropylimidazo[1,2-c]pyrimidin-5-yl)-1H-pyrazol-1-yl)azetidine-1-carboxylate (100 mg; 0.238 mmol) in 1,4-dioxane (1 mL) was added hydrogen chloride in 1,4-dioxane (2.4 mL; 4M solution). The mixture was stirred in a sealed vial for 3 hours. The solvent was removed under reduced pressure to give the product (100 mg) as an off white solid. MS (apci) m/z=320.1 (M+H).

Step C: Preparation of 2-(3-(4-(7-cyclopropylimidazo[1,2-c]pyrimidin-5-yl)-1H-pyrazol-1-yl)-1-(2,2,2-trifluoroethyl)azetidin-3-yl)acetonitrile: To a mixture of 2-(3-(4-(7-cyclopropylimidazo[1,2-c]pyrimidin-5-yl)-1H-pyrazol-1-yl)azetidin-3-yl)acetonitrile trihydrochloride (100 mg; 0.233 mmol) and acetonitrile (2 mL) was added 2,2,2-trifluoroethyl trifluoromethanesulfonate (108 mg; 0.466 mmol) and TEA (118 mg; 1.17 mmol). The mixture was stirred in a sealed vial for 15 hours. Water (40 mL) was added and the mixture was extracted into methylene chloride (3×30 mL). The combined extracts were dried (sodium sulfate and magnesium sulfate), filtered and concentrated under reduced pressure. The material was purified by chromatography on silica gel, eluting with methylene chloride/6% ammonium hydroxide in methanol (98:2-96:4 gradient) to give the desired product as a white foam (56 mg). MS (apci) m/z=402.1 (M+H).

Example 150

2-(2-(4-(7-(1-methyl-1H-pyrazol-4-yl)imidazo[1,2-c]pyrimidin-5-yl)-1H-pyrazol-1-yl)-7-oxaspiro[3.5]nonan-2-yl)acetonitrile

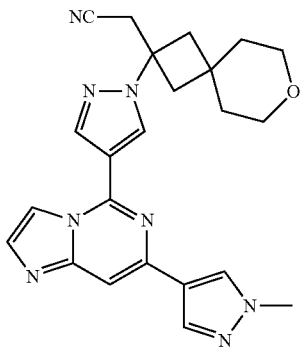 [SMILES: Cn1cc(-c2cc3nccn3c(-c3cnn(C4(CC#N)CC5(CCOCC5)C4)c3)n2)cn1]

Step A: Preparation of 4-methylenetetrahydro-2H-pyran

A solution of dihydro-2H-pyran-4(3H)-one (2.50 g; 25.0 mmol) in THF (50 mL) was sparged with nitrogen for 15 minutes. The solution was cooled to 5° C. under nitrogen with stirring. A solution of Tebbe reagent (bis(cyclopentadienyl)-μ-chloro(dimethylaluminum)-μ-methylenetitanium) (25.0 mmol; 0.50 M solution in toluene; Sigma-Aldrich Chemical Co.) was added. The mixture was allowed to warm to ambient temperature. Ether was added (400 mL). The reagent was quenched by the careful addition of 0.1M sodium hydroxide (10 mL). (The quench is highly exothermic with considerable effervescence). The resulting solution was dried (sodium sulfate) and filtered through a mixture of Celite® and alumina washing the filter cake with ether. The filtrate was partially concentrated to remove the majority of the ether at 50° C. and a pressure of 580 mm Hg. The resulting mixture was diluted with pentane, filtered through Celite® and then partially concentrated as previously (taking care not to lose the volatile product). The resulting solution in toluene/pentane was continued to the next step without characterization of the product.

Step B: Preparation of 1,1-dichloro-7-oxaspiro[3,5]nonan-2-one

Zinc was activated according to a published procedure (Synthesis 1971; 415). Hydrated copper sulfate (14 g) was dissolved in water (150 mL) and added to zinc dust (60 g). The mixture was stirred for 2 hours under nitrogen. The activated zinc was isolated by filtration, washed with acetone and dried in a vacuum oven at 100° C. prior to use. The solution of 4-methylenetetrahydro-2H-pyran from Step A was dried with sodium sulfate and magnesium sulfate and filtered through Celite® (washing the cake with ether). This removed some orange solids which had precipitated. A solution of trichloroacetyl chloride (5.00 g; 27.5 mmol) in dry ether (250 mL) was added slowly (over 4 hours) to a stirred refluxing mixture of the 4-methylenetetrahydro-2H-pyran in dry ether (250 mL) and the activated zinc (5.00 g; 76.5 mmol) under nitrogen. The mixture was stirred for 16 hours at reflux. The solution was filtered through Celite® and concentrated under reduced pressure. The material was purified by chromatography on silica gel, eluting with 10:1 hexane/ethyl acetate to give impure product (160 mg) as a colorless oil which was continued directly on to the next step.

Step C: Preparation of 7-oxaspiro[3.5]nonan-2-one

The impure 1,1-dichloro-7-oxaspiro[3.5]nonan-2-one from Step B was stirred with zinc (150 mg; 2.30 mmol) and 5 mL of acetic acid/water (1:1) for 4 hours. The mixture was stored at −20° C. for 1 day, diluted with ether (20 mL) and filtered through a pad of Celite®. The solution was neutralized with aqueous sodium bicarbonate solution and extracted into ether (5×20 mL). The combined ether extracts were dried (sodium sulfate), filtered and concentrated under reduced pressure. The material was purified by chromatography on silica gel, eluting with 1:1 ethyl acetate/hexane to give the product as a colorless oil (61 mg).

Step D: Preparation of 2-(7-oxaspiro[3.5]nonan-2-ylidene)acetonitrile

This was prepared from 7-oxaspiro[3.5]nonan-2-one (45 mg; 0.321 mg) in analogous fashion to Example 148, Step C to give the desired product (43 mg).

Step E: Preparation of 2-(2-(4-(7-(1-methyl-1H-pyrazol-4-yl)imidazo[1,2-c]pyrimidin-5-yl)-1H-pyrazol-1-yl)-7-oxaspiro[3.5]nonan-2-yl)acetonitrile This was prepared from 7-(1-methyl-1H-pyrazol-4-yl)-5-(1H-pyrazol-4-yl)imidazo[1,2-c]pyrimidine (40 mg; 0.151 mmol) and 2-(7-oxaspiro[3.5]nonan-2-ylidene)acetonitrile (37 mg; 0.226 mmol) in analogous fashion to Example 148, Step D to give the desired product (39 mg). MS (apci) m/z=429.2 (M+H).

Example 151

2-(2-(4-(7-(1-methyl-1H-pyrazol-4-yl)imidazo[1,2-c]pyrimidin-5-yl)-1H-pyrazol-1-yl)spiro[3.5]nonan-2-yl)acetonitrile

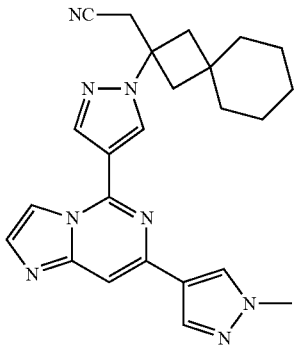 [SMILES: Cn1cc(-c2cc3nccn3c(-c3cnn(C4(CC#N)CC5(CCCCC5)C4)c3)n2)cn1]

Step A: Preparation of 1,1-dichlorospiro[3.5]nonan-2-one

This was prepared according to a literature procedure (Tetrahedron 1993, 49(36), 8159). Activated zinc (5.00 g; 76.5 mmol) (prepared according to Example 150, Step B) and methylenecyclohexane (2.40 g; 25.0 mmol) in dry ether (100 mL) under nitrogen were mixed in a 250 mL 3-neck flask with an addition funnel and condenser attached. The mixture was placed in a sonic bath at 25° C. Trichloroacetyl chloride (5.91 g; 32.5 mmol) in dry ether (50 mL) was added dropwise as the solution was sonicated. The sonication was continued for 3 hours. The mixture was filtered through Celite® and the solution was washed with saturated aqueous ammonium chloride solution (50 mL) and aqueous sodium bicarbonate solution (50 mL). The solution was dried (sodium sulfate), filtered and concentrated under reduced pressure. The residue was passed through a plug of silica gel using ether. The filtrate was evaporated to give the product as a yellow oil (5.03 g).

Step B: Preparation of spiro[3.5]nonan-2-one

According to a literature procedure (Tetrahedron 1993, 49(36), 8159). A mixture of 1,1-dichlorospiro[3.5]nonan-2-one (5.00 g; 24.1 mmol) and zinc dust (4.74 g; 72.4 mmol) was stirred in acetic acid (60 mL) and water (30 mL) for 4 hours. The solution was then stored at −20° C. for 15 hours. The mixture was filtered through Celite®, washing with ether and hexane, and then the filtrate was washed with aqueous sodium hydroxide solution (2N; 4×100 mL). (This resulted in the precipitation of white salts, which needed to be removed by filtration). The organic phase was washed with water (30 mL), dried (sodium sulfate), filtered and concentrated under reduced pressure. The material was purified by chromatography on silica gel, eluting with hexane/ether (10:1) to give the desired product as an almost colorless oil (2.56 g).

Step C: Preparation of 2-(spiro[3.5]nonan-2-ylidene)acetonitrile

This was prepared from spiro[3.5]nonan-2-one (1.25 g) using the procedure described in Example 148, Step C to give the desired product (1.14 g).

Step D: Preparation of 2-(2-(4-(7-(1-methyl-1H-pyrazol-4-yl)imidazo[1,2-c]pyrimidin-5-yl)-1H-pyrazol-1-yl)spiro[3.5]nonan-2-yl)acetonitrile This was prepared from 7-(1-methyl-1H-pyrazol-4-yl)-5-(1H-pyrazol-4-yl)imidazo[1,2-c]pyrimidine (100 mg; 0.377 mmol) and 2-(spiro[3.5]nonan-2-ylidene)acetonitrile (91 mg; 0.565 mmol) using the procedure described in Example 148, Step D to give the desired product (60 mg). MS (apci) m/z=427.2 (M+H).

Example 152

3-cyclopropyl-3-(4-(3-fluoro-7-(1-methyl-1H-pyrazol-4-yl)imidazo[1,2-c]pyrimidin-5-yl)-1H-pyrazol-1-yl)propanenitrile

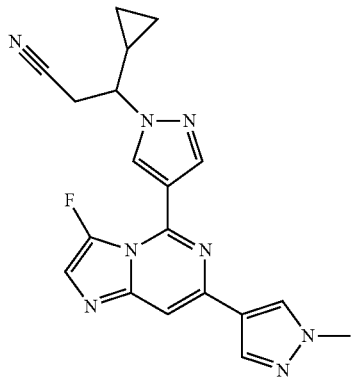 [SMILES: Cn1cc(-c2cc3ncc(F)n3c(-c3cnn(C(CC#N)C4CC4)c3)n2)cn1]

3-Cyclopropyl-3-(4-(7-(1-methyl-1H-pyrazol-4-yl)imidazo[1,2-c]pyrimidin-5-yl)-1H-pyrazol-1-yl)propanenitrile (Example 2; 0.200 g, 0.558 mmol), Selectfluor® (0.395 g, 1.12 mmol) and acetic acid (0.320 mL, 5.58 mmol) were suspended in MeCN (20 mL) and heated to 80° C. overnight. The reaction mixture was cooled to ambient temperature and the reaction mixture partitioned between saturated aqueous sodium hydrogen carbonate and ethyl acetate. The combined organic extracts were washed with brine, dried, magnesium sulfate and concentrated under reduced pressure to afford the crude material, which was purified by flash column chromatography, eluting with 1-2% (9:1 MeOH:NH$_4$OH)/dichloromethane to provide the 3-cyclopropyl-3-(4-(3-fluoro-7-(1-methyl-1H-pyrazol-4-yl)imidazo[1,2-c]pyrimidin-5-yl)-1H-pyrazol-1-yl)propanenitrile (0.042 g, 0.112 mmol, 20% yield). MS (apci) m/z=377.1 (M+H).

Example 153

2-(3-(4-(3-chloro-7-(1-(oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile

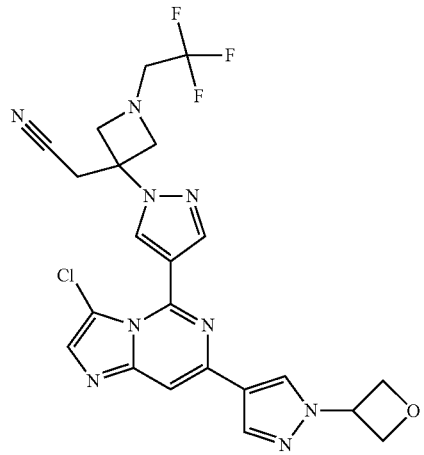 [SMILES: N#CCC1(n2cc(-c3nc(-c4cnn(C5COC5)c4)cc4ncc(Cl)n34)cn2)CN(CC(F)(F)F)C1]

2-(3-(4-(7-(1-(Oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile (Example 105; 0.040 g, 0.08274 mmol) was suspended in DCM (3 mL) and saturated aqueous NaHCO$_3$ (1 mL). n-Chlorosuccinimide (0.017 g, 0.124 mmol) was added in one portion and the reaction mixture stirred at ambient temperature overnight. Additional n-chlorosuccinimide (0.033 g, 0.248 mmol) was added and the reaction was allowed to stir at ambient temperature overnight. The reaction mixture was partitioned between saturated aqueous NaHCO$_3$ and DCM. The combined organic extracts were washed with brine, dried (MgSO$_4$), filtered and concentrated under reduced pressure to afford the crude material, which was purified by flash column chromatography, eluting with 1-2% (9:1 MeOH:NH$_4$OH)/DCM to provide 2-(3-(4-(3-chloro-7-(1-(oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile (0.012 g, 0.023 mmol, 28% yield). MS (apci) m/z=518.1 (M+H).

Example 154

2-(3-(4-(3-fluoro-7-(1-methyl-1H-pyrazol-4-yl)imidazo[1,2-c]pyrimidin-5-yl)-1H-pyrazol-1-Y1)-1-((trifluoromethyl)sulfonyl)azetidin-3-yl)acetonitrile

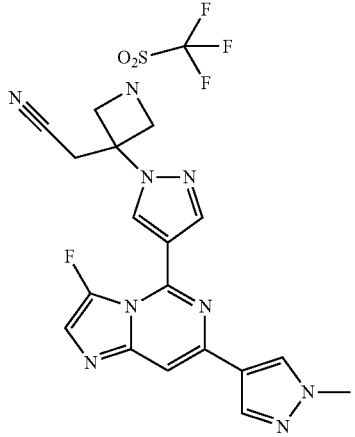

2-(3-(4-(7-(1-Methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile (Example 96; 0.200 g, 0.407 mmol), Selectfluor (0.288 g, 0.814 mmol) and acetic acid (0.233 mL, 4.07 mmol) were suspended in MeCN (20 mL) and heated to 80° C. overnight. The reaction mixture was cooled to ambient temperature and the reaction mixture was partitioned between saturated aqueous sodium hydrogen carbonate and ethyl acetate. The combined organic extracts were washed with brine, dried, magnesium sulfate and concentrated under reduced pressure to afford the crude material, which was purified by flash column chromatography, eluting with 1-2% (9:1 MeOH:NH$_4$OH)/dichloromethane to provide 2-(3-(4-(3-fluoro-7-(1-methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile (0.043 g, 0.084 mmol, 21% yield). MS (apci) m/z=510.1 (M+H).

Example 155

2-(3-(4-(3-chloro-7-(1-methyl-1H-pyrazol-4-yl)imidazo[1,2-c]pyrimidin-5-yl)-1H-pyrazol-1-yl)-1-((trifluoromethyl)sulfonyl)azetidin-3-yl)acetonitrile

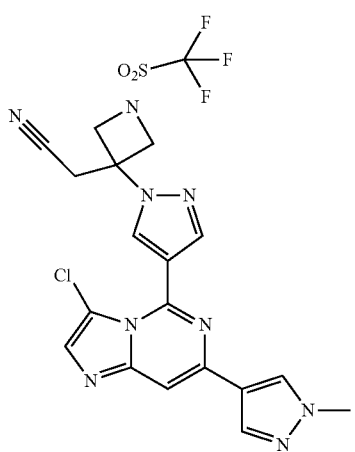

2-(3-(4-(7-(1-Methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile (Example 96; 0.150 g, 0.305 mmol) was suspended in DCM (5 mL) and saturated aqueous NaHCO$_3$ (2 mL). n-Chlorosuccinimide (0.204 g, 1.53 mmol) was added in one portion and the reaction mixture stirred at ambient temperature overnight. The reaction mixture was partitioned between saturated aqueous NaHCO$_3$ and DCM. The combined organic extracts were washed with brine, dried (MgSO$_4$), filtered and concentrated under reduced pressure to afford the crude material, which was purified by flash column chromatography, eluting with 2-3% (9:1 MeOH:NH$_4$OH)/DCM to provide 2-(3-(4-(3-chloro-7-(1-methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile (0.027 g, 0.051 mmol, 17% yield). MS (apci) m/z=526.0 (M+H).

Example 156

2-(1-(2,2-difluoroethyl)-3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile

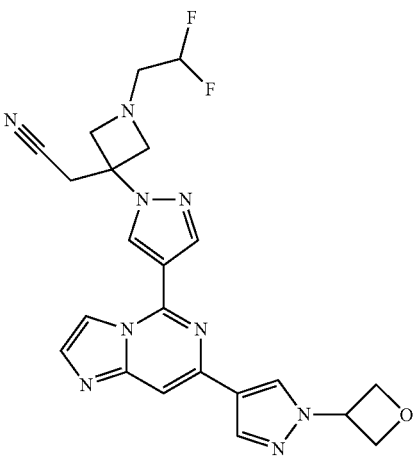 [SMILES: N#CCC1(n2cc(-c3nc(-c4cnn(C5COC5)c4)cc4nccn34)cn2)CN(CC(F)F)C1]

Step A: Preparation of tert-butyl 3-(cyanomethyl)-3-(4-(7-(1-(oxetan-3-yl)-1H-pyrazol-4-yl)imidazo[1,2-c]pyrimidin-5-yl)-1H-pyrazol-1-yl)azetidine-1-carboxylate tert-Butyl 3-(4-(7-chloroimidazo[1,2-c]pyrimidin-5-yl)-1H-pyrazol-1-yl)-3-(cyanomethyl) azetidine-1-carboxylate (Preparation N, 2.00 g, 4.83 mmol), 1-(oxetan-3-yl)-4-(4,4,5,5-tetramethyl-1,3,2-dioxaborolan-2-yl)-1H-pyrazole (Table 2, compound f; 1.81 g, 7.25 mmol), XPHOS (0.461 g, 0.967 mmol) and K$_3$PO$_4$ (7.25 mL, 14.5 mmol) were suspended in 1,4-dioxane (50 mL) and purged with Ar (g) for 10 minutes. Pd$_2$dba$_3$ (0.443 g, 0.483 mmol) was added and the system sealed and heated at 75° C. overnight. The reaction mixture was cooled to ambient temperature and partitioned between saturated aqueous NaHCO$_3$ and EtOAc. The combined organic extracts were washed with brine, dried (MgSO$_4$), filtered and concentrated under reduced pressure to afford the crude material, which was purified by flash column chromatography, eluting with 2-5% (9:1 MeOH:NH$_4$OH)/DCM to provide tert-butyl 3-(cyanomethyl)-3-(4-(7-(1-(oxetan-3-yl)-1H-pyrazol-4-yl)imidazo[1,2-c]pyrimidin-5-yl)-1H-pyrazol-1-yl)azetidine-1-carboxylate (1.46 g, 2.91 mmol, 60.2% yield). MS (apci) m/z=502.2 (M+H).

Step B: Preparation of 2-(3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile bis(2,2,2-trifluoroacetate)

tert-Butyl 3-(cyanomethyl)-3-(4-(7-(1-(oxetan-3-yl)-1H-pyrazol-4-yl)imidazo[1,2-c]pyrimidin-5-yl)-1H-pyrazol-1-yl)azetidine-1-carboxylate (0.75 g, 1.5 mmol) was suspended in DCM (15 mL) and TFA (5 mL) and stirred at ambient temperature for 2 hours. The reaction mixture was diluted with toluene and concentrated under reduced pressure. The material was transferred to another flask with DCM and MeOH and concentrated under reduced pressure to afford the crude 2-(3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile bis(2,2,2-trifluoroacetate) (1.31 g, 1.46 mmol, 97.4% yield), which was used in the next step without further purification.

Step C: Preparation of 2-(1-(2,2-difluoro ethyl)-3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile 2-(3-(4-(7-(1-(Oxetan-3-yl)-1H-pyrazol-4-yl)imidazo[1,2-c]pyrimidin-5-yl)-1H-pyrazol-1-yl)azetidin-3-yl)acetonitrile bis(2,2,2-trifluoroacetate) (0.080 g, 0.089 mmol), 2,2-difluoroethyl trifluoromethanesulfonate (0.038 g, 0.178 mmol) and N-ethyl-N-isopropylpropan-2-amine (0.093 mL, 0.534 mmol) were suspended in DMF (5 mL) and stirred at ambient temperature for 1 hour. The reaction mixture was partitioned between saturated aqueous NaHCO$_3$ and EtOAc. The combined organic extracts were washed with brine, dried (MgSO$_4$), filtered and concentrated under reduced pressure to afford the crude material, which was purified by flash column chromatography, eluting with 2.5-3.5% (9:1 MeOH: NH$_4$OH)/DCM to provide 2-(1-(2,2-difluoro ethyl)-3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile (0.005 g, 0.011 mmol, 12% yield). MS (apci) m/z=466.2 (M+H).

Example 157

2-(3-(4-(7-(1-(oxetan-3-yl)-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile

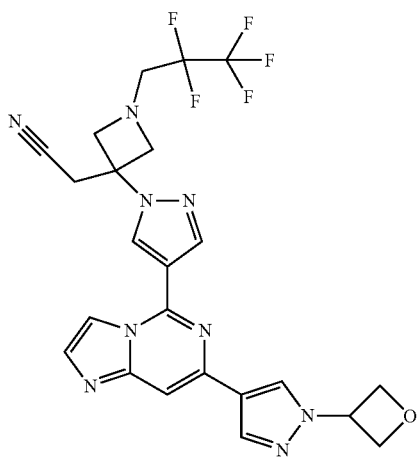 [SMILES: N#CCC1(n2cc(-c3nc(-c4cnn(C5COC5)c4)cc4nccn34)cn2)CN(CC(F)(F)C(F)(F)F)C1]

2-(3-(4-(7-(1-(Oxetan-3-yl)-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile was prepared according to the procedure of Example 156, replacing 1 trifluoromethanesulfonate with 2,2,3,3,3-pentafluoropropyl trifluoromethanesulfonate. MS (apci) m/z=534.1 (M+H).

Example 158

2-(3-(4-(7-(4-methoxyphenyl)imidazo[1,2-c]pyrimidin-5-yl)-1H-pyrazol-1-yl)-1-(trifluoromethylsulfonyl)azetidin-3-yl)acetonitrile

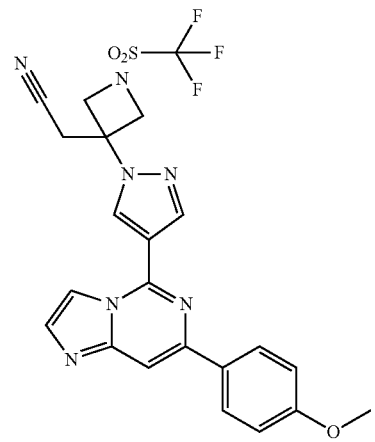

Step A: Preparation of tert-butyl 3-(cyanomethyl)-3-(4-(7-(4-methoxyphenyl)imidazo[1,2-c]pyrimidin-5-yl)-1H-pyrazol-1-yl)azetidine-1-carboxylate tert-Butyl 3-(4-(7-chloroimidazo[1,2-c]pyrimidin-5-yl)-1H-pyrazol-1-yl)-3-(cyanomethyl)azetidine-1-carboxylate (Preparation N; 2.80 g, 6.76 mmol), 4-methoxybenzeneboronic acid (1.54 g, 10.1 mmol), dicyclohexyl(2',4',6'-triisopropylbiphenyl-2-yl)phosphine (0.644 g, 1.35 mmol) and K$_3$PO$_4$ (10.1 mL, 20.3 mmol) were suspended in 1,4-dioxane (30 mL) and purged with Ar (g). Pd$_2$dba$_3$ (0.619 g, 0.676 mmol) was added and the system sealed and heated at 75° C. overnight. The reaction mixture was diluted with EtOAc and saturated aqueous NaHCO$_3$. The bi-phasic mixture was passed through a pad of Celite® to remove solids. The Celite® was washed with DCM and MeOH. The organic layer was separated and then washed with brine, dried (MgSO$_4$), filtered and concentrated under reduced pressure to afford some crude material. This was combined with the DCM and MeOH washed off the Celite® to afford the crude total material. The crude material was suspended in DCM to load onto a column. Many solids did not dissolve and were collected and identified as desired crude material. The crude material was loaded onto a column and purified by flash column chromatography, eluting with 2-4% (9:1 MeOH: NH$_4$OH)/DCM to provide tert-butyl 3-(cyanomethyl)-3-(4-(7-(4-methoxyphenyl)imidazo[1,2-c]pyrimidin-5-yl)-1H-pyrazol-1-yl)azetidine-1-carboxylate (3.42 g, 7.044 mmol, 104.3% yield). MS (apci) m/z=486.2 (M+H).

Step B: Preparation of 2-(3-(4-(7-(4-methoxyphenyl) imidazo[1,2-c]pyrimidin-5-yl)-1H-pyrazol-1-yl)azetidin-3-yl)acetonitrile dihydrochloride tert-Butyl 3-(cyanomethyl)-3-(4-(7-(4-methoxyphenyl) imidazo[1,2-c]pyrimidin-5-yl)-1H-pyrazol-1-yl)azetidine-1-carboxylate (1.60 g, 3.30 mmol) was suspended in 20 mL of 1,4-dioxane and then HCl (41.2 mL, 165 mmol) (4 M in dioxane) was added in one portion. The reaction was stirred at ambient temperature overnight, then concentrated under reduced pressure to afford the crude material, which was used in the next step without further purification.

Step C: Preparation of 2-(3-(4-(7-(4-methoxyphenyl) imidazo[1,2-c]pyrimidin-5-yl)-1H-pyrazol-1-yl)-1-(trifluoromethylsulfonyl)azetidin-3-yl)acetonitrile 2-(3-(4-(7-(4-Methoxyphenyl)imidazo[1,2-c]pyrimidin-5-yl)-1H-pyrazol-1-yl)azetidin-3-yl)acetonitrile dihydrochloride (0.300 g, 0.655 mmol) and DIEA (0.57 mL, 3.3 mmol) were suspended in DCM (10 mL) and cooled to 0° C. Trifluoromethanesulfonic anhydride (0.165 mL, 0.982 mmol) was added dropwise and the reaction mixture allowed to warm to ambient temperature overnight. The reaction mixture was partitioned between saturated aqueous $NaHCO_3$ and DCM. The combined organic extracts were dried ($MgSO_4$), filtered and concentrated under reduced pressure and the crude material purified by flash column chromatography, eluting with 2% (9:1 $MeOH:NH_4OH$)/DCM) to provide 2-(3-(4-(7-(4-methoxyphenyl)imidazo[1,2-c]pyrimidin-5-yl)-1H-pyrazol-1-yl)-1-(trifluoromethylsulfonyl)azetidin-3-yl) acetonitrile (0.188 g, 0.363 mmol, 55.5% yield). MS (apci) m/z=518.1 (M+H).

Example 159

2-(1-(cyclopropylsulfonyl)-3-(4-(7-(4-methoxyphenyl)imidazo[1,2-c]pyrimidin-5-yl)-1H-pyrazol-1-yl) azetidin-3-yl)acetonitrile

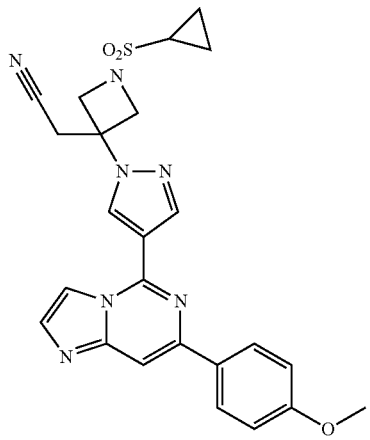

2-(1-(Cyclopropylsulfonyl)-3-(4-(7-(4-methoxyphenyl) imidazo[1,2-c]pyrimidin-5-yl)-1H-pyrazol-1-yl)azetidin-3-yl)acetonitrile was prepared according to the procedure of Example 158, replacing 1 trifluoromethanesulfonic anhydride with cyclopropanesulfonyl chloride. MS (apci) m/z=490.1 (M+H).

Example 160

2-(2-(4-(7-(1-methyl-1H-pyrazol-4-yl)imidazo[1,2-c] pyrimidin-5-yl)-1H-pyrazol-1-yl)spiro[3.3]heptan-2-yl)acetonitrile

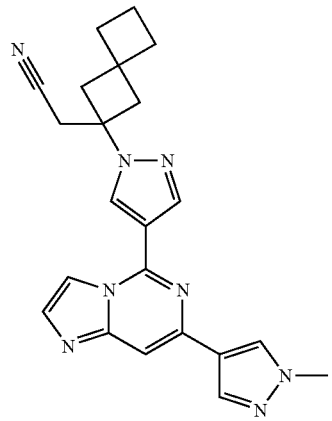 [SMILES: Cn1cc(-c2cc3nccn3c(-c3cnn(C4(CC#N)CC5(CCC5)C4)c3)n2)cn1]

Step A: Preparation of 1,1-dichlorospiro[3.3]heptan-2-one

Methylenecyclobutane (5.00 g, 70.5 mmol) and zinc dust (13.8 g, 211 mmol) were suspended in dry $Et_2O$ (200 mL) in a 3 necked round bottomed flask having an addition funnel and reflux condenser and placed in a sonic bath at 25° C. The system was sonicated and 2,2,2-trichloroacetyl chloride (10.282 mL, 91.607 mmol) (as a solution in 50 mL dry $Et_2O$) added drop-wise, during which time the reaction became warm and the $Et_2O$ began refluxing). The sonication was continued for 4 hours. The reaction mixture was filtered through a pad of Celite® and the organic layer was washed sequentially with $NH_4Cl$, $NaHCO_3$ and brine. The organic layer was dried ($MgSO_4$), filtered and concentrated under reduced pressure to afford the crude material, which was in the next step without purification.

Step B: Preparation of spiro[3.3]heptan-2-one

Crude 1,1-dichlorospiro[3.3]heptan-2-one (12.6 g, 70.5 mmol) from the previous step was suspended in acetic acid (80 mL, 1400 mmol) and water (50 mL) and stirred at ambient temperature for 5 hours. The reaction mixture was passed through a pad of Celite® and eluted with $Et_2O$. The organic layer was washed with 1 N NaOH, brine, dried ($MgSO_4$), filtered and concentrated under reduced pressure to afford the crude material, which was in the next step without purification.

Step C: Preparation of 2-(spiro[3.3]heptan-2-ylidene)acetonitrile

Diethyl cyanomethylphosphonate (3.15 mL, 20.0 mmol) was suspended in THF (30 mL) and cooled to 0° C. Potassium 2-methylpropan-2-olate (2.35 g, 21.0 mmol) was added portion-wise and stirred at 0° C. for 15 minutes. Spiro[3.3]heptan-2-one (2.100 g, 19.06 mmol) as a solution in THF (20 mL) was added dropwise and the reaction mixture was allowed to warm to ambient temperature overnight. The reaction mixture was partitioned between water, saturated aqueous NH₄Cl and EtOAc. The organic layer was washed with saturated aqueous NH₄Cl, brine, dried (MgSO₄), filtered and concentrated under reduced pressure to afford the crude material. The crude was purified by flash column chromatography, eluting with 2.5% EtOAc/Hexanes to provide 2-(spiro[3.3]heptan-2-ylidene)acetonitrile (1.40 g, 10.5 mmol, 55% yield). ¹H NMR (CDCl₃) δ 5.14-5012 (m, 1H), 2.93-2.91 (m, 2H), 2.82-2.80 (m, 2H), 2.10-2.04 (m, 4H), 1.91-1.85 (m, 2H).

Step D: Preparation of 2-(2-(4-(7-(1-methyl-1H-pyrazol-4-yl)imidazo[1,2-c]pyrimidin-5-yl)-1H-pyrazol-1-yl)spiro[3.3]heptan-2-yl)acetonitrile 7-(1-Methyl-1H-pyrazol-4-yl)-5-(1H-pyrazol-4-yl)imidazo[1,2-c]pyrimidine (Preparation K-1; 0.050 g, 0.189 mmol), 2-(spiro[3.3]heptan-2-ylidene)acetonitrile (0.050 g, 0.377 mmol) and 2,3,4,6,7,8,9,10-octahydropyrimido[1,2-a]azepine (0.014 mL, 0.094 mmol) were suspended in MeCN (3 mL) and stirred at ambient temperature overnight. The reaction mixture was concentrated under reduced pressure and the crude material purified by flash column chromatography, eluting with 1-4% (9:1 MeOH:NH₄OH)/DCM to provide 2-(2-(4-(7-(1-methyl-1H-pyrazol-4-yl)imidazo[1,2-c]pyrimidin-5-yl)-1H-pyrazol-1-yl)spiro[3.3]heptan-2-yl)acetonitrile (0.032 g, 0.080 mmol, 42% yield). MS (apci) m/z=399.2 (M+H).

Example 161

2-(2-(4-(7-(1-methyl-1H-pyrazol-4-yl)imidazo[1,2-c]pyrimidin-5-yl)-1H-pyrazol-1-yl)spiro[3.4]octan-2-yl)acetonitrile

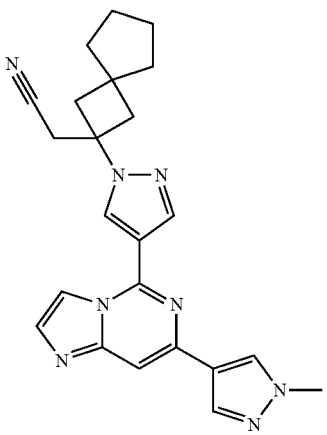 [SMILES: Cn1cc(-c2cc3nccn3c(-c3cnn(C4(CC#N)CC5(CCCC5)C4)c3)n2)cn1]

2-(2-(4-(7-(1-Methyl-1H-pyrazol-4-yl)imidazo[1,2-c]pyrimidin-5-yl)-1H-pyrazol-1-yl)spiro[3.4]octan-2-yl)acetonitrile was prepared according to the method of Example 160, using the appropriate starting materials. MS (apci) m/z=413.2 (M+H).

Example 162

2-(2-(4-(7-(1-(oxetan-3-yl)-1H-pyrazol-4-yl)imidazo[1,2-c]pyrimidin-5-yl)-1H-pyrazol-1-yl)spiro[3.3]heptan-2-yl)acetonitrile

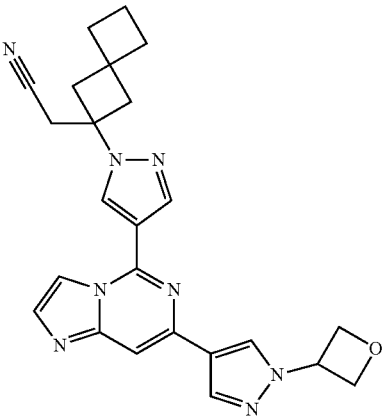 [SMILES: N#CCC1(n2cc(-c3nc(-c4cnn(C5COC5)c4)cc4nccn34)cn2)CC2(CCC2)C1]

Step A: Preparation of 2-(2-(4-(7-chloroimidazo[1,2-c]pyrimidin-5-yl)-1H-pyrazol-1-yl)spiro[3.3]heptan-2-yl)acetonitrile 7-Chloro-5-(1H-pyrazol-4-yl)imidazo[1,2-c]pyrimidine (Preparation M, Step A; 0.380 g, 1.73 mmol), 2-(spiro[3.3]heptan-2-ylidene)acetonitrile (Example 160, Steps A-C, 0.461 g, 3.46 mmol) and DBU (0.130 mL, 0.865 mmol) were suspended in MeCN (10 mL) and stirred at ambient temperature overnight. The reaction mixture was partitioned between saturated aqueous NH₄Cl and EtOAc. The organic layer was washed with brine, dried (MgSO₄), filtered concentrated under reduced pressure to afford the crude material, which was purified by flash column chromatography, eluting with 2-3% (9:1 MeOH:NH₄OH)/DCM to provide 2-(2-(4-(7-chloroimidazo[1,2-c]pyrimidin-5-yl)-1H-pyrazol-1-yl)spiro[3.3]heptan-2-yl)acetonitrile (0.493 g, 1.40 mmol, 81% yield). MS (apci) m/z=353.1 (M+H).

Step B: Preparation of 2-(2-(4-(7-(1-(oxetan-3-yl)-1H-pyrazol-4-yl)imidazo[1,2-c]pyrimidin-5-yl)-1H-pyrazol-1-yl)spiro[3.3]heptan-2-yl)acetonitrile 2-(2-(4-(7-Chloroimidazo[1,2-c]pyrimidin-5-yl)-1H-pyrazol-1-yl)spiro[3.3]heptan-2-yl)acetonitrile (0.200 g, 0.567 mmol), 1-(oxetan-3-yl)-4-(4,4,5,5-tetramethyl-1,3,2-dioxaborolan-2-yl)-1H-pyrazole (Table 2, compound f; 0.213 g, 0.850 mmol), dicyclohexyl(2',4',6'-triisopropylbiphenyl-2-yl)phosphine (0.054 g, 0.113 mmol) and K₃PO₄ (0.85 mL, 1.7 mmol) were suspended in 1,4-dioxane (10 mL) and purged with Ar (g). Pd₂dba₃ (0.052 g, 0.057 mmol) was added, and the system sealed and heated at 80° C. overnight. The reaction mixture was cooled to ambient temperature and partitioned between saturated aqueous NaHCO₃ and EtOAc. The organic layer was washed with brine, dried (MgSO₄), filtered and concentrated under reduced pressure to afford the crude material, which was purified by flash column chromatography, eluting with 2-3% (9:1 MeOH:NH₄OH)/DCM to provide 2-(2-(4-(7-(1-(oxetan-3-yl)-1H-pyrazol-4-yl)imidazo[1,2-c]pyrimidin-5-yl)-1H-pyrazol-1-yl)spiro[3.3]heptan-2-yl)acetonitrile (0.184 g, 0.418 mmol, 74% yield). MS (apci) m/z=441.2 (M+H).

What is claimed is:

1. A compound of the general Formula I

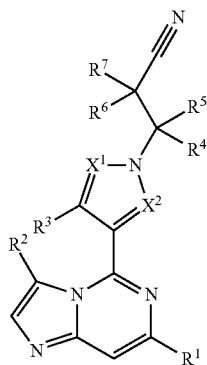

I and stereoisomers and pharmaceutically acceptable salts and solvates thereof, wherein:

$X^1$ is N or $CR^{3a}$ and $X^2$ is N or $CR^{3b}$;

$R^{3a}$ and $R^{3b}$ are independently H, (1-6C alkyl), $CF_3$, F, Cl, CN, or (3-6C)cycloalkyl;

$R^1$ is $hetAr^1$, $hetAr^2$, $hetAr^3$, $Ar^1$, $Ar^2$, $C(=O)NR^aR^b$, (3-6C)cycloalkyl, or N-(1-3C alkyl)pyridinonyl;

$hetAr^1$ is a 5 membered heteroaryl ring having 1-3 ring heteroatoms independently selected from N, O and S and optionally substituted with one or more substituents independently selected from (1-6C)alkyl, fluoro(1-6C)alkyl, difluoro(1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, $hetCyc^a$(1-2C)alkyl, $hetAr^a$(1-2C)alkyl and (1-4C alkylsulfonyl)(1-6C alkyl);

$hetCyc^a$ is a 6 membered heterocycle having 1-2 ring heteroatoms independently selected from N and O and is optionally substituted with (1-6C)alkyl;

$hetAr^a$ is a 6 membered heteroaryl having 1-2 ring nitrogen atoms;

$hetAr^2$ is a 9-membered bicyclic partially unsaturated or fully unsaturated heterocyclic ring having 3 ring nitrogen atoms and optionally substituted with one or more substituents independently selected from (1-6C)alkyl;

$hetAr^3$ is a 6 membered heteroaryl having 1-2 ring nitrogen atoms and optionally substituted with one or more substituents independently selected from (1-6C)alkyl, het-$Cyc^b$ and (1-6C)alkoxy;

$hetCyc^b$ is a 6-membered heterocycle having 1-2 ring nitrogen atoms and optionally substituted with one or more substituents independently selected from (1-6C) alkyl;

$Ar^1$ is phenyl substituted with a substituent selected from $hetCyc^c$, $hetCyc^d$, $hetAr^b$, trifluoro(1-6C)alkyl and (1-6C)alkoxy;

$hetCyc^c$ is a 6 membered heterocycle having 1-2 ring heteroatoms independently selected from N and O and optionally substituted with one or more substituents independently selected from (1-6C)alkyl;

$hetCyc^d$ is an 8-membered bridged heterocyclic ring having 1-2 ring heteroatoms independently selected from N and 0;

$hetAr^b$ is a 5-membered heteroaryl ring having 1-2 ring nitrogen atoms and optionally substituted with one or more substituents independently selected from (1-6C) alkyl;

$Ar^2$ is a benzo ring fused to a 5-6 membered azacyclic ring and is optionally substituted with one or more substituents independently selected from (1-6C)alkyl;

$R^a$ is H;

$R^b$ is (1-6C)alkyl, (3-6C)cycloalkyl or $hetAr^c$;

$hetAr^c$ is a 6-membered heteroaryl having 1-2 ring N atoms;

$R^2$ is hydrogen, halogen, (1-4C)alkyl, $CF_3$, CN, (3-4C) cycloalkyl, azetidinyl or oxetanyl;

$R^3$ is hydrogen, (1-6C)alkyl, $CF_3$, F, Cl, CN or (3-6C) cycloalkyl;

$R^4$ is H or (1-6C)alkyl, and $R^5$ is H, (1-6C)alkyl, —$CH_2CN$, (3-6C)cycloalkyl (optionally substituted by one or more halogens), $hetCyc^e$, $Ar^a$ or $hetAr^d$, or $R^4$ and $R^5$ together with the carbon atom to which they are attached form a 4-6 membered azacyclic ring optionally substituted with a substituent selected from (1-6C) alkyl, fluoro(1-6C)alkyl, difluoro(1-6C)alkyl, trifluoro (1-6C)alkyl, tetrafluoro(1-6C)alkyl, pentafluoro(1-6C) alkyl, (3-4C)alkynyl, cyano(1-4C)alkyl, benzyl, —$CH_2$ (3-6C cycloalkyl), —$CH_2hetCyc^f$, —$C(=O)O$(1-6Calkyl), —$C(=O)$(1-6Calkyl), —$C(=O)(CR'R'')$ $CF_3$, $hetAr^e$, (3-6C)cycloalkyl, a 4-6 membered oxacyclic ring and —$SO_2R^c$, or $R^4$ and $R^5$ together with the carbon atom to which they are attached form a 4-membered oxacyclic ring, or $R^4$ and $R^5$ together with the carbon atom to which they are attached form a 3-6 membered carbocyclic ring optionally substituted with (1-6C)alkyl, or $R^4$ and $R^5$ together with the carbon atom to which they are attached form a 7-9 membered bicyclic spiro carbocycle, or $R^4$ and $R^5$ together with the carbon atom to which they are attached form a 7-9 membered bicyclic spiro heterocycle having a ring heteroatom selected from O and N, wherein said ring nitrogen atom when present is optionally substituted with a substituent selected from (1-6C) alkyl, fluoro(1-6C)alkyl, difluoro (1-6C)alkyl, trifluoro (1-6C)alkyl, tetrafluoro(1-6C)alkyl, pentafluoro(1-6C) alkyl and —$SO_2R^c$;

$hetCyc^e$ is a 5-6-membered heterocycle having a ring N atom and substituted with a substituents selected from $C(=O)$(1-6C)alkyl;

$Ar^a$ is phenyl optionally substituted with one or more substituents independently selected from halogen, $CF_3$, (1-6C)alkyl and (1-6C)alkoxy;

$hetAr^d$ is a 6-membered heteroaryl having 1-2 ring nitrogen atoms and optionally substituted with one or more substituents independently selected from halogen, (1-6C)alkoxy, (1-6C)alkyl and $CF_3$;

$hetCyc^f$ is a 6-membered oxacyclic ring;

R' and R'' are independently hydrogen or methyl, or

R' and R'' together with the carbon atom to which they are attached form a cyclopropylidine ring;

$hetAr^e$ is a 6-membered heteroaryl ring having 1-2 ring nitrogen atoms;

Rc is (1-6C)alkyl, fluoro (1-3C)alkyl, difluoro(1-3C)alkyl trifluoro (1-3C)alkyl, tetrafluoro(1-3C)alkyl, pentafluoro (1-3C)alkyl, (3-6C)cycloalkyl (optionally substituted with (1-6C)alkyl), or phenyl (optionally substituted with one or more groups independently selected from (1-6C alkyl), $CF_3$, $CF_3O$— and halogen);

$R^6$ is hydrogen or methyl; and $R^7$ is hydrogen or (1-6C)alkyl.

2. A compound according to claim 1, wherein $R^1$ is $hetAr^1$ or $hetAr^2$.

3. A compound according to claim 1, wherein $R^1$ is $hetAr^1$.

4. A compound according to claim 1, wherein $hetAr^1$ is pyrazolyl, thiazolyl, oxazolyl, thiadiazolyl, imidazolyl, pyrrolyl or thiophenyl optionally substituted with one or more substituents independently selected from (1-6C)alkyl, fluoro (1-6C)alkyl, difluoro(1-6C)alkyl, trifluoro(1-6C)alkyl, (1-4C alkoxy)(1-6C)alkyl, trimethylsilyl(1-4C alkoxy)(1-6C)alkyl, (3-6C)cycloalkyl, a 4-6 membered oxacyclic ring, $hetCyc^a$(1-2C)alkyl and $hetAr^a$(1-2C)alkyl.

5. A compound according to claim 1, wherein $hetAr^1$ is pyrazol-4-yl, imidazol-1-yl or 1,3,4-thiadiazol-2-yl optionally substituted with one or more substituents independently selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl.

6. A compound according to claim 1, wherein $hetAr^1$ is pyrazol-4-yl optionally substituted with a substituent selected from methyl, ethyl, isopropyl, isobutyl, 2,2,2-trifluoroethyl, (2-isopropoxy)ethyl, trimethylsilylethoxymethyl, cyclobutyl, oxetanyl, 4-tetrahydro-2H-pyranyl, (4-methylpiperazinyl)ethyl and pyrid-3-ylmethyl.

7. A compound according to claim 1, wherein $R^1$ is hetAr2.

8. A compound according to claim 1, wherein $R^1$ is $hetAr^3$.

9. A compound according to claim 1, wherein $R^1$ is selected from $Ar^1$ and $Ar^2$.

10. A compound according to claim 1, wherein $R^1$ is $C(=O)NR^aR^b$.

11. A compound according to claim 1, wherein $R^4$ is H or (1-6C)alkyl, and $R^5$ is H, (1-6C)alkyl, —CH$_2$CN, (3-6C)cycloalkyl, $hetCyc^c$, $Ar^a$ or $hetAr^d$.

12. A compound according to claim 1, wherein $R^4$ is H or (1-6C)alkyl, and $R^5$ is H, methyl, t-butyl, 2,2-dimethylpropyl, cyanomethyl, cyclopropyl, cyclobutyl, cyclopentyl, 1-acetylpiperidin-4-yl, phenyl, trifluoromethylphenyl, chlorophenyl, pyridyl, methoxypyridyl or bromopyridyl.

13. A compound according to claim 1, wherein $R^4$ is H or (1-6C)alkyl, and $R^5$ is cyclopropyl, cyclobutyl or cyclopentyl.

14. A compound according to claim 1, wherein $R^4$ is H.

15. A compound according to claim 1, wherein $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl), —CH$_2$hetCyc$^f$, —C(=O)O(1-6Calkyl), —C(=O)(1-6Calkyl), —C(=O)(CR'R")CF$_3$, hetAr$^e$, (3-6C)cycloalkyl, a 4-6 membered oxacyclic ring and —SO$_2$R$^c$.

16. A compound according to claim 1, wherein $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, —CH$_2$(3-6C cycloalkyl), —CH$_2$-hetCyc$^f$, (3-6C)cycloalkyl and —SO$_2$R$^c$.

17. A compound according to claim 1, wherein $R^4$ and $R^5$ together with the carbon atom to which they are attached form a 4-membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl and pentafluoro(1-6C)alkyl.

18. A compound according to claim 1, wherein $R^4$ and $R^5$ together with the carbon atom to which they are attached form a 4-membered azacyclic ring substituted with —C(=O)O(1-6Calkyl), —C(=O)(1-6Calkyl), —C(=O)(CR'R")CF$_3$.

19. A compound according to claim 1, wherein $R^4$ and $R^5$ together with the carbon atom to which they are attached form a 4-membered azacyclic ring substituted with hetAr$^e$.

20. A compound according to claim 1, wherein $R^4$ and $R^5$ together with the carbon atom to which they are attached form a 4-membered azacyclic ring substituted with —SO$_2$R$^c$.

21. A compound according to claim 1, wherein $R^4$ and $R^5$ together with the carbon atom to which they are attached form a 6-membered azacyclic ring substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl), —CH$_2$hetCyc$^f$, —C(=O)O(1-6Calkyl), —C(=O)(1-6Calkyl), —C(=O)(CRR")CF$_3$, hetAr$^e$, (3-6C)cycloalkyl, a 4-6 membered oxacyclic ring and —SO$_2$R$^c$.

22. A compound of claim 1, wherein $R^4$ and $R^5$ together with the carbon atom to which they are attached form a 5 membered azacyclic ring optionally substituted with a substituent selected from (1-6C)alkyl, fluoro(1-6C)alkyl, difluoro(1-6C)alkyl, trifluoro(1-6C)alkyl, tetrafluoro(1-6C)alkyl, pentafluoro(1-6C)alkyl, (3-4C)alkynyl, cyano(1-4C)alkyl, benzyl, —CH$_2$(3-6C cycloalkyl), —CH$_2$hetCyc$^f$, —C(=O)O(1-6Calkyl), —C(=O)(1-6Calkyl), —C(=O)(CR'R")CF$_3$, hetAr$^e$, (3-6C)cycloalkyl, a 4-6 membered oxacyclic ring and —SO$_2$R$^c$.

23. A compound according to claim 1, wherein $R^4$ and $R^5$ together with the carbon atom to which they are attached form a 4-membered oxacyclic ring.

24. A compound according to claim 1, wherein $R^4$ and $R^5$ together with the carbon atom to which they are attached form a 3-6 membered carbocyclic ring.

25. A compound according to claim 1, wherein $R^7$ is hydrogen.

26. A compound according to claim 1, wherein $R^2$ is H.

27. A compound according to claim 1, wherein $R^3$ is hydrogen.

28. A compound according to claim 1, wherein $X^1$ is N and $X^2$ is $CR^{3b}$.

29. A compound according to claim 1, wherein $X^1$ is $CR^{3a}$ and $X^2$ is N.

30. A compound according to claim 1, wherein $X^1$ is $CR^{3a}$ and $X^2$ is $CR^{3b}$.

31. A compound according to claim 1, wherein $R^{3a}$ is H.

32. A compound according to claim 1, wherein $R^{3b}$ is H.

33. A pharmaceutical composition, which comprises a compound of Formula I as defined in claim 1 or a pharmaceutically acceptable salt or solvate thereof, and a pharmaceutically acceptable diluent or carrier.

34. A method for treating an autoimmune disease or inflammatory disease by the inhibition of TYK2, JAK1, JAK2 and/or JAK3 in a mammal in need thereof, which comprises administering to said mammal a therapeutically effective amount of a compound of Formula I as defined in claim 1 or a pharmaceutically acceptable salt or solvate thereof, wherein treating does not embrace preventing.

35. A method for treating organ, tissue or cell transplant rejection in a mammal in need thereof, which comprises administering to said mammal a therapeutically effective amount of a compound of Formula I as defined in claim 1 or a pharmaceutically acceptable salt or solvate thereof, wherein treating does not embrace preventing.

36. A method for treating a malignancy by the inhibition of TYK2, JAK1, JAK2 and/or JAK3 in a mammal in need thereof, which comprises administering to said mammal a therapeutically effective amount of a compound of Formula I as defined in claim 1 or a pharmaceutically acceptable salt or solvate thereof, wherein treating does not embrace preventing.

37. A process for the preparation of a compound of claim 1, which comprises:
(a) coupling a corresponding compound having the formula II or a protected derivative thereof

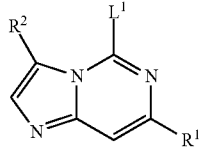

II where $L^1$ is a leaving atom and $R^1$ and $R^2$ are as defined for Formula I, with a corresponding compound having the formula III:

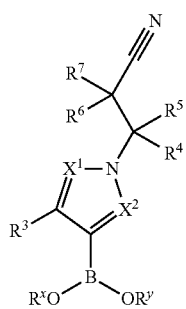

III where $R^3$, $R^4$, $R^5$, $R^6$, $R^7$, $X^1$ and $X^2$ are as defined for Formula I and $R^x$ and $R^y$ are H or (1-6C)alkyl, or $R^x$ and $R^y$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand; or (b) for compounds of Formula I wherein $R^2$ is hydrogen, cyclizing a corresponding compound having the formula IV or a protected derivative thereof

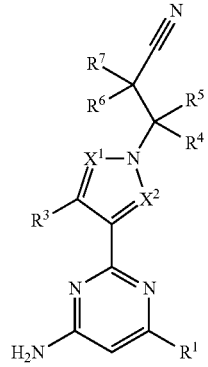

IV where $R^1$, $R^3$, $R^4$, $R^5$, $R^6$, $R^7$, $X^1$ and $X^2$ are as defined for Formula I (with the exception that $R^1$ is not C(=O)NR$^a$R$^b$), with 2-chloroacetaldehyde in the presence of a base; or (c) for a compound of Formula I wherein $R^1$ is hetAr$^1$, hetAr$^2$, hetAr$^3$, Ar$^1$ or Ar$^2$, and $R^2$ is hydrogen, coupling a corresponding compound having the formula V or a protected derivative thereof

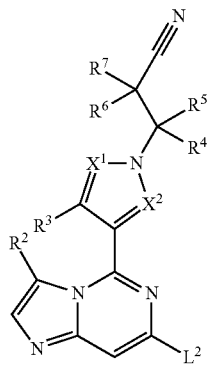

V where $R^2$ is hydrogen, $R^3$, $R^4$, $R^5$, $R^6$, $R^7$, $X^1$ and $X^2$ are as defined for Formula I and $L^2$ is a leaving atom, with a compound having the formula VIA or VIB

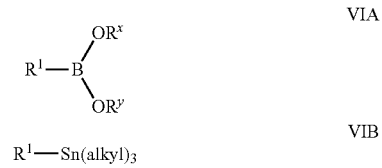

VIA

VIB wherein $R^1$ is as defined for Formula I, $R^x$ and $R^y$ are H or (1-6C)alkyl, or $R^x$ and $R^y$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand; or (d) for compounds of Formula I wherein $R^2$ is hydrogen, $R^4$ is H or (1-6C)alkyl and $R^5$ is H, (1-6C)alkyl, —CH$_2$CN, (3-6C)cycloalkyl, hetCyc$^e$, Ar$^a$ or hetAr$^d$, coupling a corresponding compound having the formula VII

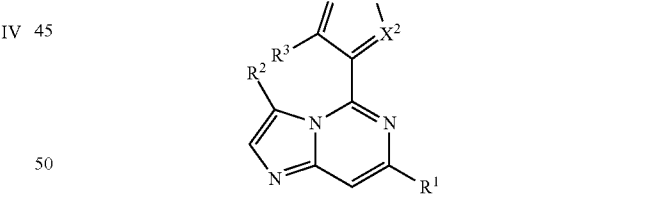

VII where $R^2$ is hydrogen, and $R^1$, $R^3$, X' and $X^2$ are as defined for Formula I, with a corresponding acrylonitrile reagent having the formula

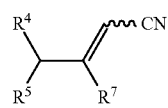

where $R^7$ is as defined for Formula I, $R^4$ is H or (1-6C)alkyl and $R^5$ is H, (1-6C)alkyl, —CH$_2$CN, (3-6C)cycloalkyl, hetCyc$^e$, Ar$^a$ or hetAr$^d$, in the presence of a base; or (e) for a compound of Formula I wherein $R^2$ is hydrogen, and $R^4$ and $R^5$ form a 4-membered oxacyclic ring, a 5-6 membered carbocyclic ring, or an unsubstituted 4 membered azacyclic ring, coupling a corresponding compound having the formula VII

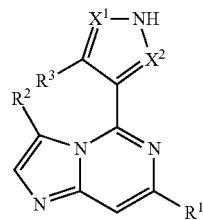

VII where $R^2$ is hydrogen, and $R^1$, $R^3$, $X^1$ and $X^2$ are as defined for Formula I, with a compound having the formula VIII-a, VIII-b, or VIII-c, respectively

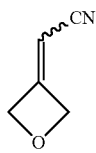

VIII-a

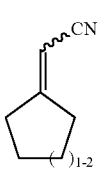

VIII-b

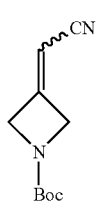

VIII-c in the presence of a base; or (f) for a compound of Formula I wherein $R^4$ and $R^5$ form a 4 or 6 membered azacyclic ring substituted with (1-6C)alkyl, fluoro(1-6C)alkyl, difluoro(1-6C)alkyl, trifluoro(1-6C)alkyl, tetrafluoro(1-6C)alkyl, pentafluoro (1-6C)alkyl, (3-4C)alkynyl, cyano(1-4C)alkyl, benzyl, —CH$_2$(3-6C cycloalkyl) or —CH$_2$hetCyc$^f$, coupling a corresponding compound having the formula IX

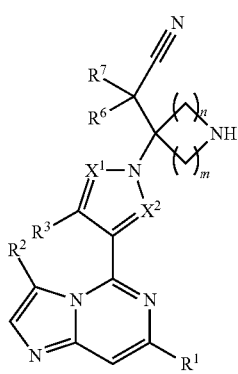

IX wherein m and n are each 1, or m and n are each 2, and $R^1$, $R^2$, $R^3$, $R^6$, $R^7$, $X^1$ and $X^2$ are as defined for Formula I, with a corresponding compound having the formula $L^3$-$R^{10}$, where $L^3$ is a leaving group or atom and $R^1$ is (1-6C)alkyl, fluoro(1-6C)alkyl, difluoro(1-6C)alkyl, trifluoro(1-6C)alkyl, tetrafluoro(1-6C)alkyl, pentafluoro (1-6C)alkyl, (3-4C)alkynyl, cyano(1-4C)alkyl, benzyl, —CH$_2$(3-6C cycloalkyl) or —CH$_2$hetCyc$^f$, in the presence of a base; or (g) for a compound of Formula I wherein $R^4$ and $R^5$ form a 4 or 6 membered azacyclic ring substituted with (1-6C)alkyl, fluoro(1-6C)alkyl, difluoro(1-6C)alkyl, trifluoro (1-6C)alkyl, tetrafluoro(1-6C)alkyl, pentafluoro(1-6C)alkyl, (3-4C)alkynyl, cyano(1-4C)alkyl, benzyl, —CH$_2$ (3-6C cycloalkyl) or —CH$_2$hetCyc$^f$, coupling a corresponding compound having the formula IX

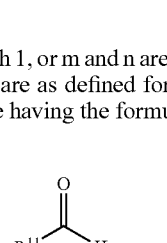

IX wherein m and n are each 1, or m and n are each 2, and $R^1$, $R^2$, $R^3$, $R^6$, $R^7$, $X^1$ and $X^2$ are as defined for Formula I, with a corresponding aldehyde having the formula

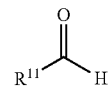

where $R^{11}$ is (1-5C)alkyl, fluoro(1-5C)alkyl, difluoro(1-5C)alkyl, trifluoro (1-5C)alkyl, tetrafluoro(1-5C)alkyl, pentafluoro(1-5C)alkyl, (3C)alkynyl, cyano(1-3C)alkyl, phenyl, -(3-6C cycloalkyl) or -hetCyc$^f$, in the presence of a base and a reducing agent; or (h) for a compound of Formula I wherein $R^4$ and $R^5$ form a 4 or 6 membered azacyclic ring substituted with cyclopropyl or oxetanyl, coupling a compound having the formula IX

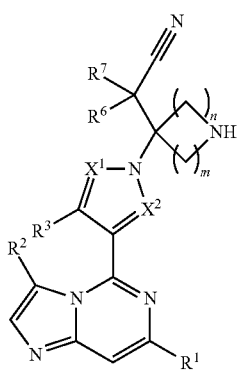

IX wherein m and n are each 1, or m and n are each 2, and $R^1$, $R^2$, $R^3$, $R^6$, $R^7$, $X^1$ and $X^2$ are as defined for Formula I, with a corresponding ketone having the formula

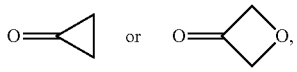

respectively, or an acetal derivative thereof, in the presence of a base and a reducing agent; or (i) for a compound of Formula I wherein $R^4$ and $R^5$ form a 4 or 6 membered azacyclic ring substituted with —C(=O)(1-6Calkyl) or —C(=O)(CR'R")CF$_3$, coupling a corresponding compound having the formula IX

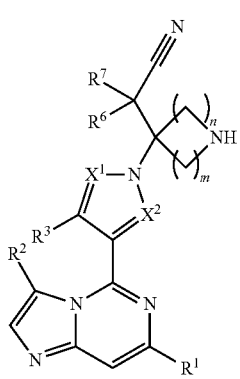

IX wherein m and n are each 1, or m and n are each 2, and $R^1$, $R^2$, $R^3$, $R^6$, $R^7$, $X^1$ and $X^2$ are as defined for Formula I, with a corresponding compound having the formula $R^{12}CO_2H$ or a corresponding anhydride thereof, where $R^{12}$ is -(1-6Calkyl) or —(CR'R")CF$_3$, in the presence of a base and optionally in the presence of a coupling reagent; or (j) for a compound of Formula I wherein $R^4$ and $R^5$ form a 4 or 6 membered azacyclic ring substituted with SO$_2$CF$_3$, reacting a compound having the formula IX

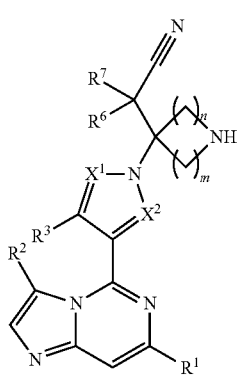

IX wherein m and n are each 1, or m and n are each 2, and $R^1$, $R^2$, $R^3$, $R^6$, $R^7$, $X^1$ and $X^2$ are as defined for Formula I, with triflic anhydride in the presence of a base; or (k) for a compound of Formula I wherein $R^4$ and $R^5$ form a 4 or 6 membered azacyclic ring substituted with SO$_2$R$^c$ where $R^c$ is as defined for Formula I, coupling a corresponding compound having the formula IX

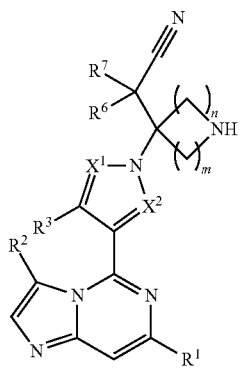

IX wherein m and n are 1, or m and n are 2, and $R^1$, $R^2$, $R^3$, $R^6$, $R^7$, $X^1$ and $X^2$ are as defined for Formula I, with a corresponding compound having the formula Cl—SO$_2$R$^c$ in the presence of a base; or (l) for a compound of Formula I wherein R' is C(=O)NR$^a$R$^b$, coupling a corresponding compound having the formula X

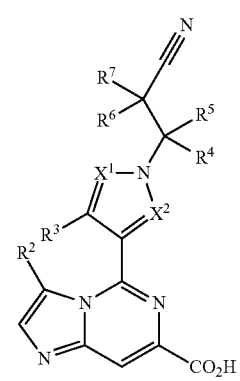

X wherein $R^2$, $R^3$, $R^4$, $R^5$, $R^6$, $R^7$, $X^1$ and $X^2$ are as defined for Formula I, with a corresponding compound having the formula HNR$^a$R$^b$ in the presence of a base and a coupling agent; or (m) for a compound of Formula I wherein $R^2$ is Cl, reacting a corresponding compound of Formula XI

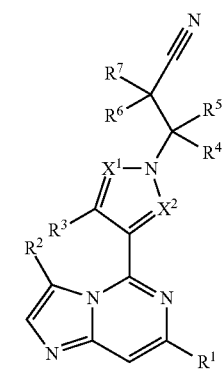

XI wherein $R^2$ is hydrogen, and $R^1$, $R^2$, $R^3$, $R^4$, $R^5$, $R^6$, $R^7$, $X^1$ and $X^2$ are as defined for Formula I, with 1-chloropyrrolidine-2,5-dione; or (n) for a compound of Formula I wherein R² is CN, reacting a corresponding compound of Formula XI

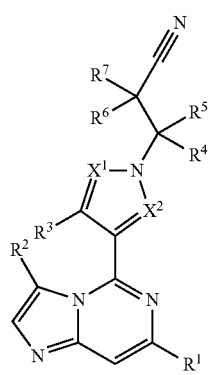

XI wherein R² is hydrogen, and R¹, R³, R⁴, R⁵, R⁶, R⁷, X¹ and X² are as defined for Formula I, with 1-iodopyrrolidinine-2,5-dione followed by treatment of the resulting 3-iodo-substituted derivative of XI with CuCN; or (o) for a compound of Formula I wherein R⁴ is hydrogen and R⁵ is CH₂CN, reacting a corresponding compound having the formula XII

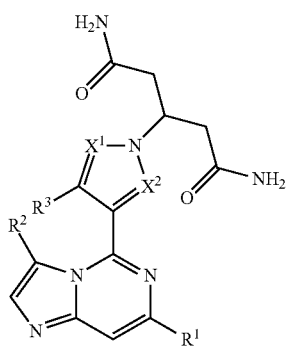

XII wherein R¹, R², R³, X¹ and X² are as defined for Formula I, with a dehydrating agent; or (p) for a compound of Formula I wherein R² is F, reacting a corresponding compound of Formula XI

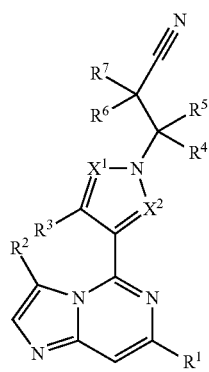

XI wherein R² is hydrogen, and R¹, R³, R⁴, R⁵, R⁶, R⁷, X¹ and X² are as defined for Formula I, with an electrophilic fluorinating agent; or (q) for a compound of Formula I wherein R² is F, reacting a corresponding compound of Formula XIII

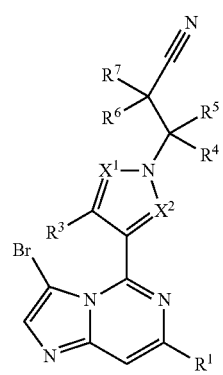

XIII with an alkyl lithium or alkyl magnesium halide reagent, followed by treatment with an electrophilic fluorinating agent; or (r) for a compound of Formula I wherein R² is F, reacting a corresponding compound of Formula IV

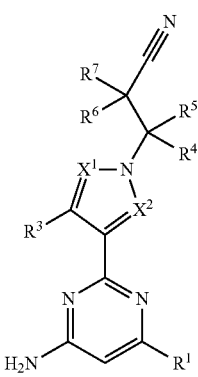

IV with 2-chloro-2-fluoroacetaldehyde or 2-bromo-2-fluoroacetaldehyde; and optionally removing any protecting groups and optionally preparing a salt or solvate thereof.

38. A compound of claim 1, selected from:
3-(4-(7-(1-methyl-1H-pyrazol-4-yl)imidazo[1,2-c]pyrimidin-5-yl)-1H-pyrazol-1-yl)pentanedinitrile;
3-Cyclopropyl-3-(4-(7-(1-methyl-1H-pyrazol-4-yl)imidazo[1,2-c]pyrimidin-5-yl)-1H-pyrazol-1-yl)propanenitrile;
Enantiomer 1 of 3-cyclopropyl-3-(4-(7-(1-methyl-1H-pyrazol-4-yl)imidazo[1,2-c]pyrimidin-5-yl)-1H-pyrazol-1-yl)propanenitrile;
Enantiomer 2 of 3-cyclopropyl-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)pentanedinitrile;
3-(4-(7-(1-methyl-1H-pyrazol-4-yl)imidazo[1,2-c]pyrimidin-5-yl)-1H-pyrazol-1-yl)-3-(pyridin-2-yl)propanenitrile;
3-(4-(7-(1-methyl-1H-pyrazol-4-yl)imidazo[1,2-c]pyrimidin-5-yl)-1H-pyrazol-1-yl)-3-(pyridin-4-yl)propanenitrile;
3-(5-methoxypyridin-3-yl)-3-(4-(7-(1-methyl-1H-pyrazol-4-yl)imidazo[1,2-c]pyrimidin-5-yl)-1H-pyrazol-1-yl)propanenitrile;

3-(5-bromopyridin-3-yl)-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)-3-phenylpropanenitrile;
3-(2-chlorophenyl)-3-(4-(7-(1-methyl-1H-pyrazol-4-yl)imidazo[1,2-c]pyrimidin-5-yl)-1H-pyrazol-1-yl)propanenitrile;
3-(3-chlorophenyl)-3-(4-(7-(1-methyl-1H-pyrazol-4-yl)imidazo[1,2-c]pyrimidin-5-yl)-1H-pyrazol-1-yl)propanenitrile;
3-(4-chlorophenyl)-3-(4-(7-(1-methyl-1H-pyrazol-4-yl)imidazo[1,2-c]pyrimidin-5-yl)-1H-pyrazol-1-yl)propanenitrile;
3-(4-(7-(1-methyl-1H-pyrazol-4-yl)imidazo[1,2-c]pyrimidin-5-yl)-1H-pyrazol-1-yl)-3-(3-(trifluoromethyl)phenyl)propanenitrile;
3-(4-(7-(1-methyl-1H-pyrazol-4-yl)imidazo[1,2-c]pyrimidin-5-yl)-1H-pyrazol-1-yl)-3-phenylbutanenitrile;
3-cyclopentyl-3-(4-(7-(1-methyl-1H-pyrazol-4-yl)imidazo[1,2-c]pyrimidin-5-yl)-1H-pyrazol-1-yl)propanenitrile;
4,4-dimethyl-3-(4-(7-(1-methyl-1H-pyrazol-4-yl)imidazo[1,2-c]pyrimidin-5-yl)-1H-pyrazol-1-yl)pentanenitrile;
3-(4-(7-(1-methyl-1H-pyrazol-4-yl)imidazo[1,2-c]pyrimidin-5-yl)-1H-pyrazol-1-yl)propanenitrile;
3-cyclobutyl-3-(4-(7-(1-methyl-1H-pyrazol-4-yl)imidazo[1,2-c]pyrimidin-5-yl)-1H-pyrazol-1-yl)propanenitrile;
tert-butyl 4-(cyanomethyl)-4-(4-(7-(1-methyl-1H-pyrazol-4-yl)imidazo[1,2-c]pyrimidin-5-yl)-1H-pyrazol-1-yl)piperidine-1-carboxylate;
2-(1-(4-(7-(1-methyl-1H-pyrazol-4-yl)imidazo[1,2-c]pyrimidin-5-yl)-1H-pyrazol-1-yl)cyclohexyl)acetonitrile;
2-(1-(4-(7-(1-methyl-1H-pyrazol-4-yl)imidazo[1,2-c]pyrimidin-5-yl)-1H-pyrazol-1-yl)cyclopentyl)acetonitrile;
2-(3-(4-(7-(1-methyl-1H-pyrazol-4-yl)imidazo[1,2-c]pyrimidin-5-yl)-1H-pyrazol-1-yl)oxetan-3-yl)acetonitrile;
3-(4-(3-chloro-7-(1-methyl-1H-pyrazol-4-yl)imidazo[1,2-c]pyrimidin-5-yl)-1H-pyrazol-1-yl)-3-cyclopropylpropanenitrile;
5-(1-(2-cyano-1-cyclopropylethyl)-1H-pyrazol-4-yl)-7-(1-methyl-1H-pyrazol-4-yl)imidazo[1,2-c]pyrimidine-3-carbonitrile;
3-(1-acetylpiperidin-4-yl)-3-(4-(7-(1-methyl-1H-pyrazol-4-yl)imidazo[1,2-c]pyrimidin-5-yl)-1H-pyrazol-1-yl)propanenitrile;
2-(1-methyl-4-(4-(7-(1-methyl-1H-pyrazol-4-yl)imidazo[1,2-c]pyrimidin-5-yl)-1H-pyrazol-1-yl)piperidin-4-yl)acetonitrile;
2-(1-ethyl-4-(4-(7-(1-methyl-1H-pyrazol-4-yl)imidazo[1,2-c]pyrimidin-5-yl)-1H-pyrazol-1-yl)piperidin-4-yl)acetonitrile;
2-(4-(4-(7-(1-methyl-1H-pyrazol-4-yl)imidazo[1,2-c]pyrimidin-5-yl)-1H-pyrazol-1-yl)-1-propylpiperidin-4-yl)acetonitrile;
2-(4-(4-(7-(1-methyl-1H-pyrazol-4-yl)imidazo[1,2-c]pyrimidin-5-yl)-1H-pyrazol-1-yl)-1-(2,2,2-trifluoroethyl)piperidin-4-yl)acetonitrile;
3-cyclopropyl-3-(4-(7-(1-((2-(timethylsilyl)ethoxy)methyl)-1H-pyrazol-4-yl)imidazo[1,2-c]pyrimidin-5-yl)-1H-pyrazol-1-yl)propanenitrile;
3-(4-(7-(1H-pyrazol-4-yl)imidazo[1,2-c]pyrimidin-5-yl)-1H-pyrazol-1-yl)-3-cyclopropylpropanenitrile;
3-Cyclopropyl-3-(4-(7-(1-isopropyl-1H-pyrazol-4-yl)imidazo[1,2-c]pyrimidin-5-yl)-1H-pyrazol-1-yl)propanenitrile;
3-cyclopropyl-3-(4-(7-(1-(pyridin-3-ylmethyl)-1H-pyrazol-4-yl)imidazo[1,2-c]pyrimidin-5-yl)-1H-pyrazol-1-yl)propanenitrile;
3-cyclopropyl-3-(4-(7-(1-(tetrahydro-2H-pyran-4-yl)-1H-pyrazol-4-yl)imidazo[1,2-c]pyrimidin-5-yl)-1H-pyrazol-1-yl)propanenitrile;
3-cyclopropyl-3-(4-(7-1-isobutyl-1H-pyrazol-4-yl)imidazo[1,2-c]pyrimidin-5-yl)-1H-pyrazol-1-yl)propanenitrile;
3-Cyclopropyl-3-(4-(7-(1-(oxetan-3-yl)-1H-pyrazol-4-yl)imidazo[1,2-c]pyrimidin-5-yl)-1H-pyrazol-1-yl)propanenitrile;
3-cyclopropyl-3-(4-(7-(1-(2,2,2-trifluoroethyl)-1H-pyrazol-4-yl)imidazo[1,2-c]pyrimidin-5-yl)-1H-pyrazol-1-yl)propanenitrile;
3-cyclopropyl-3-(4-(7-(1-ethyl-1H-pyrazol-4-yl)imidazo[1,2-c]pyrimidin-5-yl)-1H-pyrazol-1-yl)propanenitrile;
3-cyclopropyl-3-(4-(7-(1-(2-isopropoxyethyl)-1H-pyrazol-4-yl)imidazo[1,2-c]pyrimidin-5-yl)-1H-pyrazol-1 yl)propanenitrile;
3-(4-(7-(1-cyclobutyl-1H-pyrazol-4-yl)imidazo[1,2-c]pyrimidin-5-yl)-1H-pyrazol-1-yl)-3-cyclopropylpropanenitrile;
3-cyclopropyl-3-(4-(7-(oxazol-5-yl)imidazo[1,2-c]pyrimidin-5-yl)-1H-pyrazol-1-yl)propanenitrile;
3-cyclopropyl-3-(4-(7-(1-(2-(4-methylpiperazin-1-yl)ethyl)-1H-pyrazol-4-yl)imidazo[1,2-c]pyrimidin-5-yl)-1H-pyrazol-1-yl)propanenitrile;
3-Cyclopropyl-3-(4-(7-(5-methyl-1,3,4-thiadiazol-2-yl)imidazo[1,2-c]pyrimidin-5-yl)-1H-pyrazol-1-yl)propanenitrile;
3-Cyclopropyl-3-(4-(7-(4-methyl-1H-imidazol-1-yl)imidazo[1,2-c]pyrimidin-5-yl)-1H-pyrazol-1-yl)propanenitrile;
3-Cyclopropyl-3-(4-(7-(thiazol-5-yl)imidazo[1,2-c]pyrimidin-5-yl)-1H-pyrazol-1-yl)propanenitrile;
3-cyclopropyl-3-(4-(7-(2-methylthiazol-5-yl)imidazo[1,2-c]pyrimidin-5-yl)-1H-pyrazol-1-yl)propanenitrile;
3-Cyclopropyl-3-(4-(7-(6-methylpyridin-3-yl)imidazo[1,2-c]pyrimidin-5-yl)-1H-pyrazol-1-yl)propanenitrile;
3-cyclopropyl-3-(4-(7-(2-methylpyridin-4-yl)imidazo[1,2-c]pyrimidin-5-yl)-1H-pyrazol-1-yl)propanenitrile;
3-cyclopropyl-3-(4-(7-(6-(4-methylpiperazin-1-yl)pyridin-3-yl)imidazo[1,2-c]pyrimidin-5-yl)-1H-pyrazol-1-yl)propanenitrile;
3-Cyclopropyl-3-(4-(7-(1,2,3,4-tetrahydroisoquinolin-6-yl)imidazo[1,2-c]pyrimidin-5-yl)-1H-pyrazol-1-yl)propanenitrile;
3-Cyclopropyl-3-(4-(7-(2-methyl-1,2,3,4-tetrahydroisoquinolin-6-yl)imidazo[1,2-c]pyrimidin-5-yl)-1H-pyrazol-1-yl)propanenitrile;
3-Cyclopropyl-3-(4-(7-(1,2,3,4-tetrahydroisoquinolin-7-yl)imidazo[1,2-c]pyrimidin-5-yl)-1H-pyrazol-1-yl)propanenitrile;
3-Cyclopropyl-3-(4-(7-(2-methyl-1,2,3,4-tetrahydroisoquinolin-7-yl)imidazo[1,2-c]pyrimidin-5-yl)-1H-pyrazol-1-yl)propanenitrile;
3-Cyclopropyl-3-(4-(7-(5,6,7,8-tetrahydroimidazo[1,2-a]pyrazin-3-yl)imidazo[1,2-c]pyrimidin-5-yl)-1H-pyrazol-1-yl)propanenitrile;
3-cyclopropyl-3-(4-(7-(7-methyl-5,6,7,8-tetrahydroimidazo[1,2-a]pyrazin-3-yl)imidazo[1,2-c]pyrimidin-5-yl)-1H-pyrazol-1-yl)propanenitrile;
3-(4-(7-(4-(8-Oxa-3-azabicyclo[3.2.1]octan-3-yl)phenyl)imidazo[1,2-c]pyrimidin-5-yl)-1H-pyrazol-1-yl)-3-cyclopropylpropanenitrile;
3-Cyclopropyl-3-(4-(7-(4-(4-methylpiperazin-1-yl)phenyl)imidazo[1,2-c]pyrimidin-5-yl)-1H-pyrazol-1-yl)propanenitrile;
Tert-butyl 3-(cyanomethyl)-3-(4-(7-(1-methyl-1H-pyrazol-4-yl)imidazo[1,2-c]pyrimidin-5-yl)-1H-pyrazol-1-yl)azetidine-1-carboxylate;

2-(3-(4-(7-(1-Methyl-1H-pyrazol-4-yl)imidazo[1,2-c]pyrimidin-5-yl)-1H-pyrazol-1-yl)azetidin-3-yl)acetonitrile;

2-(1-Acetyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(3,3,3-trifluoropropanoyl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(1-(trifluoromethyl)cyclopropanecarbonyl)azetidin-3-yl)acetonitrile;

2-(1-Cyclopropyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(oxetan-3-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(pyrimidin-2-yl)azetidin-3-yl)acetonitrile;

2-(1-(2,2-dDifluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-Methyl-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(1-ethyl-3-(4-(7-(1-methyl-1H-pyrazol-4-yl)imidazo[1,2-c]pyrimidin-5-yl)-1H-pyrazol-1-yl)azetidin-3-yl)acetonitrile;

2,2'-(3-(4-(7-(1-methyl-1H-pyrazol-4-yl)imidazo[1,2-c]pyrimidin-5-yl)-1H-pyrazol-1-yl)azetidine-1,3-diyl)diacetonitrile;

2-(1-(3-fluoropropyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-(but-2-ynyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(prop-2-ynyl)azetidin-3-yl)acetonitrile;

2-(1-(2-fluoroethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

3-(3-(cyanomethyl)-3-(4-(7-(1-methyl-1H-pyrazol-4-yl)imidazo[1,2-c]pyrimidin-5-yl)-1H-pyrazol-1-yl)azetidin-1-yl)propanenitrile;

2-(1-(1,3-difluoropropan-2-yl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,3,3-tetrafluoropropyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-propylazetidin-3-yl)acetonitrile;

2-(1-isopropyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-methyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-(cyclopropylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-isobutyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(3,3,3-trifluoropropyl)azetidin-3-yl)acetonitrile;

2-(1-(cyclobutylmethyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-benzyl-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-((tetrahydro-2H-pyran-4-yl)methyl)azetidin-3-yl)acetonitrile;

2-(3-(4-(3-Chloro-7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(1-(Isopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(methyl sulfonyl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(propylsulfonyl)azetidin-3-yl)acetonitrile;

2-(1-(cyclohexylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(trifluoromethylsulfonyl)azetidin-3-yl)acetonitrile;

2-(1-(ethylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(3,3,3-trifluoropropylsulfonyl) azetidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(phenylsulfonyl)azetidin-3-yl)acetonitrile;

2-(3-(4-(7-(1-Isopropyl-1-H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-Isopropyl-1H-pyrazol-4-yl)imidazo[1,2-c]pyrimidin-5-yl)-1H-pyrazol-1-yl)-1-(trifluoromethylsulfonyl)azetidine-3-yl)acetonitrile;

2-(3-(4-(7-(2-Methylthiazol-5-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-Cyclobutyl-1H-pyrazol-4-yl)imidazo[1,2-c]pyrimidin-5-yl)-1H-pyrazol-1-yl)-1-(2,2,2-trifluoroethyl)azetidin-3-yl)acetonitril e;

2-(3-(4-(7-(1-Ethyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(1-(Oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

3-(3-methyl-4-(7-(1-methyl-1H-pyrazol-4-yl)imidazo[1,2-c]pyrimidin-5-yl)-1H-pyrazol-1-yl)propanenitrile;

3-(5-methyl-4-(7-(1-methyl-1H-pyrazol-4-yl)imidazo[1,2-c]pyrimidin-5-yl)-1H-pyrazol-1-yl)propanenitrile;

2-(3-(3-methyl-4-(7-(1-methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

3-Cyclopropyl-3-(3-methyl-4-(7-(1-methyl-1H-pyrazol-4-yl)imidazo[1,2-c]pyrimidin-5-yl)-1H-pyrazol-1-yl)propanenitrile;

3-Cyclopentyl-3-(4-(7-(4-(1-methylpiperidin-4-yl)phenyl)imidazo[1,2-c]pyrimidin-5-yl)-1H-pyrazol-1-yl)propanenitrile;

Enantiomer 1 of 3-cyclopentyl-3-(4-(7-(4-(1-methylpiperidin-4-yl)phenyl)imidazo[1,2-c]pyrimidin-5-yl)-1H-pyrazol-1-yl)propanenitrile;

Enantiomer 2 of 3-cyclopentyl-3-(4-(7-(4-(1-methylpiperidin-4-yl)phenyl)imidazo[1,2-c]pyrimidin-5-yl)-1H-pyrazol-1-yl)propanenitrile;

3-Cyclopentyl-3-(4-(7-(4-morpholinophenyl)imidazo[1,2-c]pyrimidin-5-yl)-1H-pyrazol-1-yl)propanenitrile;

Enantiomer 1 of 3-cyclopentyl-3-(4-(7-(4-morpholinophenyl)imidazo[1,2-c]pyrimidin-5-yl)-1H-pyrazol-1-yl)propanenitrile;

Enantiomer 2 of 3-cyclopentyl-3-(4-(7-(4-morpholinophenyl)imidazo[1,2-c]pyrimidin-5-yl)-1H-pyrazol-1-yl)propanenitrile;

3-methyl-3-(4-(7-(4-morpholinophenyl)imidazo[1,2-c]pyrimidin-5-yl)-1H-pyrazol-1-yl)butanenitrile;

3-cyclopropyl-3-(4-(7-(4-morpholinophenyl)imidazo[1,2-c]pyrimidin-5-yl)-1H-pyrazol-1-yl)propanenitrile;

3-(4-(7-(4-morpholinophenyl)imidazo[1,2-c]pyrimidin-5-yl)-1H-pyrazol-1-yl)butanenitrile;

2-methyl-3-(4-(7-(4-morpholinophenyl)imidazo[1,2-c]pyrimidin-5-yl)-1H-pyrazol-1-yl)propanenitrile;

3-(4-(7-(4-morpholinophenyl) imidazo[1,2-c]pyrimidin-5-yl)-1H-pyrazol-1-yl)propanenitrile;

3-Cyclopentyl-3-(3-methyl-4-(7-(4-morpholinophenyl)imidazo[1,2-c]pyrimidin-5-yl)-1H-pyrazol-1-yl)propanenitrile;

N-tert-butyl-5-(1-(2-cyano-1-cyclopropylethyl)-1H-pyrazol-4-yl)imidazo[1,2-c]pyrimidine-7-carboxamide;

5-(1-(2-Cyano-1-cyclopropylethyl)-1H-pyrazol-4-yl)-N-cyclohexylimidazo[1,2-c]pyrimidine-7-carboxamide;

5-(1-(2-Cyano-1-cyclopropylethyl)-1H-pyrazol-4-yl)-N-cyclobutylimidazo[1,2-c]pyrimidine-7-carboxamide;

5-(1-(2-cyano-1-cyclopropylethyl)-1H-pyrazol-4-yl)-N-(pyridin-2-yl)imidazo[1,2-c]pyrimidine-7-carboxamide;

3-Cyclopropyl-3-(3-(7-(1-methyl-1H-pyrazol-4-yl)imidazo[1,2-c]pyrimidin-5-yl)-1H-pyrrol-1-yl)propanenitrile;

2-(3-(3-(7-(1-Methyl-1H-pyrazol-4-yl)imidazo[1,2-c]pyrimidin-5-yl)-1H-pyrrol-1-yl)azetidin-3-yl)acetonitrile;

2-(3-(3-(7-(1-Methyl-1H-pyrazol-4-yl)imidazo[1,2-c]pyrimidin-5-yl)-1H-pyrrol-1-yl)-1-(2,2,2-trifluoroethyl)azetidin-3-yl)acetonitrile;

Tert-butyl 3-(cyanomethyl)-3-(3-(7-(1-methyl-1H-pyrazol-4-yl)imidazo[1,2-c]pyrimidin-5-yl)-1H-pyrazol-1-yl)azetidine-1-carboxylate;

2-(3-(3-(7-(1-Methyl-1H-pyrazol-4-yl)imidazo[1,2-c]pyrimidin-5-yl)-1H-pyrazol-1-yl)azetidin-3-yl)acetonitrile;

2-(3-(3-(7-(1-Methyl-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

3-Cyclopropyl-3-(3-(7-(1-methyl-1H-pyrazol-4-yl)imidazo[1,2-c]pyrimidin-5-yl)-1H-pyrazol-1-yl)propanenitrile;

2-(3-(4-(7-(1-methyl-1H-pyrazol-4-yl)imidazo[1,2-c]pyrimidin-5-yl)-1H-pyrazol-1-yl)-1-(trifluoromethylsulfonyl)pyrrolidin-3-yl)acetonitrile;

2-(1-acetyl-3-(4-(7-(1-methyl-1H-pyrazol-4-yl)imidazo[1,2-c]pyrimidin-5-yl)-1H-pyrazol-1-yl)pyrrolidin-3-yl)acetonitrile;

2-(3-(4-(7-(1-methyl-1H-pyrazol-4-yl)imidazo[1,2-c]pyrimidin-5-yl)-1H-pyrazol-1-yl)-1-(2,2,2-trifluoroethyl)pyrrolidin-3-yl)acetonitrile;

2-(1-(cyclopropylsulfonyl)-3-(4-(7-(1-methyl-1H-pyrazol-4-yl)imidazo[1,2-c]pyrimidin-5-yl)-1H-pyrazol-1-yl)azetidin-3-yl)acetonitrile;

2-(3-(4-(7-(4-(4-methylpiperazin-1-yl)phenyl)imidazo[1,2-c]pyrimidin-5-yl)-1H-pyrazol-1-yl)-1-(2,2,2-trifluoroethyl)azetidin-3-yl)acetonitrile;

2-(3-(4-(7-(4-(4-methylpiperazin-1-yl)phenyl)imidazo[1,2-c]pyrimidin-5-yl)-1H-pyrazol-1-yl)-1-(trifluoromethylsulfonyl)azetidin-3-yl)acetonitrile;

2-(3-(4-(7-(2-methylthiazol-5-yl)imidazo[1,2-c]pyrimidin-5-yl)-1H-pyrazol-1-yl)-1-(trifluoromethylsulfonyl)azetidin-3-yl)acetonitrile;

2-(1-(cyclopropylsulfonyl)-3-(4-(7-(2-methylthiazol-5-yl)imidazo[1,2-c]pyrimidin-5-yl)-1H-pyrazol-1-yl)azetidin-3-yl)acetonitrile;

2-(1-(cyclopropylsulfonyl)-3-(4-(7-(2-methoxypyrimidin-5-yl)imidazo[1,2-c]pyrimidin-5-yl)-1H-pyrazol-1-yl)azetidin-3-yl)acetonitrile;

2-(3-(4-(7-(2-methoxypyrimidin-5-yl)imidazo[1,2-c]pyrimidin-5-yl)-1H-pyrazol-1-yl)-1-(trifluoromethylsulfonyl)azetidin-3-yl)acetonitrile;

2-(3-(3-(7-(1-(2-(methylsulfonyl)ethyl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(3-(7-(1-methyl-2-oxo-1,2-dihydropyridin-4-yl)imidazo[1,2-c]pyrimidin-5-yl)-1H-pyrazol-1-yl)-1-(2,2,2-trifluoroethyl)azetidin-3-yl)acetonitrile;

2-(3-(3-(7-(1-methyl-6-oxo-1,6-dihydropyridin-3-yl)imidazo[1,2-c]pyrimidin-5-yl)-1H-pyrazol-1-yl)-1-(2,2,2-trifluoroethyl)azetidin-3-yl)acetonitrile;

2-(3-(4-(7-(4-(trifluoromethyl)phenyl)imidazo[1,2-c]pyrimidin-5-yl)-1H-pyrazol-1-yl)-1-(trifluoromethylsulfonyl)azetidin-3-yl)acetonitrile;

3-(2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

(S)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

R)-3-((S)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

(S)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

(R)-3-((R)-2,2-difluorocyclopropyl)-3-(4-(7-(1-methyl-1H-pyrazol-4-yl)imidazo[1,2-c]pyrimidin-5-yl)-1H-pyrazol-1-yl)propanenitrile;

2-(6-(4-(7-(1-methyl-1H-pyrazol-4-yl)imidazo[1,2-c]pyrimidin-5-yl)-1H-pyrazol-1-yl)-2-oxaspiro[3.3]heptan-6-yl)acetonitrile;

2-(3-(4-(7-cyclopropylimidazo[1,2-c]pyrimidin-5-yl)-1H-pyrazol-1-yl)-1-(2,2,2-trifluoroethyl)azetidin-3-yl)acetonitrile;

2-(2-(4-(7-(1-methyl-1H-pyrazol-4-yl)imidazo[1,2-c]pyrimidin-5-yl)-1H-pyrazol-1-yl)-7-oxaspiro[3.5]nonan-2-yl)acetonitrile;

3-cyclopropyl-3-(4-(3-fluoro-7-(1-methyl-1H-pyrazol-4-yl)imidazo[1,2-c]pyrimidin-5-yl)-1H-pyrazol-1-yl)propanenitrile;

2-(3-(4-(3-chloro-7-(1-(oxetan-3-yl)-1H-pyrazol-4-yl)imidazo[1,2-c]pyrimidin-5-yl)-1H-pyrazol-1-yl)-1-(2,2,2-trifluoroethyl)azetidin-3-yl)acetonitrile;

2-(3-(4-(3-fluoro-7-(1-methyl-1H-pyrazol-4-yl)imidazo[1,2-c]pyrimidin-5-yl)-1H-pyrazol-1-yl)-1-((trifluoromethyl)sulfonyl)azetidin-3-yl)acetonitrile;

2-(3-(4-(3-chloro-7-(1-methyl-1H-pyrazol-4-yl)imidazo[1,2-c]pyrimidin-5-yl)-1H-pyrazol-1-yl)-1-((trifluoromethyl)sulfonyl)azetidin-3-yl)acetonitrile;

2-(1-(2,2-difluoroethyl)-3-(4-(7-(1-(oxetan-3-yl)-1H-pyrazol-4-yl)imidazo[1,2-c]pyrimidin-5-yl)-1H-pyrazol-1-yl)azetidin-3-yl)acetonitrile;

2-(3-(4-(7-(1-(oxetan-3-yl)-1H-pyrazol-4-yl)imidazo[1,2-c]pyrimidin-5-yl)-1H-pyrazol-1-yl)-1-(2,2,3,3,3-pentafluoropropyl)azetidin-3-yl)acetonitrile;

2-(3-(4-(7-(4-methoxyphenyl)imidazo[1,2-c]pyrimidin-5-yl)-1H-pyrazol-1-yl)-1-(trifluoromethylsulfonyl)azetidin-3-yl)acetonitrile;

2-(1-(cyclopropylsulfonyl)-3-(4-(7-(4-methoxyphenyl)imidazo[1,2-c]pyrimidin-5-yl)-1H-pyrazol-1-yl)azetidin-3-yl)acetonitrile;

2-(2-(4-(7-(1-methyl-1H-pyrazol-4-yl)imidazo[1,2-c]pyrimidin-5-yl)-1H-pyrazol-1-yl)spiro[3.3]heptan-2-yl)acetonitrile;

2-(2-(4-(7-(1-methyl-1H-pyrazol-4-yl)imidazo[1,2-c]pyrimidin-5-yl)-1H-pyrazol-1-yl)spiro[3.4]octan-2-yl)acetonitrile;

2-(2-(4-(7-(1-(oxetan-3-yl)-1H-pyrazol-4-yl)imidazo[1,2-c]pyrimidin-5-yl)-1H-pyrazol-1-yl)spiro[3.3]heptan-2-yl)acetonitrile;

or a pharmaceutically acceptable salt or solvate thereof.

* * * * *